(12) United States Patent
Lieberman Aiden et al.

(10) Patent No.: US 11,214,800 B2
(45) Date of Patent: Jan. 4, 2022

(54) METHODS AND COMPOSITIONS FOR ALTERING FUNCTION AND STRUCTURE OF CHROMATIN LOOPS AND/OR DOMAINS

(71) Applicants: THE BROAD INSTITUTE, INC., Cambridge, MA (US); BAYLOR COLLEGE OF MEDICINE, Houston, TX (US)

(72) Inventors: Erez Lieberman Aiden, Houston, TX (US); Eric S. Lander, Cambridge, MA (US); Suhas Rao, Stanford, CA (US); Su-Chen Huang, Houston, TX (US); Adrian L. Sanborn, Houston, TX (US); Neva C. Durand, Houston, TX (US); Miriam Huntley, Houston, TX (US); Andrew Jewett, Houston, TX (US)

(73) Assignees: THE BROAD INSTITUTE, INC., Cambridge, MA (US); BAYLOR COLLEGE OF MEDICINE, Houston, TX (US)

( * ) Notice: Subject to any disclaimer, the term of this patent is extended or adjusted under 35 U.S.C. 154(b) by 0 days.

(21) Appl. No.: 15/753,318

(22) PCT Filed: Aug. 18, 2016

(86) PCT No.: PCT/US2016/047644
§ 371 (c)(1),
(2) Date: Feb. 18, 2018

(87) PCT Pub. No.: WO2017/031370
PCT Pub. Date: Feb. 23, 2017

(65) Prior Publication Data
US 2018/0245079 A1    Aug. 30, 2018

Related U.S. Application Data

(60) Provisional application No. 62/347,585, filed on Jun. 8, 2016, provisional application No. 62/239,135, filed on Oct. 8, 2015, provisional application No. 62/206,606, filed on Aug. 18, 2015.

(51) Int. Cl.
*C12N 15/113* (2010.01)
*C07K 14/47* (2006.01)
*C12N 15/11* (2006.01)

(52) U.S. Cl.
CPC ............ *C12N 15/113* (2013.01); *C07K 14/47* (2013.01); *C07K 14/4702* (2013.01); *C12N 15/11* (2013.01); *C12N 2310/14* (2013.01); *C12N 2310/20* (2017.05)

(58) Field of Classification Search
None
See application file for complete search history.

(56) References Cited

U.S. PATENT DOCUMENTS

| | | | |
|---|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 5,427,930 A | 6/1995 | Birkenmeyer et al. |
| 5,543,158 A | 8/1996 | Gref et al. |
| 5,580,859 A | 12/1996 | Felgner et al. |
| 5,589,466 A | 12/1996 | Felgner et al. |
| 5,593,972 A | 1/1997 | Weiner et al. |
| 5,744,311 A | 4/1998 | Fraiser et al. |
| 5,846,946 A | 12/1998 | Huebner et al. |
| 5,855,913 A | 1/1999 | Hanes et al. |

(Continued)

FOREIGN PATENT DOCUMENTS

| | | |
|---|---|---|
| EP | 1 519 714 A1 | 4/2005 |
| EP | 1 664 316 A1 | 6/2006 |

(Continued)

OTHER PUBLICATIONS

Karpf, A.R., A Potential Role for Epigenetic Modulatory Drugs in the Enhancement of Cancer/Germ-Line Antigen Vaccine Efficacy; Epigenetics, vol. 1, No. 3, pp. 116-120, 2006 (Year: 2006).*

(Continued)

*Primary Examiner* — Nancy J Leith

(74) *Attorney, Agent, or Firm* — F. Brent Nix, Esq.; Michael B. Scher, Esq.; Johnson, Marcou, Isaacs & Nix, LLC

(57) ABSTRACT

Chromatin 3D structure modulating agents in the context of the present invention are intended to interfere or manipulate the function of loop anchor motifs, such as CTCF motifs. In certain example embodiments, the present invention may block formation of an loop anchor or chromatin domain or induce formation of a loop anchor or chromatin domain at a targeted genomic location. For instance, a loop anchor motif can be altered, such as by mutating (including inverting) a binding motif so as to remove such a motif, or by adding new binding motifs in new locations within a loop domain, so as to reduce the size of an existing loop, so as to modify the size of an existing loop, or combinations thereof. Alternatively, the chromatin 3D structure modulating agent may bind a target region and mask a loop anchor motif, thereby preventing a loop anchor or chromatin domain from forming. The chromatin 3D structure modulating agent may bind a target region and cause a loop anchor of chromatin domain to form.

32 Claims, 24 Drawing Sheets

Specification includes a Sequence Listing.

(56) References Cited

U.S. PATENT DOCUMENTS

| | | |
|---|---|---|
| 5,866,366 A | 2/1999 | Kallender |
| 5,985,309 A | 11/1999 | Edwards et al. |
| 6,007,845 A | 12/1999 | Domb et al. |
| 6,025,134 A | 2/2000 | Sooknanan |
| 6,027,889 A | 2/2000 | Barany et al. |
| 6,479,626 B1 | 11/2002 | Kim et al. |
| 6,534,261 B1 | 3/2003 | Cox et al. |
| 6,603,061 B1 | 8/2003 | Armstrong et al. |
| 6,607,882 B1 | 8/2003 | Cox et al. |
| 6,746,838 B1 | 6/2004 | Choo et al. |
| 6,794,136 B1 | 9/2004 | Eisenberg et al. |
| 6,824,978 B1 | 11/2004 | Cox et al. |
| 6,866,997 B1 | 3/2005 | Choo et al. |
| 6,903,185 B2 | 6/2005 | Kim et al. |
| 6,933,113 B2 | 8/2005 | Case et al. |
| 6,979,539 B2 | 12/2005 | Cox et al. |
| 7,013,219 B2 | 3/2006 | Case et al. |
| 7,030,215 B2 | 4/2006 | Liu et al. |
| 7,220,719 B2 | 5/2007 | Case et al. |
| 7,241,573 B2 | 7/2007 | Choo et al. |
| 7,241,574 B2 | 7/2007 | Choo et al. |
| 7,259,015 B2 | 8/2007 | Kingsman et al. |
| 7,303,910 B2 | 12/2007 | Bebbington et al. |
| 7,351,585 B2 | 4/2008 | Mitrophanous et al. |
| 7,585,849 B2 | 9/2009 | Liu et al. |
| 7,595,376 B2 | 9/2009 | Kim et al. |
| 7,745,651 B2 | 6/2010 | Heyes et al. |
| 7,799,565 B2 | 9/2010 | MacLachlan et al. |
| 7,803,397 B2 | 9/2010 | Heyes et al. |
| 7,838,658 B2 | 11/2010 | MacLachlan et al. |
| 7,868,149 B2 | 1/2011 | Boukharov et al. |
| 7,901,708 B2 | 3/2011 | MacLachlan et al. |
| 7,915,399 B2 | 3/2011 | MacLachlan et al. |
| 7,982,027 B2 | 7/2011 | MacLachlan et al. |
| 8,021,867 B2 | 9/2011 | Smith et al. |
| 8,044,019 B2 | 10/2011 | Uno et al. |
| 8,058,069 B2 | 11/2011 | Yaworski et al. |
| 8,101,741 B2 | 1/2012 | MacLachlan et al. |
| 8,119,361 B2 | 2/2012 | Smith et al. |
| 8,119,381 B2 | 2/2012 | Smith et al. |
| 8,124,369 B2 | 2/2012 | Smith et al. |
| 8,129,134 B2 | 3/2012 | Smith et al. |
| 8,133,697 B2 | 3/2012 | Smith et al. |
| 8,163,514 B2 | 4/2012 | Smith et al. |
| 8,188,263 B2 | 5/2012 | MacLachlan et al. |
| 8,236,943 B2 | 8/2012 | Lee et al. |
| 8,283,333 B2 | 10/2012 | Yaworski et al. |
| 8,372,951 B2 | 2/2013 | Chang et al. |
| 8,404,658 B2 | 3/2013 | Hajjar et al. |
| 8,440,431 B2 | 5/2013 | Voytas et al. |
| 8,440,432 B2 | 5/2013 | Voytas et al. |
| 8,450,471 B2 | 5/2013 | Voytas et al. |
| 8,454,972 B2 | 6/2013 | Nabel et al. |
| 8,575,305 B2 | 11/2013 | Gait et al. |
| 8,614,194 B1 | 12/2013 | Chen et al. |
| 8,697,359 B1 | 4/2014 | Zhang |
| 8,709,843 B2 | 4/2014 | Shakuda |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 2004/0013648 A1 | 1/2004 | Kingsman et al. |
| 2005/0019923 A1 | 1/2005 | Uchegbu et al. |
| 2006/0281180 A1 | 12/2006 | Radcliffe et al. |
| 2007/0025970 A1 | 2/2007 | Kingsman et al. |
| 2007/0054961 A1 | 3/2007 | Maden et al. |
| 2008/0267903 A1 | 10/2008 | Uchegbu et al. |
| 2009/0007284 A1 | 1/2009 | Radcliffe et al. |
| 2009/0017543 A1 | 1/2009 | Wilkes et al. |
| 2009/0100536 A1 | 4/2009 | Adams et al. |
| 2009/0111106 A1 | 4/2009 | Mitrophanous et al. |
| 2010/0317109 A1 | 12/2010 | Maden et al. |
| 2011/0117189 A1 | 5/2011 | Mazzone et al. |
| 2011/0195123 A1 | 8/2011 | Shemi |
| 2011/0293571 A1 | 12/2011 | Widdowson et al. |
| 2011/0293703 A1 | 12/2011 | Mahon et al. |
| 2012/0115227 A1 | 5/2012 | Cohen-Haguenauer et al. |
| 2012/0251560 A1 | 10/2012 | Dahlman et al. |
| 2012/0251618 A1 | 10/2012 | Schrum et al. |
| 2012/0295960 A1 | 11/2012 | Palfi et al. |
| 2013/0079231 A1 | 3/2013 | Pushkarev et al. |
| 2013/0244279 A1 | 9/2013 | de Fougerolles et al. |
| 2013/0245107 A1 | 9/2013 | de Fougerolles et al. |
| 2013/0252281 A1 | 9/2013 | de Fougerolles et al. |
| 2013/0302401 A1 | 11/2013 | Ma et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0310830 A1 | 10/2014 | Zhang et al. |
| 2016/0186208 A1* | 6/2016 | Jaenisch .............. C12N 15/907 800/18 |
| 2017/0007679 A1* | 1/2017 | Maeder .............. C12N 15/1138 |

FOREIGN PATENT DOCUMENTS

| | | |
|---|---|---|
| EP | 1 766 035 A1 | 3/2007 |
| EP | 1 781 593 A2 | 5/2007 |
| EP | 2 764 103 A2 | 8/2014 |
| EP | 2 771 468 A1 | 9/2014 |
| EP | 2 784 162 A1 | 10/2014 |
| EP | 3 009 511 A2 | 4/2016 |
| EP | 3 337 908 A1 | 6/2018 |
| WO | 90/01069 A1 | 2/1990 |
| WO | 2012/135025 A2 | 10/2012 |
| WO | 2014/018423 A2 | 1/2014 |
| WO | 2014/093595 A1 | 6/2014 |
| WO | 2014/093622 A2 | 6/2014 |
| WO | 2014/093635 A1 | 6/2014 |
| WO | 2014/093655 A2 | 6/2014 |
| WO | 2014/093661 A2 | 6/2014 |
| WO | 2014/093694 A1 | 6/2014 |
| WO | 2014/093701 A1 | 6/2014 |
| WO | 2014/093709 A1 | 6/2014 |
| WO | 2014/093712 A1 | 6/2014 |
| WO | 2014/093718 A1 | 6/2014 |
| WO | 2014172470 A2 | 10/2014 |
| WO | 2014/204723 A1 | 12/2014 |
| WO | 2014/204724 A1 | 12/2014 |
| WO | 2014/204725 A1 | 12/2014 |
| WO | 2014/204726 A1 | 12/2014 |
| WO | 2014/204727 A1 | 12/2014 |
| WO | 2014/204728 A1 | 12/2014 |
| WO | 2014/204729 A1 | 12/2014 |
| WO | 2015033293 A1 | 3/2015 |
| WO | 2015/089419 A2 | 6/2015 |
| WO | 2015/089486 A2 | 6/2015 |
| WO | 2017/031370 A1 | 2/2017 |

OTHER PUBLICATIONS

Nichols et al., "A CTCF Code for 3D Genome Architecture" 162 Cell 703-705 (Year: 2015).*

(56) References Cited

OTHER PUBLICATIONS

Invitation to Pay Additional Fees for PCT International Application No. PCT/US2016/047644, Nov. 15, 2016, 2.
International Search Report and Written Opinion for PCT International Application No. PCT/US2016/047644, dated Feb. 1, 2017, 18.
Alpour, et al., "Self-organization of Domain Structures by DNA-loop-extruding Enzymes", Nucleic Acids Res, vol. 40, No. 22, Dec. 2012, 11202-11212.
Guo, et al., "CRISPR Inversion of CTCF Sites Alters Genome Topology and Enhancer/Promoter Function", Cell, vol. 162, Aug. 13, 2015, 900-910.
Sanborn, et al., "Chromatin Extrusion Explains Key Features of Loop and Domain Formation in Wild-Type and Engineered Genomes", PNAS ePub, vol. 112, No. 47, Oct. 23, 2015, E6456-E6465.
Wittmann-Regis, "PCT International Preliminary Report on Patentability issued in PCT/US2016/047544 dated Mar. 1, 2018", Mar. 1, 2018, 1-9.
"Extended European Search Report issued in European Application No. 16837870.1", dated Jan. 2, 2019, 10 pages.
Aiden, et al., "Comprehensive Mapping of Long Range Interactions Reveals Folding Principles of the Human Genome", Science, vol. 326, Issue 5950, Oct. 9, 2009, 289-293.
Alipour, et al., "Self-organization of Domain Structures by DNA-loop-extruding Enzymes", Nucleic Acids Research, vol. 40, No. 22, 2012, 1-11.
Banerji, et al., "Expression of a beta-globin Gene is Enhanced by Remote SV40 DNA Sequences", Cell, vol. 27, Dec. 1981, 299-308.
Barbieri, et al., "Complexity of Chromatin Folding is Captured by the Strings and Binders Switch Model", Proceedings of the National Academy of Sciences, vol. 109, 16173-16178.
Barski, et al., "High-resolution Profiling Of Histone Methylations In The Human Genome", Cell, vol. 129, No. 4, May 18, 2007, 823-837.
Bickmore, Wendy A.., "The Spatial Organization of the Human Genome", Annual Review of Genomics and Human Genetics, vol. 14, 2013, 67-84.
Blackwood, et al., "Going the Distance: A Current View of Enhancer Action", Science, vol. 281, No. 5373, 1998, 60-63.
Bohn, et al., "Diffusion-Driven Looping Provides a Consistent Framework for Chromatin Organization", PloS One, vol. 5, 2010, 14 pages.
Bulger, et al., "Looping Versus Linking: Toward a Model for Long-distance Gene Activation", Genes & Development, vol. 13, 1999, 2465-2477.
Chadwick, et al., "DXZ4 Chromatin Adopts an Opposing Conformation to that of the Surrounding Chromosome and Acquires a Novel Inactive X-Specific Role Involving CTCF and Antisense Transcripts", Genome Research, vol. 18, 2008, 1259-1269.
Cremer, et al., "Chromosome Territories, Nuclear Architecture and Gene Regulation in Mammalian Cells", Nature Reviews Genetics, vol. 2, No. 4, 2001, 292-301.
Cullen, et al., "Interaction Between Transcription Regulatory Regions Of Prolactin Chromatin", Science, vol. 261, No. 5118, Jul. 9, 1993, 203-206.
De Gennes, P.G., "Kinetics of Collapse for a Flexible Coil", Journal de Physique Lettres, vol. 48, No. 14, 1985, 639-642.
Dekker, et al., "Capturing Chromosome Conformation", Science, vol. 295, No. 5558, Feb. 15, 2002, 1306-1311.
Dixon, et al., "Topological Domains In Mammalian Genomes Identified By Analysis Of Chromatin Interactions", Nature, vol. 485, No. 7398, Apr. 11, 2012, 376-380.
Dostie, et al., "Chromosome Conformation Capture Carbon Copy (5C): A Massively Parallel Solution For Mapping Interactions Between Genomic Elements", Genome Research, vol. 16, No. 10, Oct. 2006, 1299-1309.
Durand, et al., "Juicer Provides a One-Click System for Analyzing Loop-Resolution Hi-C Experiments", Cell Systems, vol. 3, Issue 1, Jul. 27, 2016, p. 95-98.
Fullwood, "An Oestrogen Receptor ?-bound Human Chromatin Interactome", Nature, vol. 462, No. 7269, Nov. 5, 2009, 58-64.
Gaszner, et al., "Insulators: Exploiting Transcriptional And Epigenetic Mechanisms", Nature Reviews Genetics, vol. 7, No. 9, Sep. 2006, 703-713.
Gerasimova, et al., "A Chromatin Insulator Determines the Nuclear Localization of DNA", Molecular Cell, vol. 6, No. 5, Nov. 2000, 1025-1035.
Hahn, et al., "Relationship between Gene Body DNA Methylation and Intragenic H3K9me3 and H3K36me3 Chromatin Marks", PLoS ONE, vol. 6, No. 4, e18844, Apr. 2011, 12 pages.
Horakova, et al., "The Macrosatellite DXZ4 Mediates CTCF-Dependent Long-Range Intrachromosomal Interactions on the Human Inactive X Chromosome", Human Molecular Genetics, vol. 21 No. 20, Jul. 2012, 4367-4377.
Horakova, et al., "The Mouse DXZ4 Homolog Retains Ctcf Binding and Proximity to Pls3 Despite Substantial Organizational Differences Compared to the Primate Macrosatellite", Genome Biology, vol. 13, Article No. R70, 2012, 17 pages.
Jin, et al., "A High-resolution Map of Three-dimensional Chromatin Interactome in Human Cells", Nature, vol. 503, 2013, 290-294.
Kalhor, et al., "Genome Architectures Revealed By Tethered Chromosome Conformation Capture And Population-based Modeling", Nature Biotechnology, vol. 30, No. 1, Jan. 2012, 90-98.
Kim, et al., "Analysis of the Vertebrate Insulator Protein CTCF Binding Sites in the Human Genome", Cell, vol. 128, No. 6, Mar. 23, 2007, 1231-1245.
Lupianez, et al., "Disruptions of Topological Chromatin Domains cause Pathogenic Rewiring of Gene-enhancer Interactions", Cell, vol. 16, Issue 5, May 21, 2015, p. 1012-p. 1025.
Marshall, et al., "CTCF and BORIS in Genome Regulation and Cancer", Current Opinion in Genetics & Development, vol. 24C, No. 1, Dec. 2013, 8-15.
Mateos-Langerak, et al., "Spatially Confined Folding of Chromatin in the Interphase Nucleus", Proceedings of the National Academy of Sciences, vol. 106, No. 10, Mar. 10, 2009, 3812-3817.
Minajigi, et al., "A Comprehensive Xist Interactome Reveals Cohesin Repulsion and an RNA-directed Chromosome Conformation", Science, vol. 349, No. 6245, Jul. 17, 2015, 6 pages.
Mukherjee, et al., "Enhancer-Origin Interaction in Plasmid R6K Involves a DNA Loop Mediated by Initiator Protein", Cell, vol. 52, Issue 3, Feb. 12, 1988, 375-383.
Murrell, et al., "Interaction Between Differentially Methylated Regions Partitions The Imprinted Genes Igf2 And H19 Into Parent-specific Chromatin Loops", Nature Genetics, vol. 36, No. 8, Aug. 2004, 889-893.
Narendra, et al., "CTCF Establishes Discrete Functional Chromatin Domains at the Hox Clusters during Differentiation", Science, vol. 347, No. 6225, Feb. 27, 2015, 1017-1021.
Nasmyth, Kim, "Disseminating the Genome: Joining, Resolving, and Separating Sister Chromatids During Mitosis and Meiosis", Annual Review of Genetics, vol. 35, 2001, 673-745.
Naumova, et al., "Organization of the Mitotic Chromosome", Science, vol. 34, No. 6161, 2013, 948-953.
Nora, et al., "Spatial Partitioning of the Regulatory Landscape of the Xinactivation Center", Nature, vol. 485, No. 7398, 2012, 381-385.
Rao, et al., "A 3D Map Of The Human Genome At Kilobase Resolution Reveals Principles Of Chromatin Looping", Cell, vol. 159, No. 7, Dec. 18, 2014, 1665-1680.
Ren, et al., "A CRISPR Connection between Chromatin Topology and Genetic Disorders", Cell, vol. 161, No. 5, May 21, 2015, 955-957.
Rosa, et al., "Structure and Dynamics of Interphase Chromosomes", PLOS Computational Biology, vol. 4, No. 8, 2008, 16 pages.
Sachs, et al., "A Random-walk/giant-loop Model for Interphase Chromosomes", Proceedings of the National Academy of Sciences, vol. 92, Mar. 1995, 2710-2714.
Schleif, Robert, "DNA Looping", Annual Review of Biochemistry, vol. 61, 1992, 199-223.
Schmidt, et al., "Waves of Retrotransposon Expansion Remodel Genome Organization And Ctcf Binding in Multiple Mammalian Lineages", Cell, vol. 148, No. (1-2), Jan. 20, 2012, 335-348.

(56) References Cited

OTHER PUBLICATIONS

Schram, et al., "On the Stability of Fractal Globules", The Journal of Chemical Physics, vol. 138, 2013, 12 pages.
Sexton, et al., "Gene Regulation through Nuclear Organization", Nature Structural & Molecular Biology, vol. 14, 2007, 1049-1055.
Sexton, et al., "Three-dimensional Folding And Functional Organization Principles Of The *Drosophila* Genome", Cell, vol. 148, No. 3, Feb. 3, 2012, 458-472.
Tolhuis, et al., "Looping And Interaction Between Hypersensitive Sites In The Active ?-Globin Locus", Molecular Cell, vol. 10, No. 6, Dec. 2002, 1453-1465.
Zhang, et al., "Chromosomal Translocations are Guided by the Spatial Organization of the Genome", Cell, vol. 148, No. 5, 2012, 908-921.
Guo, et al., "CRISPR Inversion of CTCF Sites Alters Genome Topology and Enhancer/Promoter Function.", Cell, vol. 162, No. 4, XP055365405, pp. 900-910, Aug. 13, 2015.
Sanborn et al., "Chromatin extrusion explains key features of loop and domain formation in wild-type and engineered genomes.", PNAS, vol. 112, No. 47, XP055365407, pp. E6456-E6465, Published online: Oct. 23, 2015.
"Communication pursuant to Article 94(3) EPC", issued by the European Patent Office dated Oct. 29, 2020 for counterpart European Application No. 16837870.1.
Qi, Lei S., et al., "Repurposing CRISPR as an RNA-Guided Platform for Sequence-Specific Control of Gene Expression", Cell, vol. 152, No. 5, pp. 1173-1183, Feb. 28, 2013.
"Communication pursuant to Article 94(3) EPC", issued by the European Patent Office (EPO) for counterpart EP Application No. 16837870.1 dated May 31, 2021.

\* cited by examiner

METHODS AND COMPOSITIONS FOR ALTERING FUNCTION AND STRUCTURE OF CHROMATIN LOOPS AND/OR DOMAINS

REFERENCE TO RELATED APPLICATIONS

This application is the U.S. National Stage of International Application No. PCT/US2016/047644, filed Aug. 18, 2016, published in English under PCT Article 21(2), which claims priority to U.S. Provisional Application No. 62/206,606 filed Aug. 18, 2015 and entitled "Principles and Applications of Chromatin Looping," U.S. Provisional Application No. 62/239,135 filed Oct. 8, 2015 and entitled "Principles and Applications of Chromatin Looping," and U.S. Provisional Application No. 62/347,585 filed Jun. 8, 2016 and entitled "Methods and Compositions for Altering Function and Structure of Chromatin Loops and/or Domains," the complete disclosures of which are hereby fully incorporated herein by reference.

STATEMENT OF GOVERNMENT SUPPORT

This invention was made with government support under Grant No. HG003067 awarded by the National Institutes of Health. The government has certain rights in the invention.

REFERENCE TO AN ELECTRONIC SEQUENCE LISTING

The contents of the electronic sequence listing ("BROD-0552US_ST25.txt"; Size is 15,441 bytes and it was created on Jan. 19, 2021) is herein incorporated by reference in its entirety.

FIELD OF THE INVENTION

The present invention is in the field of genetic engineering and medicine. The present invention provides methods and tools for altering chromatin three dimensional (3D) structure in a cell, in particular chromatin loop formation and structure. The present invention allows the altering the transcriptional activity of chromatin domains or genomic loci, including such domains and loci associated with a disease, such as cancer or a genetic disease, through use of such methods and tools. The present invention provides methods of treatment comprising altering chromatin 3D structure or gene expression within a chromatin domain. The present invention further provides methods of modulating chromatin loop formation to thereby interfere with higher-order chromatin structure, and ultimately control gene expression.

Also, the present invention provides a method for probing higher order structures formed by the chromatin loops, using in situ proximity ligation of multiple extremely short fragments produced by restriction enzyme cleavage in combination with chromosome conformation capture and deep sequencing methods in intact nuclei (in situ Hi-C) for creating 3D genome maps. The method for probing such higher order structures is particularly useful for determining the proximity among three or more loci. The methods of the invention rely on a systematic approach of causing single and combinatorial genome-wide perturbations in cells, with subsequent molecular profiling at the single cell level. Applications include dissection of cell circuitry and delineation of functional or molecular pathways. The present invention is also relevant for therapeutics target discovery.

The present invention further provides methods for sequencing and assembling target genomes using 3D contact maps of chromatin loop structures in a target genome defining spatial proximity relationships between genomic loci in the genome. Such methods are in particularly useful when implemented on a computer.

BACKGROUND

It has been suggested that the three-dimensional structure of nucleic acids in a cell may be involved in complex biological regulation, for example compartmentalizing the nucleus and bringing widely separated functional elements into close spatial proximity. Understanding how nucleic acids interact, and perhaps more importantly how this interaction, or lack thereof, regulates cellular processes, presents a new frontier of exploration. For example, understanding chromosomal folding and the patterns therein can provide insight into the complex relationships between chromatin structure, gene activity, and the functional state of the cell. Adding ribonucleic acids (RNAs) into the mix adds a further complexity.

Typically, deoxyribonucleic acid (DNA) is viewed as a linear molecule, with little attention paid to the three-dimensional organization. However chromosomes are not rigid, and while the linear distance between two genomic loci need may be vast, when folded, the special distance may be small. For example, while regions of chromosomal DNA may be separated by many megabases, they can also can be immediately adjacent in 3-dimensional space. Much the same way a protein can fold to bring sequence elements together to form an active site, from the standpoint of gene regulation, long-range interactions between genomic loci may for the same sort of active centers. For example, gene enhancers, silencers, and insulator elements might function across vast genomic distances.

The existence of long-range interactions complicates efforts to understand the pathways that regulate cellular processes, because the interacting regulatory elements could lie at a great genomic distance from a target gene, even on another chromosome. In the case of oncogenes and other disease-associated genes, identification of long-range genetic regulators would be of great use in identifying the genomic variants responsible for the disease state and the process by which the disease state is brought about.

The roughly two meters of DNA in the human genome is intricately packaged to form the chromatin and chromosomes in each cell nucleus. In addition to its structural role, this organization has critical regulatory functions. In particular, the formation of loops in the human genome plays an essential role in regulating genes. We herein demonstrate the ability to create reliable maps of these loops, using an in situ Hi-C method for three-dimensional genome sequencing, and to control the formation of such loops, thereby altering gene expression. Hi-C characterizes the three-dimensional configuration of the genome by determining the frequency of physical contact between all pairs of loci, genome-wide.

In order to control the regulatory function of chromatin folding, it would be required to provide methods for altering chromatin three dimensional (3D) structure in a cell, to remove or otherwise modify existing chromatin loop structures, or to introduce new chromatin loop structures where their presence is required or beneficial, for instance, in the context of treatment of disease conditions, such as cancer or genetic disease. However, to date, no such methods exist. The present invention aims to provide essential methods and tools for altering chromatin three dimensional (3D) structure.

In order to associate the dynamics of chromatin loop structure to cellular processes in health and disease, the chromatin three dimensional (3D) structure from a large number of cells in different stages of development, from diseased and healthy subjects, and from a wide variety of cellular lineages and biological species need to be analysed and their genomes sequenced. Such studies are hampered by costs. There is therefore a need for further improvements in methods for de novo assembly of whole genomes and genomic fragments. The present invention aims to provide such improved methods.

Further, while existing methods for assessing chromatin three dimensional (3D) structure are very suitable for indicating that two loci are spatially co-localized in the nucleus, it may be expected that there are multiple loci spatially co-localized in a living cell. Yet, methods that can indicate simultaneous co-localization of more than 2, such as up to 10 or more different loci are not available. The present invention aims to provide such methods.

SUMMARY

The present invention provides a method to engineer chromatin loops and contact domains in one or more target regions of chromatin DNA inside the nucleus of a cell, said method comprising interfering with the function of CTCF and/or cohesion.

In one embodiment, the present invention provides a method to engineer chromatin loops and contact domains in a target region of chromatin DNA inside the nucleus of a cell, said method comprising the step of interfering with the function of CTCF and/or cohesin during the extrusion process wherein chromatin DNA is extruded by each of the two subunits of a CTCF and/or cohesin-comprising extrusion complex in opposite direction with respect to the genome and halted by a forward and reverse CTCF or cohesin binding motif in convergent orientation on opposite strands of the extruded chromatin DNA.

In one embodiment of the method of the invention, the interfering results in the removal of one or more existing chromatin loops or contact domains, the introduction of one or more new chromatin loops or contact domains, or the modification of one or more existing loops or contact domains.

In one embodiment of the method of the invention, the removal of one or more existing chromatin loops or contact domains comprises the targeted removal or modification of one or more existing forward and/or reverse CTCF or cohesin binding motifs in or proximate to said target region.

In one embodiment of the method of the invention, the introduction of one or more new chromatin loops or contact domains comprises the targeted introduction of one or more new forward and/or reverse CTCF or cohesin binding motifs in or proximate to said target region.

In one embodiment of the method of the invention, the modification of one or more existing loops or contact domains comprises the targeted introduction of one or more new forward and/or reverse CTCF or cohesin binding motifs.

In one embodiment of the method of the invention, the modification of one or more existing loops or contact domains comprises the targeted introduction of one or more extrusion-blocking proteins or protein-binding sites in or proximate to said target region to thereby prevent or attenuate the extrusion of at least one chromatin strand through the extrusion complex whereby a smaller loop is formed or a loop is blocked from forming, preferably said introduction being in a location between the forward and reverse CTCF or cohesin binding motifs at an existing loop or contact domain boundary, more preferably in a location within 150,000 base pairs, 125,000 base pairs, 100,000 base pairs, 90,000 base pairs, 80,000 base pairs, 70,000 base pairs, 60,000 base pairs, 50,000 base pairs, 40,000 base pairs, 30,000 base pairs, 20,000 base pairs, 10,000 base pairs, 9,000 base pairs, 8,000 base pairs, 7,000 base pairs, 6,000 base pairs, 5,000 base pairs, 4,000 base pairs, 3,000 base pairs, 2,000 base pairs, 1000 base pairs, 900 base pairs, 800 base pairs, 700 base pairs, 600 base pairs, 500 base pairs, 400 base pairs, 300 base pairs, 200 base pairs, 100 base pairs, 50 base pairs, 25 base pairs, 10 base pairs, or 5 base pairs of an existing forward CTCF or cohesin binding motif See FIG. 24A.

In one embodiment of the invention, extrusion-blocking proteins or protein binding sites may be introduced upstream or downstream of an existing CTCF or cohesin binding motif in order to introduce a new loop anchor to which a new chromatin loop may form. In certain example embodiments, the distance from an existing CTCF or cohesin motif may be within 1,000-150,000 base pairs of an existing CTCF or cohesin domain, or any sub-range therebetween. The target sites for introduction of an extrusion-blocking protein or protein binding site will depend on the distance from an existing CTCT or cohesin domain. For example, if the extrusion-blocking protein is a dCa9 the corresponding gRNA will be based on the genomic distance located at the desired distance from the existing CTCF or cohesin domain.

In one embodiment of the method of the invention, the removal of one or more contact domains comprises the targeted removal or modification of one or more, preferably all, CTCF or cohesin binding motifs located at the contact domain boundary.

In one embodiment of the method of the invention, the introduction of one or more new contact domains comprises the targeted introduction of one or more new forward and/or reverse CTCF or cohesin binding motifs in or proximate to said target region to thereby create two consecutive CTCF or cohesin binding motifs that do not loop to one another.

In one embodiment of the method of the invention, the targeted removal or modification comprises the mutation or inversion of said one or more CTCF or cohesin binding motifs, preferably wherein said targeted removal or modification comprises the mutation of at least a single base pair in said one or more CTCF binding motifs.

In one embodiment of the method of the invention, the targeted introduction comprises the introduction of one or more CTCF or cohesin binding motifs, preferably in convergent orientation on opposite strands of the chromatin DNA.

In one embodiment of the method of the invention, the targeted removal, modification or introduction comprises genome editing.

In one embodiment of the method of the invention, the targeted removal, modification or introduction comprises the use of a CRISPR/Cas system, an inactivate CRISPR/Cas system, a Cas protein, a zinc finger protein (ZFP), a zinc finger nuclease (ZFN), a transcription activator-like effector (TALE), a transcription activator-like effector nuclease (TALEN), or a meganuclease.

In one embodiment of the method of the invention, the CTCF or cohesin binding motif is the CTCF motif.

In one embodiment of the method of the invention, the domain is an exclusion domain, and wherein said exclusion domain is introduced by inserting, a CTCF or cohesin binding motif downstream or upstream from an adjacent CTCF or cohesin binding motifs in convergent orientation. In one embodiment of the method of the invention, the domain is an exclusion domain and wherein said exclusion domain is deleted by deleting a CTCF or cohesion binding motif downstream or upstream from an adjacent CTCF or cohesion binding motif, or inverting a CTCF or cohesion motif downstream or upstream of an adjacent CTCF such that the inverted CTCF or cohesion motif is not in a convergent orientation with the adjacent CTCF motif or cohesin motif.

In one embodiment of the method of the invention, in addition to the step of interfering with the function of CTCF and/or cohesin, said method comprises the step of performing in situ Hi-C on said cell prior to or following said step of interfering with the function of CTCF and/or cohesin, optionally combined with HYbrid Capture on the in situ Hi-C library generated.

In one embodiment of the method of the invention, the method is for altering chromatin three dimensional (3D) structure in a cell.

In one embodiment of the method of the invention, the method comprises delivering to a cell one or more sequence-specific DNA targeting agents directed to said target region or proximate thereto, preferably wherein said one or more sequence-specific DNA targeting agents are selected from the group consisting of a CRISPR/Cas system, a Cas protein, a catalytically inactive CRISPR-Cas system or Cas protein, a zinc finger protein (ZFP), a zinc finger nuclease (ZFN), a transcription activator-like effector (TALE), a transcription activator-like effector nuclease (TALEN), and a meganuclease. In certain example embodiment the one or more sequence-specific DNA targeting agents are delivered to the nucleus of the cell.

In one embodiment of the method of the invention, the target region comprises genes the expression of which is to be modified, preferably wherein said proximity to the target region is less than 2,000, 1,000, 900, 800, 700, 600, 500, 400, 300, 200, or 100 base pairs.

In one embodiment of the method of the invention, the target region is located in or overlaps with an existing chromatin loop or contact domain, or wherein said target region is to be formed into or is to be made part of a new chromatin loop or contact domain.

In one embodiment of the method of the invention, the delivering of the one or more sequence-specific DNA targeting agents to the nucleus of a cell comprises delivering one or more vectors encoding the one or more sequence-specific DNA targeting agents.

In one embodiment of the method of the invention, the delivering of the one or more sequence-specific DNA targeting agents comprises delivering a cell-permeable reagent, preferably a pyrrole-imidazole polyamide.

In one embodiment of the method of the invention, the one or more sequence-specific DNA targeting agents bind to and mask one or more existing CTCF or cohesin binding motifs such that an existing loop or contact domain is masked and a chromatin loop is attenuated or removed. In other example embodiments, the one or more sequence-specific DNA targeting agents bind to and mask one or more existing CTCF or cohesion binding motifs such that an extrusion complex is not arrested at the existing CTCF or cohesin binding motif thereby allowing the extrusion complex to arrest at a subsequent existing CTCF or cohesin binding motif. In certain example embodiments, the arresting at a subsequent existing CTCF results in formation of a new loop or contact domain and/or formation of a new chromatin loop anchored at the subsequent CTCF or cohesion binding motif.

In one embodiment of the method of the invention, the one or more sequence-specific DNA targeting agents comprise a DNA methyltransferase domain, wherein methylation of one or more existing CTCF or cohesin binding motifs masks the existing CTCF or cohesin binding motif preventing CTCF or cohesin from binding to the masked CTCF or cohesin binding motif, thereby preventing a loop or contact domain from forming at the masked CTCF or cohesin binding motif, preventing a chromatin loop anchored at the masked CTCF or cohesin motif from forming, or whereby an extrusion complex is not arrested at the existing CTCF or cohesin binding motif. In other example embodiments, the one or more sequence-specific DNA targeting agents comprise DNA demethyltransferase, wherein demethylation of one or more existing CTCF or cohesin binding motifs unmasks the existing CTCF or cohesin binding motif thereby allowing a loop or contact domain to form at the unmasked CTCF or cohesin binding motif, a loop anchored at the unmasked CTCF or cohesin binding motif to form, or an extrusion complex In one embodiment of the method of the invention, the extrusion complex comprises one or more members selected from the group consisting of CTCF, SA1/2, Smc3, Smc1, cohesin and Rad21.

In one embodiment of the method of the invention, one or more members of the extrusion complex, or a part thereof, are fused to a sequence-specific DNA targeting agent as defined hereinabove, wherein biding of the sequence-specific DNA targeting agent to a target region results in formation of a a new chromatin loop anchor and/or new chromatin loop structure.

In one embodiment of the method of the invention, two or more multimerizable sequence-specific DNA targeting agents are targeted to two or more target regions in order to bring them into physical proximity.

In one embodiment of the method of the invention, the multimerizable sequence-specific DNA targeting agents comprise a catalytically inactive CRISPR-Cas system, a zinc finger protein (ZFP), or a transcription activator-like effector (TALE) fused to a dimerization domain.

In one embodiment of the method of the invention, the dimerization domain is inducible upon addition of a ligand.

In one embodiment of the method of the invention, the one or more sequence-specific DNA targeting agents comprises a site-specific nuclease.

In one embodiment of the method of the invention, the site-specific nuclease comprises a CRISPR-Cas system, a zinc finger nuclease (ZFN), or a transcription activator-like effector nuclease (TALEN).

In one embodiment of the method of the invention, the site-specific nuclease comprises a nickase.

In one embodiment of the method of the invention, the one or more agents comprise one or more recombination templates.

In one embodiment of the method of the invention, the one or more site-specific nucleases inserts one or more new CTCF or cohesin binding motifs or inverts an existing CTCF or cohesin binding motif upon binding to the one or more target regions, whereby a new pair of convergent CTCF or cohesin binding motifs is formed.

In one embodiment of the method of the invention, the site-specific nuclease inserts one or more convergent pairs of CTCF or cohesin binding motifs, whereby each convergent CTCF or cohesin binding motif pair generates a new chromatin loop structure.

In one embodiment of the method of the invention, the site-specific nuclease deletes one or more CTCF or cohesin binding motifs.

In one embodiment of the method of the invention, the site-specific nuclease inserts, deletes or substitutes one or more nucleotides in a loop binding motif.

In one embodiment of the method of the invention, the site-specific nuclease inserts an array of CTCF or cohesin binding motifs in a target chromosome, preferably wherein the array comprises between 10-100 copies of a CTCF or cohesin binding motif, so as to alter chromatin 3D structure at chromosome scale.

In one embodiment of the method of the invention, the array is a DXZ4 element.

In one embodiment of the method of the invention, the chromatin loop or contact domain is associated with an actively transcribed gene. In one embodiment of the method of the invention, modification or deletion of the chromatin loop anchor or chromatin loop structure results in preventing the mRNA splicing machinery associated with said actively transcribed gene from interacting with a transcription initiation complex, so as to alter mRNA splicing. In another example embodiment, modification or deletion of the chromatin loop anchor or chromatin loop structure results in allowing a mRNA splicing machinery associated with said actively transcribed gene to interact with a transcription initiation complex, so as to alter mRNA splicing. In certain other example embodiments, introduction of a new chromatin loop anchor or chromain loop structure results in allowing a mRNA splicing machinery to associate diwth an initiation complex of an actively transcribed genes, so as to alter mRNA splicing.

In one embodiment of the method of the invention, a different promoter/transcription start site is utilized, and/or whereby a different mRNA isoform is produced.

In one embodiment of the method of the invention, an enhancer element, silencer element or insulator element is insulated from or brought into contact with said chromatin loop or contact domain or with the promoter of said gene.

In one embodiment of the method of the invention, the method for altering chromatin domain activity comprises delivering to a cell or population of cells one or more sequence-specific DNA targeting agents directed to one or more target regions of chromatin DNA comprising an existing chromatin domain, wherein binding of the one or more DNA targeting agents to one or more target regions alters the transcriptional activity of a chromatin domain.

In one embodiment of such a method of the invention, the sequence-specific DNA targeting agent targets a DNA contact site opposite a promoter site in the chromatin domain.

In one embodiment of the method of the invention, the DNA contact site is at a CTCF or cohesin binding motif.

In one embodiment of the method of the invention, the sequence-specific DNA targeting agents comprise a transcription factor domain and a DNA targeting domain, whereby the transcription factor domain is brought into contact with a contact domain, or a proximity sufficient to allow for interaction with the chromatin domain.

In one embodiment of the method of the invention, the transcription factor domain is selected from the group consisting of an activator protein, a repressor protein, an elongation factor, and a histone modifying enzyme.

In one embodiment of the method of the invention, the histone modifying enzyme is selected from the group consisting of a DNA methyltransferase, a histone methyltransferase, a histone demethylase, histone deacetylase and a histone acetyltransferase.

In one embodiment of the method of the invention, the DNA targeting domain comprises a CRISPR-Cas system, a zinc finger protein (ZFP), or a transcription activator-like effector (TALE).

The method of any one of the preceding claims, wherein the one or more vectors are delivered in vivo.

In one embodiment of the method of the invention, the the one or more sequence-specific DNA targeting agents are under the inducible control of a vector promoter.

In one embodiment of the method of the invention, the vector promoter is a tissue-specific promoter or a ubiquitous expression promoter.

In one embodiment of the method of the invention, the vector is a viral vector.

In one embodiment of the method of the invention, the viral vector is selected from the group consisting of lentiviral, adenoviral, adeno-associated viral, and herpes simplex virus vectors.

In one embodiment of the method of the invention, the CRISPR-Cas system is self-inactivating, whereby the self-inactivation of the CRISPR-Cas system limits duration of its activity and/or expression in targeted cells.

In one embodiment of the method of the invention, the target region is associated with a disease.

In one embodiment of the method of the invention, the disease associated with aberrant chromatin folding.

In one embodiment of the method of the invention, the disease is cancer, a genetic disease, or infectious disease.

In one embodiment of the method of the invention, the target region comprises an oncogene or tumor suppressor gene.

In one embodiment of the method of the invention, a target region associated with aberrant expression of an oncogene is targeted, whereby expression of the oncogene is repressed.

In one embodiment of the method of the invention, a target region associated with aberrant expression of a tumor suppressor is targeted, whereby expression of the tumor suppressor is activated.

In one embodiment of the method of the invention, the genetic disease selected from the disorders identified in Tables A B or C herein below.

In one embodiment of the method of the invention, the genetic disease is a disorder associated with genomic imprinting.

In one embodiment of the method of the invention, the imprinted gene is unsilenced.

In one embodiment of the method of the invention, the gene is silenced by establishing imprinting.

In one embodiment of the method of the invention, the target region comprises a virus integration site of an infectious virus, preferably wherein the virus is a retrovirus, an adenovirus, an adeno-associated virus (AAV), a lentivirus or a herpesvirus.

In one embodiment of the method of the invention, the target region is associated with improved yields, disease resistance, drought resistance or salt tolerance in plants or animals.

In one embodiment of the method of the invention, the cells or population of cells are part of a mammal.

In one embodiment of the method of the invention, the cells or population of cells are part of a plant.

The present invention further provides a method of treatment comprising altering chromatin 3D structure or gene expression within a chromatin domain according to any of the preceding methods in a subject in need thereof suffering from a disease associated with aberrant chromatin 3D structure or aberrant gene expression within a chromatin domain.

The present invention also provides a method of treatment comprising altering chromatin 3D structure around an inserted therapeutic gene according to any of the preceding methods in a subject in need thereof, in order to ensure proper regulation of the inserted therapeutic gene and the surrounding endogenous genes.

In one embodiment of the method of treatment of the invention, the one or more vectors are delivered to the subject, wherein the one or more sequence-specific DNA targeting agents introduced by the one or more vectors corrects the aberrant loop chromatin 3D structure or aberrant gene expression within a chromatin domain.

In one embodiment of the method of treatment of the invention, one or more vectors are delivered to the subject suffering from a genetic defect such that the one or more sequence-specific DNA targeting agents introduced by the one or more vectors silences expression of one or more defective genes or rescues expression of one or more silenced functional genes.

In one embodiment of the method of treatment of the invention, one or more vectors are delivered to a subject suffering from a cancer such that the one or more sequence-specific DNA targeting agents introduced by the one or more vectors silences expression of one or more oncogenes or induces expression of one or more tumor suppressors.

In any and all embodiments of the methods the invention as described above, in addition to the step of interfering with the function of CTCF and/or cohesin, said method may comprise the step of performing in situ Hi-C on said cell prior to or following said step of interfering with the function of CTCF and/or cohesin, optionally combined with HYbrid Capture on the in situ Hi-C library generated, wherein said in situ HiC method identifies target chromatin loop modification sites or monitors the result of chromatin loop or contact domain modification in a target region, said method comprising performing prior to or following said step of interfering with the function of CTCF and/or cohesin the steps of generating a 3D contact map of the genome of said cell; identifying a target modification site from the 3D contact map, wherein the target modification site comprises either an existing loop or domain or a target nucleic acid sequence for introducing a new chromatin loop or domain, or identifying modified sites from the 3D contact map, wherein a modified site comprises a modified loop or domain.

In one embodiment of such combined methods of the invention, the method further comprises the steps of: generating a set of vectors wherein each vector encodes one or more chromatin loop perturbations, wherein expression of the one or more vectors results in removal of one or more existing chromatin loops or domains, introduction of one or more new chromatin loops or domains, or modification of one or more existing loops or domains at one of the identified target modification sites; delivering each vector in the set of vectors to a different cell or cell population to determine an impact of the introduced chromatin loop perturbations on cell function; and identifying one or more vectors that introduce the one or more chromatin perturbations with a minimal negative impact on cell function.

In a further embodiment of this method of the invention, cell function is assessed by changes in gene expression and/or changes in cell phenotype.

In another aspect, the present invention provide an agent for use as a medicament or for use in the treatment of a disorder in a human or animal subject in need thereof, wherein said agent comprises one or more sequence-specific DNA targeting agents selected from the group consisting of a CRISPR-Cas system, a zinc finger protein (ZFP), a zinc finger nuclease (ZFN), a transcription activator-like effector (TALE), a transcription activator-like effector nuclease (TALEN), a catalytically inactive CRISPR-Cas system, and a self-inactivating CRISPR/Cas system, wherein binding of the sequence-specific DNA targeting agents to the one or more genomic loci removes one or more existing chromatin loop or domain structures, introduces one or more new chromatin loop or domain structures, or modifies one or more existing chromatin loop or domain structures in a cell of said subject.

In one embodiment of said aspect the agent introduces, masks, mutates or inverts one or more existing forward and/or reverse CTCF or cohesin binding motifs or prevents the extrusion of at least one chromatin strand through a CTCF and/or cohesin-comprising extrusion complex in said cell.

In one embodiment of said aspect the agent comprises a DNA-targeting element comprising a nucleotide sequence that hybridizes to one or more CTCF or cohesin binding motifs or to a DNA target region in said chromatin DNA proximate to a location where one or more CTCF or cohesin binding motifs are to be introduced into the genome.

In one embodiment of said aspect the agent comprises a DNA-targeting element comprising a zinc finger motif that binds to one or more CTCF or cohesin binding motifs or to a DNA target region in said chromatin DNA proximate to a location where one or more CTCF or cohesin binding motifs are to be introduced into the genome.

In one embodiment of said aspect the agent is encoded by a vector for delivering said agent to the nucleus of said cell.

In one embodiment of said aspect the vector is a viral vector.

In one embodiment of said aspect the viral vector is selected from the group consisting of lentiviral, adenoviral, adeno-associated viral, and herpes simplex virus vectors.

It is expressly foreseen that embodiments of the method of treatment as disclosed herein are also an embodiment of the agent for medical use as disclosed, including purposes, structures and diseases.

Further embodiments of this invention include a method to engineer chromatin loops and contact domains in a target region of chromatinized DNA inside the nucleus of a cell, said method comprising the step of modifying, adding, or removing a CTCF or cohesin binding motif. Preferable, in such an embodiment, only a single loop anchor or domain boundary is engineered.

Further embodiments of this invention include a method to engineer chromatin loops and contact domains in a target region of chromatin DNA inside the nucleus of a cell, said method comprising the step of interfering with the function of CTCF and/or cohesin.

Still further embodiments of this invention include a method to engineer chromatin loops and contact domains in a target region of chromatin DNA inside the nucleus of a cell, said method comprising the step of interfering with the function of CTCF and/or cohesin. Preferable, in such an embodiment, only a single loop anchor or domain boundary is engineered. Preferably, in such a method said interfering comprises interfering with a CTCF or cohesin binding motif. Preferably, interfering with a CTCF or cohesin binding motif comprises removing nucleotides, adding nucleotides, methylating nucleotides, and/or changing the orientation of all or part of the motif.

Alternatively, or in addition thereto, in embodiments of the methods described above, said interfering comprises adding a new CTCF or cohesin binding motif.

Alternatively, or in addition thereto, in embodiments of the methods described above, said said interfering comprises modifying the native CTCF or cohesin proteins.

Alternatively, or in addition thereto, in embodiments of the methods described above, said interfering comprises introducing modified CTCF or cohesin proteins.

Alternatively, or in addition thereto, in embodiments of the methods described above, said said interfering comprises introducing a protein which interferes with the normal function of CTCF. Preferably said protein is catalytically deactivated CRISPR/Cas protein, such as a catalytically deactivated Cas9 (dCas9). In certain example embodiments the dCas9 targets a CTCF or cohesin binding motif or a region proximate to a CTCF or cohesin motif using one or more guide RNAs. In one example embodiment, one or more gRNAs are used to tile a target region proximate to and/or including an existing CTCF or cohesin motif to cause binding of multiple dCas9s in the target region. In certain example embodiments, the gRNAs target a region within 10 to 5,000 base pairs of an existing CTCF or cohesin motif.

Still further embodiments of this invention include a non-naturally occurring or engineered composition comprising the agents described herein. In one preferred embodiment, wherein the agent is a nucleic acid molecule, said molecule is cloned into an expression vector.

Still further embodiments of this invention include a kit comprising the agents described herein, or the expression vector as described herein, and further comprising instructions for performing a method of the invention as described herein.

Still further embodiments of this invention include a composition as described herein comprising agent as described herein or the expression vector comprising the agent; and optionally one or more pharmaceutically acceptable excipients. In a preferred embodiment, said composition is for use in therapy.

Still further embodiments of this invention include an in vitro method of modifying chromatin loops or contact domains as described herein in a target region (or a genomic locus of interest, which terms are interchangeable), comprising contacting the genomic locus with an agent or composition of the invention as described herein.

Still further embodiments of this invention include the use of an agent or composition of the invention as described herein or the expression vector as described to modify chromatin loops or contact domains as described herein in a mammalian cell.

BRIEF DESCRIPTION OF THE DRAWINGS

FIG. 15. Loops between promoters and enhancers are strongly associated with gene activation. (A) Histogram showing loop count at promoters (left); restricted to loops where the distal peak locus contains an enhancer (right). (B) Genes whose promoters participate in a loop in GM12878 but not in a second cell type are frequently upregulated in GM12878, and vice-versa. (C) Left: a loop in GM12878, with one anchor at the SELL promoter and the other at a distal enhancer. The gene is on. Right: The loop is absent in IMR90, where the gene is off (D) Left: Two loops in GM12878 are anchored at the promoter of the inactive ADAMTS1 gene. Right: A series of loops and domains appear, along with evident transitive looping. ADAMTS1 is on.

DETAILED DESCRIPTION OF SEVERAL EMBODIMENTS

I. Summary of Terms

Figure 1:
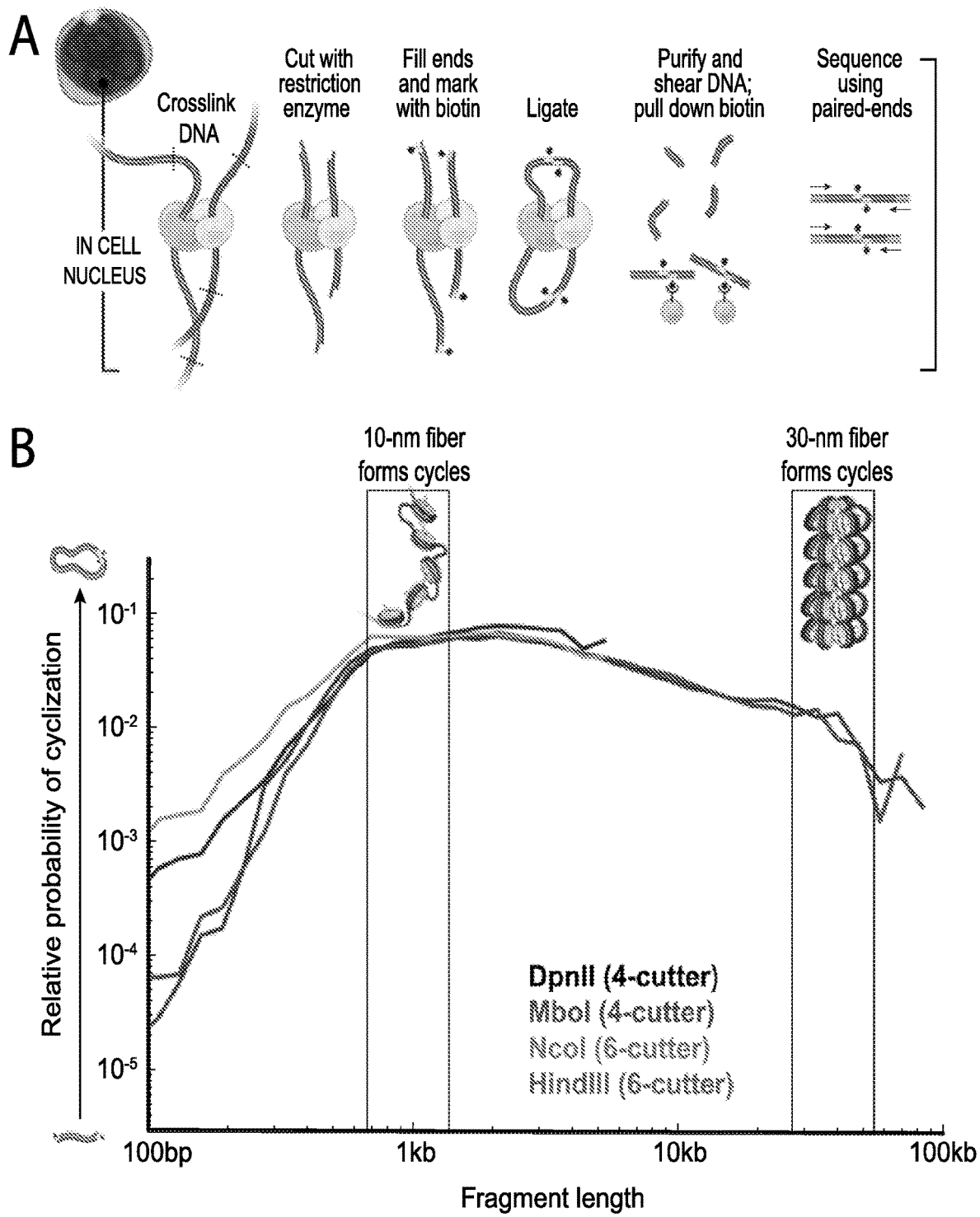
FIG. 1. Chromatin is bendable at the kilobase scale. (A) in situ Hi-C couples DNA-DNA proximity ligation with high-throughput paired-end sequencing to map contacts occurring in intact nuclei, genome-wide. (B) Top: probability that a single restriction fragment will form a cycle is shown as a function of fragment length for Hi-C experiments performed using four different restriction enzymes. Cycle formation in all experiments increased rapidly for fragments up to 800 bp and then plateaued, suggesting a Kuhn length for chromatin of around 1 kb. Computer simulations of 30 nm fiber flexibility predict a peak at 30 kb (yellow shading, right). Thus, our findings suggest that continuous 30 nm fibers are rare in nuclear chromatin. In graph: distribution of restriction fragment lengths when the human genome is cut with DpnII (restriction site: GATC), MboI (GATC), NcoI (CCATGG), or HindIII (AAGCTT).

Unless otherwise noted, technical terms are used according to conventional usage. Definitions of common terms in molecular biology may be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710).

The singular terms "a," "an," and "the" include plural referents unless context clearly indicates otherwise. Similarly, the word "or" is intended to include "and" unless the context clearly indicates otherwise. The term "comprises" means "includes." In case of conflict, the present specification, including explanations of terms, will control.

To facilitate review of the various embodiments of this disclosure, the following explanations of specific terms are provided:

Amplification: To increase the number of copies of a nucleic acid molecule, such as one or more end joined nucleic acid fragments that includes a junction, such as a ligation junction. The resulting amplification products are called "amplicons." Amplification of a nucleic acid molecule (such as a DNA or RNA molecule) refers to use of a technique that increases the number of copies of a nucleic acid molecule (including fragments).

An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. This cycle can be repeated. The product of amplification can be characterized by such techniques as electrophoresis, restriction endonuclease cleavage patterns, oligonucleotide hybridization or ligation, and/or nucleic acid sequencing.

Other examples of in vitro amplification techniques include quantitative real-time PCR; reverse transcriptase PCR (RT-PCR); real-time PCR (rt PCR); real-time reverse transcriptase PCR (rt RT-PCR); nested PCR; strand displacement amplification (see U.S. Pat. No. 5,744,311); transcription-free isothermal amplification (see U.S. Pat. No. 6,033,881, repair chain reaction amplification (see WO 90/01069); ligase chain reaction amplification (see European patent publication EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134) amongst others.

Binding or stable binding (of an oligonucleotide): An oligonucleotide, such as a nucleic acid probe that specifically binds to a target junction in an end joined nucleic acid fragment, binds or stably binds to a target nucleic acid if a sufficient amount of the oligonucleotide forms base pairs or is hybridized to its target nucleic acid. For example depending in the hybridization conditions, there need not be complete matching between the probe and the nucleic acid target, for example there can be mismatch, or a nucleic acid bubble. Binding can be detected by either physical or functional properties.

Binding site: A region on a protein, DNA, or RNA to which other molecules stably bind. In one example, a binding site is the site on an end joined nucleic acid fragment.

Biotin-14-CTP: A biologically active analog of cytosine-5'-triphosphate that is readily incorporated into a nucleic acid by polymerase or a reverse transcriptase. In some examples, biotin-14-CTP is incorporated into a nucleic acid fragment that has a 3' overhang.

Capture moieties: Molecules or other substances that when attached to a nucleic acid molecule, such as an end joined nucleic acid, allow for the capture of the nucleic acid molecule through interactions of the capture moiety and something that the capture moiety binds to, such as a particular surface and/or molecule, such as a specific binding molecule that is capable of specifically binding to the capture moiety.

Chromatin loop: Chromatin fibers are arranged in living cells as independent loops anchored to the nuclear matrix or chromosomal scaffold. Specific DNA sequences act as anchors for these loops but it is not clear how flexible the anchors are. In order to fit DNA into the nucleus, it must be packaged into a highly compacted structure known as chromatin. In the first step of this process DNA is condensed into a 11 nm fiber that represents an approximate 6-fold level of compaction. This is achieved through nucleosome assembly, produced through interactions between DNA and histone proteins. Despite the extensive knowledge on the structure of the 11 nm nucleosome fiber, as well as metaphase chromosomes, the intermediate chromatin structures commonly described were largely hypothetical and had yet to be observed in vivo. The present invention has enabled to directly examine long-range interactions between chromosomal sequences in situ. This has produced convincing evidence that genes are configured into looped structures or chromatin loops that juxtapose regulatory elements to activate or repress transcription. The detection of loops in situ and the discovery how the majority of such loops is formed, now provides clear indiation of the factors that are involved in forming, maintaining and resolving such loops, and how they impact on gene expression. The present inventors have, through the use of in situ Hi-C technology, discovered that chromatin looping in the intact nucleus of a cell can be dynamically observed, quantified, and manipulated. Chromatin loop formation is the result of the presence of a pair of CTCF binding motifs in the convergent orientation on opposite strands of the DNA. Disruption of one of these motifs results in disappearance of the loop.

Complementary: A double-stranded DNA or RNA strand consists of two complementary strands of base pairs. Complementary binding occurs when the base of one nucleic acid molecule forms a hydrogen bond to the base of another nucleic acid molecule. Normally, the base adenine (A) is complementary to thymidine (T) and uracil (U), while cytosine (C) is complementary to guanine (G). For example, the sequence 5'-ATCG-3' of one ssDNA molecule can bond to 3'-TAGC-5' of another ssDNA to form a dsDNA. In this example, the sequence 5'-ATCG-3' is the reverse complement of 3'-TAGC-5'. Nucleic acid molecules can be complementary to each other even without complete hydrogen-bonding of all bases of each molecule. For example, hybridization with a complementary nucleic acid sequence can occur under conditions of differing stringency in which a complement will bind at some but not all nucleotide positions.

Contacting: Placement in direct physical association, including both in solid or liquid form, for example contacting a sample with a crosslinking agent or a probe.

Control: A reference standard. A control can be a known value or range of values indicative of basal levels or amounts or present in a tissue or a cell or populations thereof. A control can also be a cellular or tissue control, for example a tissue from a non-diseased state and/or exposed to different environmental conditions. A difference between a test sample and a control can be an increase or conversely a decrease. The difference can be a qualitative difference or a quantitative difference, for example a statistically significant difference.

Covalently linked: Refers to a covalent linkage between atoms by the formation of a covalent bond characterized by the sharing of pairs of electrons between atoms. In one example, a covalent link is a bond between an oxygen and a phosphorous, such as phosphodiester bonds in the backbone of a nucleic acid strand. In another example, a covalent link is one between a nucleic acid protein, another protein and/or nucleic acid that has been crosslinked by chemical means. In another example, a covalent link is one between fragmented nucleic acids.

Crosslinking agent: A chemical agent or even light, which facilitates the attachment of one molecule to another molecule. Crosslinking agents can be protein-nucleic acid crosslinking agents, nucleic acid-nucleic acid crosslinking agents, and protein-protein crosslinking agents. Examples of such agents are known in the art. In some embodiments, a crosslinking agent is a reversible crosslinking agent. In some embodiments, a crosslinking agent is a non-reversible crosslinking agent.

CTCF: Transcriptional repressor CTCF (UniProtKB P49711) also known as 11-zinc finger protein or CCCTC-binding factor is a transcription factor that in humans is encoded by the CTCF gene (Gene ID: 10664). This gene is a member of the BORIS+CTCF gene family and encodes a transcriptional regulator protein with 11 highly conserved zinc finger (ZF) domains. This nuclear protein is able to use different combinations of the ZF domains to bind different DNA target sequences and proteins. Depending upon the context of the site, the protein can bind a histone acetyltransferase (HAT)-containing complex and function as a transcriptional activator or bind a histone deacetylase (HDAC)-containing complex and function as a transcriptional repressor. If the protein is bound to a transcriptional insulator element, it can block communication between enhancers and upstream promoters, thereby regulating imprinted expression. Mutations in this gene have been associated with invasive breast cancers, prostate cancers, and Wilms' tumors. Alternatively spliced transcript variants encoding different isoforms have been found for this gene. Such variants and orthologs are in some embodiments incorporated in aspects of this invention. CTCF binds to a DNA sequence having sufficient sequence similarity (e.g. >70% sequence similarity over the length of the sequence) to the consensus CTCF binding DNA sequence 5'-CCGCGNGGNGGCAG-3' (SEQ ID NO: 13) (in IUPAC notation), dubbed herein the CTCF binding motif or CTCF binding site. The binding to this sequence is defined by 11 zinc finger motifs in the CTCF protein structure. The binding of CTCF to DNA can be disrupted by CpG methylation of the binding site. The CpG sites or CG sites are regions of DNA where a cytosine nucleotide is followed by a guanine nucleotide in the linear sequence of bases along its 5'→3' direction separated by only one phosphate (5'-C-phosphate-G-3'). Cytosines in CpG dinucleotides or CpG islands can be methylated to form 5-methylcytosine. The methyl group is added by DNA methyltransferases. Hence, site-specific methylation of the CTCF binding motif by methyltransferases can be used to disrupt binding of CTCF, and thereby loop formation.

Detect: To determine if an agent (such as a signal or particular nucleic acid or protein) is present or absent. In some examples, this can further include quantification in a sample, or a fraction of a sample, such as a particular cell or cells within a tissue.

Detectable label: A compound or composition that is conjugated directly or indirectly to another molecule to facilitate detection of that molecule. Specific, non-limiting examples of labels include fluorescent tags, enzymatic linkages, and radioactive isotopes and other physical tags, such as biotin. In some examples, a label is attached to a nucleic acid, such as an end-joined nucleic acid, to facilitate detection and/or isolation of the nucleic acid.

DNA sequencing: The process of determining the nucleotide order of a given DNA molecule. Generally, the sequencing can be performed using automated Sanger sequencing (AB13730xl genome analyzer), pyrosequencing on a solid support (454 sequencing, Roche), sequencing-by-synthesis with reversible terminations (ILLUMINA® Genome Analyzer), sequencing-by-ligation (ABI SOLiD®) or sequencing-by-synthesis with virtual terminators (HELISCOPE®). In some embodiments, DNA sequencing is performed using a chain termination method developed by Frederick Sanger, and thus termed "Sanger based sequencing" or "SBS." This technique uses sequence-specific termination of a DNA synthesis reaction using modified nucleotide substrates. Extension is initiated at a specific site on the template DNA by using a short oligonucleotide primer complementary to the template at that region. The oligonucleotide primer is extended using DNA polymerase in the presence of the four deoxynucleotide bases (DNA building blocks), along with a low concentration of a chain terminating nucleotide (most commonly a di-deoxynucleotide). Limited incorporation of the chain terminating nucleotide by the DNA polymerase results in a series of related DNA fragments that are terminated only at positions where that particular nucleotide is present. The fragments are then size-separated by electrophoresis a polyacrylamide gel, or in a narrow glass tube (capillary) filled with a viscous polymer. An alternative to using a labeled primer is to use labeled terminators instead; this method is commonly called "dye terminator sequencing." "Pyrosequencing" is an array based method, which has been commercialized by 454 Life Sciences. In some embodiments of the array-based methods, single-stranded DNA is annealed to beads and amplified via EmPCR®. These DNA-bound beads are then placed into wells on a fiber-optic chip along with enzymes that produce light in the presence of ATP. When free nucleotides are washed over this chip, light is produced as the PCR amplification occurs and ATP is generated when nucleotides join with their complementary base pairs. Addition of one (or more) nucleotide(s) results in a reaction that generates a light signal that is recorded, such as by the charge coupled device (CCD) camera, within the instrument. The signal strength is proportional to the number of nucleotides, for example, homopolymer stretches, incorporated in a single nucleotide flow.

Domain: A self-interacting segment of mammalian chromatin manifested as squares of enriched contacts revealed along the diagonal of a Hi-C contact map. The inventors have shown that a genome is partitioned into domains that are associated with particular patterns of histone marks that segregates into sub-compartments, distinguished by unique long-range contact patterns. Domain includes reference to superdomain and loop domain. A loop domain is a domain whose endpoints are anchored to form a chromatin loop. Loops are anchored at DNA sites bound by higher-order "loop anchor complexes" containing loop anchor proteins, including CTCF and cohesin, and other factors. Many loops demarcate domains; the vast majority of loops are anchored at a pair of convergent CTCF/RAD21/SMC3 binding sites. The pairs of CTCF motifs that anchor a loop are nearly all found in the convergent orientation. The inactive X chromosome (Xi) is found to be partitioned into two large "superdomains" whose boundary lies near the locus of the lncRNA DXZ4 (Chadwick, 2008). We also detect a network of extremely long-range (7-74 Mb) "superloops", the strongest of which are anchored at locations containing lncRNA genes (loc550643, XIST, DXZ4, and FIRRE). With the exception of XIST, all of these lncRNAs contain CTCF-binding tandem repeats that bind CTCF only on the inactive X.

Exclusion domain: A contact domain formed as a result of the formation of a loop by an extrusion complex between adjacent forward and reverse motifs in the convergent orientation, wherein a third CTCF motif downstream of the revers or upstream of the forward motif causes the an extrusion complex that lands in the interval between the two reverse or two forward motives is obstructed on both sides, tends to remain inside the Interval, thereby resulting in the formation of a domain.

Fluorophore: A chemical compound, which when excited by exposure to a particular stimulus such as a defined wavelength of light, emits light (fluoresces), for example at a different wavelength (such as a longer wavelength of light). Fluorophores are part of the larger class of luminescent compounds. Luminescent compounds include chemiluminescent molecules, which do not require a particular wavelength of light to luminesce, but rather use a chemical source of energy. Therefore, the use of chemiluminescent molecules (such as aequorin) eliminates the need for an external source of electromagnetic radiation, such as a laser.

Examples of particular fluorophores that can be used in the probes disclosed herein are provided in U.S. Pat. No. 5,866,366 to Nazarenko et al., such as 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (*Lucifer* Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron™. Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives; LightCycler Red 640; Cy5.5; and Cy56-carboxyfluorescein; 5-carboxyfluorescein (5-FAM); boron dipyrromethene difluoride (BODIPY); N,N,N',N'-tetramethyl-6-carboxyrhodamine (TAMRA); acridine, stilbene, -6-carboxy-fluorescein (HEX), TET (Tetramethyl fluorescein), 6-carboxy-X-rhodamine (ROX), Texas Red, 2',7'-dimethoxy-4',5'-dichloro-6-carboxyfluorescein (JOE), Cy3, Cy5, VIC® (Applied Biosystems), LC Red 640, LC Red 705, Yakima yellow amongst others.

Genome or nucleic acid editing and the like: In some embodiments, editing of a genome, for example as described herein, includes inserting, deleting, or otherwise altering the nucleic acid sequence of the genome, for example in a cell. In certain embodiments this can include using a genome editing system, such as a CRISPR/Cas, system, a TALEN system, a ZFN system, a meganuclease and the like. As disclosed herein, editing can be made by way of an RNA-guided endonuclease system, such as the CRISPR/Cas system. In particular embodiments, the CRISPR/Cas system is a Cas9 system, a Cpf1 system or any other suitable CRISPR/Cas system. With respect to general information on CRISPR/Cas Systems, components thereof, and delivery of such components, including methods, materials, delivery vehicles, vectors, particles, and making and using thereof, including as to amounts and formulations, as well as CRISPR/Cas-expressing eukaryotic cells, CRISPR/Cas expressing eukaryotes, such as a mouse, reference is made to: U.S. Pat. Nos. 8,697,359, 8,771,945, 8,795,965, 8,865,406, 8,871,445, 8,889,356, 8,889,418, 8,895,308, 8,932,814, 8,945,839, 8,906,616; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); European Patents/Patent Applications: EP 2 771 468 (EP13818570.7), EP 2 764 103 (EP13824232.6), and EP 2 784 162 (EP14170383.5); and PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO2014/093701 (PCT/US2013/074800), WO2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809), European patent application EP3009511 and *Multiplex genome engineering using CRISPR/Cas systems.*

Cong, L., Ran, F. A., Cox, D., Lin, S., Barretto, R., Habib, N., Hsu, P. D., Wu, X., Jiang, W., Marraffini, L. A., & Zhang, F. *Science* Febuary 15; 339(6121):819-23 (2013); *RNA-guided editing of bacterial genomes using CRISPR-Cas systems*. Jiang W., Bikard D., Cox D., Zhang F, Marraffini L A. Nat Biotechnol March; 31(3):233-9 (2013); *One-Step Generation of Mice Carrying Mutations in Multiple Genes by CRISPR/Cas-Mediated Genome Engineering*. Wang H., Yang H., Shivalila C S., Dawlaty M M., Cheng A W., Zhang F., Jaenisch R. Cell May 9; 153(4):910-8 (2013); *Optical control of mammalian endogenous transcription and epigenetic states*. Konermann S, Brigham M D, Trevino A E, Hsu P D, Heidenreich M, Cong L, Platt R J, Scott D A, Church G M, Zhang F. Nature. 2013 Aug. 22; 500(7463): 472-6. doi: 10.1038/Nature12466. Epub 2013 Aug. 23; *Double Nicking by RNA-Guided CRISPR Cas9 for Enhanced Genome Editing Specificity*. Ran, F A., Hsu, P D., Lin, C Y., Gootenberg, J S., Konermann, S., Trevino, A E., Scott, D A., Inoue, A., Matoba, S., Zhang, Y., & Zhang, F. *Cell* August 28. pii: S0092-8674(13)01015-5. (2013); *DNA targeting specificity of RNA-guided Cas9 nucleases*. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. *Nat Biotechnol* doi:10.1038/nbt.2647 (2013); *Genome engineering using the CRISPR-Cas9 system*. Ran, F A., Hsu, P D., Wright, J., Agarwala, V., Scott, D A., Zhang, F. Nature Protocols November; 8(11):2281-308. (2013); *Genome-Scale CRISPR-Cas9 Knockout Screening in Human Cells*. Shalem, O., Sanjana, N E., Hartenian, E., Shi, X., Scott, D A., Mikkelson, T., Heckl, D., Ebert, B L., Root, D E., Doench, J G., Zhang, F. *Science* December 12. (2013). [Epub ahead of print]; *Crystal structure of cas9 in complex with guide RNA and target DNA*. Nishimasu, H., Ran, F A., Hsu, P D., Konermann, S., Shehata, S I., Dohmae, N., Ishitani, R., Zhang, F., Nureki, O. *Cell* February 27. (2014). 156(5):935-49; *Genome-wide binding of the CRISPR endonuclease Cas9 in mammalian cells*. Wu X., Scott D A., Kriz A J., Chiu A C., Hsu P D., Dadon D B., Cheng A W., Trevino A E., Konermann S., Chen S., Jaenisch R., Zhang F., Sharp P A. *Nat Biotechnol*. (2014) April 20. doi: 10.1038/nbt.2889; *CRISPR-Cas9 Knockin Mice for Genome Editing and Cancer Modeling*, Platt et al., Cell 159(2): 440-455 (2014) DOI: 10.1016/j.cell.2014.09.014; *Development and Applications of CRISPR-Cas9 for Genome Engineering*, Hsu et al, Cell 157, 1262-1278 (Jun. 5, 2014) (Hsu 2014); *Genetic screens in human cells using the CRISPR/Cas9 system*, Wang et al., Science. 2014 Jan. 3; 343(6166): 80-84. doi:10.1126/science.1246981; *Rational design of highly active sgRNAs for CRISPR-Cas9-mediated gene inactivation*, Doench et al., Nature Biotechnology 32(12):1262-7 (2014) published online 3 Sep. 2014; doi:10.1038/nbt.3026, and *In vivo interrogation of gene function in the mammalian brain using CRISPR-Cas9*, Swiech et al, Nature Biotechnology 33, 102-106 (2015) published online 19 Oct. 2014; doi:10.1038/nbt.3055, *Cpf1 Is a Single RNA-Guided Endonuclease of a Class 2 CRISPR-Cas System*, Zetsche et al., Cell 163, 1-13 (2015).

Each of these publications, patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention.

All documents (e.g., these patents, patent publications and applications and the appln cited documents) are incorporated herein by reference to the same extent as if each individual document was specifically and individually indicated to be incorporated by reference.

As disclosed herein editing can be made by way of the transcription activator-like effector nucleases (TALENs) system. Transcription activator-like effectors (TALEs) can be engineered to bind practically any desired DNA sequence. Exemplary methods of genome editing using the TALEN system can be found for example in Cermak T. Doyle E L. Christian M. Wang L. Zhang Y. Schmidt C, et al. Efficient design and assembly of custom TALEN and other TAL effector-based constructs for DNA targeting. Nucleic Acids Res. 2011; 39:e82; Zhang F. Cong L. Lodato S. Kosuri S. Church G M. Arlotta P Efficient construction of sequence-specific TAL effectors for modulating mammalian transcription. Nat Biotechnol. 2011; 29:149-153 and U.S. Pat. Nos. 8,450,471, 8,440,431 and 8,440,432, all of which are specifically incorporated by reference.

As disclosed herein editing can be made by way of the zinc-finger nucleases (ZFNs) system. The ZFN system uses artificial restriction enzymes generated by fusing a zinc finger DNA-binding domain to a DNA-cleavage domain that can be engineered to target desired DNA sequences. Exemplary methods of genome editing using ZFNs can be found for example in U.S. Pat. Nos. 6,534,261, 6,607,882, 6,746, 838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference.

As disclosed herein editing can be made by way of meganucleases, which are endodeoxyribonucleases characterized by a large recognition site (double-stranded DNA sequences of 12 to 40 base pairs). Exemplary method for using meganucleases can be found in U.S. Pat. Nos. 8,163, 514; 8,133,697; 8,021,867; 8,119,361; 8,119,381; 8,124, 369; and 8,129,134, which are specifically incorporated by reference.

High throughput technique: Through a combination of robotics, data processing and control software, liquid handling devices, and detectors, high throughput techniques allows the rapid screening of potential reagents, conditions, or targets in a short period of time, for example in less than 24, less than 12, less than 6 hours, or even less than 1 hour.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence. "Specifically hybridizable" and "specifically complementary" are terms that indicate a sufficient degree of complementarity such that stable and specific binding occurs between the oligonucleotide (or it's analog) and the DNA, RNA, and or DNA-RNA hybrid target. The oligonucleotide or oligonucleotide analog need not be 100% complementary to its target sequence to be specifically hybridizable. An oligonucleotide or analog is specifically hybridizable when there is a sufficient degree of complementarity to avoid non-specific binding of the oligonucleotide or analog to non-target sequences under conditions where specific binding is desired. Such binding is referred to as specific hybridization.

Isolated: An "isolated" biological component (such as the end joined fragmented nucleic acids described herein) has been substantially separated or purified away from other biological components in the cell of the organism, in which the component naturally occurs, for example, extra-chromatin DNA and RNA, proteins and organelles. Nucleic acids and proteins that have been "isolated" include nucleic acids and proteins purified by standard purification methods, for example from a sample. The term also embraces nucleic acids and proteins prepared by recombinant expression in a host cell as well as chemically synthesized nucleic acids. It is understood that the term "isolated" does not imply that the biological component is free of trace contamination, and can include nucleic acid molecules that are at least 50% isolated, such as at least 75%, 80%, 90%, 95%, 98%, 99%, or even 100% isolated.

Junction: A site where two nucleic acid fragments or joined, for example using the methods described herein. A junction encodes information about the proximity of the nucleic acid fragments that participate in formation of the junction. For example, junction formation between to nucleic acid fragments indicates that these two nucleic acid sequences where in close proximity when the junction was formed, although they may not be in proximity in liner nucleic acid sequence space. Thus, a junction can define ling range interactions. In some embodiments, a junction is labeled, for example with a labeled nucleotide, for example to facilitate isolation of the nucleic acid molecule that includes the junction.

Motif: A nucleic acid sequence to which a protein will bind to directly (e.g. through a zinc finger) or indirectly (e.g. via a protein mediator). One example of a motif is a CTCF motif capable of binding CTCF.

Nucleic acid (molecule or sequence): A deoxyribonucleotide or ribonucleotide polymer including without limitation, cDNA, mRNA, genomic DNA, and synthetic (such as chemically synthesized) DNA or RNA or hybrids thereof. The nucleic acid can be double-stranded (ds) or single-stranded (ss). Where single-stranded, the nucleic acid can be the sense strand or the antisense strand. Nucleic acids can include natural nucleotides (such as A, T/U, C, and G), and can also include analogs of natural nucleotides, such as labeled nucleotides. Some examples of nucleic acids include the probes disclosed herein. The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U). Nucleotides include those nucleotides containing modified bases, modified sugar moieties, and modified phosphate backbones, for example as described in U.S. Pat. No. 5,866,336 to Nazarenko et al.

Examples of modified base moieties which can be used to modify nucleotides at any position on its structure include, but are not limited to: 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N~6-sopentenyladenine, 1-methylguanine, 1-methylinosine, 2,2-dimethylguanine, 2-methyladenine, 2-methylguanine, 3-methylcytosine, 5-methyl cytosine, N6-adenine, 7-methylguanine, 5-methylaminomethyluracil, methoxyarninomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil, 3-(3-amino-3-N-2-carboxypropyl) uracil, 2,6-diaminopurine and biotinylated analogs, amongst others.

Examples of modified sugar moieties which may be used to modify nucleotides at any position on its structure include, but are not limited to arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

Loop anchor: The present inventors herein describe new, one-kilobase-resolution contact maps of the human genome created by using in situ Hi-C, which couples DNA-DNA proximity ligation in intact nuclei (nuclear ligation assay) with high-throughput sequencing. The maps—containing over 15 billion contacts—allowed the inventors to annotate nearly 9,000 contact domains, which are contiguous genomic intervals in which there is an enhanced probability of contact among all loci. Contact domains range in size from tens of kilo bases to several megabases, with a median size of 185 kb. The inventors found that many contact domains are also "loop domains"—that is, contact domains whose boundaries are demarcated by the endpoints of a chromatin loop. These endpoints are revealed in the contact maps from Hi-C data as numerous nodes (local maxima) that correspond to loop anchor loci at the boundary of a domain. The inventors founds that contact domains often correspond to loops—that is, the two boundaries of the domain lie at the loop's two anchor loci, which are spatially proximate. The inventors dubbed this common configuration a "loop domain." The maps allowed the inventors to annotate over 10,000 loops. These loops typically lie between convergent DNA motifs (i.e., motifs pointing toward one another) that bind a complex containing CTCF and cohesin. Thus, each anchor site typically contains a motif that binds a complex containing CTCF and cohesin. The ubiquity of the convergent orientation or configuration of these CTCF binding motifs suggests that the binding of CTCF and cohesin is responsible for the formation of loops and domains at precise genomic coordinates. The CTCF binding motif is a loop anchor motif, forming a loop anchor for the "extrusion complex" containing CTCF and cohesin, which stabilizes the domain loop at its anchor point(s).

Primers: Short nucleic acid molecules, such as a DNA oligonucleotide, which can be annealed to a complementary target nucleic acid molecule by nucleic acid hybridization to form a hybrid between the primer and the target nucleic acid strand. A primer can be extended along the target nucleic acid molecule by a polymerase enzyme. Therefore, primers can be used to amplify a target nucleic acid molecule, wherein the sequence of the primer is specific for the target nucleic acid molecule, for example so that the primer will hybridize to the target nucleic acid molecule under very high stringency hybridization conditions. The specificity of a primer increases with its length. Thus, for example, a primer that includes 30 consecutive nucleotides will anneal to a target sequence with a higher specificity than a corresponding primer of only 15 nucleotides. Thus, to obtain greater specificity, probes and primers can be selected that include at least 5, 10, 15, 20, 25, 30, 35, 40, 45, 50 or more consecutive nucleotides. In particular examples, a primer is at least 15 nucleotides in length, such as at least 5 contiguous nucleotides complementary to a target nucleic acid molecule. Particular lengths of primers that can be used to practice the methods of the present disclosure include primers having at least 5, at least 10, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, or more contiguous nucleotides complementary to the target nucleic acid molecule to be amplified, such as a primer of 5-60 nucleotides, 15-50 nucleotides, 15-30 nucleotides or greater. Primer pairs can be used for amplification of a nucleic acid sequence, for example, by PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence. In general, at least one forward and one reverse primer are included in an amplification reaction. PCR primer pairs can be derived from a known sequence, for example, by using computer programs intended for that purpose such as Primer (Version 0.5, © 1991, Whitehead Institute for Biomedical Research, Cambridge, Mass.). Methods for preparing and using primers are described in, for example, Sambrook et al. (1989) *Molecular Cloning: A Laboratory Manual*, Cold Spring Harbor, N.Y.; Ausubel et al. (1987) *Current Protocols in Molecular Biology*, Greene Publ. Assoc. & Wiley-Intersciences.

Probe: A probe comprises an isolated nucleic acid capable of hybridizing to a target nucleic acid (such as end joined nucleic acid fragment). A detectable label or reporter molecule can be attached to a probe. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example, in Sambrook et al., Molecular Cloning: A Laboratory Manual, Cold Spring Harbor Laboratory Press (1989) and Ausubel et al., Current Protocols in Molecular Biology, Greene Publishing Associates and Wiley-Intersciences (1987). Probes are generally at least 5 nucleotides in length, such as at least 10, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50 at least 51, at least 52, at least 53, at least 54, at least 55, at least 56, at least 57, at least 58, at least 59, at least 60, or more contiguous nucleotides complementary to the target nucleic acid molecule, such as 50-60 nucleotides, 20-50 nucleotides, 20-40 nucleotides, 20-30 nucleotides or greater.

Targeting probe: A probe that includes an isolated nucleic acid capable of hybridizing to a junction in a end joined nucleic acid fragment, wherein the probe specifically hybridizes to the end joined nucleic acid fragment both 5' and 3' of the site of the junction and spans the site of the junction.

Target junction: Any nucleic acid present or thought to be present in a sample that the information of a junction between an end joined nucleic acid fragment about which information would like to be obtained, such as its presence or absence.

Sample: A sample, such as a biological sample, that includes biological materials (such as nucleic acid and proteins, for example double-stranded nucleic acid binding proteins) obtained from an organism or a part thereof, such as a plant, animal, bacteria, and the like. In particular embodiments, the biological sample is obtained from an animal subject, such as a human subject. A biological sample is any solid or fluid sample obtained from, excreted by or secreted by any living organism, including without limitation, single celled organisms, such as bacteria, yeast, protozoans, and amebas among others, multicellular organisms (such as plants or animals, including samples from a healthy or apparently healthy human subject or a human patient affected by a condition or disease to be diagnosed or investigated, such as cancer). For example, a biological sample can be a biological fluid obtained from, for example, blood, plasma, serum, urine, bile, ascites, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease, such as a rheumatoid arthritis, osteoarthritis, gout or septic arthritis). A sample can also be a sample obtained from any organ or tissue (including a biopsy or autopsy specimen, such as a tumor biopsy) or can include a cell (whether a primary cell or cultured cell) or medium conditioned by any cell, tissue or organ.

Specific Binding Agent: An agent that binds substantially or preferentially only to a defined target such as a protein, enzyme, polysaccharide, oligonucleotide, DNA, RNA, recombinant vector or a small molecule. In an example, a "specific binding agent that specifically binds to the label" is capable of binding to a label that is covalently linked to a targeting probe. A nucleic acid-specific binding agent binds substantially only to the defined nucleic acid, such as DNA, or to a specific region within the nucleic acid, for example a nucleic acid probe. A protein-specific binding agent binds substantially only the defined protein, or to a specific region within the protein. For example, a "specific binding agent" includes antibodies and other agents that bind substantially to a specified polypeptide. Antibodies can be monoclonal or polyclonal antibodies that are specific for the polypeptide, as well as immunologically effective portions ("fragments") thereof. The determination that a particular agent binds substantially only to a specific polypeptide may readily be made by using or adapting routine procedures. One suitable in vitro assay makes use of the Western blotting procedure (described in many standard texts, including Harlow and Lane, Using Antibodies: A Laboratory Manual, CSHL, New York, 1999).

Test agent: Any agent that that is tested for its effects, for example its effects on a cell. In some embodiments, a test agent is a chemical compound, such as a chemotherapeutic agent, antibiotic, or even an agent with unknown biological properties.

Tissue: A plurality of functionally related cells. A tissue can be a suspension, a semi-solid, or solid. Tissue includes cells collected from a subject such as blood, cervix, uterus, lymph nodes breast, skin, and other organs.

Treatment: "Treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

Under conditions that permit binding: A phrase used to describe any environment that permits the desired activity, for example conditions under which two or more molecules, such as nucleic acid molecules and/or protein molecules, can bind.

Suitable methods and materials for the practice or testing of this disclosure are described below. Such methods and materials are illustrative only and are not intended to be limiting. Other methods and materials similar or equivalent to those described herein can be used. For example, conventional methods well known in the art to which this disclosure pertains are described in various general and more specific references, including, for example, Sambrook et al., Molecular Cloning: A Laboratory Manual, 2d ed., Cold Spring Harbor Laboratory Press, 1989; Sambrook et al., Molecular Cloning: A Laboratory Manual, 3d ed., Cold Spring Harbor Press, 2001; Ausubel et al., Current Protocols in Molecular Biology, Greene Publishing Associates, 1992 (and Supplements to 2000); Ausubel et al., Short Protocols in Molecular Biology: A Compendium of Methods from Current Protocols in Molecular Biology, 4th ed., Wiley & Sons, 1999; Harlow and Lane, Antibodies: A Laboratory Manual, Cold Spring Harbor Laboratory Press, 1990; and Harlow and Lane, Using Antibodies: A Laboratory Manual, Cold Spring Harbor Laboratory Press, 1999. In addition, the materials, methods, and examples are illustrative only and not intended to be limiting

II. Description of Several Embodiments

A major goal in modern biology is defining the interactions between different biological actors in vivo. Over the past few decades, major advances have been made in developing methods to identify the molecular interactions with any given protein. With nucleic acids and in particular genomic DNA it is difficult to determine the interactions in a cell in part because of enormity, at the sequence level, of genomic DNA in a cell. It is believed that genomic DNA adopts a fractal globule state in which the DNA organized in three dimensions such that functionally related genomic elements, for example enhancers and their target genes, are directly interacting or are located in very close spatial proximity. Such close physical proximity between such elements is further believed to play a role in genome biology both in normal development and homeostasis and in disease. During the cell cycle the particular proximity relationships change, further complicating the study of genome dynamics. Understanding, and perhaps controlling, these tertiary interactions at the nucleic acid level has enormous potential to further our understating of the complexities cellular dynamics and perhaps fostering the development of new classes of therapeutics. Thus, methods are needed to investigate these interactions. This disclosure meets those needs.

Genes are located at a particular position on a particular chromosome, but the elements that regulate their activity can lie far away. Understanding these distal regulatory sequences is essential to understanding how genes turn on and off in a healthy person, and how this process goes awry in disease. But finding distal regulatory sequences has been an open problem for over 30 years.

Using the three-dimensional genome sequencing approach disclosed herein, it is now possible to comprehensively identify all distal regulators of all genes in a sample population of cells. The information available, will make it possible to assess the impact of candidate drugs on specific cellular circuits, hastening the process of drug discovery and for biological research in general. The information available will also enable the mapping of genomic structural and sequence variations. The methods as disclosed herein will further allow the modification of gene expression through modification of chromatin loops and domains, which finds application in all types of industry, and in medicine.

Figure 9:
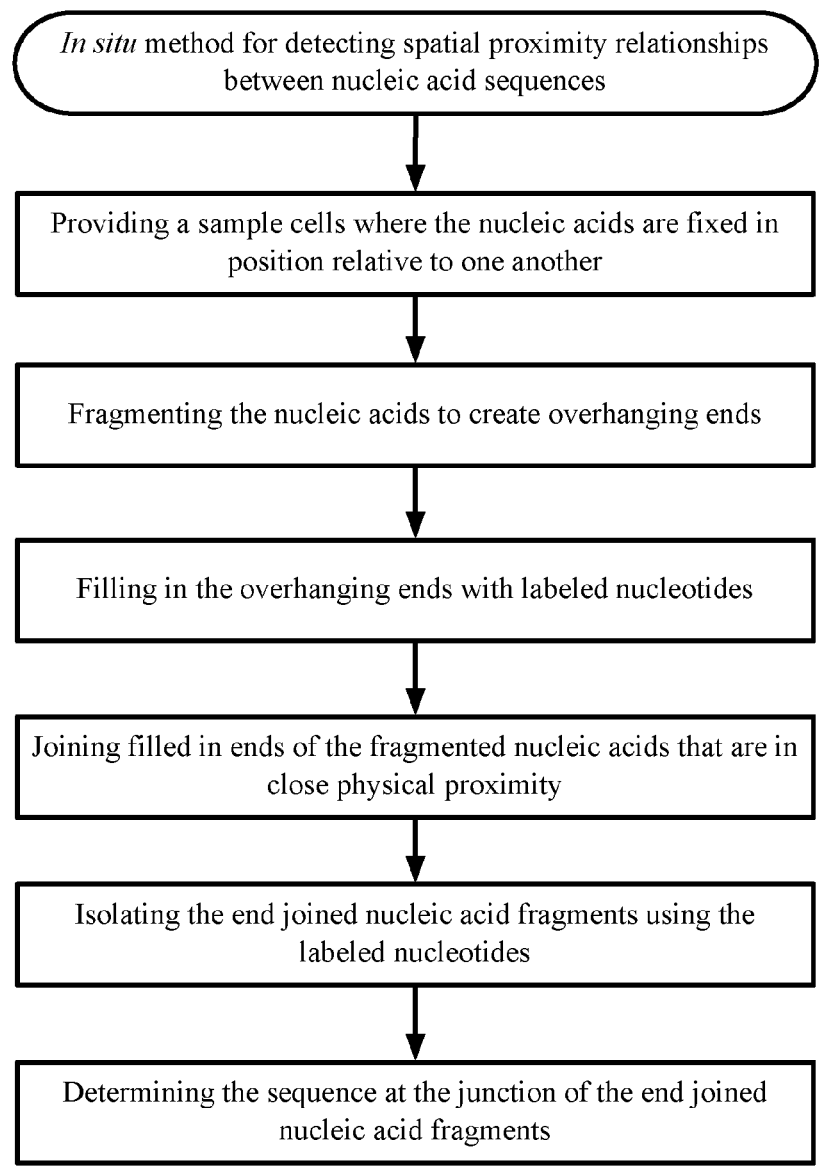
FIG. 9 is an exemplary flow diagram of exemplary methods disclosed herein. The flow diagram is for illustrative purposes only and it is envisioned that the method disclosed herein can have more or fewer steps than shown in the diagram.

Disclosed herein is a method for detecting spatial proximity relationships between DNA in situ. By combining DNA-DNA proximity ligation with high throughput sequencing in order to measure how frequently positions in the human genome come into close physical proximity, the disclosed method can simultaneously map substantially all of the interactions of DNAs in a cell, including spatial arrangements of DNA. An flowchart depicting a non-limiting example of the methods disclosed is given in FIG. 9. Some of the advantages of the disclosed method are that is can be completed on a small sample of cells, without dilution of the sample. This lack of dilution yields many more contacts than previous methods used to define DNA/DNA interactions, such as chromosome Conformation Capture (3C) and Hi-C technology (see Dekker et al., Science 295:1306-1311 (2002) and Lieberman-Aiden et al., Science 326:289-93 (2009).

As demonstrated in Example 1 below, in situ determination of nucleic acid proximity as described results in surprising superior results over the Hi-C protocol. As shown in Example 1, the disclosed methods yield a result with greater complexity, which indicates more interactions that can be mapped and consequently more information. In addition, method disclosed herein provide more information on long distance intra-chromosomal contacts. These contacts are the most informative ones, as they can pin down the long-range interactions in the cell.

In order to determine the target for intervention, the methods for determining spatial proximity relationships between nucleic acid sequences are elemental. Further, the methods can also be used to monitor the result of interventions in chromatin looping. In the paragraphs below, the methods for detecting spatial nucleic acid proximity, agents for modulating chromatin 3D structure, and methods and tools for delivering such agents are discussed in detail, as will methods for intervention in chromatin loop formation using genome editing tools.

A. In Situ Methods for Detecting Spatial Nucleic Acid Proximity

Disclosed herein are in situ methods for detecting spatial proximity relationships between nucleic acid sequences in a sample, such as DNA sequences, for example in a cell or multiple cells. Preferred methods include in situ Hi-C methods. The methods include providing a sample of one or more cells, nuclear extract, cellular milieu or system of nucleic acids of interest that include nucleic acids. In some embodiments, the spatial relationships in the cell is locked in, for example cross-linked or otherwise stabilized. For example, a sample of cells can be treated with a cross-linker to lock in the spatial information or relationship about the molecules in the cells, such as the DNA in the cell. The nucleic acids present are fragmented to yield nucleic acids with overhanging ends, such as a 5' overhanging end. The overhanging ends are then filled in, for example using a DNA polymerase, such as available from a commercial source. The filled in nucleic acid fragments are thus blunt ended at the end filled 5' end. The fragments are then end joined at the filled in end, for example, by ligation using a commercially available nucleic acid ligase, or otherwise attached to another fragment that is in close physical proximity. The ligation, or other attachment procedure, for example nick translation or strand displacement, creates one or more end joined nucleic acid fragments having a junction, for example a ligation junction, wherein the site of the junction, or at least within a few bases, includes one or more labeled nucleic acids, for example, one or more fragmented nucleic acids that have had their overhanging ends filled and joined together. While this step typically involves a ligase, it is contemplated that any means of joining the fragments can be used, for example any chemical or enzymatic means. Further, it is not necessary that the ends be joined in a typical 3'-5' ligation.

To identify the created ligation junction, a labeled nucleotide is used. In one example embodiment, one or more labeled nucleotides are incorporated into the ligated junction. For example, the overhanging ends may be filled in using a DNA polymerase that incorporates one or more labeled nucleotides during the filling in step described above.

In some embodiments the nucleic acids are cross-linked, either directly, or indirectly, and the information about spatial relationships between the different DNA fragments in the cell, or cells, is maintained during this joining step, and substantially all of the end joined nucleic acid fragments formed at this step were in spatial proximity in the cell prior to the crosslinking step. Therefore, at this point the information about which sequences were in spatial proximity to other sequences in the cell is locked into the end joined fragments. It has been found however, that in some situations, it is not necessary to hold the nucleic acids in place using a chemical fixative or crosslinking agent. Thus in some embodiments, no crosslinking agent is used. In still other embodiments, the nucleic acids are held in position relative to each other by the application of non-crosslinking means, such as by using agar or other polymer to hold the nucleic acids in position.

The labeled nucleotide is present in the junction is used to isolate the one or more end joined nucleic acid fragments using the labeled nucleotide. The sequence is determined at the junction of the one or more end joined nucleic acid fragments, thereby detecting spatial proximity relationships between nucleic acid sequences in a cell. In some embodiments, such as for genome assembly, essentially all of the sequence of the end joined fragments is determined. In some embodiments, determining the sequence of the junction of the one or more end joined nucleic acid fragments includes nucleic acid sequencing. In some embodiments, determining the sequence of the junction of the one or more end joined nucleic acid fragments includes using a probe that specifically hybridizes to the nucleic acid sequences both 5' and 3' of the junction of the one or more end joined nucleic acid fragments, for example using an RNA probe, a DNA probe, a locked nucleic acid (LNA) probe, a peptide nucleic acid (PNA) probe, or a hybrid RNA-DNA probe. In exemplary embodiments of the disclosed method, the location is determined or identified for nucleic acid sequences both 5' and 3' of the ligation junction of the one or more end joined nucleic acid fragments relative to source genome and/or chromosome. In some embodiments, the junction identified is correlated with a disease state. In some embodiments, the junction identified is correlated with an environmental condition. In some embodiments, the sequenced end joined fragments are assembled to create an assembled genome or portion thereof, such as a chromosome or sub-fraction thereof. In some embodiments, information from one or more ligation junctions derived from a sample consisting of a mixture of cells from different organisms, such as mixture of microbes, is used to identify the organisms present in the sample and their relative proportions. In some example, the sample is derived from patient samples.

Typically, the end joined fragments are desired to be between about 100 and about 1000 bases in length, although longer and shorter fragments are contemplated. In some embodiments, the nucleic acid fragments are between about 100 and about 1000 bases in length, such as about 100, about 150, about 200, about 250, about 300, about 350, about 400, about 450, about 500, about 550, about 600, about 650, about 700, about 750, about 800, about 850, about 900, about 950 or about 1000 bases in length, for example form about 100 to about 1000, about 200 to about 800, about 500 to about 850, about 100 to about 500 and about 300 to about 775 base pairs in length and the like. In specific examples, end joined fragments are selected for sequence determination that are between about 300 and 500 base pairs in length.

In some embodiments, in order to create discrete portions of nucleic acid that can be joined together in subsequent steps of the methods, the nucleic acids present in the cells, such as cross-linked cells, are fragmented. The fragmentation can be done by a variety of methods, such as enzymatic and chemical cleavage. For example, DNA can be fragmented using an endonuclease that cuts a specific sequence of DNA and leaves behind a DNA fragment with a 5' overhang, thereby yielding fragmented DNA. In other examples an endonuclease can be selected that cuts the DNA at random spots and yields overhangs or blunt ends. In some embodiments, fragmenting the nucleic acid present in the one or more cells comprises enzymatic digestion with an endonuclease that leaves 5' overhanging ends. Enzymes that fragment, or cut, nucleic acids and yield an overhanging sequence are known in the art and can be obtained from such commercial sources as New England BioLabs® and Promega®. One of ordinary skill in the art can choose the restriction enzyme with out undue experimentation. One of ordinary skill in the art will appreciate that using different fragmentation techniques, such as different enzymes with different sequence requirements, will yield different fragmentation patterns and therefore different nucleic acid ends. The process of fragmenting the sample can yield ends that are capable of being joined.

In some embodiments, the end joined DNA that includes a labeled nucleotide is captured with a specific binding agent that specifically binds a capture moiety, such as biotin, on the labeled nucleotide. In some embodiments, the capture moiety is adsorbed or otherwise captured on a surface. In specific embodiments, the end target joined DNA is labeled with biotin, for instance by incorporation of biotin-14-CTP or other biotinylated nucleotide during the filling in of the 5' overhang, for example with a DNA polymerase, allowing capture by streptavidin. Other means for labeling, capturing, and detecting nucleic acid probes include: incorporation of aminoallyl-labeled nucleotides, incorporation of sulfhydryl-labeled nucleotides, incorporation of allyl- or azide-containing nucleotides, and many other methods described in Bioconjugate Techniques (2nd Ed), Greg T. Hermanson, Elsevier (2008), which is specifically incorporated herein by reference. In some embodiments the specific binding agent has been immobilized for example on a solid support, thereby isolating the target nucleic molecule of interest. By "solid support or carrier" is intended any support capable of binding a targeting nucleic acid. Well-known supports or carriers include glass, polystyrene, polypropylene, polyethylene, dextran, nylon, amylases, natural and modified celluloses, polyacrylamides, agarose, gabbros and magnetite. The nature of the carrier can be either soluble to some extent or insoluble for the purposes of the present disclosure. The support material may have virtually any possible structural configuration so long as the coupled molecule is capable of binding to targeting probe. Thus, the support configuration may be spherical, as in a bead, or cylindrical, as in the inside surface of a test tube, or the external surface of a rod. Alternatively, the surface may be flat such as a sheet or test strip. After capture, these end joined nucleic acid fragments are available for further analysis, for example to determine the sequences that contributed to the information encoded by the ligation junction, which can be used to determine which DNA sequences are close in spatial proximity in the cell, for example to map the three dimensional structure of DNA in a cell such as genomic and/or chromatin bound DNA. In some embodiments, the sequence is determined by PCR, hybridization of a probe and/or sequencing, for example by sequencing using high-throughput paired end sequencing. In some embodiments determining the sequence at the one or more junctions of the one or more end joined nucleic acid fragments comprises nucleic acid sequencing, such as short-read sequencing technologies or long-read sequencing technologies. In some embodiments, nucleic acid sequencing is used to determine two or more junctions within an end-joined concatemer simultaneously.

In some embodiments, determining the sequence of a junction includes using a probe that specifically binds to the junction at the site of the two joined nucleic acid fragments. In particular embodiments, the probe specifically hybridizes to the junction both 5' and 3' of the site of the join and spans the site of the join. A probe that specifically binds to the junction at the site of the join can be selected based on known interactions, for example in a diagnostic setting where the presence of a particular target junction, or set of target junctions, has been correlated with a particular disease or condition. It is further contemplated that once a target junction is known, a probe for that target junction can be synthesized.

In some embodiments, the end joined nucleic acids are selectively amplified. In some examples, to selectively amplify the end joined nucleic acids, a 3' DNA adaptor and a 5' RNA, or conversely a 5' DNA adaptor and a 3' RNA adaptor can be ligated to the ends of the molecules can be used to mark the end joined nucleic acids. Using primers specific for these adaptors only end joined nucleic acids will be amplified during an amplification procedure such as PCR. In some embodiments, the target end joined nucleic acid is amplified using primers that specifically hybridize to the adaptor nucleic acid sequences present at the 3' and 5' ends of the end joined nucleic acids. In some embodiments, the non-ligated ends of the nucleic acids are end repaired. In some embodiments attaching sequencing adapters to the ends of the end ligated nucleic acid fragments.

In some embodiments, the cells are lysed to release the cellular contents, for example after crosslinking. In some examples the nuclei are lysed as well, while in other examples, the nuclei are maintained intact, which can then be isolated and optionally lysed, for example using an reagent that selectively targets the nuclei or other separation technique known in the art. In some examples, the sample is a sample of permeablized nuclei, multiple nuclei, isolated nuclei, synchronized cells, (such at various points in the cell cycle, for example metaphase) or acellular. In some embodiments, the nucleic acids present in the sample are purified, for example using ethanol precipitation. In example embodiments of the disclosed method the cells and/or cell nuclei are not subjected to mechanical lysis. In some example embodiments, the sample is not subjected to RNA degradation. In specific embodiments, the sample is not contacted with an exonuclease to remove of biotin from un-ligated ends. In some embodiments, the sample is not subjected to phenol/chloroform extraction.

In some embodiments of the disclosed method the nucleic acids present in the cell or cells are fixed in position relative to each other by chemical crosslinking, for example by contacting the cells with one or more chemical cross linkers. This treatment locks in the spatial relationships between portions of nucleic acids in a cell. Any method of fixing the nucleic acids in their positions can be used. In some embodiments, the cells are fixed, for example with a fixative, such as an aldehyde, for example formaldehyde or gluteraldehyde. In some embodiments, a sample of one or more cells is cross-linked with a cross-linker to maintain the spatial relationships in the cell. For example, a sample of cells can be treated with a cross-linker to lock in the spatial information or relationship about the molecules in the cells, such as the DNA and RNA in the cell. In other embodiments, the relative positions of the nucleic acid can be maintained without using crosslinking agents. For example the nucleic acids can be stabilized using spermine and spermidine (see Cullen et al., Science 261, 203 (1993), which is specifically incorporated herein by reference in its entirety). Other methods of maintaining the positional relationships of nucleic acids are known in the art. In some embodiments, nuclei are stabilized by embedding in a polymer such as agarose. In some embodiments, the cross-linker is a reversible cross-linker. In some embodiments, the cross-linker is reversed, for example after the fragments are joined. In specific examples, the nucleic acids are released from the cross-linked three-dimensional matrix by treatment with an agent, such as a proteinase, that degrade the proteinaceous material form the sample, thereby releasing the end ligated nucleic acids for further analysis, such as determination of the nucleic acid sequence. In specific embodiments, the sample is contacted with a proteinase, such as Proteinase K. In some embodiments of the disclosed methods, the cells are contacted with a crosslinking agent to provide the cross-linked cells. In some examples, the cells are contacted with a protein-nucleic acid crosslinking agent, a nucleic acid-nucleic acid crosslinking agent, a protein-protein crosslinking agent or any combination thereof. By this method, the nucleic acids present in the sample become resistant to special rearrangement and the spatial information about the relative locations of nucleic acids in the cell is maintained. In some examples, a cross-linker is a reversible—, such that the cross-linked molecules can be easily separated in subsequent steps of the method. In some examples, a cross-linker is a non-reversible cross-linker, such that the cross-linked molecules cannot be easily separated. In some examples, a cross-linker is light, such as UV light. In some examples, a cross linker is light activated. These cross-linkers include formaldehyde, disuccinimidyl glutarate, UV light, psoralens and their derivatives such as aminomethyl-trioxsalen, glutaraldehyde, ethylene glycol bis[succinimidylsuccinate], bissulfosuccinimidyl suberate, 1-Ethyl-3-[3-dimethylaminopropyl]carbodiimide (EDC) bis [sulfosuccinimidyl] suberate (BS3) and other compounds known to those skilled in the art, including those described in the Thermo Scientific Pierce Crosslinking Technical Handbook, Thermo Scientific (2009) as available on the world wide web at piercenet.com/files/1601673_Crosslink_HB_Intl.pdf.

The disclosed methods are also particularly suited to monitoring disease states, such as disease state in an organism, for example a plant or an animal subject, such as a mammalian subject, for example a human subject. Certain disease states may be caused and/or characterized by the differential formation of certain target joins. For example, certain interactions may occur in a diseased cell but not in a normal cell. In other examples, certain interactions may occur in a normal cell but not in diseased cell. Thus, using the disclosed methods a profile of the interaction between DNA sequences in vivo, can be correlated with a disease state. The target join profile correlated with a disease can be used as a "fingerprint" to identify and/or diagnose a disease in a cell, by virtue of having a similar "fingerprint." In addition, the profile can be used to monitor a disease state, for example to monitor the response to a therapy, disease progression and/or make treatment decisions for subjects.

The ability to obtain an interaction profile allows for the diagnosis of a disease state, for example by comparison of the profile present in a sample with the correlated with a specific disease state, wherein a similarity in profile indicates a particular disease state.

Accordingly, aspects of the disclosed methods relate to diagnosing a disease state based on target junction profile correlated with a disease state, for example cancer, or an infection, such as a viral or bacterial infection. It is understood that a diagnosis of a disease state could be made for any organism, including without limitation plants, and animals, such as humans.

Aspects of the present disclosure relate to the correlation of an environmental stress or state with an target junction profile, such as a sample of cells, for example a culture of cells, can be exposed to an environmental stress, such as but not limited to heat shock, osmolarity, hypoxia, cold, oxidative stress, radiation, starvation, a chemical (for example a therapeutic agent or potential therapeutic agent) and the like. After the stress is applied, a representative sample can be subjected to analysis, for example at various time points, and compared to a control, such as a sample from an organism or cell, for example a cell from an organism, or a standard value.

In some embodiments, the disclosed methods can be used to screen chemical libraries for agents that modulate DNA interaction profiles, for example that alter the interaction profile from an abnormal one, for example correlated to a disease state to one indicative of a disease free state. By exposing cells, or fractions thereof, tissues, or even whole animals, to different members of the chemical libraries, and performing the methods described herein, different members of a chemical library can be screened for their effect on interaction profiles simultaneously in a relatively short amount of time, for example using a high throughput method.

In some embodiments, the sequence information determined by the disclosed methods may be used to phase polymorphisms and/or assemble individual haplotypes, distinguish between heterozygous and homozygous structural variations, resolve genomic structural genomic variation, including copy number variations, estimate the 1D distance between two fragments of DNA from the same chromosome, assess syntenic relationships between two or more organisms at arbitrary resolution, and/or generate phylogenetic trees and/or ancestral genomes.

In some embodiments, screening of test agents involves testing a combinatorial library containing a large number of potential modulator compounds. A combinatorial chemical library may be a collection of diverse chemical compounds generated by either chemical synthesis or biological synthesis, by combining a number of chemical "building blocks" such as reagents. For example, a linear combinatorial chemical library, such as a polypeptide library, is formed by combining a set of chemical building blocks (amino acids) in every possible way for a given compound length (for example the number of amino acids in a polypeptide compound). Millions of chemical compounds can be synthesized through such combinatorial mixing of chemical building blocks.

Appropriate agents can be contained in libraries, for example, synthetic or natural compounds in a combinatorial library. Numerous libraries are commercially available or can be readily produced; means for random and directed synthesis of a wide variety of organic compounds and biomolecules, including expression of randomized oligonucleotides, such as antisense oligonucleotides and oligopeptides, also are known. Alternatively, libraries of natural compounds in the form of bacterial, fungal, plant and animal extracts are available or can be readily produced. Additionally, natural or synthetically produced libraries and compounds are readily modified through conventional chemical, physical and biochemical means, and may be used to produce combinatorial libraries. Such libraries are useful for the screening of a large number of different compounds.

The compounds identified using the methods disclosed herein can serve as conventional "lead compounds" or can themselves be used as potential or actual therapeutics. In some instances, pools of candidate agents can be identified and further screened to determine which individual or subpools of agents in the collective have a desired activity.

Appropriate samples for use in the methods disclosed herein include any conventional biological sample obtained from an organism or a part thereof, such as a plant, animal, and the like. In particular embodiments, the biological sample is obtained from an animal subject, such as a human subject. A biological sample is any solid or fluid sample obtained from, excreted by or secreted by any living organism, including without limitation, single celled organisms, such as yeast, protozoans, and amoebas among others, multicellular organisms (such as plants or animals, including samples from a healthy or apparently healthy human subject or a human patient affected by a condition or disease to be diagnosed or investigated, such as cancer). For example, a biological sample can be a biological fluid obtained from, for example, blood, plasma, serum, urine, bile, ascites, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease, such as a rheumatoid arthritis, osteoarthritis, gout or septic arthritis). A sample can also be a sample obtained from any organ or tissue (including a biopsy or autopsy specimen, such as a tumor biopsy) or can include a cell (whether a primary cell or cultured cell) or medium conditioned by any cell, tissue or organ. Exemplary samples include, without limitation, cells, cell lysates, blood smears, cyto-centrifuge preparations, cytology smears, bodily fluids (e.g., blood, plasma, serum, saliva, sputum, urine, bronchoalveolar lavage, semen, etc.), tissue biopsies (e.g., tumor biopsies), fine-needle aspirates, and/or tissue sections (e.g., cryostat tissue sections and/or paraffin-embedded tissue sections). In other examples, the sample includes circulating tumor cells (which can be identified by cell surface markers). In particular examples, samples are used directly (e.g., fresh or frozen), or can be manipulated prior to use, for example, by fixation (e.g., using formalin) and/or embedding in wax (such as formalin-fixed paraffin-embedded (FFPE) tissue samples). It will appreciated that any method of obtaining tissue from a subject can be utilized, and that the selection of the method used will depend upon various factors such as the type of tissue, age of the subject, or procedures available to the practitioner. Standard techniques for acquisition of such samples are available. See, for example Schluger et al., J. Exp. Med. 176:1327-33 (1992); Bigby et al., Am. Rev. Respir. Dis. 133:515-18 (1986); Kovacs et al., NEJM 318: 589-93 (1988); and Ognibene et al., Am. Rev. Respir. Dis. 129:929-32 (1984).

This disclosure also provides integrated systems for high-throughput testing, or automated testing. The systems typically include a robotic armature that transfers fluid from a source to a destination, a controller that controls the robotic armature, a detector, a data storage unit that records detection, and an assay component such as a microtiter dish comprising a well having a reaction mixture for example media.

In some embodiments of the disclosed methods, determining the identity of a nucleic acid, such as a target junction, includes detection by nucleic acid hybridization. Nucleic acid hybridization involves providing a probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA:DNA, PNA:DNA, RNA:RNA, or RNA:DNA) will form even where the annealed sequences are not perfectly complementary. Thus, specificity of hybridization is reduced at lower stringency. Conversely, at higher stringency (e.g., higher temperature or lower salt) successful hybridization requires fewer mismatches. One of skill in the art will appreciate that hybridization conditions can be designed to provide different degrees of stringency.

In general, there is a tradeoff between hybridization specificity (stringency) and signal intensity. Thus, in one embodiment, the wash is performed at the highest stringency that produces consistent results and that provides a signal intensity greater than approximately 10% of the background intensity. Thus, the hybridized array may be washed at successively higher stringency solutions and read between each wash. Analysis of the data sets thus produced will reveal a wash stringency above which the hybridization pattern is not appreciably altered and which provides adequate signal for the particular oligonucleotide probes of interest. In some examples, RNA is detected using Northern blotting or in situ hybridization (Parker & Barnes, Methods in Molecular Biology 106:247-283, 1999); RNAse protection assays (Hod, Biotechniques 13:852-4, 1992); and PCR-based methods, such as reverse transcription polymerase chain reaction (RT-PCR) (Weis et al., Trends in Genetics 8:263-4, 1992).

In one embodiment, the hybridized nucleic acids are detected by detecting one or more labels attached to the sample nucleic acids. The labels can be incorporated by any of a number of methods. In one example, the label is simultaneously incorporated during the amplification step in the preparation of the sample nucleic acids. Thus, for example, polymerase chain reaction (PCR) with labeled primers or labeled nucleotides will provide a labeled amplification product. In one embodiment, transcription amplification, as described above, using a labeled nucleotide (such as fluorescein-labeled UTP and/or CTP) incorporates a label into the transcribed nucleic acids.

Detectable labels suitable for use include any composition detectable by spectroscopic, photochemical, biochemical, immunochemical, electrical, optical or chemical means. Useful labels include biotin for staining with labeled streptavidin conjugate, magnetic beads (for example Dynabeads™), fluorescent dyes (for example, fluorescein, Texas red, rhodamine, green fluorescent protein, and the like), radiolabels (for example, 3 H, 125 I, 35 S, 14 C, or 32 P), enzymes (for example, horseradish peroxidase, alkaline phosphatase and others commonly used in an ELISA), and colorimetric labels such as colloidal gold or colored glass or plastic (for example, polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are also well known. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

The label may be added to the target (sample) nucleic acid(s) prior to, or after, the hybridization. So-called "direct labels" are detectable labels that are directly attached to or incorporated into the target (sample) nucleic acid prior to hybridization. In contrast, so-called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected (see Laboratory Techniques in Biochemistry and Molecular Biology, Vol. 24: Hybridization With Nucleic Acid Probes, P. Tijssen, ed. Elsevier, N.Y., 1993).

In some embodiments, the identity of a nucleic acid is determined by DNA or RNA sequencing. Generally, the sequencing can be performed using automated Sanger sequencing (AB13730xl genome analyzer), pyrosequencing on a solid support (454 sequencing, Roche), sequencing-by-synthesis with reversible terminations (ILLUMINA® Genome Analyzer), sequencing-by-ligation (ABI SOLiD®) or sequencing-by-synthesis with virtual terminators (HELISCOPE®); Moleculo sequencing (see Voskoboynik et al. eLife 2013 2:e00569 and U.S. patent application Ser. No. 13/608,778, filed Sep. 10, 2012); DNA nanoball sequencing; Single molecule real time (SMRT) sequencing; Nanopore DNA sequencing; Sequencing by hybridization; Sequencing with mass spectrometry; and Microfluidic Sanger sequencing. Examples of information that can be obtained from the disclosed methods and the analysis of the results thereof, include without limitation uni- or multiplex, 3 dimensional genome mapping, genome assembly, one dimensional genome mapping, the use of single nucleotide polymorphisms to phase genome maps, for example to determine the patterns of chromosome inactivation, such as for analysis of genomic imprinting, the use of specific junctions to determine karyotypes, including but not limited to chromosome number alterations (such as unisomies, uniparental disomies, and trisomies), translocations, inversions, duplications, deletions and other chromosomal rearrangements, the use of specific junctions correlated with disease to aid in diagnosis.

Furthermore, the methods disclosed herein can readily be combined with other techniques, such as hybrid capture after library generation (to target specific parts of the genome), chromatin immunoprecipitation after ligation (to examine the chromatin environment of regions associated with specific proteins), bisulfite treatment, (to probe the methylation state of DNA). For examples the information from one or more ligation junctions is used to infer and/or determine the three dimensional structure of the genome. In some embodiments, the information from one or more ligation junctions is used to simultaneously map protein-DNA interactions and DNA-DNA interactions or RNA-DNA interactions and DNA-DNA interactions. In some embodiments, the information from one or more ligation junctions is used to simultaneously map methylation and three-dimensional structure. In some embodiments, the information from more than one ligation junction is used to assemble whole genomes or parts of genomes. In some embodiments, the sample is treated to accentuate interactions between contiguous regions of the genome. In some embodiments, the cells in the sample are synchronized in metaphase.

In one example embodiment, hybrid capture after library generation comprises treating a library of end joined nucleic acid fragments generated using the methods described above with an agent that isolates end joined nucleic acid fragments comprising specific nucleic acid sequence (target sequence). In certain example embodiments, the specific nucleic acid sequence is at least 50, at least 60, at least 70, at least 80, at least 90, at least 100, at least 110, at least 120, at least 130, at least 140, at least 150, at least 160, at least 170, at least 180, at least 190, or at least 200 base pairs long. In certain example embodiments, the specific nucleic acid sequence is within at least 50, at least 60, at least 70, at least, 80, at least 90, or at least 100 base pairs, in either the 5' or 3' direction, of a restriction site. In certain example embodiments, the specific nucleic sequence comprises less than ten repetitive bases. In certain other example embodiments, the GC content of the specific nucleic acid sequence is between 25% and 80%, between 40% and 70%, or between 50% and 60%.

In certain example embodiments, the agent that isolates the end joined nucleic acid fragments comprising the specific nucleic acid sequence is a probe. The probe may be labeled. In certain example embodiments, the probe is radiolabeled, fluorescently-labeled, enzymatically-labeled, or chemically labeled. In certain other example embodiments, the probe may be labeled with a capture moiety, such as a biotin-label. Wherein, the probe is labeled with a capture moiety, the capture moiety may be used to isolate the end joined nucleic acid fragments using techniques such as those known in the art and described previously. The exact sequence of the isolated end-joined nucleic acid fragments may then be determined, for example, by sequencing as described previously.

Considering the wealth of information that can be gained using the methods described herein, with respect to genome architecture at the primary, secondary, tertiary and beyond (see Examples below), the methods disclosed herein can be used to apply genome engineering techniques for the treatment of disease as well as the study of biological questions. In some embodiments, the organizational structure of a genome is determined using the methods disclosed herein. For example the methods disclosed herein have been demonstrated (see Example 1) to generate very dense contact maps. In some examples sequences obtained using the methods disclosed herein are mapped to a genome of an organism, such as a animal, plant, fungi, or microorganism, for example a bacterial, yeast, virus and the like. In some examples, using single nucleotide polymorphisms (SNPs), diploid maps corresponding to each chromosomal homolog are constructed. These maps, as well as others that can be generated using the disclosed technology provide a picture, such as a three-dimensional picture, of genomic architecture with high resolution, such as a resolution of 1 kilobase or even lower, for example less then 500 bases.

As disclosed herein, the inventors have shown that a genome is partitioned into domains that are associated with particular patterns of histone marks that segregates into sub-compartments, distinguished by unique long-range contact patterns. Using the maps, the inventors have identified 10,000 distinct loops across the genome and studied their properties, including their strong association with gene activation. Using the maps constructed with the methods described herein as a starting place, targeted alterations in genome structure can be made.

Such genetic and epigenetic control of cells with genome engineering technologies enables a broad range of applications from basic biology to biotechnology and medicine. Manipulating transcriptional regulation or chromatin states at particular loci can reveal how genetic material is organized and utilized within a cell, illuminating relationships between the architecture of the genome and its functions. In addition, once the organization is determined, for example using the methods disclosed herein, manipulation of the genome can be used as a treatment for certain diseases as well as reconstruction of useful biological systems, for example for drug development processes and medical therapeutics. A series of programmable nuclease-based genome editing technologies have developed (see Hsu et al., Cell 157, Jun. 5, 2014 1262-1278 for review). Among these, the clustered regularly interspaced short palindromic repeats (CRISPR)/CRISPR-associated (Cas) system provides for a preferred embodiment in aspects of this invention (see e.g.; Platt et al., Cell 159(2), 440-455 (2014); Shalem et al., Science 3 84-87 (2014); Le Cong et al., Science 339, 819 (2013); and WO2015/089486).

Disclosed herein are methods of altering or modulating the spatial proximity relationships between nucleic acids inside a cell. The methods include providing a sample of one or more cells comprising nucleic acids and providing one or more agents targeting one or more specific genomic regions of interest. The agents are introduced into the one or more cells in order to introduce or remove a sequence or nucleic acid/histone modification associated with a particular spatial proximity arrangement of nucleic acids. In some embodiments the genomic regions of interest are identified with the methods disclosed herein. In some embodiments, a particular sequence is deleted/inserted in order to abrogate/establish a chromatin loop. In some embodiments, the chromatin loop is altered in a tissue specific manner. In some embodiments, the chromatin loop is involved in the regulation of the expression of a gene. In some embodiments, the chromatin loop or specific genomic regions participating in the chromatin loop are indicative of a disease or condition. In some embodiments, a particular sequence is deleted/inserted in order to abrogate/establish a chromatin domain with elevated contacts between all pairs of loci within a contiguous interval. In some embodiments, the chromatin domain is altered in a tissue specific manner. In some embodiments, the chromatin domain is involved in the regulation of the expression of a gene. In some embodiments, the chromatin domain or specific genomic regions participating in the chromatin domain are indicative of a disease or condition. In some embodiments, an agent is introduced to alter the histone modifications at a specific genomic region. In some embodiments, specific histone modifications are introduced at genomic region to target the region to a nuclear compartment. In some preferred embodiments, the agent introduced to target specific genomic regions is a CRISPR/Cas system.

The present invention thus provides methods of altering or modulating the spatial proximity relationships between nucleic acids inside a cell, wherein said methods include providing a sample of one or more cells comprising nucleic acids and providing one or more agents targeting one or more specific genomic regions of interest, wherein the agents are introduced into the one or more cells in order to introduce or remove a sequence or nucleic acid/histone modification associated with a particular spatial proximity arrangement of nucleic acids, and preferably wherein the one or more specific genomic regions of interest comprise at least one CTCF binding motif.

B. Agents for Modulating 3D Chromatin Structure

Chromatin 3D structure modulating agents in the context of the present invention are intended to interfere or manipulate the function of loop anchor motifs, such as CTCF motifs in any possible way. In certain example embodiments, the present invention may block formation of an loop anchor or chromatin domain or induce formation of a loop anchor or chromatin domain at a targeted genomic location. For instance, a loop anchor motif can be altered, such as by mutating (including inverting) a binding motif so as to remove such a motif, or by adding new binding motifs in new locations within a loop domain, so as to reduce the size of an existing loop, so as to modify the size of an existing loop, or combinations thereof. Alternatively, the chromatin 3D structure modulating agent may bind a target region and mask a loop anchor motif, thereby preventing a loop anchor or chromatin domain from forming. The chromatin 3D structure modulating agent may bind a target region and cause a loop anchor of chromatin domain to form. For example, the chromatin 3D structure modulating agent may arrest an extrusion complex at the targeted genomic region faciliating the formation of a new loop anchor or chromatin domain.

1. CRISPR/Cas Systems

Apart from altering the CTCF binding motif or introducing new CTCF binding motifs, it is also envisaged that binding and accumulation of a bulky DNA-binding agent, such as a Cas enzyme, optionally multiple Cas enzymes, at the genomic locus of interest, preferably inside the loop domain defined by two converging CTCF motifs, suffices to prevent proper loop formation and/or extrusion, and thereby alter loop architecture. Hence, as an example of such an embodiment, the agent may be a CRISPR/Cas vector system comprising one or more vectors encoding a Cas protein, preferably a Cas9 protein or a Cpf1 protein, such as a catalytically inactive Cas, and one or more guide RNAs, wherein said one or more guide RNAs are targeted to various genomic loci upstream or downstream of a loop anchor site, preferably outside a loop domain, wherein the bound Cas protein(s) form a bloc. The exact location may be optimized according to degree of loop modulation desired. This system provides for a programmable and reversible method for altering chromatin three dimensional (3D) structure in a cell. In such embodiments, it is preferred that the two active cutting sites (HNH and RuvC) of the Cas protein are disabled, so as to render it catalytically inactive, while its ability to home in on its target DNA are preserved. Such methods are known to one of skill in the art.

Preferred agents in the context of this invention comprise a CRISPR/Cas system. The CRISPR/Cas system does not require the generation of customized proteins to target specific sequences but rather a single Cas protein can be programmed by an RNA guide to recognize a specific DNA target, in other words the Cas protein can be recruited to a specific DNA target or genomic locus of interest using said RNA guide. Adding the CRISPR/Cas system to the repertoire of genome sequencing techniques and analysis methods significantly simplifies the methodology to alter genome structure.

CRISPR/Cas genome editing is preferably carried out with a Type II or type V CRISPR system.

In general, the CRISPR-Cas or CRISPR system is as used in the foregoing documents, such as WO 2014/093622 (PCT/US2013/074667) and refers collectively to transcripts and other elements involved in the expression of or directing the activity of CRISPR-associated ("Cas") genes, including sequences encoding a Cas gene and one or more of, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and, where applicable, transactivating (tracr) RNA or a single guide RNA (sgRNA) (chimeric RNA)) or other sequences. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise any polynucleotide, such as DNA or RNA polynucleotides. In some embodiments, a target sequence is located in the nucleus or cytoplasm of a cell. As used herein, the term "crRNA" or "guide RNA" or "single guide RNA" or "sgRNA" or "one or more nucleic acid components" of a CRISPR-Cas locus effector protein, as applicable, comprises any polynucleotide sequence having sufficient complementarity with a target nucleic acid sequence to hybridize with the target nucleic acid sequence and direct sequence-specific binding of a nucleic acid-targeting complex to the target nucleic acid sequence. In some embodiments, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, Calif.), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as known by the skilled person. Similarly, cleavage of a target nucleic acid sequence may be evaluated in a test tube by providing the target nucleic acid sequence, components of a nucleic acid-targeting complex, including the guide sequence to be tested and a control guide sequence different from the test guide sequence, and comparing binding or rate of cleavage at the target sequence between the test and control guide sequence reactions. Other assays are possible, and will occur to those skilled in the art. A guide sequence, and hence a nucleic acid-targeting guide RNA may be selected to target any target nucleic acid sequence. The target sequence may be DNA. The target sequence may be any RNA sequence. In certain embodiments, the spacer length of the guide RNA is from 15 to 35 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer.

In particular embodiments, the CRISPR/Cas system requires a tracrRNA. The "tracrRNA" sequence or analogous terms includes any polynucleotide sequence that has sufficient complementarity with a crRNA sequence to hybridize. In some embodiments, the degree of complementarity between the tracrRNA sequence and crRNA sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and crRNA sequence are contained within a single transcript, such that hybridization between the two produces a transcript having a secondary structure, such as a hairpin. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In a hairpin structure the portion of the sequence 5' of the final "N" and upstream of the loop corresponds to the tracr mate sequence, and the portion of the sequence 3' of the loop corresponds to the tracr sequence. In alternative embodiments, the CRISPR/Cas system does not require a tracrRNA.

In particular embodiments according to the invention, the guide RNA (capable of guiding Cas to a target locus) may comprise (1) a guide sequence capable of hybridizing to a genomic target locus in the eukaryotic cell; and (2) a tracr mate or direct repeat sequence. In particular embodiments, the CRISPR/Cas protein is characterized in that it makes use of a guide RNA comprising a guide sequence capable of hybridizing to a genomic target locus in the eukaryotic cell and a direct repeat sequence, and does not require a tracrRNA. In particular embodiments, where the CRISPR/Cas protein is characterized in that it makes use of a tracrRNA, the guide sequence, tracr mate and tracr sequence may reside in a single RNA, i.e. an sgRNA (arranged in a 5' to 3' orientation), or the tracr RNA may be a different RNA than the RNA containing the guide and tracr mate sequence. In these embodiments, the tracr hybridizes to the tracr mate sequence and directs the CRISPR/Cas complex to the target sequence.

In one aspect, the invention provides methods for using one or more elements of a CRISPR system. The CRISPR complex of the invention provides an effective means for modifying a target polynucleotide. The CRISPR complex of the invention has a wide variety of utility including modifying (e.g., deleting, inserting, translocating, inactivating, activating) a target polynucleotide in a multiplicity of cell types. As such the CRISPR complex of the invention has a broad spectrum of applications in, e.g., gene therapy, drug screening, disease diagnosis, and prognosis. An exemplary CRISPR complex comprises a CRISPR enzyme complexed with a guide RNA comprising a guide sequence capable of hybridizing to a target sequence within the target polynucleotide.

A template nucleic acid, as that term is used herein, refers to a nucleic acid sequence which can be used in conjunction with a CRISPR/Cas system, such as, but not limited to a CRISPR/Cas9 system to alter the structure of a target position. In an embodiment, the target nucleic acid is modified to have some or all of the sequence of the template nucleic acid, typically at or near cleavage site(s). In an embodiment, the template nucleic acid is single stranded. In an alternate embodiment, the template nucleic acid is double stranded. In an embodiment, the template nucleic acid is DNA, e.g., double stranded DNA. In an alternate embodiment, the template nucleic acid is single stranded DNA.

In an embodiment, the template nucleic acid alters the structure of the target position by participating in homologous recombination. In an embodiment, the template nucleic acid alters the sequence of the target position. In an embodiment, the template nucleic acid results in the incorporation of a modified, or non-naturally occurring base into the target nucleic acid.

The template sequence may undergo a breakage mediated or catalyzed recombination with the target sequence. In an embodiment, the template nucleic acid may include sequence that corresponds to a site on the target sequence that is cleaved by a CRISPR/Cas mediated cleavage event. In an embodiment, the template nucleic acid may include sequence that corresponds to both, a first site on the target sequence that is cleaved in a first CRISPR/Cas mediated event, and a second site on the target sequence that is cleaved in a second CRISPR/Cas mediated event.

In certain embodiments, the template nucleic acid can include sequence which results in an alteration in the coding sequence of a translated sequence, e.g., one which results in the substitution of one amino acid for another in a protein product, e.g., transforming a mutant allele into a wild type allele, transforming a wild type allele into a mutant allele, and/or introducing a stop codon, insertion of an amino acid residue, deletion of an amino acid residue, or a nonsense mutation. In certain embodiments, the template nucleic acid can include sequence which results in an alteration in a non-coding sequence, e.g., an alteration in an exon or in a 5' or 3' non-translated or non-transcribed region. Such alterations include an alteration in a control element, e.g., a promoter, enhancer, and an alteration in a cis-acting or trans-acting control element.

A template nucleic acid having homology with a target position in a target gene may be used to alter the structure of a target sequence. The template sequence may be used to alter an unwanted structure, e.g., an unwanted or mutant nucleotide. The template nucleic acid may include sequence which, when integrated, results in: decreasing the activity of a positive control element; increasing the activity of a positive control element; decreasing the activity of a negative control element; increasing the activity of a negative control element; decreasing the expression of a gene; increasing the expression of a gene; increasing resistance to a disorder or disease; increasing resistance to viral entry; correcting a mutation or altering an unwanted amino acid residue conferring, increasing, abolishing or decreasing a biological property of a gene product, e.g., increasing the enzymatic activity of an enzyme, or increasing the ability of a gene product to interact with another molecule.

The template nucleic acid may include sequence which results in: a change in sequence of 1, 2, 3, 4, 5, 6, 7, 8, 9, 10, 11, 12 or more nucleotides of the target sequence. In an embodiment, the template nucleic acid may be 20+/−10, 30+/−10, 40+/−10, 50+/−10, 60+/−10, 70+/−10, 80+/−10, 90+/−10, 100+/−10, 1 10+/−10, 120+/−10, 130+/−10, 140+/−10, 150+/−10, 160+/−10, 170+/−10, 180+/−10, 190+/−10, 200+/−10, 210+/−10, of 220+/−10 nucleotides in length. In an embodiment, the template nucleic acid may be 30+/−20, 40+/−20, 50+/−20, 60+/−20, 70+/−20, 80+/−20, 90+/−20, 100+/−20, 1 10+/−20, 120+/−20, 130+/−20, 140+/−20, I 50+/−20, 160+/−20, 170+/−20, 180+/−20, 190+/−20, 200+/−20, 210+/−20, of 220+/−20 nucleotides in length. In an embodiment, the template nucleic acid is 10 to 1,000, 20 to 900, 30 to 800, 40 to 700, 50 to 600, 50 to 500, 50 to 400, 50 to 300, 50 to 200, or 50 to 100 nucleotides in length.

A template nucleic acid comprises the following components: [5' homology arm]-[replacement sequence]-[3' homology arm]. The homology arms provide for recombination into the chromosome, thus replacing the undesired element, e.g., a mutation or signature, with the replacement sequence. In an embodiment, the homology arms flank the most distal cleavage sites. In an embodiment, the 3' end of the 5' homology arm is the position next to the 5' end of the replacement sequence. In an embodiment, the 5' homology arm can extend at least 10, 20, 30, 40, 50, 100, 200, 300, 400, 500, 600, 700, 800, 900, 1000, 1500, or 2000 nucleotides 5' from the 5' end of the replacement sequence. In an embodiment, the 5' end of the 3' homology arm is the position next to the 3' end of the replacement sequence. In an embodiment, the 3' homology arm can extend at least 10, 20, 30, 40, 50, 100, 200, 300, 400, 500, 600, 700, 800, 900, 1000, 1500, or 2000 nucleotides 3' from the 3' end of the replacement sequence.

In certain embodiments, one or both homology arms may be shortened to avoid including certain sequence repeat elements. For example, a 5' homology arm may be shortened to avoid a sequence repeat element. In other embodiments, a 3' homology arm may be shortened to avoid a sequence repeat element. In some embodiments, both the 5' and the 3' homology arms may be shortened to avoid including certain sequence repeat elements.

In certain embodiments, a template nucleic acids for correcting a mutation may designed for use as a single-stranded oligonucleotide. When using a single-stranded oligonucleotide, 5' and 3' homology arms may range up to about 200 base pairs (bp) in length, e.g., at least 25, 50, 75, 100, 125, 150, 175, or 200 bp in length.

a. DNA Repair and NHEJ

In certain embodiments, nuclease-induced non-homologous end-joining (NHEJ) can be used to target gene-specific knockouts. Nuclease-induced NHEJ can also be used to remove (e.g., delete) sequence in a gene of interest. Generally, NHEJ repairs a double-strand break in the DNA by joining together the two ends; however, generally, the original sequence is restored only if two compatible ends, exactly as they were formed by the double-strand break, are perfectly ligated. The DNA ends of the double-strand break are frequently the subject of enzymatic processing, resulting in the addition or removal of nucleotides, at one or both strands, prior to rejoining of the ends. This results in the presence of insertion and/or deletion (indel) mutations in the DNA sequence at the site of the NHEJ repair. Two-thirds of these mutations typically alter the reading frame and, therefore, produce a non-functional protein. Additionally, mutations that maintain the reading frame, but which insert or delete a significant amount of sequence, can destroy functionality of the protein. This is locus dependent as mutations in critical functional domains are likely less tolerable than mutations in non-critical regions of the protein. The indel mutations generated by NHEJ are unpredictable in nature; however, at a given break site certain indel sequences are favored and are over represented in the population, likely due to small regions of microhomology. The lengths of deletions can vary widely; most commonly in the 1-50 bp range, but they can easily be greater than 50 bp, e.g., they can easily reach greater than about 100-200 bp. Insertions tend to be shorter and often include short duplications of the sequence immediately surrounding the break site. However, it is possible to obtain large insertions, and in these cases, the inserted sequence has often been traced to other regions of the genome or to plasmid DNA present in the cells.

Because NHEJ is a mutagenic process, it may also be used to delete small sequence motifs as long as the generation of a specific final sequence is not required. If a double-strand break is targeted near to a short target sequence, the deletion mutations caused by the NHEJ repair often span, and therefore remove, the unwanted nucleotides. For the deletion of larger DNA segments, introducing two double-strand breaks, one on each side of the sequence, can result in NHEJ between the ends with removal of the entire intervening sequence. Both of these approaches can be used to delete specific DNA sequences; however, the error-prone nature of NHEJ may still produce indel mutations at the site of repair.

Both double strand cleaving by the CRISPR/Cas system can be used in the methods and compositions described herein to generate NHEJ-mediated indels. NHEJ-mediated indels targeted to the gene, e.g., a coding region, e.g., an early coding region of a gene of interest can be used to knockout (i.e., eliminate expression of) a gene of interest. For example, early coding region of a gene of interest includes sequence immediately following a transcription start site, within a first exon of the coding sequence, or within 500 bp of the transcription start site (e.g., less than 500, 450, 400, 350, 300, 250, 200, 150, 100 or 50 bp).

In an embodiment, in which the CRISPR/Cas system generates a double strand break for the purpose of inducing NHEJ-mediated indels, a guide RNA may be configured to position one double-strand break in close proximity to a nucleotide of the target position. In an embodiment, the cleavage site may be between 0-500 bp away from the target position (e.g., less than 500, 400, 300, 200, 100, 50, 40, 30, 25, 20, 15, 10, 9, 8, 7, 6, 5, 4, 3, 2 or 1 bp from the target position).

In an embodiment, in which two guide RNAs complexing with CRISPR/Cas system nickases induce two single strand breaks for the purpose of inducing NHEJ-mediated indels, two guide RNAs may be configured to position two single-strand breaks to provide for NHEJ repair a nucleotide of the target position.

b. dCas9 and Functional Effectors

Unlike CRISPR-Cas-mediated gene knockout, which permanently eliminates expression by mutating the gene at the DNA level, CRISPR-Cas knockdown allows for temporary reduction of gene expression through the use of artificial transcription factors. Mutating key residues in cleavage domains of the Cas protein results in the generation of a catalytically inactive Cas protein. A catalytically inactive Cas protein complexes with a guide RNA and localizes to the DNA sequence specified by that guide RNA's targeting domain, however, it does not cleave the target DNA. Fusion of the inactive Cas protein to an effector domain also referred to herein as a functional domain, e.g., a transcription repression domain, enables recruitment of the effector to any DNA site specified by the guide RNA.

In certain example embodiments, inactivated Cas protein may be delivered to one or more target regions. For example, using the in situ Hi-C methods described herein chromatin loop domains may be identified in a sample. From the Hi-C contact map target genome regions may be identified where abrogation of a loop or insertion of a new chromatin loop is desired. Accordingly an inactivated Cas protein may be delivered to the target region. In certain example embodiments, the inactivated Cas protein binds to or proximate to an existing loop anchor motif to mask or otherwise interfer with formation of a chromatin loop anchor. In certain other example embodiments, one or more inactivated Cas proteins may be delivered to one or more target regions such that upon binding the one or more inactivated Cas proteins arrest an chromatin loop extrusion complex resulting in formation of a new chromatin loop or modification of an existing chromatin loop (i.e. increasing or decreasing the size of a given chromatin domain).

The inactivated CRISPR/Cas protein may have associated (e.g., via fusion protein) one or more functional domains, including for example, one or more domains from the group comprising, consisting essentially of, or consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g., light inducible). Preferred domains are Fok1, VP64, P65, HSF1, MyoD1. In the event that Fok1 is provided, it is advantageous that multiple Fok1 functional domains are provided to allow for a functional dimer and that guide RNAs are designed to provide proper spacing for functional use (Fok1) as specifically described in Tsai et al. Nature Biotechnology, Vol. 32, Number 6, June 2014). The adaptor protein may utilize known linkers to attach such functional domains. In certain example embodiments, the inactivated Cas protein may be fused to one or more of CTCF, SA1/2, Smc3, Smc1, cohesin and Rad21, such that binding of the fusion protein causes a loop anchor to form or an extrusion complex arrest at the site of inactivated Cas binding. When more than one functional domain is included, the functional domains may be the same or different.

In general, the positioning of the one or more functional domain on the inactivated CRISPR/Cas protein is one which allows for correct spatial orientation for the functional domain to affect the target with the attributed functional effect. For example, if the functional domain is a transcription activator (e.g., VP64 or p65), the transcription activator is placed in a spatial orientation which allows it to affect the transcription of the target. Likewise, a transcription repressor will be advantageously positioned to affect the transcription of the target, and a nuclease (e.g., Fok1) will be advantageously positioned to cleave or partially cleave the target. This may include positions other than the N-/C-terminus of the CRISPR protein.

In certain embodiments, Cas protein may be fused to a transcriptional repression domain and recruited to the promoter region of a gene. Especially for gene repression, it is contemplated herein that blocking the binding site of an endogenous transcription factor would aid in downregulating gene expression. In another embodiment, an inactive Cas protein can be fused to a chromatin modifying protein. Altering chromatin status can result in decreased expression of the target gene. This § could be adapted to describe the "Road block" embodiment described by Erez In an embodiment, a guide RNA molecule can be targeted to a known transcription response elements (e.g., promoters, enhancers, etc.), a known upstream activating sequences, and/or sequences of unknown or known function that are suspected of being able to control expression of the target DNA. Idem: adapt to refer to regions with the motifs of interest In some methods, a target polynucleotide can be inactivated to effect the modification of the expression in a cell. For example, upon the binding of a CRISPR complex to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein is not produced. idem c. Delivery of CRISPR System Through this disclosure and the knowledge in the art, CRISPR-Cas system, or components thereof or nucleic acid molecules thereof (including, for instance HDR template) or nucleic acid molecules encoding or providing components thereof may be delivered by a delivery system herein described both generally and in detail.

In certain aspects the invention involves vectors, e.g. for delivering or introducing in a cell Cas and/or RNA capable of guiding Cas to a target locus (i.e. guide RNA), but also for propagating these components (e.g. in prokaryotic cells). A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

The guide RNA-encoding sequences and/or Cas encoding sequences, can be functionally or operatively linked to regulatory element(s) and hence the regulatory element(s) drive expression. The promoter(s) can be constitutive promoter(s) and/or conditional promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the β-actin promoter, the phosphoglycerol kinase (PGK) promoter, and the EF1α promoter. An advantageous promoter is the promoter is U6.

Vector delivery, e.g., plasmid, viral delivery: The CRISPR enzyme, for instance a Cas9 or any other CRISPR/Cas protein, and/or any of the present RNAs, for instance a guide RNA, can be delivered using any suitable vector, e.g., plasmid or viral vectors, such as adeno associated virus (AAV), lentivirus, adenovirus or other viral vector types, or combinations thereof. The CRISPR/CAs protein and one or more guide RNAs can be packaged into one or more vectors, e.g., plasmid or viral vectors. In some embodiments, the vector, e.g., plasmid or viral vector is delivered to the tissue of interest by, for example, an intramuscular injection, while other times the delivery is via intravenous, transdermal, intranasal, oral, mucosal, or other delivery methods. Such delivery may be either via a single dose, or multiple doses. One skilled in the art understands that the actual dosage to be delivered herein may vary greatly depending upon a variety of factors, such as the vector choice, the target cell, organism, or tissue, the general condition of the subject to be treated, the degree of transformation/modification sought, the administration route, the administration mode, the type of transformation/modification sought, etc.

Means of delivery of RNA also preferred include delivery of RNA via nanoparticles (Cho, S., Goldberg, M., Son, S., Xu, Q., Yang, F., Mei, Y., Bogatyrev, S., Langer, R. and Anderson, D., Lipid-like nanoparticles for small interfering RNA delivery to endothelial cells, Advanced Functional Materials, 19: 3112-3118, 2010) or exosomes (Schroeder, A., Levins, C., Cortez, C., Langer, R., and Anderson, D., Lipid-based nanotherapeutics for siRNA delivery, Journal of Internal Medicine, 267: 9-21, 2010, PMID: 20059641). Indeed, exosomes have been shown to be particularly useful in delivery siRNA, a system with some parallels to the CRISPR system. For instance, El-Andaloussi S, et al. ("Exosome-mediated delivery of siRNA in vitro and in vivo." Nat Protoc. 2012 December; 7(12):2112-26. doi: 10.1038/nprot.2012.131. Epub 2012 Nov. 15.) describe how exosomes are promising tools for drug delivery across different biological barriers and can be harnessed for delivery of siRNA in vitro and in vivo. Their approach is to generate targeted exosomes through transfection of an expression vector, comprising an exosomal protein fused with a peptide ligand. The exosomes are then purify and characterized from transfected cell supernatant, then RNA is loaded into the exosomes. Delivery or administration according to the invention can be performed with exosomes, in particular but not limited to the brain. Vitamin E (α-tocopherol) may be conjugated with CRISPR Cas and delivered to the brain along with high density lipoprotein (HDL), for example in a similar manner as was done by Uno et al. (HUMAN GENE THERAPY 22:711-719 (June 2011)) for delivering short-interfering RNA (siRNA) to the brain. Mice were infused via Osmotic minipumps (model 1007D; Alzet, Cupertino, Calif.) filled with phosphate-buffered saline (PBS) or free TocsiBACE or Toc-siBACE/HDL and connected with Brain Infusion Kit 3 (Alzet). A brain-infusion cannula was placed about 0.5 mm posterior to the bregma at midline for infusion into the dorsal third ventricle. Uno et al. found that as little as 3 nmol of Toc-siRNA with HDL could induce a target reduction in comparable degree by the same ICV infusion method. A similar dosage of CRISPR Cas conjugated to α-tocopherol and co-administered with HDL targeted to the brain may be contemplated for humans in the present invention, for example, about 3 nmol to about 3 μmol of CRISPR Cas targeted to the brain may be contemplated. Zou et al. ((HUMAN GENE THERAPY 22:465-475 (April 2011)) describes a method of lentiviral-mediated delivery of short-hairpin RNAs targeting PKCγ for in vivo gene silencing in the spinal cord of rats. Zou et al. administered about 10 μl of a recombinant lentivirus having a titer of $1\times10^9$ transducing units (TU)/ml by an intrathecal catheter. A similar dosage of CRISPR Cas expressed in a lentiviral vector targeted to the brain may be contemplated for humans in the present invention, for example, about 10-50 ml of CRISPR Cas targeted to the brain in a lentivirus having a titer of $1\times10^9$ transducing units (TU)/ml may be contemplated.

Several types of particle delivery systems and/or formulations are known to be useful in a diverse spectrum of biomedical applications. In general, a particle is defined as a small object that behaves as a whole unit with respect to its transport and properties. Particles are further classified according to diameter. Coarse particles cover a range between 2,500 and 10,000 nanometers. Fine particles are sized between 100 and 2,500 nanometers. Ultrafine particles, or nanoparticles, are generally between 1 and 100 nanometers in size. The basis of the 100-nm limit is the fact that novel properties that differentiate particles from the bulk material typically develop at a critical length scale of under 100 nm.

As used herein, a particle delivery system/formulation is defined as any biological delivery system/formulation which includes a particle in accordance with the present invention. A particle in accordance with the present invention is any entity having a greatest dimension (e.g. diameter) of less than 100 microns (μm). In some embodiments, inventive particles have a greatest dimension of less than 10 m. In some embodiments, inventive particles have a greatest dimension of less than 2000 nanometers (nm). In some embodiments, inventive particles have a greatest dimension of less than 1000 nanometers (nm). In some embodiments, inventive particles have a greatest dimension of less than 900 nm, 800 nm, 700 nm, 600 nm, 500 nm, 400 nm, 300 nm, 200 nm, or 100 nm. Typically, inventive particles have a greatest dimension (e.g., diameter) of 500 nm or less. In some embodiments, inventive particles have a greatest dimension (e.g., diameter) of 250 nm or less. In some embodiments, inventive particles have a greatest dimension (e.g., diameter) of 200 nm or less. In some embodiments, inventive particles have a greatest dimension (e.g., diameter) of 150 nm or less. In some embodiments, inventive particles have a greatest dimension (e.g., diameter) of 100 nm or less. Smaller particles, e.g., having a greatest dimension of 50 nm or less are used in some embodiments of the invention. In some embodiments, inventive particles have a greatest dimension ranging between 25 nm and 200 nm.

It will be appreciated that reference made herein to particles or nanoparticles can be interchangeable, where appropriate. CRISPR enzyme mRNA and guide RNA may be delivered simultaneously using particles or lipid envelopes; for instance, CRISPR protein and RNA of the invention, e.g., as a complex, can be delivered via a particle as in Dahlman et al., WO2015089419 A2 and documents cited therein, such as 7C1 (see, e.g., James E. Dahlman and Carmen Barnes et al. Nature Nanotechnology (2014) published online 11 May 2014, doi:10.1038/nnano.2014.84), e.g., delivery particle comprising lipid or lipidoid and hydrophilic polymer, e.g., cationic lipid and hydrophilic polymer, for instance wherein the the cationic lipid comprises 1,2-dioleoyl-3-trimethylammonium-propane (DOTAP) or 1,2-ditetradecanoyl-sn-glycero-3-phosphocholine (DMPC) and/or wherein the hydrophilic polymer comprises ethylene glycol or polyethylene glycol (PEG); and/or wherein the particle further comprises cholesterol (e.g., particle from formulation 1=DOTAP 100, DMPC 0, PEG 0, Cholesterol 0; formulation number 2=DOTAP 90, DMPC 0, PEG 10, Cholesterol 0; formulation number 3=DOTAP 90, DMPC 0, PEG 5, Cholesterol 5), wherein particles are formed using an efficient, multistep process wherein first, effector protein and RNA are mixed together, e.g., at a 1:1 molar ratio, e.g., at room temperature, e.g., for 30 minutes, e.g., in sterile, nuclease free 1×PBS; and separately, DOTAP, DMPC, PEG, and cholesterol as applicable for the formulation are dissolved in alcohol, e.g., 100% ethanol; and, the two solutions are mixed together to form particles containing the complexes).

Delivery or administration according to the invention can be performed with liposomes. Liposomes are spherical vesicle structures composed of a uni- or multilamellar lipid bilayer surrounding internal aqueous compartments and a relatively impermeable outer lipophilic phospholipid bilayer. Liposomes have gained considerable attention as drug delivery carriers because they are biocompatible, non-toxic, can deliver both hydrophilic and lipophilic drug molecules, protect their cargo from degradation by plasma enzymes, and transport their load across biological membranes and the blood brain barrier (BBB) (see, e.g., Spuch and Navarro, Journal of Drug Delivery, vol. 2011, Article ID 469679, 12 pages, 2011. doi:10.1155/2011/469679 for review).

Liposomes can be made from several different types of lipids; however, phospholipids are most commonly used to generate liposomes as drug carriers. Although liposome formation is spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi:10.1155/2011/469679 for review).

Other cationic lipids, such as amino lipid 2,2-dilinoleyl-4-dimethylaminoethyl-[1,3]-dioxolane (DLin-KC2-DMA) may be utilized to encapsulate CRISPR Cas or components thereof or nucleic acid molecule(s) coding therefor e.g., similar to SiRNA (see, e.g., Jayaraman, Angew. Chem. Int. Ed. 2012, 51, 8529-8533), and hence may be employed in the practice of the invention. A preformed vesicle with the following lipid composition may be contemplated: amino lipid, distearoylphosphatidylcholine (DSPC), cholesterol and (R)-2,3-bis(octadecyloxy) propyl-1-(methoxy poly(ethylene glycol)2000)propylcarbamate (PEG-lipid) in the molar ratio 40/10/40/10, respectively, and a FVII siRNA/total lipid ratio of approximately 0.05 (w/w). To ensure a narrow particle size distribution in the range of 70-90 nm and a low polydispersity index of 0.11+0.04 (n=56), the particles may be extruded up to three times through 80 nm membranes prior to adding the guide RNA. Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Michael S D Kormann et al. ("Expression of therapeutic proteins after delivery of chemically modified mRNA in mice: Nature Biotechnology, Volume:29, Pages: 154-157 (2011)) describes the use of lipid envelopes to deliver RNA. Use of lipid envelopes is also preferred in the present invention.

Supercharged proteins are a class of engineered or naturally occurring proteins with unusually high positive or negative net theoretical charge and may be employed in delivery of CRISPR Cas system(s) or component(s) thereof or nucleic acid molecule(s) coding therefor. Both supernegatively and superpositively charged proteins exhibit a remarkable ability to withstand thermally or chemically induced aggregation. Superpositively charged proteins are also able to penetrate mammalian cells. Associating cargo with these proteins, such as plasmid DNA, RNA, or other proteins, can enable the functional delivery of these macromolecules into mammalian cells both in vitro and in vivo. David Liu's lab reported the creation and characterization of supercharged proteins in 2007 (Lawrence et al., 2007, Journal of the American Chemical Society 129, 10110-10112).

The nonviral delivery of RNA and plasmid DNA into mammalian cells are valuable both for research and therapeutic applications (Akinc et al., 2010, Nat. Biotech. 26, 561-569). Purified +36 GFP protein (or other superpositively charged protein) is mixed with RNAs in the appropriate serum-free media and allowed to complex prior addition to cells. Inclusion of serum at this stage inhibits formation of the supercharged protein-RNA complexes and reduces the effectiveness of the treatment. The following protocol has been found to be effective for a variety of cell lines (McNaughton et al., 2009, Proc. Natl. Acad. Sci. USA 106, 6111-6116). However, pilot experiments varying the dose of protein and RNA should be performed to optimize the procedure for specific cell lines.

(1) One day before treatment, plate $1 \times 10^5$ cells per well in a 48-well plate.
(2) On the day of treatment, dilute purified +36 GFP protein in serumfree media to a final concentration 200 nM. Add RNA to a final concentration of 50 nM. Vortex to mix and incubate at room temperature for 10 min.
(3) During incubation, aspirate media from cells and wash once with PBS.

(4) Following incubation of +36 GFP and RNA, add the protein-RNA complexes to cells.
(5) Incubate cells with complexes at 37° C. for 4 h.
(6) Following incubation, aspirate the media and wash three times with 20 U/mL heparin PBS. Incubate cells with serum-containing media for a further 48 h or longer depending upon the assay for activity.
(7) Analyze cells by immunoblot, qPCR, phenotypic assay, or other appropriate method.

In particular embodiments, cell penetrating peptides (CPPs) are contemplated for the delivery of the CRISPR Cas system. CPPs are short peptides that facilitate cellular uptake of various molecular cargo (from nanosize particles to small chemical molecules and large fragments of DNA). The term "cargo" as used herein includes but is not limited to the group consisting of therapeutic agents, diagnostic probes, peptides, nucleic acids, antisense oligonucleotides, plasmids, proteins, particles including nanoparticles, liposomes, chromophores, small molecules and radioactive materials. In aspects of the invention, the cargo may also comprise any component of the CRISPR Cas system or the entire functional CRISPR Cas system. Aspects of the present invention further provide methods for delivering a desired cargo into a subject comprising: (a) preparing a complex comprising the cell penetrating peptide of the present invention and a desired cargo, and (b) orally, intraarticularly, intraperitoneally, intrathecally, intrarterially, intranasally, intraparenchymally, subcutaneously, intramuscularly, intravenously, dermally, intrarectally, or topically administering the complex to a subject. The cargo is associated with the peptides either through chemical linkage via covalent bonds or through non-covalent interactions.

2. Zinc Finger Systems

Other preferred tools for genome editing for use in the context of this invention include zinc finger systems and TALE systems. One type of programmable DNA-binding domain is provided by artificial zinc-finger (ZF) technology, which involves arrays of ZF modules to target new DNA-binding sites in the genome. Each finger module in a ZF array targets three DNA bases. A customized array of individual zinc finger domains is assembled into a ZF protein (ZFP).

ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms.

3. Tale Systems

In advantageous embodiments of the invention, the methods provided herein use isolated, non-naturally occurring, recombinant or engineered DNA binding proteins that comprise TALE monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", or "TALE monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is X1-11-(X12X13)-X14-33 or 34 or 35, where the subscript indicates the amino acid position and X represents any amino acid. X12X13 indicate the RVDs. In some polypeptide monomers, the variable amino acid at position 13 is missing or absent and in such polypeptide monomers, the RVD consists of a single amino acid. In such cases the RVD may be alternatively represented as X*, where X represents X12 and (*) indicates that X13 is absent. The DNA binding domain comprises several repeats of TALE monomers and this may be represented as (X1-11-(X12X13)-X14-33 or 34 or 35)z, where in an advantageous embodiment, z is at least 5 to 40. In a further advantageous embodiment, z is at least 10 to 26.

The TALE monomers have a nucleotide binding affinity that is determined by the identity of the amino acids in its RVD. For example, polypeptide monomers with an RVD of NI preferentially bind to adenine (A), polypeptide monomers with an RVD of NG preferentially bind to thymine (T), polypeptide monomers with an RVD of HD preferentially bind to cytosine (C) and polypeptide monomers with an RVD of NN preferentially bind to both adenine (A) and guanine (G). In yet another embodiment of the invention, polypeptide monomers with an RVD of IG preferentially bind to T. Thus, the number and order of the polypeptide monomer repeats in the nucleic acid binding domain of a TALE determines its nucleic acid target specificity. In still further embodiments of the invention, polypeptide monomers with an RVD of NS recognize all four base pairs and may bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011), each of which is incorporated by reference in its entirety.

The TALE polypeptides used in methods of the invention are isolated, non-naturally occurring, recombinant or engineered nucleic acid-binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In a preferred embodiment of the invention, polypeptide monomers having RVDs RN, NN, NK, SN, NH, KN, HN, NQ, HH, RG, KH, RH and SS preferentially bind to guanine. In a much more advantageous embodiment of the invention, polypeptide monomers having RVDs RN, NK, NQ, HH, KH, RH, SS and SN preferentially bind to guanine and thereby allow the generation of TALE polypeptides with high binding specificity for guanine containing target nucleic acid sequences. In an even more advantageous embodiment of the invention, polypeptide monomers having RVDs HH, KH, NH, NK, NQ, RH, RN and SS preferentially bind to guanine and thereby allow the generation of TALE polypeptides with high binding specificity for guanine containing target nucleic acid sequences. In a further advantageous embodiment, the RVDs that have high binding specificity for guanine are RN, NH RH and KH. Furthermore, polypeptide monomers having an RVD of NV preferentially bind to adenine and guanine. In more preferred embodiments of the invention, polypeptide monomers having RVDs of H*, HA, KA, N*, NA, NC, NS, RA, and S* bind to adenine, guanine, cytosine and thymine with comparable affinity.

mer and this half repeat may be referred to as a half-monomer (FIG. 8), which is included in the term "TALE monomer". Therefore, it follows that the length of the nucleic acid or DNA being targeted is equal to the number of full polypeptide monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in certain embodiments, the TALE polypeptides described herein further comprise an N-terminal capping region and/or a C-terminal capping region.

An exemplary amino acid sequence of a N-terminal capping region is:

```
                                                          (SEQ ID NO: 14)
            M D P I R S R T P S P A R E L L S G P Q P D G V Q P T A D R G V S P

P A G G P L D G L P A R R T M S R T R L P S P P A P S P A F S A D S

F S D L L R Q F D P S L F N T S L F D S L P P F G A H H T E A A T G

E W D E V Q S G L R A A D A P P P T M R V A V T A A R P P R A K P A

P R R R A A Q P S D A S P A A Q V D L R T L G Y S Q Q Q Q E K I K P

K V R S T V A Q H H E A L V G H G F T H A H I V A L S Q H P A A L G

T V A V K Y Q D M I A A L P E A T H E A I V G V G K Q W S G A R A L

E A L L T V A G E L R G P P L Q L D T G Q L L K I A K R G G V T A V

E A V H A W R N A L T G A P L N
```

The predetermined N-terminal to C-terminal order of the one or more polypeptide monomers of the nucleic acid or DNA binding domain determines the corresponding predetermined target nucleic acid sequence to which the TALE polypeptides will bind. As used herein the polypeptide monomers and at least one or more half polypeptide monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases this region may be referred to as repeat 0. In animal genomes, TALE binding sites do not necessarily have to begin with a thymine (T) and TALE polypeptides may target DNA sequences that begin with T, A, G or C. The tandem repeat of TALE monomers always ends with a half-length repeat or a stretch of sequence that may share identity with only the first 20 amino acids of a repetitive full length TALE mono- An exemplary amino acid sequence of a C-terminal capping region is:

```
                                                          (SEQ ID NO: 15)
            R P A L E S I V A Q L S R P D P A L A A L T N D H L V A L A C L G

G R P A L D A V K K G L P H A P A L I K R T N R R I P E R T S H R

V A D H A Q V V R V L G F F Q C H S H P A Q A F D D A M T Q F G M

S R H G L L Q L F R R V G V T E L E A R S G T L P P A S Q R W D R

I L Q A S G M K R A K P S P T S T Q T P D Q A S L H A F A D S L E

R D L D A P S P M H E G D Q T R A S
```

As used herein the predetermined "N-terminus" to "C terminus" orientation of the N-terminal capping region, the DNA binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, fragments of the N-terminal and/or C-terminal capping regions are included in the TALE polypeptides described herein.

In certain embodiments, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., Nature Biotechnology 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full length capping region, while fragments that include the C-terminal 20 amino acids retain greater than 50% of the efficacy of the full length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies may be generated by any of a number of computer programs known in the art, which include but are not limited to BLAST or FASTA. Suitable computer program for carrying out alignments like the GCG Wisconsin Bestfit package may also be used. Once the software has produced an optimal alignment, it is possible to calculate % homology, preferably % sequence identity. The software typically does this as part of the sequence comparison and generates a numerical result.

In advantageous embodiments described herein, the TALE polypeptides of the invention include a nucleic acid binding domain linked to the one or more effector domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments of the TALE polypeptides described herein, the activity mediated by the effector domain is a biological activity. For example, in some embodiments the effector domain is a transcriptional inhibitor (i.e., a repressor domain), such as an mSin interaction domain (SID). SID4X domain or a Krüppel-associated box (KRAB) or fragments of the KRAB domain. In some embodiments the effector domain is an enhancer of transcription (i.e. an activation domain), such as the VP16, VP64 or p65 activation domain. In some embodiments, the nucleic acid binding is linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal.

In some embodiments, the effector domain is a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination the activities described herein.

C. Tools and Methods for Delivery of Certain Chromatin 3D Structure Modulating Agents 1. Delivery Through this disclosure, knowledge in the art, and the above disclosure regarding delivery of CRISPR-Cas systems, Zinc Finger systems, TALEs, and other modulating agents, or components thereof, or nucleic acid molecules thereof (including, for instance HDR template), or nucleic acid molecules encoding or providing components thereof, may be delivered by a delivery system herein described both generally and in detail.

Vector delivery, e.g., plasmid, viral delivery: the chromatin 3D structure modulating agents, can be delivered using any suitable vector, e.g., plasmid or viral vectors, such as adeno associated virus (AAV), lentivirus, adenovirus or other viral vector types, or combinations thereof. In some embodiments, the vector, e.g., plasmid or viral vector is delivered to the tissue of interest by, for example, an intramuscular injection, while other times the delivery is via intravenous, transdermal, intranasal, oral, mucosal, or other delivery methods. Such delivery may be either via a single dose, or multiple doses. One skilled in the art understands that the actual dosage to be delivered herein may vary greatly depending upon a variety of factors, such as the vector choice, the target cell, organism, or tissue, the general condition of the subject to be treated, the degree of transformation/modification sought, the administration route, the administration mode, the type of transformation/modification sought, etc.

Such a dosage may further contain, for example, a carrier (water, saline, ethanol, glycerol, lactose, sucrose, calcium phosphate, gelatin, dextran, agar, pectin, peanut oil, sesame oil, etc.), a diluent, a pharmaceutically-acceptable carrier (e.g., phosphate-buffered saline), a pharmaceutically-acceptable excipient, and/or other compounds known in the art. The dosage may further contain one or more pharmaceutically acceptable salts such as, for example, a mineral acid salt such as a hydrochloride, a hydrobromide, a phosphate, a sulfate, etc.; and the salts of organic acids such as acetates, propionates, malonates, benzoates, etc. Additionally, auxiliary substances, such as wetting or emulsifying agents, pH buffering substances, gels or gelling materials, flavorings, colorants, microspheres, polymers, suspension agents, etc. may also be present herein. In addition, one or more other conventional pharmaceutical ingredients, such as preservatives, humectants, suspending agents, surfactants, antioxidants, anticaking agents, fillers, chelating agents, coating agents, chemical stabilizers, etc. may also be present, especially if the dosage form is a reconstitutable form. Suitable exemplary ingredients include microcrystalline cellulose, carboxymethylcellulose sodium, polysorbate 80, phenylethyl alcohol, chlorobutanol, potassium sorbate, sorbic acid, sulfur dioxide, propyl gallate, the parabens, ethyl vanillin, glycerin, phenol, parachlorophenol, gelatin, albumin and a combination thereof. A thorough discussion of pharmaceutically acceptable excipients is available in REMINGTON'S PHARMACEUTICAL SCIENCES (Mack Pub. Co., N.J. 1991) which is incorporated by reference herein.

In an embodiment herein the delivery is via an adenovirus, which may be at a single booster dose containing at least $1 \times 10^5$ particles (also referred to as particle units, pu) of adenoviral vector. In an embodiment herein, the dose preferably is at least about $1 \times 10^6$ particles (for example, about $1 \times 10^6$-$1 \times 10^{12}$ particles), more preferably at least about $1 \times 10^7$ particles, more preferably at least about $1 \times 10^8$ particles (e.g., about $1 \times 10^8$-$1 \times 10^{11}$ particles or about $1 \times 10^8$-$1 \times 10^{12}$ particles), and most preferably at least about $1 \times 10^0$ particles (e.g., about $1 \times 10^9$-$1 \times 10^{10}$ particles or about $1 \times 10^9$-$1 \times 10^{12}$ particles), or even at least about $1 \times 10^{10}$ particles (e.g., about $1 \times 10^{10}$-$1 \times 10^{12}$ particles) of the adenoviral vector. Alternatively, the dose comprises no more than about $1 \times 10^{14}$ particles, preferably no more than about $1 \times 10^{13}$ particles, even more preferably no more than about $1 \times 10^{12}$ particles, even more preferably no more than about $1 \times 10^{11}$ particles, and most preferably no more than about $1 \times 10^{10}$ particles (e.g., no more than about $1 \times 10^9$ articles). Thus, the dose may contain a single dose of adenoviral vector with, for example, about $1 \times 10^6$ particle units (pu), about $2 \times 10^6$ pu, about $4 \times 10^6$ pu, about $1 \times 10^7$ pu, about $2 \times 10^7$ pu, about $4 \times 10^7$ pu, about $1 \times 10^8$ pu, about $2 \times 10^8$ pu, about $4 \times 10^8$ pu, about $1 \times 10^9$ pu, about $2 \times 10^9$ pu, about $4 \times 10^9$ pu, about $1 \times 10^{10}$ pu, about $2 \times 10^{10}$ pu, about $4 \times 10^{10}$ pu, about $1 \times 10^{11}$ pu, about $2 \times 10^{11}$ pu, about $4 \times 10^{11}$ pu, about $1 \times 10^{12}$ pu, about $2 \times 10^{12}$ pu, or about $4 \times 10^{12}$ pu of adenoviral vector. See, for example, the adenoviral vectors in U.S. Pat. No. 8,454,972 B2 to Nabel, et. al., granted on Jun. 4, 2013; incorporated by reference herein, and the dosages at col 29, lines 36-58 thereof. In an embodiment herein, the adenovirus is delivered via multiple doses.

In an embodiment herein, the delivery is via an AAV. A therapeutically effective dosage for in vivo delivery of the AAV to a human is believed to be in the range of from about 20 to about 50 ml of saline solution containing from about $1 \times 10^{10}$ to about $1 \times 10^{10}$ functional AAV/ml solution. The dosage may be adjusted to balance the therapeutic benefit against any side effects. In an embodiment herein, the AAV dose is generally in the range of concentrations of from about $1 \times 10^5$ to $1 \times 10^{50}$ genomes AAV, from about $1 \times 10^8$ to $1 \times 10^{20}$ genomes AAV, from about $1 \times 10^{10}$ to about $1 \times 10^{16}$ genomes, or about $1 \times 10^{11}$ to about $1 \times 10^{16}$ genomes AAV. A human dosage may be about $1 \times 10^{13}$ genomes AAV. Such concentrations may be delivered in from about 0.001 ml to about 100 ml, about 0.05 to about 50 ml, or about 10 to about 25 ml of a carrier solution. Other effective dosages can be readily established by one of ordinary skill in the art through routine trials establishing dose response curves. See, for example, U.S. Pat. No. 8,404,658 B2 to Hajjar, et al., granted on Mar. 26, 2013, at col. 27, lines 45-60.

In an embodiment herein the delivery is via a plasmid. In such plasmid compositions, the dosage should be a sufficient amount of plasmid to elicit a response. For instance, suitable quantities of plasmid DNA in plasmid compositions can be from about 0.1 to about 2 mg, or from about 1 µg to about 10 µg per 70 kg individual. Plasmids of the invention will generally comprise (i) a promoter; (ii) a sequence encoding a CRISPR enzyme, operably linked to said promoter; (iii) a selectable marker; (iv) an origin of replication; and (v) a transcription terminator downstream of and operably linked to (ii). The plasmid can also encode the RNA components of a CRISPR complex, but one or more of these may instead be encoded on a different vector.

The doses herein are based on an average 70 kg individual. The frequency of administration is within the ambit of the medical or veterinary practitioner (e.g., physician, veterinarian), or scientist skilled in the art. It is also noted that mice used in experiments are typically about 20 g and from mice experiments one can scale up to a 70 kg individual.

In some embodiments the RNA molecules of the invention are delivered in liposome or lipofectin formulations and the like and can be prepared by methods well known to those skilled in the art. Such methods are described, for example, in U.S. Pat. Nos. 5,593,972, 5,589,466, and 5,580,859, which are herein incorporated by reference. Delivery systems aimed specifically at the enhanced and improved delivery of siRNA into mammalian cells have been developed, (see, for example, Shen et al FEBS Let. 2003, 539: 111-114; Xia et al., Nat. Biotech. 2002, 20:1006-1010; Reich et al., Mol. Vision. 2003, 9: 210-216; Sorensen et al., J. Mol. Biol. 2003, 327: 761-766; Lewis et al., Nat. Gen. 2002, 32: 107-108 and Simeoni et al., NAR 2003, 31, 11: 2717-2724) and may be applied to the present invention. siRNA has recently been successfully used for inhibition of gene expression in primates (see for example. Tolentino et al., Retina 24(4):660 which may also be applied to the present invention.

Indeed, RNA delivery is a useful method of in vivo delivery. It is possible to deliver a CRISPR/Cas protein and one or more RNA polynucleotides (for instance, guide RNA and/or HR repair template) into cells using liposomes or particles. Thus delivery of the CRISPR enzyme, such as a Cas9 and/or delivery of the RNAs of the invention may be in RNA form and via microvesicles, liposomes or particles as described above. For example, Cas protein encoding mRNA and gRNA can be packaged into liposomal particles for delivery in vivo. Liposomal transfection reagents such as lipofectamine from Life Technologies and other reagents on the market can effectively deliver RNA molecules into the liver.

Means of delivery of RNA also preferred include delivery of RNA via nanoparticles (Cho, S., Goldberg, M., Son, S., Xu, Q., Yang, F., Mei, Y., Bogatyrev, S., Langer, R. and Anderson, D., Lipid-like nanoparticles for small interfering RNA delivery to endothelial cells, Advanced Functional Materials, 19: 3112-3118, 2010) or exosomes (Schroeder, A., Levins, C., Cortez, C., Langer, R., and Anderson, D., Lipid-based nanotherapeutics for siRNA delivery, Journal of Internal Medicine, 267: 9-21, 2010, PMID: 20059641).

Indeed, exosomes have been shown to be particularly useful in delivery siRNA, a system with some parallels to the CRISPR system. For instance, El-Andaloussi S, et al. ("Exosome-mediated delivery of siRNA in vitro and in vivo." Nat Protoc. 2012 December; 7(12):2112-26. doi: 10.1038/nprot.2012.131. Epub 2012 Nov. 15.) describe how exosomes are promising tools for drug delivery across different biological barriers and can be harnessed for delivery of siRNA in vitro and in vivo. Their approach is to generate targeted exosomes through transfection of an expression vector, comprising an exosomal protein fused with a peptide ligand. The exosomes are then purify and characterized from transfected cell supernatant, then RNA is loaded into the exosomes. Delivery or administration according to the invention can be performed with exosomes, in particular but not limited to the brain. Vitamin E ($\alpha$-tocopherol) may be conjugated with CRISPR Cas and delivered to the brain along with high density lipoprotein (HDL), for example in a similar manner as was done by Uno et al. (HUMAN GENE THERAPY 22:711-719 (June 2011)) for delivering short-interfering RNA (siRNA) to the brain. Mice were infused via Osmotic minipumps (model 1007D; Alzet, Cupertino, Calif.) filled with phosphate-buffered saline (PBS) or free TocsiBACE or Toc-siBACE/HDL and connected with Brain Infusion Kit 3 (Alzet). A brain-infusion cannula was placed about 0.5 mm posterior to the bregma at midline for infusion into the dorsal third ventricle. Uno et al. found that as little as 3 nmol of Toc-siRNA with HDL could induce a target reduction in comparable degree by the same ICV infusion method. A similar dosage of CRISPR Cas conjugated to $\alpha$-tocopherol and co-administered with HDL targeted to the brain may be contemplated for humans in the present invention, for example, about 3 nmol to about 3 µmol of CRISPR Cas targeted to the brain may be contemplated. Zou et al. ((HUMAN GENE THERAPY 22:465-475 (April 2011)) describes a method of lentiviral-mediated delivery of short-hairpin RNAs targeting PKC$\gamma$ for in vivo gene silencing in the spinal cord of rats. Zou et al. administered about 10 µl of a recombinant lentivirus having a titer of $1 \times 10^9$ transducing units (TU)/ml by an intrathecal catheter. A similar dosage of CRISPR Cas expressed in a lentiviral vector targeted to the brain may be contemplated for humans in the present invention, for example, about 10-50 ml of CRISPR Cas targeted to the brain in a lentivirus having a titer of $1 \times 10^9$ transducing units (TU)/ml may be contemplated.

In terms of local delivery to the brain, this can be achieved in various ways. For instance, material can be delivered intrastriatally e.g. by injection. Injection can be performed stereotactically via a craniotomy.

a. Adeno Associated Virus (AAV)

Cas9 and one or more guide RNA can be delivered using adeno associated virus (AAV), lentivirus, adenovirus or other plasmid or viral vector types, in particular, using formulations and doses from, for example, U.S. Pat. No. 8,454,972 (formulations, doses for adenovirus), U.S. Pat. No. 8,404,658 (formulations, doses for AAV) and U.S. Pat. No. 5,846,946 (formulations, doses for DNA plasmids) and from clinical trials and publications regarding the clinical trials involving lentivirus, AAV and adenovirus. For examples, for AAV, the route of administration, formulation and dose can be as in U.S. Pat. No. 8,454,972 and as in clinical trials involving AAV. For Adenovirus, the route of administration, formulation and dose can be as in U.S. Pat. No. 8,404,658 and as in clinical trials involving adenovirus. For plasmid delivery, the route of administration, formulation and dose can be as in U.S. Pat. No. 5,846,946 and as in clinical studies involving plasmids. Doses may be based on or extrapolated to an average 70 kg individual (e.g. a male adult human), and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed. The viral vectors can be injected into the tissue of interest. For cell-type specific genome modification, the expression of Cas9 can be driven by a cell-type specific promoter. For example, liver-specific expression might use the Albumin promoter and neuron-specific expression (e.g. for targeting CNS disorders) might use the Synapsin I promoter.

In terms of in vivo delivery, AAV is advantageous over other viral vectors for a couple of reasons:
Low toxicity (this may be due to the purification method not requiring ultra centrifugation of cell particles that can activate the immune response)
Low probability of causing insertional mutagenesis because it doesn't integrate into the host genome.

b. Lentivirus

Lentiviruses are complex retroviruses that have the ability to infect and express their genes in both mitotic and post-mitotic cells. The most commonly known lentivirus is the human immunodeficiency virus (HIV), which uses the envelope glycoproteins of other viruses to target a broad range of cell types.

Lentiviruses may be prepared as follows. After cloning pCasES10 (which contains a lentiviral transfer plasmid backbone), HEK293FT at low passage (p=5) were seeded in a T-75 flask to 50% confluence the day before transfection in DMEM with 10% fetal bovine serum and without antibiotics. After 20 hours, media was changed to OptiMEM (serum-free) media and transfection was done 4 hours later. Cells were transfected with 10 µg of lentiviral transfer plasmid (pCasES10) and the following packaging plasmids: 5 µg of pMD2.G (VSV-g pseudotype), and 7.5 ug of psPAX2 (gag/pol/rev/tat). Transfection was done in 4 mL OptiMEM with a cationic lipid delivery agent (50 uL Lipofectamine 2000 and 100 ul Plus reagent). After 6 hours, the media was changed to antibiotic-free DMEM with 10% fetal bovine serum. These methods use serum during cell culture, but serum-free methods are preferred.

Lentivirus may be purified as follows. Viral supernatants were harvested after 48 hours. Supernatants were first cleared of debris and filtered through a 0.45 um low protein binding (PVDF) filter. They were then spun in a ultracentrifuge for 2 hours at 24,000 rpm. Viral pellets were resuspended in 50 ul of DMEM overnight at 4 C. They were then aliquoted and immediately frozen at −80° C.

In another embodiment, minimal non-primate lentiviral vectors based on the equine infectious anemia virus (EIAV) are also contemplated, especially for ocular gene therapy (see, e.g., Balagaan, J Gene Med 2006; 8: 275-285). In another embodiment, RetinoStat®, an equine infectious anemia virus-based lentiviral gene therapy vector that expresses angiostatic proteins endostatin and angiostatin that is delivered via a subretinal injection for the treatment of the web form of age-related macular degeneration is also contemplated (see, e.g., Binley et al., HUMAN GENE THERAPY 23:980-991 (September 2012)) and this vector may be modified for the CRISPR-Cas system of the present invention.

In another embodiment, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2:36ra43) may be used/and or adapted to the CRISPR-Cas system of the present invention. A minimum of 2.5×106 CD34+ cells per kilogram patient weight may be collected and prestimulated for 16 to 20 hours in X-VIVO 15 medium (Lonza) containing 2 μmonglutamine, stem cell factor (100 ng/ml), Flt-3 ligand (Flt-3L) (100 ng/ml), and thrombopoietin (10 ng/ml) (CellGenix) at a density of 2×106 cells/ml. Prestimulated cells may be transduced with lentiviral at a multiplicity of infection of 5 for 16 to 24 hours in 75-cm2 tissue culture flasks coated with fibronectin (25 mg/cm2) (RetroNectin, Takara Bio Inc.).

Lentiviral vectors have been disclosed as in the treatment for Parkinson's Disease, see, e.g., US Patent Publication No. 20120295960 and U.S. Pat. Nos. 7,303,910 and 7,351,585. Lentiviral vectors have also been disclosed for the treatment of ocular diseases, see e.g., US Patent Publication Nos. 20060281180, 20090007284, US20110117189; US20090017543; US20070054961, US20100317109. Lentiviral vectors have also been disclosed for delivery to the brain, see, e.g., US Patent Publication Nos. US20110293571; US20110293571, US20040013648, US20070025970, US20090111106 and U.S. Pat. No. 7,259,015.

c. RNA Delivery

RNA delivery: The chromatin 3D structure modulating agents, such as the CRISPR protein, and/or any other of the components of the CRISPR/Cas system, for instance a guide RNA, can also be delivered in the form of RNA. Cas enzyme encoding mRNA can be generated using in vitro transcription. For example, Cas9 mRNA can be synthesized using a PCR cassette containing the following elements: T7_promoter-kozak sequence (GCCACC)-Cas9-3' UTR from beta globin-polyA tail (a string of 120 or more adenines). The cassette can be used for transcription by T7 polymerase. Guide RNAs can also be transcribed using in vitro transcription from a cassette containing T7_promoter-GG-guide RNA sequence.

To enhance expression and reduce possible toxicity, the CRISPR enzyme-coding sequence and/or the guide RNA can be modified to include one or more modified nucleoside e.g. using pseudo-U or 5-Methyl-C.

mRNA delivery methods are especially promising for liver delivery currently.

Much clinical work on RNA delivery has focused on RNAi or antisense, but these systems can be adapted for delivery of RNA for implementing the present invention. References below to RNAi etc. should be read accordingly.

d. Particle Delivery Systems and/or Formulations:

Several types of particle delivery systems and/or formulations are known to be useful in a diverse spectrum of biomedical applications. In general, a particle is defined as a small object that behaves as a whole unit with respect to its transport and properties. Particles are further classified according to diameter Coarse particles cover a range between 2,500 and 10,000 nanometers. Fine particles are sized between 100 and 2,500 nanometers. Ultrafine particles, or nanoparticles, are generally between 1 and 100 nanometers in size. The basis of the 100-nm limit is the fact that novel properties that differentiate particles from the bulk material typically develop at a critical length scale of under 100 nm.

As used herein, a particle delivery system/formulation is defined as any biological delivery system/formulation which includes a particle in accordance with the present invention. A particle in accordance with the present invention is any entity having a greatest dimension (e.g. diameter) of less than 100 microns (m). In some embodiments, inventive particles have a greatest dimension of less than 10 m. In some embodiments, inventive particles have a greatest dimension of less than 2000 nanometers (nm). In some embodiments, inventive particles have a greatest dimension of less than 1000 nanometers (nm). In some embodiments, inventive particles have a greatest dimension of less than 900 nm, 800 nm, 700 nm, 600 nm, 500 nm, 400 nm, 300 nm, 200 nm, or 100 nm. Typically, inventive particles have a greatest dimension (e.g., diameter) of 500 nm or less. In some embodiments, inventive particles have a greatest dimension (e.g., diameter) of 250 nm or less. In some embodiments, inventive particles have a greatest dimension (e.g., diameter) of 200 nm or less. In some embodiments, inventive particles have a greatest dimension (e.g., diameter) of 150 nm or less. In some embodiments, inventive particles have a greatest dimension (e.g., diameter) of 100 nm or less. Smaller particles, e.g., having a greatest dimension of 50 nm or less are used in some embodiments of the invention. In some embodiments, inventive particles have a greatest dimension ranging between 25 nm and 200 nm.

Particle characterization (including e.g., characterizing morphology, dimension, etc.) is done using a variety of different techniques. Common techniques are electron microscopy (TEM, SEM), atomic force microscopy (AFM), dynamic light scattering (DLS), X-ray photoelectron spectroscopy (XPS), powder X-ray diffraction (XRD), Fourier transform infrared spectroscopy (FTIR), matrix-assisted laser desorption/ionization time-of-flight mass spectrometry (MALDI-TOF), ultraviolet-visible spectroscopy, dual polarisation interferometry and nuclear magnetic resonance (NMR). Characterization (dimension measurements) may be made as to native particles (i.e., preloading) or after loading of the cargo (herein cargo refers to e.g., one or more components of CRISPR-Cas system e.g., CRISPR enzyme or mRNA or guide RNA, or any combination thereof, and may include additional carriers and/or excipients) to provide particles of an optimal size for delivery for any in vitro, ex vivo and/or in vivo application of the present invention. In certain preferred embodiments, particle dimension (e.g., diameter) characterization is based on measurements using dynamic laser scattering (DLS). Mention is made of U.S. Pat. Nos. 8,709,843; 6,007,845; 5,855,913; 5,985,309; 5,543,158; and the publication by James E. Dahlman and Carmen Barnes et al. Nature Nanotechnology (2014) published online 11 May 2014, doi:10.1038/nnano.2014.84, concerning particles, methods of making and using them and measurements thereof.

Particles delivery systems within the scope of the present invention may be provided in any form, including but not limited to solid, semi-solid, emulsion, or colloidal particles. As such any of the delivery systems described herein, including but not limited to, e.g., lipid-based systems, liposomes, micelles, microvesicles, exosomes, or gene gun may be provided as particle delivery systems within the scope of the present invention.

The chromatin 3D structure modulating agents, such as but not limited to CRISPR protein mRNA and guide RNA may be delivered simultaneously using particles or lipid envelopes; for instance, CRISPR enzyme and RNA of the invention, e.g., as a complex, can be delivered via a particle as in Dahlman et al., WO2015089419 A2 and documents cited therein, such as 7C1 (see, e.g., James E. Dahlman and Carmen Barnes et al. Nature Nanotechnology (2014) published online 11 May 2014, doi:10.1038/nnano.2014.84), e.g., delivery particle comprising lipid or lipidoid and hydrophilic polymer, e.g., cationic lipid and hydrophilic polymer, for instance wherein the the cationic lipid comprises 1,2-dioleoyl-3-trimethylammonium-propane (DOTAP) or 1,2-ditetradecanoyl-sn-glycero-3-phosphocholine (DMPC) and/or wherein the hydrophilic polymer comprises ethylene glycol or polyethylene glycol (PEG); and/or wherein the particle further comprises cholesterol (e.g., particle from formulation 1=DOTAP 100, DMPC 0, PEG 0, Cholesterol 0; formulation number 2=DOTAP 90, DMPC 0, PEG 10, Cholesterol 0; formulation number 3=DOTAP 90, DMPC 0, PEG 5, Cholesterol 5), wherein particles are formed using an efficient, multistep process wherein first, effector protein and RNA are mixed together, e.g., at a 1:1 molar ratio, e.g., at room temperature, e.g., for 30 minutes, e.g., in sterile, nuclease free 1×PBS; and separately, DOTAP, DMPC, PEG, and cholesterol as applicable for the formulation are dissolved in alcohol, e.g., 100% ethanol; and, the two solutions are mixed together to form particles containing the complexes).

For example, Su X, Fricke J, Kavanagh D G, Irvine D J ("In vitro and in vivo mRNA delivery using lipid-enveloped pH-responsive polymer nanoparticles" Mol Pharm. 2011 Jun. 6; 8(3):774-87. doi: 10.1021/mp100390w. Epub 2011 Apr. 1) describes biodegradable core-shell structured particles with a poly(β-amino ester) (PBAE) core enveloped by a phospholipid bilayer shell. These were developed for in vivo mRNA delivery. The pH-responsive PBAE component was chosen to promote endosome disruption, while the lipid surface layer was selected to minimize toxicity of the polycation core. Such are, therefore, preferred for delivering RNA of the present invention.

In one embodiment, particles based on self assembling bioadhesive polymers are contemplated, which may be applied to oral delivery of peptides, intravenous delivery of peptides and nasal delivery of peptides, all to the brain. Other embodiments, such as oral absorption and ocular delivery of hydrophobic drugs are also contemplated. The molecular envelope technology involves an engineered polymer envelope which is protected and delivered to the site of the disease (see, e.g., Mazza, M. et al. ACS Nano, 2013. 7(2): 1016-1026; Siew, A., et al. Mol Pharm, 2012. 9(1):14-28; Lalatsa, A., et al. J Contr Rel, 2012. 161(2):523-36; Lalatsa, A., et al., Mol Pharm, 2012. 9(6):1665-80; Lalatsa, A., et al. Mol Pharm, 2012. 9(6):1764-74; Garrett, N. L., et al. J Biophotonics, 2012. 5(5-6):458-68; Garrett, N. L., et al. J Raman Spect, 2012. 43(5):681-688; Ahmad, S., et al. J Royal Soc Interface 2010. 7:S423-33; Uchegbu, I. F. Expert Opin Drug Deliv, 2006. 3(5):629-40; Qu, X., et al. Biomacromolecules, 2006. 7(12):3452-9 and Uchegbu, I. F., et al. Int J Pharm, 2001. 224:185-199). Doses of about 5 mg/kg are contemplated, with single or multiple doses, depending on the target tissue.

In one embodiment, particles that can deliver RNA to a cancer cell to stop tumor growth developed by Dan Anderson's lab at MIT may be used/and or adapted to the CRISPR Cas system of the present invention. In particular, the Anderson lab developed fully automated, combinatorial systems for the synthesis, purification, characterization, and formulation of new biomaterials and nanoformulations. See, e.g., Alabi et al., Proc Natl Acad Sci USA. 2013 Aug. 6; 110(32):12881-6; Zhang et al., Adv Mater. 2013 Sep. 6; 25(33):4641-5; Jiang et al., Nano Lett. 2013 Mar. 13; 13(3):1059-64; Karagiannis et al., ACS Nano. 2012 Oct. 23; 6(10):8484-7; Whitehead et al., ACS Nano. 2012 Aug. 28; 6(8):6922-9 and Lee et al., Nat Nanotechnol. 2012 Jun. 3; 7(6):389-93.

US patent application 20110293703 relates to lipidoid compounds are also particularly useful in the administration of polynucleotides, which may be applied to deliver the CRISPR Cas system of the present invention. In one aspect, the aminoalcohol lipidoid compounds are combined with an agent to be delivered to a cell or a subject to form microparticles, particles, liposomes, or micelles. The agent to be delivered by the particles, liposomes, or micelles may be in the form of a gas, liquid, or solid, and the agent may be a polynucleotide, protein, peptide, or small molecule. The minoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

US Patent Publication No. 20110293703 also provides methods of preparing the aminoalcohol lipidoid compounds. One or more equivalents of an amine are allowed to react with one or more equivalents of an epoxide-terminated compound under suitable conditions to form an aminoalcohol lipidoid compound of the present invention. In certain embodiments, all the amino groups of the amine are fully reacted with the epoxide-terminated compound to form tertiary amines. In other embodiments, all the amino groups of the amine are not fully reacted with the epoxide-terminated compound to form tertiary amines thereby resulting in primary or secondary amines in the aminoalcohol lipidoid compound. These primary or secondary amines are left as is or may be reacted with another electrophile such as a different epoxide-terminated compound. As will be appreciated by one skilled in the art, reacting an amine with less than excess of epoxide-terminated compound will result in a plurality of different aminoalcohol lipidoid compounds with various numbers of tails. Certain amines may be fully functionalized with two epoxide-derived compound tails while other molecules will not be completely functionalized with epoxide-derived compound tails. For example, a diamine or polyamine may include one, two, three, or four epoxide-derived compound tails off the various amino moieties of the molecule resulting in primary, secondary, and tertiary amines. In certain embodiments, all the amino groups are not fully functionalized. In certain embodiments, two of the same types of epoxide-terminated compounds are used. In other embodiments, two or more different epoxide-terminated compounds are used. The synthesis of the aminoalcohol lipidoid compounds is performed with or without solvent, and the synthesis may be performed at higher temperatures ranging from 30-100° C., preferably at approximately 50-90° C. The prepared aminoalcohol lipidoid compounds may be optionally purified. For example, the mixture of aminoalcohol lipidoid compounds may be purified to yield an aminoalcohol lipidoid compound with a particular number of epoxide-derived compound tails. Or the mixture may be purified to yield a particular stereo- or regioisomer. The aminoalcohol lipidoid compounds may also be alkylated using an alkyl halide (e.g., methyl iodide) or other alkylating agent, and/or they may be acylated.

US Patent Publication No. 20110293703 also provides libraries of aminoalcohol lipidoid compounds prepared by the inventive methods. These aminoalcohol lipidoid compounds may be prepared and/or screened using high-throughput techniques involving liquid handlers, robots, microtiter plates, computers, etc. In certain embodiments, the aminoalcohol lipidoid compounds are screened for their ability to transfect polynucleotides or other agents (e.g., proteins, peptides, small molecules) into the cell.

US Patent Publication No. 20130302401 relates to a class of poly(beta-amino alcohols) (PBAAs) has been prepared using combinatorial polymerization. The inventive PBAAs may be used in biotechnology and biomedical applications as coatings (such as coatings of films or multilayer films for medical devices or implants), additives, materials, excipients, non-biofouling agents, micropatterning agents, and cellular encapsulation agents. When used as surface coatings, these PBAAs elicited different levels of inflammation, both in vitro and in vivo, depending on their chemical structures. The large chemical diversity of this class of materials allowed us to identify polymer coatings that inhibit macrophage activation in vitro. Furthermore, these coatings reduce the recruitment of inflammatory cells, and reduce fibrosis, following the subcutaneous implantation of carboxylated polystyrene microparticles. These polymers may be used to form polyelectrolyte complex capsules for cell encapsulation. The invention may also have many other biological applications such as antimicrobial coatings, DNA or siRNA delivery, and stem cell tissue engineering. The teachings of US Patent Publication No. 20130302401 may be applied to the CRISPR Cas system of the present invention.

In another embodiment, lipid particles (LNPs) are contemplated. An antitransthyretin small interfering RNA has been encapsulated in lipid particles and delivered to humans (see, e.g., Coelho et al., N Engl J Med 2013; 369:819-29), and such a system may be adapted and applied to the CRISPR Cas system of the present invention. Doses of about 0.01 to about 1 mg per kg of body weight administered intravenously are contemplated. Medications to reduce the risk of infusion-related reactions are contemplated, such as dexamethasone, acetampinophen, diphenhydramine or cetirizine, and ranitidine are contemplated. Multiple doses of about 0.3 mg per kilogram every 4 weeks for five doses are also contemplated.

LNPs have been shown to be highly effective in delivering siRNAs to the liver (see, e.g., Tabernero et al., Cancer Discovery, April 2013, Vol. 3, No. 4, pages 363-470) and are therefore contemplated for delivering RNA encoding CRISPR Cas to the liver. A dosage of about four doses of 6 mg/kg of the LNP every two weeks may be contemplated. Tabernero et al. demonstrated that tumor regression was observed after the first 2 cycles of LNPs dosed at 0.7 mg/kg, and by the end of 6 cycles the patient had achieved a partial response with complete regression of the lymph node metastasis and substantial shrinkage of the liver tumors. A complete response was obtained after 40 doses in this patient, who has remained in remission and completed treatment after receiving doses over 26 months. Two patients with RCC and extrahepatic sites of disease including kidney, lung, and lymph nodes that were progressing following prior therapy with VEGF pathway inhibitors had stable disease at all sites for approximately 8 to 12 months, and a patient with PNET and liver metastases continued on the extension study for 18 months (36 doses) with stable disease.

However, the charge of the LNP must be taken into consideration. As cationic lipids combined with negatively charged lipids to induce nonbilayer structures that facilitate intracellular delivery. Because charged LNPs are rapidly cleared from circulation following intravenous injection, ionizable cationic lipids with pKa values below 7 were developed (see, e.g., Rosin et al, Molecular Therapy, vol. 19, no. 12, pages 1286-2200, December 2011). Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethylammonium-propane (DLinDAP), 1,2-dilinoleyloxy-3-N,N-dimethylaminopropane (DLinDMA), 1,2-dilineyloxy-keto-N,N-dimethyl-3-aminopropane (DLinKDMA), and 1,2-dilinoleyl-4-(2-dimethylaminoethyl)-[1,3]-dioxolane (DLinKC2-DMA). It has been shown that LNP siRNA systems containing these lipids exhibit remarkably different gene silencing properties in hepatocytes in vivo, with potencies varying according to the series DLinKC2-DMA>DLinKDMA>DLinDMA>>DLinDAP employing a Factor VII gene silencing model (see, e.g., Rosin et al, Molecular Therapy, vol. 19, no. 12, pages 1286-2200, December 2011). A dosage of 1 μg/ml of LNP or CRISPR-Cas RNA in or associated with the LNP may be contemplated, especially for a formulation containing DLinKC2-DMA.

Preparation of LNPs and encapsulation of the chromatin 3D structure modulating agents may be used/and or adapted from Rosin et al, Molecular Therapy, vol. 19, no. 12, pages 1286-2200, December 2011). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinKDMA), 1,2-dilinoleyl-4-(2-dimethylaminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG), and R-3-[(ω)-methoxy-poly(ethylene glycol)2000) carbamoyl]-1,2-dimyristyloxlpropyl-3-amine (PEG-C-DOMG) may be provided by Tekmira Pharmaceuticals (Vancouver, Canada) or synthesized. Cholesterol may be purchased from Sigma (St Louis, Mo.). The specific CRISPR Cas RNA may be encapsulated in LNPs containing DLinDAP, DLinDMA, DLinK-DMA, and DLinKC2-DMA (cationic lipid:DSPC:CHOL: PEGS-DMG or PEG-C-DOMG at 40:10:40:10 molar ratios). When required, 0.2% SP-DiOC18 (Invitrogen, Burlington, Canada) may be incorporated to assess cellular uptake, intracellular delivery, and biodistribution. Encapsulation may be performed by dissolving lipid mixtures comprised of cationic lipid:DSPC:cholesterol:PEG-c-DOMG (40:10:40:10 molar ratio) in ethanol to a final lipid concentration of 10 mmol/l. This ethanol solution of lipid may be added drop-wise to 50 mmol/l citrate, pH 4.0 to form multilamellar vesicles to produce a final concentration of 30% ethanol vol/vol. Large unilamellar vesicles may be formed following extrusion of multilamellar vesicles through two stacked 80 nm Nuclepore polycarbonate filters using the Extruder (Northern Lipids, Vancouver, Canada). Encapsulation may be achieved by adding RNA dissolved at 2 mg/ml in 50 mmol/l citrate, pH 4.0 containing 30% ethanol vol/vol drop-wise to extruded preformed large unilamellar vesicles and incubation at 31° C. for 30 minutes with constant mixing to a final RNA/lipid weight ratio of 0.06/1 wt/wt. Removal of ethanol and neutralization of formulation buffer were performed by dialysis against phosphate-buffered saline (PBS), pH 7.4 for 16 hours using Spectra/Por 2 regenerated cellulose dialysis membranes. Particle size distribution may be determined by dynamic light scattering using a NICOMP 370 particle sizer, the vesicle/intensity modes, and Gaussian fitting (Nicomp Particle Sizing, Santa Barbara, Calif.). The particle size for all three LNP systems may be ~70 nm in diameter. RNA encapsulation efficiency may be determined by removal of free RNA using VivaPureD MiniH columns (Sartorius Stedim Biotech) from samples collected before and after dialysis. The encapsulated RNA may be extracted from the eluted particles and quantified at 260 nm. RNA to lipid ratio was determined by measurement of cholesterol content in vesicles using the Cholesterol E enzymatic assay from Wako Chemicals USA (Richmond, Va.). In conjunction with the herein discussion of LNPs and PEG lipids, PEGylated liposomes or LNPs are likewise suitable for delivery of a CRISPR-Cas system or components thereof.

Preparation of large LNPs may be used/and or adapted from Rosin et al, Molecular Therapy, vol. 19, no. 12, pages 1286-2200, December 2011. A lipid premix solution (20.4 mg/ml total lipid concentration) may be prepared in ethanol containing DLinKC2-DMA, DSPC, and cholesterol at 50:10:38.5 molar ratios. Sodium acetate may be added to the lipid premix at a molar ratio of 0.75:1 (sodium acetate: DLinKC2-DMA). The lipids may be subsequently hydrated by combining the mixture with 1.85 volumes of citrate buffer (10 mmol/l, pH 3.0) with vigorous stirring, resulting in spontaneous liposome formation in aqueous buffer containing 35% ethanol. The liposome solution may be incubated at 37° C. to allow for time-dependent increase in particle size. Aliquots may be removed at various times during incubation to investigate changes in liposome size by dynamic light scattering (Zetasizer Nano ZS, Malvern Instruments, Worcestershire, UK). Once the desired particle size is achieved, an aqueous PEG lipid solution (stock=10 mg/ml PEG-DMG in 35% (vol/vol) ethanol) may be added to the liposome mixture to yield a final PEG molar concentration of 3.5% of total lipid. Upon addition of PEG-lipids, the liposomes should their size, effectively quenching further growth. RNA may then be added to the empty liposomes at an RNA to total lipid ratio of approximately 1:10 (wt:wt), followed by incubation for 30 minutes at 37° C. to form loaded LNPs. The mixture may be subsequently dialyzed overnight in PBS and filtered with a 0.45-μm syringe filter.

Spherical Nucleic Acid (SNA™) constructs and other particles (particularly gold particles) are also contemplated as a means to delivery CRISPR-Cas system to intended targets. Significant data show that AuraSense Therapeutics' Spherical Nucleic Acid (SNA™) constructs, based upon nucleic acid-functionalized gold particles, are useful.

Literature that may be employed in conjunction with herein teachings include: Cutler et al., J. Am. Chem. Soc. 2011 133:9254-9257, Hao et al., Small. 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19):7625-7630, Jensen et al., Sci. Transl. Med. 5, 209ra152 (2013) and Mirkin, et al., Small, 10:186-192.

Self-assembling particles with RNA may be constructed with polyethyleneimine (PEI) that is PEGylated with an Arg-Gly-Asp (RGD) peptide ligand attached at the distal end of the polyethylene glycol (PEG). This system has been used, for example, as a means to target tumor neovasculature expressing integrins and deliver siRNA inhibiting vascular endothelial growth factor receptor-2 (VEGF R2) expression and thereby achieve tumor angiogenesis (see, e.g., Schiffelers et al., Nucleic Acids Research, 2004, Vol. 32, No. 19). Nanoplexes may be prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. A dosage of about 100 to 200 mg of CRISPR Cas is envisioned for delivery in the self-assembling particles of Schiffelers et al.

The nanoplexes of Bartlett et al. (PNAS, Sep. 25, 2007, vol. 104, no. 39) may also be applied to the present invention. The nanoplexes of Bartlett et al. are prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. The DOTA-siRNA of Bartlett et al. was synthesized as follows: 1,4,7,10-tetraazacyclododecane-1,4,7,10-tetraacetic acid mono(N-hydroxysuccinimide ester) (DOTA-NHSester) was ordered from Macrocyclics (Dallas, Tex.). The amine modified RNA sense strand with a 100-fold molar excess of DOTA-NHS-ester in carbonate buffer (pH 9) was added to a microcentrifuge tube. The contents were reacted by stirring for 4 h at room temperature. The DOTA-RNAsense conjugate was ethanol-precipitated, resuspended in water, and annealed to the unmodified antisense strand to yield DOTA-siRNA. All liquids were pretreated with Chelex-100 (Bio-Rad, Hercules, Calif.) to remove trace metal contaminants. Tf-targeted and nontargeted siRNA particles may be formed by using cyclodextrin-containing polycations. Typically, particles were formed in water at a charge ratio of 3 (+/−) and an siRNA concentration of 0.5 g/liter. One percent of the adamantane-PEG molecules on the surface of the targeted particles were modified with Tf (adamantane-PEG-Tf). The particles were suspended in a 5% (wt/vol) glucose carrier solution for injection.

Davis et al. (Nature, Vol 464, 15 Apr. 2010) conducts a RNA clinical trial that uses a targeted particle-delivery system (clinical trial registration number NCT00689065). Patients with solid cancers refractory to standard-of-care therapies are administered doses of targeted particles on days 1, 3, 8 and 10 of a 21-day cycle by a 30-min intravenous infusion. The particles consist of a synthetic delivery system containing: (1) a linear, cyclodextrin-based polymer (CDP), (2) a human transferrin protein (TF) targeting ligand displayed on the exterior of the particle to engage TF receptors (TFR) on the surface of the cancer cells, (3) a hydrophilic polymer (polyethylene glycol (PEG) used to promote particle stability in biological fluids), and (4) siRNA designed to reduce the expression of the RRM2 (sequence used in the clinic was previously denoted siR2B+5). The TFR has long been known to be unregulated in malignant cells, and RRM2 is an established anti-cancer target. These particles (clinical version denoted as CALAA-01) have been shown to be well tolerated in multi-dosing studies in non-human primates. Although a single patient with chronic myeloid leukaemia has been administered siRNA by liposomal delivery, Davis et al.'s clinical trial is the initial human trial to systemically deliver siRNA with a targeted delivery system and to treat patients with solid cancer. To ascertain whether the targeted delivery system can provide effective delivery of functional siRNA to human tumours, Davis et al. investigated biopsies from three patients from three different dosing cohorts; patients A, B and C, all of whom had metastatic melanoma and received CALAA-01 doses of 18, 24 and 30 mg m-2 siRNA, respectively. Similar doses may also be contemplated for the the chromatin 3D structure modulating agents of the present invention. The delivery of the invention may be achieved with particles containing a linear, cyclodextrin-based polymer (CDP), a human transferrin protein (TF) targeting ligand displayed on the exterior of the particle to engage TF receptors (TFR) on the surface of the cancer cells and/or a hydrophilic polymer (for example, polyethylene glycol (PEG) used to promote particle stability in biological fluids).

It is preferred to have the chromatin 3D structure modulating agents, such as one or more components of CRISPR complex, e.g., CRISPR protein or mRNA or guide RNA delivered using particles or lipid envelopes. Other delivery systems or vectors are may be used in conjunction with the particle aspects of the invention.

In general, a "nanoparticle" refers to any particle having a diameter of less than 1000 nm. In certain preferred embodiments, nanoparticles of the invention have a greatest dimension (e.g., diameter) of 500 nm or less. In other preferred embodiments, nanoparticles of the invention have a greatest dimension ranging between 25 nm and 200 nm. In other preferred embodiments, nanoparticles of the invention have a greatest dimension of 100 nm or less. In other preferred embodiments, particles of the invention have a greatest dimension ranging between 35 nm and 60 nm. In other preferred embodiments, the particles of the invention are not nanoparticles.

Particles encompassed in the present invention may be provided in different forms, e.g., as solid particles (e.g., metal such as silver, gold, iron, titanium), non-metal, lipid-based solids, polymers), suspensions of particles, or combinations thereof. Metal, dielectric, and semiconductor particles may be prepared, as well as hybrid structures (e.g., core-shell particles). Particles made of semiconducting material may also be labeled quantum dots if they are small enough (typically sub 10 nm) that quantization of electronic energy levels occurs. Such nanoscale particles are used in biomedical applications as drug carriers or imaging agents and may be adapted for similar purposes in the present invention.

Semi-solid and soft particles have been manufactured, and are within the scope of the present invention. A prototype particle of semi-solid nature is the liposome. Various types of liposome particles are currently used clinically as delivery systems for anticancer drugs and vaccines. Particles with one half hydrophilic and the other half hydrophobic are termed Janus particles and are particularly effective for stabilizing emulsions. They can self-assemble at water/oil interfaces and act as solid surfactants.

U.S. Pat. No. 8,709,843, incorporated herein by reference, provides a drug delivery system for targeted delivery of therapeutic agent-containing particles to tissues, cells, and intracellular compartments. The invention provides targeted particles comprising comprising polymer conjugated to a surfactant, hydrophilic polymer or lipid. U.S. Pat. No. 6,007,845, incorporated herein by reference, provides particles which have a core of a multiblock copolymer formed by covalently linking a multifunctional compound with one or more hydrophobic polymers and one or more hydrophilic polymers, and contain a biologically active material. U.S. Pat. No. 5,855,913, incorporated herein by reference, provides a particulate composition having aerodynamically light particles having a tap density of less than 0.4 g/cm3 with a mean diameter of between 5 µm and 30 µm, incorporating a surfactant on the surface thereof for drug delivery to the pulmonary system. U.S. Pat. No. 5,985,309, incorporated herein by reference, provides particles incorporating a surfactant and/or a hydrophilic or hydrophobic complex of a positively or negatively charged therapeutic or diagnostic agent and a charged molecule of opposite charge for delivery to the pulmonary system. U.S. Pat. No. 5,543,158, incorporated herein by reference, provides biodegradable injectable particles having a biodegradable solid core containing a biologically active material and poly(alkylene glycol) moieties on the surface. WO2012135025 (also published as US20120251560), incorporated herein by reference, describes conjugated polyethyleneimine (PEI) polymers and conjugated aza-macrocycles (collectively referred to as "conjugated lipomer" or "lipomers"). In certain embodiments, it can envisioned that such conjugated lipomers can be used in the context of the CRISPR-Cas system to achieve in vitro, ex vivo and in vivo genomic perturbations to modify gene expression, including modulation of protein expression.

In one embodiment, the particle may be epoxide-modified lipid-polymer, advantageously 7C1 (see, e.g., James E. Dahlman and Carmen Barnes et al. Nature Nanotechnology (2014) published online 11 May 2014, doi:10.1038/nnano.2014.84). C71 was synthesized by reacting C15 epoxide-terminated lipids with PEI600 at a 14:1 molar ratio, and was formulated with C14PEG2000 to produce particles (diameter between 35 and 60 nm) that were stable in PBS solution for at least 40 days.

An epoxide-modified lipid-polymer may be utilized to deliver the CRISPR-Cas system of the present invention to pulmonary, cardiovascular or renal cells, however, one of skill in the art may adapt the system to deliver to other target organs. Dosage ranging from about 0.05 to about 0.6 mg/kg are envisioned. Dosages over several days or weeks are also envisioned, with a total dosage of about 2 mg/kg.

e. Exosomes

Exosomes are endogenous nano-vesicles that transport RNAs and proteins, and which can deliver agents to the brain and other target organs. To reduce immunogenicity, Alvarez-Erviti et al. (2011, Nat Biotechnol 29: 341) used self-derived dendritic cells for exosome production. Targeting to the brain was achieved by engineering the dendritic cells to express Lamp2b, an exosomal membrane protein, fused to the neuron-specific RVG peptide. Purified exosomes were loaded with exogenous RNA by electroporation. Intravenously injected RVG-targeted exosomes delivered GAPDH siRNA specifically to neurons, microglia, oligodendrocytes in the brain, resulting in a specific gene knockdown. Pre-exposure to RVG exosomes did not attenuate knockdown, and non-specific uptake in other tissues was not observed. The therapeutic potential of exosome-mediated siRNA delivery was demonstrated by the strong mRNA (60%) and protein (62%) knockdown of BACE1, a therapeutic target in Alzheimer's disease.

To obtain a pool of immunologically inert exosomes, Alvarez-Erviti et al. harvested bone marrow from inbred C57BL/6 mice with a homogenous major histocompatibility complex (MHC) haplotype. As immature dendritic cells produce large quantities of exosomes devoid of T-cell activators such as MHC-II and CD86, Alvarez-Erviti et al. selected for dendritic cells with granulocyte/macrophage-colony stimulating factor (GM-CSF) for 7 d. Exosomes were purified from the culture supernatant the following day using well-established ultracentrifugation protocols. The exosomes produced were physically homogenous, with a size distribution peaking at 80 nm in diameter as determined by particle tracking analysis (NTA) and electron microscopy. Alvarez-Erviti et al. obtained 6-12 µg of exosomes (measured based on protein concentration) per 106 cells.

Next, Alvarez-Erviti et al. investigated the possibility of loading modified exosomes with exogenous cargoes using electroporation protocols adapted for nanoscale applications. As electroporation for membrane particles at the nanometer scale is not well-characterized, non-specific Cy5-labeled RNA was used for the empirical optimization of the electroporation protocol. The amount of encapsulated RNA was assayed after ultracentrifugation and lysis of exosomes. Electroporation at 400 V and 125 µF if resulted in the greatest retention of RNA and was used for all subsequent experiments.

Alvarez-Erviti et al. administered 150 µg of each BACE1 siRNA encapsulated in 150 µg of RVG exosomes to normal C57BL/6 mice and compared the knockdown efficiency to four controls: untreated mice, mice injected with RVG exosomes only, mice injected with BACE1 siRNA complexed to an in vivo cationic liposome reagent and mice injected with BACE1 siRNA complexed to RVG-9R, the RVG peptide conjugated to 9 D-arginines that electrostatically binds to the siRNA. Cortical tissue samples were analyzed 3 d after administration and a significant protein knockdown (45%, P<0.05, versus 62%, P<0.01) in both siRNA-RVG-9R-treated and siRNARVG exosome-treated mice was observed, resulting from a significant decrease in BACE1 mRNA levels (66% [+ or −] 15%, P<0.001 and 61% [+ or −] 13% respectively, P<0.01). Moreover, Applicants demonstrated a significant decrease (55%, P<0.05) in the total [beta]-amyloid 1-42 levels, a main component of the amyloid plaques in Alzheimer's pathology, in the RVG-exosome-treated animals. The decrease observed was greater than the β-amyloid 1-40 decrease demonstrated in normal mice after intraventricular injection of BACE1 inhibitors. Alvarez-Erviti et al. carried out 5'-rapid amplification of cDNA ends (RACE) on BACE1 cleavage product, which provided evidence of RNAi-mediated knockdown by the siRNA.

Finally, Alvarez-Erviti et al. investigated whether RNA-RVG exosomes induced immune responses in vivo by assessing IL-6, IP-10, TNFα and IFN-α serum concentrations. Following exosome treatment, nonsignificant changes in all cytokines were registered similar to siRNA-transfection reagent treatment in contrast to siRNA-RVG-9R, which potently stimulated IL-6 secretion, confirming the immunologically inert profile of the exosome treatment. Given that exosomes encapsulate only 20% of siRNA, delivery with RVG-exosome appears to be more efficient than RVG-9R delivery as comparable mRNA knockdown and greater protein knockdown was achieved with fivefold less siRNA without the corresponding level of immune stimulation. This experiment demonstrated the therapeutic potential of RVG-exosome technology, which is potentially suited for long-term silencing of genes related to neurodegenerative diseases. The exosome delivery system of Alvarez-Erviti et al. may be applied to deliver the CRISPR-Cas system of the present invention to therapeutic targets, especially neurodegenerative diseases. A dosage of about 100 to 1000 mg of CRISPR Cas encapsulated in about 100 to 1000 mg of RVG exosomes may be contemplated for the present invention.

El-Andaloussi et al. (Nature Protocols 7, 2112-2126 (2012)) discloses how exosomes derived from cultured cells can be harnessed for delivery of RNA in vitro and in vivo. This protocol first describes the generation of targeted exosomes through transfection of an expression vector, comprising an exosomal protein fused with a peptide ligand. Next, El-Andaloussi et al. explain how to purify and characterize exosomes from transfected cell supernatant. Next, El-Andaloussi et al. detail crucial steps for loading RNA into exosomes. Finally, El-Andaloussi et al. outline how to use exosomes to efficiently deliver RNA in vitro and in vivo in mouse brain. Examples of anticipated results in which exosome-mediated RNA delivery is evaluated by functional assays and imaging are also provided. The entire protocol takes ~3 weeks. Delivery or administration according to the invention may be performed using exosomes produced from self-derived dendritic cells. From the herein teachings, this can be employed in the practice of the invention.

In another embodiment, the plasma exosomes of Wahlgren et al. (Nucleic Acids Research, 2012, Vol. 40, No. 17 e130) are contemplated. Exosomes are nano-sized vesicles (30-90 nm in size) produced by many cell types, including dendritic cells (DC), B cells, T cells, mast cells, epithelial cells and tumor cells. These vesicles are formed by inward budding of late endosomes and are then released to the extracellular environment upon fusion with the plasma membrane. Because exosomes naturally carry RNA between cells, this property may be useful in gene therapy, and from this disclosure can be employed in the practice of the instant invention.

Exosomes from plasma can be prepared by centrifugation of buffy coat at 900 g for 20 min to isolate the plasma followed by harvesting cell supernatants, centrifuging at 300 g for 10 min to eliminate cells and at 16 500 g for 30 min followed by filtration through a 0.22 mm filter. Exosomes are pelleted by ultracentrifugation at 120 000 g for 70 min. Chemical transfection of siRNA into exosomes is carried out according to the manufacturer's instructions in RNAi Human/Mouse Starter Kit (Quiagen, Hilden, Germany). siRNA is added to 100 ml PBS at a final concentration of 2 mmol/ml. After adding HiPerFect transfection reagent, the mixture is incubated for 10 min at RT. In order to remove the excess of micelles, the exosomes are re-isolated using aldehyde/sulfate latex beads. The chemical transfection of CRISPR Cas into exosomes may be conducted similarly to siRNA. The exosomes may be co-cultured with monocytes and lymphocytes isolated from the peripheral blood of healthy donors. Therefore, it may be contemplated that exosomes containing CRISPR Cas may be introduced to monocytes and lymphocytes of and autologously reintroduced into a human. Accordingly, delivery or administration according to the invention may be performed using plasma exosomes.

f. Liposomes

Delivery or administration according to the invention can be performed with liposomes. Liposomes are spherical vesicle structures composed of a uni- or multilamellar lipid bilayer surrounding internal aqueous compartments and a relatively impermeable outer lipophilic phospholipid bilayer. Liposomes have gained considerable attention as drug delivery carriers because they are biocompatible, nontoxic, can deliver both hydrophilic and lipophilic drug molecules, protect their cargo from degradation by plasma enzymes, and transport their load across biological membranes and the blood brain barrier (BBB) (see, e.g., Spuch and Navarro, Journal of Drug Delivery, vol. 2011, Article ID 469679, 12 pages, 2011. doi:10.1155/2011/469679 for review).

Liposomes can be made from several different types of lipids; however, phospholipids are most commonly used to generate liposomes as drug carriers. Although liposome formation is spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi:10.1155/2011/469679 for review).

Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. Further, liposomes are prepared from hydrogenated egg phosphatidylcholine or egg phosphatidylcholine, cholesterol, and dicetyl phosphate, and their mean vesicle sizes were adjusted to about 50 and 100 nm. (see, e.g., Spuch and Navarro, Journal of Drug Delivery, vol. 2011, Article ID 469679, 12 pages, 2011. doi:10.1155/2011/469679 for review).

A liposome formulation may be mainly comprised of natural phospholipids and lipids such as 1,2-distearoryl-sn-glycero-3-phosphatidyl choline (DSPC), sphingomyelin, egg phosphatidylcholines and monosialoganglioside. Since this formulation is made up of phospholipids only, liposomal formulations have encountered many challenges, one of the ones being the instability in plasma. Several attempts to overcome these challenges have been made, specifically in the manipulation of the lipid membrane. One of these attempts focused on the manipulation of cholesterol. Addition of cholesterol to conventional formulations reduces rapid release of the encapsulated bioactive compound into the plasma or 1,2-dioleoyl-sn-glycero-3-phosphoethanolamine (DOPE) increases the stability (see, e.g., Spuch and Navarro, Journal of Drug Delivery, vol. 2011, Article ID 469679, 12 pages, 2011. doi:10.1155/2011/469679 for review).

In a particularly advantageous embodiment, Trojan Horse liposomes (also known as Molecular Trojan Horses) are desirable and protocols may be found at cshprotocols.cshlp.org/content/2010/4/pdb.prot5407.long. These particles allow delivery of a transgene to the entire brain after an intravascular injection. Without being bound by limitation, it is believed that neutral lipid particles with specific antibodies conjugated to surface allow crossing of the blood brain barrier via endocytosis. Applicant postulates utilizing Trojan Horse Liposomes to deliver the CRISPR family of nucleases to the brain via an intravascular injection, which would allow whole brain transgenic animals without the need for embryonic manipulation. About 1-5 g of DNA or RNA may be contemplated for in vivo administration in liposomes.

In another embodiment, the the chromatin 3D structure modulating agents such as the CRISPR Cas system may be administered in liposomes, such as a stable nucleic-acid-lipid particle (SNALP) (see, e.g., Morrissey et al., Nature Biotechnology, Vol. 23, No. 8, August 2005). Daily intravenous injections of about 1, 3 or 5 mg/kg/day of a specific CRISPR Cas targeted in a SNALP are contemplated. The daily treatment may be over about three days and then weekly for about five weeks. In another embodiment, a specific CRISPR Cas encapsulated SNALP) administered by intravenous injection to at doses of about 1 or 2.5 mg/kg are also contemplated (see, e.g., Zimmerman et al., Nature Letters, Vol. 441, 4 May 2006). The SNALP formulation may contain the lipids 3-N-[(wmethoxypoly(ethylene glycol) 2000) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar percent ratio (see, e.g., Zimmerman et al., Nature Letters, Vol. 441, 4 May 2006).

In another embodiment, stable nucleic-acid-lipid particles (SNALPs) have proven to be effective delivery molecules to highly vascularized HepG2-derived liver tumors but not in poorly vascularized HCT-116 derived liver tumors (see, e.g., Li, Gene Therapy (2012) 19, 775-780). The SNALP liposomes may be prepared by formulating D-Lin-DMA and PEG-C-DMA with distearoylphosphatidylcholine (DSPC), Cholesterol and siRNA using a 25:1 lipid/siRNA ratio and a 48/40/10/2 molar ratio of Cholesterol/D-Lin-DMA/DSPC/PEG-C-DMA. The resulted SNALP liposomes are about 80-100 nm in size.

In yet another embodiment, a SNALP may comprise synthetic cholesterol (Sigma-Aldrich, St Louis, Mo., USA), dipalmitoylphosphatidylcholine (Avanti Polar Lipids, Alabaster, Ala., USA), 3-N-[(w-methoxy poly(ethylene glycol) 2000)carbamoyl]-1,2-dimyrestyloxypropylamine, and cationic 1,2-dilinoleyloxy-3-N,Ndimethylaminopropane (see, e.g., Geisbert et al., Lancet 2010; 375: 1896-905). A dosage of about 2 mg/kg total CRISPR Cas per dose administered as, for example, a bolus intravenous infusion may be contemplated.

In yet another embodiment, a SNALP may comprise synthetic cholesterol (Sigma-Aldrich), 1,2-distearoyl-sn-glycero-3-phosphocholine (DSPC; Avanti Polar Lipids Inc.), PEG-cDMA, and 1,2-dilinoleyloxy-3-(N;N-dimethyl)aminopropane (DLinDMA) (see, e.g., Judge, J. Clin. Invest. 119:661-673 (2009)). Formulations used for in vivo studies may comprise a final lipid/RNA mass ratio of about 9:1.

The safety profile of RNAi nanomedicines has been reviewed by Barros and Gollob of Alnylam Pharmaceuticals (see, e.g., Advanced Drug Delivery Reviews 64 (2012) 1730-1737). The stable nucleic acid lipid particle (SNALP) is comprised of four different lipids—an ionizable lipid (DLinDMA) that is cationic at low pH, a neutral helper lipid, cholesterol, and a diffusible polyethylene glycol (PEG)-lipid. The particle is approximately 80 nm in diameter and is charge-neutral at physiologic pH. During formulation, the ionizable lipid serves to condense lipid with the anionic RNA during particle formation. When positively charged under increasingly acidic endosomal conditions, the ionizable lipid also mediates the fusion of SNALP with the endosomal membrane enabling release of RNA into the cytoplasm. The PEG-lipid stabilizes the particle and reduces aggregation during formulation, and subsequently provides a neutral hydrophilic exterior that improves pharmacokinetic properties.

To date, two clinical programs have been initiated using SNALP formulations with RNA. Tekmira Pharmaceuticals recently completed a phase I single-dose study of SNALP-ApoB in adult volunteers with elevated LDL cholesterol. ApoB is predominantly expressed in the liver and jejunum and is essential for the assembly and secretion of VLDL and LDL. Seventeen subjects received a single dose of SNALP-ApoB (dose escalation across 7 dose levels). There was no evidence of liver toxicity (anticipated as the potential dose-limiting toxicity based on preclinical studies). One (of two) subjects at the highest dose experienced flu-like symptoms consistent with immune system stimulation, and the decision was made to conclude the trial.

Alnylam Pharmaceuticals has similarly advanced ALN-TTR01, which employs the SNALP technology described above and targets hepatocyte production of both mutant and wild-type TTR to treat TTR amyloidosis (ATTR). Three ATTR syndromes have been described: familial amyloidotic polyneuropathy (FAP) and familial amyloidotic cardiomyopathy (FAC)—both caused by autosomal dominant mutations in TTR; and senile systemic amyloidosis (SSA) cause by wildtype TTR. A placebo-controlled, single dose-escalation phase I trial of ALN-TTR01 was recently completed in patients with ATTR. ALN-TTR01 was administered as a 15-minute IV infusion to 31 patients (23 with study drug and 8 with placebo) within a dose range of 0.01 to 1.0 mg/kg (based on siRNA). Treatment was well tolerated with no significant increases in liver function tests. Infusion-related reactions were noted in 3 of 23 patients at ≥0.4 mg/kg; all responded to slowing of the infusion rate and all continued on study. Minimal and transient elevations of serum cytokines IL-6, IP-10 and IL-1ra were noted in two patients at the highest dose of 1 mg/kg (as anticipated from preclinical and NHP studies). Lowering of serum TTR, the expected pharmacodynamics effect of ALN-TTR01, was observed at 1 mg/kg.

In yet another embodiment, a SNALP may be made by solubilizing a cationic lipid, DSPC, cholesterol and PEG-lipid e.g., in ethanol, e.g., at a molar ratio of 40:10:40:10, respectively (see, Semple et al., Nature Niotechnology, Volume 28 Number 2 Feb. 2010, pp. 172-177). The lipid mixture was added to an aqueous buffer (50 mM citrate, pH 4) with mixing to a final ethanol and lipid concentration of 30% (vol/vol) and 6.1 mg/ml, respectively, and allowed to equilibrate at 22° C. for 2 min before extrusion. The hydrated lipids were extruded through two stacked 80 nm pore-sized filters (Nuclepore) at 22° C. using a Lipex Extruder (Northern Lipids) until a vesicle diameter of 70-90 nm, as determined by dynamic light scattering analysis, was obtained. This generally required 1-3 passes. The siRNA (solubilized in a 50 mM citrate, pH 4 aqueous solution containing 30% ethanol) was added to the pre-equilibrated (35° C.) vesicles at a rate of ~5 ml/min with mixing. After a final target siRNA/lipid ratio of 0.06 (wt/wt) was reached, the mixture was incubated for a further 30 min at 35° C. to allow vesicle reorganization and encapsulation of the siRNA. The ethanol was then removed and the external buffer replaced with PBS (155 mM NaCl, 3 mM Na2HPO4, 1 mM KH2PO4, pH 7.5) by either dialysis or tangential flow diafiltration. siRNA were encapsulated in SNALP using a controlled step-wise dilution method process. The lipid constituents of KC2-SNALP were DLin-KC2-DMA (cationic lipid), dipalmitoylphosphatidylcholine (DPPC; Avanti Polar Lipids), synthetic cholesterol (Sigma) and PEG-C-DMA used at a molar ratio of 57.1:7.1:34.3:1.4. Upon formation of the loaded particles, SNALP were dialyzed against PBS and filter sterilized through a 0.2 µm filter before use. Mean particle sizes were 75-85 nm and 90-95% of the siRNA was encapsulated within the lipid particles. The final siRNA/lipid ratio in formulations used for in vivo testing was ~0.15 (wt/wt). LNP-siRNA systems containing Factor VII siRNA were diluted to the appropriate concentrations in sterile PBS immediately before use and the formulations were administered intravenously through the lateral tail vein in a total volume of 10 ml/kg. This method and these delivery systems may be extrapolated to the CRISPR Cas system of the present invention.

g. Other Lipids

Other cationic lipids, such as amino lipid 2,2-dilinoleyl-4-dimethylaminoethyl-[1,3]-dioxolane (DLin-KC2-DMA) may be utilized to encapsulate the chromatin 3D structure modulating agents such as CRISPR Cas or components thereof or nucleic acid molecule(s) coding therefor e.g., similar to SiRNA (see, e.g., Jayaraman, Angew. Chem. Int. Ed. 2012, 51, 8529-8533), and hence may be employed in the practice of the invention. A preformed vesicle with the following lipid composition may be contemplated: amino lipid, distearoylphosphatidylcholine (DSPC), cholesterol and (R)-2,3-bis(octadecyloxy) propyl-1-(methoxy poly(ethylene glycol)2000)propylcarbamate (PEG-lipid) in the molar ratio 40/10/40/10, respectively, and a FVII siRNA/total lipid ratio of approximately 0.05 (w/w). To ensure a narrow particle size distribution in the range of 70-90 nm and a low polydispersity index of 0.11+0.04 (n=56), the particles may be extruded up to three times through 80 nm membranes prior to adding the CRISPR Cas RNA. Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Michael S D Kormann et al. ("Expression of therapeutic proteins after delivery of chemically modified mRNA in mice: Nature Biotechnology, Volume:29, Pages: 154-157 (2011)) describes the use of lipid envelopes to deliver RNA. Use of lipid envelopes is also preferred in the present invention.

In another embodiment, lipids may be formulated with the the chromatin 3D structure modulating agents, such as the CRISPR Cas system, of the present invention to form lipid particles (LNPs). Lipids include, but are not limited to, DLin-KC2-DMA4, C12-200 and colipids disteroylphosphatidyl choline, cholesterol, and PEG-DMG may be formulated with CRISPR Cas instead of siRNA (see, e.g., Novobrantseva, Molecular Therapy—Nucleic Acids (2012) 1, e4; doi:10.1038/mtna.2011.3) using a spontaneous vesicle formation procedure. The component molar ratio may be about 50/10/38.5/1.5 (DLin-KC2-DMA or C12-200/disteroylphosphatidyl choline/cholesterol/PEG-DMG). The final lipid:siRNA weight ratio may be ~12:1 and 9:1 in the case of DLin-KC2-DMA and C12-200 lipid particles (LNPs), respectively. The formulations may have mean particle diameters of ~80 nm with >90% entrapment efficiency. A 3 mg/kg dose may be contemplated.

Tekmira has a portfolio of approximately 95 patent families, in the U.S. and abroad, that are directed to various aspects of LNPs and LNP formulations (see, e.g., U.S. Pat. Nos. 7,982,027; 7,799,565; 8,058,069; 8,283,333; 7,901,708; 7,745,651; 7,803,397; 8,101,741; 8,188,263; 7,915,399; 8,236,943 and 7,838,658 and European Pat. Nos 1766035; 1519714; 1781593 and 1664316), all of which may be used and/or adapted to the present invention.

The the chromatin 3D structure modulating agents such as the CRISPR Cas system or components thereof or nucleic acid molecule(s) coding therefor may be delivered encapsulated in PLGA Microspheres such as that further described in US published applications 20130252281 and 20130245107 and 20130244279 (assigned to Moderna Therapeutics) which relate to aspects of formulation of compositions comprising modified nucleic acid molecules which may encode a protein, a protein precursor, or a partially or fully processed form of the protein or a protein precursor. The formulation may have a molar ratio 50:10:38.5:1.5-3.0 (cationic lipid:fusogenic lipid:cholesterol:PEG lipid). The PEG lipid may be selected from, but is not limited to PEG-c-DOMG, PEG-DMG. The fusogenic lipid may be DSPC. See also, Schrum et al., Delivery and Formulation of Engineered Nucleic Acids, US published application 20120251618.

Nanomerics' technology addresses bioavailability challenges for a broad range of therapeutics, including low molecular weight hydrophobic drugs, peptides, and nucleic acid based therapeutics (plasmid, siRNA, miRNA). Specific administration routes for which the technology has demonstrated clear advantages include the oral route, transport across the blood-brain-barrier, delivery to solid tumours, as well as to the eye. See, e.g., Mazza et al., 2013, ACS Nano. 2013 Feb. 26; 7(2):1016-26; Uchegbu and Siew, 2013, J Pharm Sci. 102(2):305-10 and Lalatsa et al., 2012, J Control Release. 2012 Jul. 20; 161(2):523-36.

US Patent Publication No. 20050019923 describes cationic dendrimers for delivering bioactive molecules, such as polynucleotide molecules, peptides and polypeptides and/or pharmaceutical agents, to a mammalian body. The dendrimers are suitable for targeting the delivery of the bioactive molecules to, for example, the liver, spleen, lung, kidney or heart (or even the brain). Dendrimers are synthetic 3-dimensional macromolecules that are prepared in a step-wise fashion from simple branched monomer units, the nature and functionality of which can be easily controlled and varied. Dendrimers are synthesised from the repeated addition of building blocks to a multifunctional core (divergent approach to synthesis), or towards a multifunctional core (convergent approach to synthesis) and each addition of a 3-dimensional shell of building blocks leads to the formation of a higher generation of the dendrimers. Polypropyleneimine dendrimers start from a diaminobutane core to which is added twice the number of amino groups by a double Michael addition of acrylonitrile to the primary amines followed by the hydrogenation of the nitriles. This results in a doubling of the amino groups. Polypropyleneimine dendrimers contain 100% protonable nitrogens and up to 64 terminal amino groups (generation 5, DAB 64). Protonable groups are usually amine groups which are able to accept protons at neutral pH. The use of dendrimers as gene delivery agents has largely focused on the use of the polyamidoamine. and phosphorous containing compounds with a mixture of amine/amide or N-P(O2)S as the conjugating units respectively with no work being reported on the use of the lower generation polypropyleneimine dendrimers for gene delivery. Polypropyleneimine dendrimers have also been studied as pH sensitive controlled release systems for drug delivery and for their encapsulation of guest molecules when chemically modified by peripheral amino acid groups. The cytotoxicity and interaction of polypropyleneimine dendrimers with DNA as well as the transfection efficacy of DAB 64 has also been studied.

US Patent Publication No. 20050019923 is based upon the observation that, contrary to earlier reports, cationic dendrimers, such as polypropyleneimine dendrimers, display suitable properties, such as specific targeting and low toxicity, for use in the targeted delivery of bioactive molecules, such as genetic material. In addition, derivatives of the cationic dendrimer also display suitable properties for the targeted delivery of bioactive molecules. See also, Bioactive Polymers, US published application 20080267903, which discloses "Various polymers, including cationic polyamine polymers and dendrimeric polymers, are shown to possess anti-proliferative activity, and may therefore be useful for treatment of disorders characterised by undesirable cellular proliferation such as neoplasms and tumours, inflammatory disorders (including autoimmune disorders), psoriasis and atherosclerosis. The polymers may be used alone as active agents, or as delivery vehicles for other therapeutic agents, such as drug molecules or nucleic acids for gene therapy. In such cases, the polymers' own intrinsic anti-tumour activity may complement the activity of the agent to be delivered." The disclosures of these patent publications may be employed in conjunction with herein teachings for delivery of CRISPR Cas system(s) or component(s) thereof or nucleic acid molecule(s) coding therefor.

h. Supercharged Proteins

Supercharged proteins are a class of engineered or naturally occurring proteins with unusually high positive or negative net theoretical charge and may be employed in delivery of the chromatin 3D structure modulating agents, such as the CRISPR Cas system(s) or component(s) thereof or nucleic acid molecule(s) coding therefor. Both supernegatively and superpositively charged proteins exhibit a remarkable ability to withstand thermally or chemically induced aggregation. Superpositively charged proteins are also able to penetrate mammalian cells. Associating cargo with these proteins, such as plasmid DNA, RNA, or other proteins, can enable the functional delivery of these macromolecules into mammalian cells both in vitro and in vivo. David Liu's lab reported the creation and characterization of supercharged proteins in 2007 (Lawrence et al., 2007, Journal of the American Chemical Society 129, 10110-10112).

The nonviral delivery of RNA and plasmid DNA into mammalian cells are valuable both for research and therapeutic applications (Akinc et al., 2010, Nat. Biotech. 26, 561-569). Purified +36 GFP protein (or other superpositively charged protein) is mixed with RNAs in the appropriate serum-free media and allowed to complex prior addition to cells. Inclusion of serum at this stage inhibits formation of the supercharged protein-RNA complexes and reduces the effectiveness of the treatment. The following protocol has been found to be effective for a variety of cell lines (McNaughton et al., 2009, Proc. Natl. Acad. Sci. USA 106, 6111-6116) (However, pilot experiments varying the dose of protein and RNA should be performed to optimize the procedure for specific cell lines): (1) One day before treatment, plate 1×105 cells per well in a 48-well plate. (2) On the day of treatment, dilute purified +36 GFP protein in serumfree media to a final concentration 200 nM. Add RNA to a final concentration of 50 nM. Vortex to mix and incubate at room temperature for 10 min. (3) During incubation, aspirate media from cells and wash once with PBS. (4) Following incubation of +36 GFP and RNA, add the protein-RNA complexes to cells. (5) Incubate cells with complexes at 37° C. for 4 h. (6) Following incubation, aspirate the media and wash three times with 20 U/mL heparin PBS. Incubate cells with serum-containing media for a further 48 h or longer depending upon the assay for activity. (7) Analyze cells by immunoblot, qPCR, phenotypic assay, or other appropriate method.

David Liu's lab has further found +36 GFP to be an effective plasmid delivery reagent in a range of cells. As plasmid DNA is a larger cargo than siRNA, proportionately more +36 GFP protein is required to effectively complex plasmids. For effective plasmid delivery Applicants have developed a variant of +36 GFP bearing a C-terminal HA2 peptide tag, a known endosome-disrupting peptide derived from the influenza virus hemagglutinin protein. The following protocol has been effective in a variety of cells, but as above it is advised that plasmid DNA and supercharged protein doses be optimized for specific cell lines and delivery applications: (1) One day before treatment, plate 1×105 per well in a 48-well plate. (2) On the day of treatment, dilute purified 1)36 GFP protein in serumfree media to a final concentration 2 mM. Add 1 mg of plasmid DNA. Vortex to mix and incubate at room temperature for 10 min. (3) During incubation, aspirate media from cells and wash once with PBS. (4) Following incubation of 1)36 GFP and plasmid DNA, gently add the protein-DNA complexes to cells. (5) Incubate cells with complexes at 37 C for 4 h. (6) Following incubation, aspirate the media and wash with PBS. Incubate cells in serum-containing media and incubate for a further 24-48 h. (7) Analyze plasmid delivery (e.g., by plasmid-driven gene expression) as appropriate. See also, e.g., McNaughton et al., Proc. Natl. Acad. Sci. USA 106, 6111-6116 (2009); Cronican et al., ACS Chemical Biology 5, 747-752 (2010); Cronican et al., Chemistry & Biology 18, 833-838 (2011); Thompson et al., Methods in Enzymology 503, 293-319 (2012); Thompson, D. B., et al., Chemistry & Biology 19 (7), 831-843 (2012). The methods of the super charged proteins may be used and/or adapted for delivery of the CRISPR Cas system of the present invention. These systems of Dr. Lui and documents herein in in conjunction with herein teachints can be employed in the delivery of CRISPR Cas system(s) or component(s) thereof or nucleic acid molecule(s) coding therefor.

i. Cell Penetrating Peptides (CPPs)

In yet another embodiment, cell penetrating peptides (CPPs) are contemplated for the delivery of the the chromatin 3D structure modulating agents, such the CRISPR Cas system as described above. CPPs are short peptides that facilitate cellular uptake of various molecular cargo (from nanosize particles to small chemical molecules and large fragments of DNA). The term "cargo" as used herein includes but is not limited to the group consisting of therapeutic agents, diagnostic probes, peptides, nucleic acids, antisense oligonucleotides, plasmids, proteins, particles, liposomes, chromophores, small molecules and radioactive materials. In aspects of the invention, the cargo may also comprise any component of the CRISPR Cas system or the entire functional CRISPR Cas system. Aspects of the present invention further provide methods for delivering a desired cargo into a subject comprising: (a) preparing a complex comprising the cell penetrating peptide of the present invention and a desired cargo, and (b) orally, intraarticularly, intraperitoneally, intrathecally, intrarterially, intranasally, intraparenchymally, subcutaneously, intramuscularly, intravenously, dermally, intrarectally, or topically administering the complex to a subject. The cargo is associated with the peptides either through chemical linkage via covalent bonds or through non-covalent interactions.

The function of the CPPs are to deliver the cargo into cells, a process that commonly occurs through endocytosis with the cargo delivered to the endosomes of living mammalian cells. Cell-penetrating peptides are of different sizes, amino acid sequences, and charges but all CPPs have one distinct characteristic, which is the ability to translocate the plasma membrane and facilitate the delivery of various molecular cargoes to the cytoplasm or an organelle. CPP translocation may be classified into three main entry mechanisms: direct penetration in the membrane, endocytosis-mediated entry, and translocation through the formation of a transitory structure. CPPs have found numerous applications in medicine as drug delivery agents in the treatment of different diseases including cancer and virus inhibitors, as well as contrast agents for cell labeling. Examples of the latter include acting as a carrier for GFP, MRI contrast agents, or quantum dots. CPPs hold great potential as in vitro and in vivo delivery vectors for use in research and medicine. CPPs typically have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPPs are the hydrophobic peptides, containing only apolar residues, with low net charge or have hydrophobic amino acid groups that are crucial for cellular uptake. One of the initial CPPs discovered was the trans-activating transcriptional activator (Tat) from Human Immunodeficiency Virus 1 (HIV-1) which was found to be efficiently taken up from the surrounding media by numerous cell types in culture. Since then, the number of known CPPs has expanded considerably and small molecule synthetic analogues with more effective protein transduction properties have been generated. CPPs include but are not limited to Penetratin, Tat (48-60), Transportan, and (R-AhX-R4) (Ahx=aminohexanoyl).

U.S. Pat. No. 8,372,951, provides a CPP derived from eosinophil cationic protein (ECP) which exhibits highly cell-penetrating efficiency and low toxicity. Aspects of delivering the CPP with its cargo into a vertebrate subject are also provided. Further aspects of CPPs and their delivery are described in U.S. Pat. Nos. 8,575,305; 8,614,194 and 8,044,019.

j. Implantable Devices

In another embodiment, implantable devices are also contemplated for delivery of the the chromatin 3D structure modulating agents or nucleic acid molecule(s) coding therefor. For example, US Patent Publication 20110195123 discloses an implantable medical device which elutes a drug locally and in prolonged period is provided, including several types of such a device, the treatment modes of implementation and methods of implantation. The device comprising of polymeric substrate, such as a matrix for example, that is used as the device body, and drugs, and in some cases additional scaffolding materials, such as metals or additional polymers, and materials to enhance visibility and imaging. An implantable delivery device can be advantageous in providing release locally and over a prolonged period, where drug is released directly to the extracellular matrix (ECM) of the diseased area such as tumor, inflammation, degeneration or for symptomatic objectives, or to injured smooth muscle cells, or for prevention. One kind of drug is RNA, as disclosed above, and this system may be used/and or adapted to the the chromatin 3D structure modulating agents such as the CRISPR Cas system envisaged herein. The modes of implantation in some embodiments are existing implantation procedures that are developed and used today for other treatments, including brachytherapy and needle biopsy. In such cases the dimensions of the new implant described in this invention are similar to the original implant. Typically a few devices are implanted during the same treatment procedure.

As described in US Patent Publication 20110195123, there is provided a drug delivery implantable or insertable system, including systems applicable to a cavity such as the abdominal cavity and/or any other type of administration in which the drug delivery system is not anchored or attached, comprising a biostable and/or degradable and/or bioabsorbable polymeric substrate, which may for example optionally be a matrix. It should be noted that the term "insertion" also includes implantation. The drug delivery system is preferably implemented as a "Loder" as described in US Patent Publication 20110195123.

The polymer or plurality of polymers are biocompatible, incorporating an agent and/or plurality of agents, enabling the release of agent at a controlled rate, wherein the total volume of the polymeric substrate, such as a matrix for example, in some embodiments is optionally and preferably no greater than a maximum volume that permits a therapeutic level of the agent to be reached. As a non-limiting example, such a volume is preferably within the range of 0.1 m3 to 1000 mm3, as required by the volume for the agent load. The Loder may optionally be larger, for example when incorporated with a device whose size is determined by functionality, for example and without limitation, a knee joint, an intra-uterine or cervical ring and the like.

The drug delivery system (for delivering the composition) is designed in some embodiments to preferably employ degradable polymers, wherein the main release mechanism is bulk erosion; or in some embodiments, non degradable, or slowly degraded polymers are used, wherein the main release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the surface is preferably maintained effectively constant during a significant period of the total drug releasing period, and therefore the diffusion rate is effectively constant (termed "zero mode" diffusion). By the term "constant" it is meant a diffusion rate that is preferably maintained above the lower threshold of therapeutic effectiveness, but which may still optionally feature an initial burst and/or may fluctuate, for example increasing and decreasing to a certain degree. The diffusion rate is preferably so maintained for a prolonged period, and it can be considered constant to a certain level to optimize the therapeutically effective period, for example the effective silencing period.

The drug delivery system optionally and preferably is designed to shield the nucleotide based therapeutic agent from degradation, whether chemical in nature or due to attack from enzymes and other factors in the body of the subject.

The drug delivery system as described in US Patent Publication 20110195123 is optionally associated with sensing and/or activation appliances that are operated at and/or after implantation of the device, by non and/or minimally invasive methods of activation and/or acceleration/deceleration, for example optionally including but not limited to thermal heating and cooling, laser beams, and ultrasonic, including focused ultrasound and/or RF (radiofrequency) methods or devices.

According to some embodiments of US Patent Publication 20110195123, the site for local delivery may optionally include target sites characterized by high abnormal proliferation of cells, and suppressed apoptosis, including tumors, active and or chronic inflammation and infection including autoimmune diseases states, degenerating tissue including muscle and nervous tissue, chronic pain, degenerative sites, and location of bone fractures and other wound locations for enhancement of regeneration of tissue, and injured cardiac, smooth and striated muscle.

The site for implantation of the composition, or target site, preferably features a radius, area and/or volume that is sufficiently small for targeted local delivery. For example, the target site optionally has a diameter in a range of from about 0.1 mm to about 5 cm.

The location of the target site is preferably selected for maximum therapeutic efficacy. For example, the composition of the drug delivery system (optionally with a device for implantation as described above) is optionally and preferably implanted within or in the proximity of a tumor environment, or the blood supply associated thereof.

For example the composition (optionally with the device) is optionally implanted within or in the proximity to pancreas, prostate, breast, liver, via the nipple, within the vascular system and so forth.

The target location is optionally selected from the group consisting of (as non-limiting examples only, as optionally any site within the body may be suitable for implanting a Loder): 1. brain at degenerative sites like in Parkinson or Alzheimer disease at the basal ganglia, white and gray matter; 2. spine as in the case of amyotrophic lateral sclerosis (ALS); 3. uterine cervix to prevent HPV infection; 4. active and chronic inflammatory joints; 5. dermis as in the case of psoriasis; 6. sympathetic and sensoric nervous sites for analgesic effect; 7. Intra osseous implantation; 8. acute and chronic infection sites; 9. Intra vaginal; 10. Inner ear-auditory system, labyrinth of the inner ear, vestibular system; 11. Intra tracheal; 12. Intra-cardiac; coronary, epicardiac; 13. urinary bladder; 14. biliary system; 15. parenchymal tissue including and not limited to the kidney, liver, spleen; 16. lymph nodes; 17. salivary glands; 18. dental gums; 19. Intra-articular (into joints); 20. Intra-ocular; 21. Brain tissue; 22. Brain ventricles; 23. Cavities, including abdominal cavity (for example but without limitation, for ovary cancer); 24. Intra esophageal and 25. Intra rectal.

Optionally insertion of the system (for example a device containing the composition) is associated with injection of material to the ECM at the target site and the vicinity of that site to affect local pH and/or temperature and/or other biological factors affecting the diffusion of the drug and/or drug kinetics in the ECM, of the target site and the vicinity of such a site.

Optionally, according to some embodiments, the release of said agent could be associated with sensing and/or activation appliances that are operated prior and/or at and/or after insertion, by non and/or minimally invasive and/or else methods of activation and/or acceleration/deceleration, including laser beam, radiation, thermal heating and cooling, and ultrasonic, including focused ultrasound and/or RF (radiofrequency) methods or devices, and chemical activators.

According to other embodiments of US Patent Publication 20110195123, the drug preferably comprises a RNA, for example for localized cancer cases in breast, pancreas, brain, kidney, bladder, lung, and prostate as described below. Although exemplified with RNAi, many drugs are applicable to be encapsulated in Loder, and can be used in association with this invention, as long as such drugs can be encapsulated with the Loder substrate, such as a matrix for example, and this system may be used and/or adapted to deliver the the chromatin 3D structure modulating agents such as the CRISPR Cas systems envisaged in the context of the present invention.

As another example of a specific application, neuro and muscular degenerative diseases develop due to abnormal gene expression. Local delivery of RNAs may have therapeutic properties for interfering with such abnormal gene expression. Local delivery of anti apoptotic, anti inflammatory and anti degenerative drugs including small drugs and macromolecules may also optionally be therapeutic. In such cases the Loder is applied for prolonged release at constant rate and/or through a dedicated device that is implanted separately. All of this may be used and/or adapted to the the chromatin 3D structure modulating agents of the present invention.

As yet another example of a specific application, psychiatric and cognitive disorders are treated with gene modifiers. Gene knockdown is a treatment option. Loders locally delivering agents to central nervous system sites are therapeutic options for psychiatric and cognitive disorders including but not limited to psychosis, bi-polar diseases, neurotic disorders and behavioral maladies. The Loders could also deliver locally drugs including small drugs and macromolecules upon implantation at specific brain sites. All of this may be used and/or adapted to the the chromatin 3D structure modulating agents of the present invention.

As another example of a specific application, silencing of innate and/or adaptive immune mediators at local sites enables the prevention of organ transplant rejection. Local delivery of RNAs and immunomodulating reagents with the Loder implanted into the transplanted organ and/or the implanted site renders local immune suppression by repelling immune cells such as CD8 activated against the transplanted organ. All of this may be used/and or adapted to the the chromatin 3D structure modulating agents of the present invention.

As another example of a specific application, vascular growth factors including VEGFs and angiogenin and others are essential for neovascularization. Local delivery of the factors, peptides, peptidomimetics, or suppressing their repressors is an important therapeutic modality; silencing the repressors and local delivery of the factors, peptides, macromolecules and small drugs stimulating angiogenesis with the Loder is therapeutic for peripheral, systemic and cardiac vascular disease.

The method of insertion, such as implantation, may optionally already be used for other types of tissue implantation and/or for insertions and/or for sampling tissues, optionally without modifications, or alternatively optionally only with non-major modifications in such methods. Such methods optionally include but are not limited to brachytherapy methods, biopsy, endoscopy with and/or without ultrasound, such as ERCP, stereotactic methods into the brain tissue, Laparoscopy, including implantation with a laparoscope into joints, abdominal organs, the bladder wall and body cavities.

Implantable device technology herein discussed can be employed with herein teachings and hence by this disclosure and the knowledge in the art, the chromatin 3D structure modulating agents or nucleic acid molecules thereof or encoding or providing components may be delivered via an implantable device.

Figure 10:
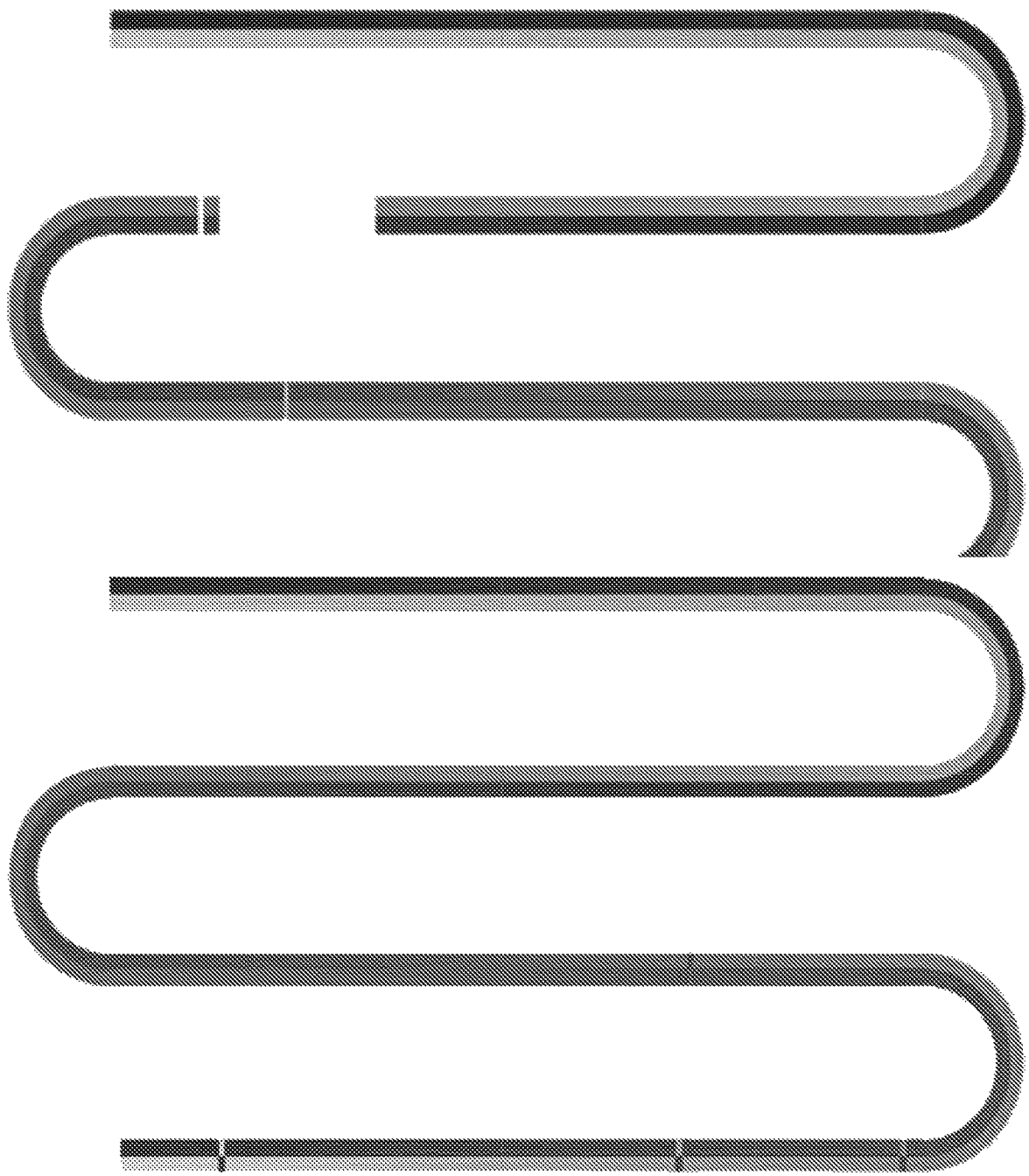
FIG. 10 is a schematic that demonstrates that the disclosed methods can be used to assemble genomes de novo.

One of the other major advances enabled by the methods disclosed herein, is de novo assembly genome. As shown in FIG. 10, the combination of the disclosed methods and high through put sequencing can be used to assemble genomes de novo. The image at top represents the correct assembly of human chromosome 20. At bottom is shown a de novo assembly of human chromosome 20 from 100 kb fragments, created using data generated with the methods disclosed herein. With the exception of a few small inversions, the assembly is perfect. The maps allow the creation of de novo genome assemblies without the use of mate pair reads.

D. Modifying Gene Expression and Disease Treatment

A method of the invention may be used to create a plant, an animal or cell that may be used to model and/or study genetic or epigenetic conditions of interest, such as a through a model of mutations of interest or a as a disease model. As used herein, "disease" refers to a disease, disorder, or indication in a subject. For example, a method of the invention may be used to create an animal or cell that comprises a modification in one or more nucleic acid sequences associated with a disease, or a plant, animal or cell in which the expression of one or more nucleic acid sequences associated with a disease are altered. Such a nucleic acid sequence may encode a disease associated protein sequence or may be a disease associated control sequence. Accordingly, it is understood that in embodiments of the invention, a plant, subject, patient, organism or cell can be a non-human subject, patient, organism or cell. Thus, the invention provides a plant, animal or cell, produced by the present methods, or a progeny thereof. The progeny may be a clone of the produced plant or animal, or may result from sexual reproduction by crossing with other individuals of the same species to introgress further desirable traits into their offspring. The cell may be in vivo or ex vivo in the cases of multicellular organisms, particularly animals or plants. In the instance where the cell is in cultured, a cell line may be established if appropriate culturing conditions are met and preferably if the cell is suitably adapted for this purpose (for instance a stem cell). Bacterial cell lines produced by the invention are also envisaged. Hence, cell lines are also envisaged.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R.I. Freshney, ed. (1987)).

In some embodiments, the methods described herein are used to produce a non-human transgenic animal or transgenic plant having altered gene expression due to chromatin loop or domain modification. In some embodiments, the transgenic animal is a mammal, such as a mouse, rat, or rabbit. In certain embodiments, the organism or subject is a plant. In certain embodiments, the organism or subject or plant is algae. Methods for producing transgenic plants and animals are known in the art, and generally begin with a method of cell transfection, such as described herein. Transgenic animals are also provided, as are transgenic plants, especially crops and algae. The transgenic animal or plant may be useful in applications outside of providing a disease model. These may include food or feed production through expression of, for instance, higher protein, carbohydrate, nutrient or vitamins levels than would normally be seen in the wildtype. In this regard, transgenic plants, especially pulses and tubers, and animals, especially mammals such as livestock (cows, sheep, goats and pigs), but also poultry and edible insects, are preferred.

Transgenic algae or other plants such as rape may be particularly useful in the production of vegetable oils or biofuels such as alcohols (especially methanol and ethanol), for instance. These may be engineered to express or overexpress high levels of oil or alcohols for use in the oil or biofuel industries.

In one aspect, the invention provides for methods of modifying the expression of a target polynucleotide in a eukaryotic cell. In some embodiments, the method comprises allowing a CRISPR complex to bind to the target polynucleotide associated with chromatin extrusion and loop formation, to effect cleavage of said target polynucleotide thereby modifying the target polynucleotide, wherein the CRISPR complex comprises a CRISPR protein complexed with a guide sequence hybridized to a target sequence within said target polynucleotide.

In one aspect, the invention provides a method of modifying expression of a polynucleotide in a eukaryotic cell. In some embodiments, the method comprises allowing a CRISPR complex to bind to the polynucleotide, such as a CTCF binding motif, such that said binding results in chromatin loop or domain modification, thereby altering locus interaction and increased or decreased expression of a polynucleotide in said loop or domain; wherein the CRISPR complex comprises a CRISPR protein complexed with a guide RNA comprising a guide sequence hybridized to a target sequence within said polynucleotide.

With recent advances in crop genomics, the ability to use the methods disclosed herein to perform efficient and cost effective gene editing and manipulation will allow the rapid selection and comparison of single and and multiplexed genetic manipulations to transform such genomes for improved production and enhanced traits. In this regard reference is made to US patents and publications: U.S. Pat. No. 6,603,061—*Agrobacterium*-Mediated Plant Transformation Method; U.S. Pat. No. 7,868,149—Plant Genome Sequences and Uses Thereof and US 2009/0100536—Transgenic Plants with Enhanced Agronomic Traits, all the contents and disclosure of each of which are herein incorporated by reference in their entirety. In the practice of the invention, the contents and disclosure of Morrell et al "Crop genomics:advances and applications" Nat Rev Genet. 2011 Dec. 29; 13(2):85-96 are also herein incorporated by reference in their entirety. In an advantageous embodiment of the invention, the methods disclosed herein are used to engineer microalgae (Example 14). Accordingly, reference herein to animal cells may also apply, mutatis mutandis, to plant cells unless otherwise apparent.

In one aspect, the invention provides for methods of modifying a target polynucleotide in a eukaryotic cell, which may be in vivo, ex vivo or in vitro. In some embodiments, the method comprises sampling a cell or population of cells from a human or non-human animal or plant (including micro-algae), and modifying the cell or cells. Culturing may occur at any stage ex vivo. The cell or cells may even be re-introduced into the non-human animal or plant (including micro-algae). Methods in aspects of this invention may thus include ex vivo methods or in vitro methods.

In one aspect, the invention provides kits containing any one or more of the elements disclosed in the above methods and compositions. In some embodiments, the kit comprises a vector system and instructions for using the kit. In some embodiments, the kit includes instructions in one or more languages, for example in more than one language.

In some embodiments, a kit comprises one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit comprises one or more oligonucleotides corresponding to a guide sequence for insertion into a vector so as to operably link the guide sequence and a regulatory element. In some embodiments, the kit comprises a homologous recombination template polynucleotide.

In one aspect, the invention provides methods for using one or more elements of a CRISPR system. The CRISPR complex of the invention provides an effective means for modifying a chromatin looping. The CRISPR complex of the invention has a wide variety of utility including modifying (e.g., deleting, inserting, translocating, inactivating, activating) a target polynucleotide in a multiplicity of cell types. As such the CRISPR complex for use in the invention has a broad spectrum of applications in, e.g., gene therapy, drug screening, disease diagnosis, and prognosis. An exemplary CRISPR complex comprises a CRISPR enzyme complexed with a guide RNA comprising a guide sequence hybridized to a target sequence within the target polynucleotide.

The target polynucleotide in a chromatin loop or domain, envisaged to be modified by methods of this invention, by virtue of which the expression of said target polynucleotide is modified, can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA).

The target polynucleotide in a chromatin loop or domain, modified by methods of this invention, by virtue of which the expression of said target polynucleotide is modified, may include a number of disease-associated genes and polynucleotides as well as signaling biochemical pathway-associated genes and polynucleotides as listed in U.S. provisional patent applications 61/736,527 and 61/748,427 having Broad reference BI-2011/008/WSGR Docket No. 44063-701.101 and BI-2011/008/WSGR Docket No. 44063-701.102 respectively, both entitled SYSTEMS METHODS AND COMPOSITIONS FOR SEQUENCE MANIPULATION filed on Dec. 12, 2012 and Jan. 2, 2013, respectively, the contents of all of which are herein incorporated by reference in their entirety.

Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

Examples of disease-associated genes and polynucleotides are available from McKusick-Nathans Institute of Genetic Medicine, Johns Hopkins University (Baltimore, Md.) and National Center for Biotechnology Information, National Library of Medicine (Bethesda, Md.), available on the World Wide Web.

Examples of disease-associated genes and polynucleotides are listed in Tables A and B. Disease specific information is available from McKusick-Nathans Institute of Genetic Medicine, Johns Hopkins University (Baltimore, Md.) and National Center for Biotechnology Information, National Library of Medicine (Bethesda, Md.), available on the World Wide Web. Examples of signaling biochemical pathway-associated genes and polynucleotides are listed in Table C.

Mutations in these genes and pathways can result in production of improper proteins or proteins in improper amounts which affect function. Further examples of genes, diseases and proteins are hereby incorporated by reference from U.S. Provisional applications 61/736,527 and 61/748,427. Such genes, proteins and pathways may be the target polynucleotide of a CRISPR complex.

TABLE A

| DISEASE/DISORDER | GENES |
| --- | --- |
| Neoplasia | PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR (Androgen Receptor); TSG101; IGF; IGF Receptor; Igf1 (4 variants); Igf2 (3 variants); Igf 1 Receptor; Igf 2 Receptor; Bax; Bcl2; caspases family (9 members: 1, 2, 3, 4, 6, 7, 8, 9, 12); Kras; Apc |
| Age-related Macular Degeneration | Abcr; Ccl2; Cc2; cp (ceruloplasmin); Timp3; cathepsinD; Vldlr; Ccr2 |
| Schizophrenia Disorders | Neuregulin1 (Nrg1); Erb4 (receptor for Neuregulin); Complexin1 (Cplx1); Tph1 Tryptophan hydroxylase; Tph2, Tryptophan hydroxylase 2; Neurexin 1; GSK3; GSK3a; GSK3b, 5-HTT (Slc6a4); COMT; DRD (Drd1a); SLC6A3; DAOA; DTNBP1; Dao (Dao1) |
| Trinucleotide Repeat Disorders | HTT (Huntington's Dx); SBMA/SMAX1/AR (Kennedy's Dx); FXN/X25 (Friedrich's Ataxia); ATX3 (Machado-Joseph's Dx); ATXN1 and ATXN2 (spinocerebellar ataxias); DMPK (myotonic dystrophy); Atrophin-1 and Atn1 (DRPLA Dx); CBP (Creb-BP - global instability); VLDLR (Alzheimer's); Atxn7; Atxn10 |
| Fragile X Syndrome | FMR2; FXR1; FXR2; mGLUR5 |
| Secretase Related Disorders | APH-1 (alpha and beta); Presenilin (Psen1); nicastrin (Nestn); PEN-2 |
| Others | Nos1; Parp1; Nat1; Nat2 |
| Prion - related disorders | Prp |
| ALS | SOD1; ALS2; STEX; FUS; TARDBP; VEGF (VEGF-a; VEGF-b; VEGF-c) |
| Drug addiction | Prkce (alcohol); Drd2; Drd4; ABAT (alcohol); GRIA2; Grm5; Grin1; Htrlb; Grin2a; Drd3; Pdyn; Gria1 (alcohol) |
| Autism | Mecp2; BZRAP1; MDGA2; Sema5A; Neurexin 1; Fragile X (FMR2 (AFF2); FXR1; FXR2; Mglur5) |
| Alzheimer's Disease | E1; CHIP; UCH; UBB; Tau; LRP; PICALM; Clusterin; PS1; SORL1; CR1; Vldlr; Uba1; Uba3; CHIP28 (Aqp1, Aquaporin 1); Uchl1; Uchl3; APP |
| Inflammation | IL-10; IL-1 (IL-1a; IL-1b); IL-13; IL-17 (IL-17a (CTLA8); IL-17b; IL-17c; IL-17d; IL-17f); Il-23; Cx3cr1; ptpn22; TNFa; NOD2/CARD15 for IBD; IL-6; IL-12 (IL-12a; IL-12b); CTLA4; Cx3cl1 |
| Parkinson's Disease | x-Synuclein; DJ-1; LRRK2; Parkin; PINK1 |

TABLE B

| DISEASE/DISORDER | GENES |
|---|---|
| Blood and coagulation diseases and disorders | Anemia (CDAN1, CDA1, RPS19, DBA, PKLR, PK1, NT5C3, UMPH1, PSN1, RHAG, RH50A, NRAMP2, SPTB, ALAS2, ANH1, ASB, ABCB7, ABC7, ASAT); Bare lymphocyte syndrome (TAPBP, TPSN, TAP2, ABCB3, PSF2, RING11, MHC2TA, C2TA, RFX5, RFXAP, RFX5), Bleeding disorders (TBXA2R, P2RX1, P2X1); Factor H and factor H-like 1 (HF1, CFH, HUS); Factor V and factor VIII (MCFD2); Factor VII deficiency (F7); Factor X deficiency (F10); Factor XI deficiency (F11); Factor XII deficiency (F12, HAF); Factor XIIIA deficiency (F13A1, F13A); Factor XIIIB deficiency (F13B); Fanconi anemia (FANCA, FACA, FA1, FA, FAA, FAAP95, FAAP90, FLJ34064, FANCB, FANCC, FACC, BRCA2, FANCD1, FANCD2, FANCD, FACD, FAD, FANCE, FACE, FANCF, XRCC9, FANCG, BRIP1, BACH1, FANCJ, PHF9, FANCL, FANCM, KIAA1596); Hemophagocytic lymphohistiocytosis disorders (PRF1, HPLH2, UNC13D, MUNC13-4, HPLH3, HLH3, FHL3); Hemophilia A (F8, F8C, HEMA); Hemophilia B (F9, HEMB), Hemorrhagic disorders (PI, ATT, F5); Leukocyde deficiencies and disorders (ITGB2, CD18, LCAMB, LAD, EIF2B1, EIF2BA, EIF2B2, EIF2B3, EIF2B5, LVWM, CACH, CLE, EIF2B4); Sickle cell anemia (HBB); Thalassemia (HBA2, HBB, HBD, LCRB, HBA1). |
| Cell dysregulation and oncology diseases and disorders | B-cell non-Hodgkin lymphoma (BCL7A, BCL7); Leukemia (TAL1 TCL5, SCL, TAL2, FLT3, NBS1, NBS, ZNFN1A1, IK1, LYF1, HOXD4, HOX4B, BCR, CML, PHL, ALL, ARNT, KRAS2, RASK2, GMPS, AF10, ARHGEF12, LARG, KIAA0382, CALM, CLTH, CEBPA, CEBP, CHIC2, BTL, FLT3, KIT, PBT, LPP, NPM1, NUP214, D9S46E, CAN, CAIN, RUNX1, CBFA2, AML1, WHSC1L1, NSD3, FLT3, AF1Q, NPM1, NUMA1, ZNF145, PLZF, PML, MYL, STAT5B, AF10, CALM, CLTH, ARL11, ARLTS1, P2RX7, P2X7, BCR, CML, PHL, ALL, GRAF, NF1, VRNF, WSS, NFNS, PTPN11, PTP2C, SHP2, NS1, BCL2, CCND1, PRAD1, BCL1, TCRA, GATA1, GF1, ERYF1, NFE1, ABL1, NQO1, DIA4, NMOR1, NUP214, D9S46E, CAN, CAIN). |
| Inflammation and immune related diseases and disorders | AIDS (KIR3DL1, NKAT3, NKB1, AMB11, KIR3DS1, IFNG, CXCL12, SDF1); Autoimmune lymphoproliferative syndrome (TNFRSF6, APT1, FAS, CD95, ALPS1A); Combined immunodeficiency, (IL2RG, SCIDX1, SCIDX, IMD4); HIV-1 (CCL5, SCYA5, D17S136E, TCP228), HIV susceptibility or infection (IL10, CSIF, CMKBR2, CCR2, CMKBR5, CCCKR5 (CCR5)); Immunodeficiencies (CD3E, CD3G, AICDA, AID, HIGM2, TNFRSF5, CD40, UNG, DGU, HIGM4, TNFSF5, CD40LG, HIGM1, IGM, FOXP3, IPEX, AIID, XPID, PIDX, TNFRSF14B, TACI); Inflammation (IL-10, IL-1 (IL-1a, IL-1b), IL-13, IL-17 (IL-17a (CTLA8), IL-17b, IL-17c, IL-17d, IL-17f), Il-23, Cx3cr1, ptpn22, TNFa, NOD2/CARD15 for IBD, IL-6, IL-12 (IL-12a, IL-12b), CTLA4, Cx3cl1); Severe combined immunodeficiencies (SCIDs)(JAK3, JAKL, DCLRE1C, ARTEMIS, SCIDA, RAG1, RAG2, ADA, PTPRC, CD45, LCA, IL7R, CD3D, T3D, IL2RG, SCIDX1, SCIDX, IMD4). |
| Metabolic, liver, kidney and protein diseases and disorders | Amyloid neuropathy (TTR, PALB); Amyloidosis (APOA1, APP, AAA, CVAP, AD1, GSN, FGA, LYZ, TTR, PALB); Cirrhosis (KRT18, KRT8, CIRH1A, NAIC, TEX292, KIAA1988); Cystic fibrosis (CFTR, ABCC7, CF, MRP7); Glycogen storage diseases (SLC2A2, GLUT2, G6PC, G6PT, G6PT1, GAA, LAMP2, LAMPB, AGL, GDE, GBE1, GYS2, PYGL, PFKM); Hepatic adenoma, 142330 (TCF1, HNF1A, MODY3), Hepatic failure, early onset, and neurologic disorder (SCOD1, SCO1), Hepatic lipase deficiency (LIPC), Hepatoblastoma, cancer and carcinomas (CTNNB1, PDGFRL, PDGRL, PRLTS, AXIN1, AXIN, CTNNB1, TP53, P53, LFS1, IGF2R, MPRI, MET, CASP8, MCH5; Medullary cystic kidney disease (UMOD, HNFJ, FJHN, MCKD2, ADMCKD2); Phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63). |
| Muscular/Skeletal diseases and disorders | Becker muscular dystrophy (DMD, BMD, MYF6), Duchenne Muscular Dystrophy (DMD, BMD); Emery-Dreifuss muscular dystrophy (LMNA, LMN1, EMD2, FPLD, CMD1A, HGPS, LGMD1B, LMNA, LMN1, EMD2, FPLD, CMD1A); Facioscapulohumeral muscular dystrophy (FSHMD1A, FSHD1A); Muscular dystrophy (FKRP, MDC1C, LGMD2I, LAMA2, LAMM, LARGE, KIAA0609, MDC1D, FCMD, TTID, MYOT, CAPN3, CANP3, DYSF, LGMD2B, SGCG, LGMD2C, DMDA1, SCG3, SGCA, ADL, DAG2, LGMD2D, DMDA2, SGCB, LGMD2E, SGCD, SGD, LGMD2F, CMD1L, TCAP, LGMD2G, CMD1N, TRIM32, HT2A, LGMD2H, FKRP, MDC1C, LGMD2I, TTN, CMD1G, TMD, LGMD2J, POMT1, CAV3, LGMD1C, SEPN1, SELN, RSMD1, PLEC1, PLTN, EBS1); Osteopetrosis (LRP5, BMND1, LRP7, LR3, OPPG, VBCH2, CLCN7, CLC7, OPTA2, OSTM1, GL, TCIRG1, TIRC7, OC116, OPTB1); Muscular atrophy (VAPB, VAPC, ALS8, SMN1, SMA1, SMA2, SMA3, SMA4, BSCL2, SPG17, GARS, SMAD1, CMT2D, HEXB, IGHMBP2, SMUBP2, CATF1, SMARD1). |
| Neurological and neuronal diseases and disorders | ALS (SOD1, ALS2, STEX, FUS, TARDBP, VEGF (VEGF-a, VEGF-b, VEGF-c); Alzheimer disease (APP, AAA, CVAP, AD1, APOE, AD2, PSEN2, AD4, STM2, APBB2, FE65L1, NOS3, PLAU, URK, ACE, |

TABLE B-continued

| DISEASE/DISORDER | GENES |
|---|---|
| | DCP1, ACE1, MPO, PACIP1, PAXIP1L, PTIP, A2M, BLMH, BMH, PSEN1, AD3); Autism (Mecp2, BZRAP1, MDGA2, Sema5A, Neurexin 1, GLO1, MECP2, RTT, PPMX, MRX16, MRX79, NLGN3, NLGN4, KIAA1260, AUTSX2); Fragile X Syndrome (FMR2, FXR1, FXR2, mGLUR5); Huntington's disease and disease like disorders (HD, IT15, PRNP, PRIP, JPH3, JP3, HDL2, TBP, SCA17); Parkinson disease (NR4A2, NURR1, NOT, TINUR, SNCAIP, TBP, SCA17, SNCA, NACP, PARK1, PARK4, DJ1, PARK7, LRRK2, PARK8, PINK1, PARK6, UCHL1, PARK5, SNCA, NACP, PARK1, PARK4, PRKN, PARK2, PDJ, DBH, NDUFV2); Rett syndrome (MECP2, RTT, PPMX, MRX16, MRX79, CDKL5, STK9, MECP2, RTT, PPMX, MRX16, MRX79, x-Synuclein, DJ-1); Schizophrenia (Neuregulin1 (Nrg1), Erb4 (receptor for Neuregulin), Complexin1 (Cplx1), Tph1 Tryptophan hydroxylase, Tph2, Tryptophan hydroxylase 2, Neurexin 1, GSK3, GSK3a, GSK3b, 5-HTT (Slc6a4), COMT, DRD (Drd1a), SLC6A3, DAOA, DTNBP1, Dao (Dao1)); Secretase Related Disorders (APH-1 (alpha and beta), Presenilin (Psen1), nicastrin, (Ncstn), PEN-2, Nos1, Parp1, Nat1, Nat2); Trinucleotide Repeat Disorders (HTT (Huntington's Dx), SBMA/SMAX1/AR (Kennedy's Dx), FXN/X25 (Friedrich's Ataxia), ATX3 (Machado- Joseph's Dx), ATXN1 and ATXN2 (spinocerebellar ataxias), DMPK (myotonic dystrophy), Atrophin-1 and Atn1 (DRPLA Dx), CBP (Creb-BP - global instability), VLDLR (Alzheimer's), Atxn7, Atxn10). |
| Occular diseases and disorders | Age-related macular degeneration (Abcr, Ccl2, Cc2, cp (ceruloplasmin), Timp3, cathepsinD, Vldlr, Ccr2); Cataract (CRYAA, CRYA1, CRYBB2, CRYB2, PITX3, BFSP2, CP49, CP47, CRYAA, CRYA1, PAX6, AN2, MGDA, CRYBA1, CRYB1, CRYGC, CRYG3, CCL, LIM2, MP19, CRYGD, CRYG4, BFSP2, CP49, CP47, HSF4, CTM, HSF4, CTM, MIP, AQP0, CRYAB, CRYA2, CTPP2, CRYBB1, CRYGD, CRYG4, CRYBB2, CRYB2, CRYGC, CRYG3, CCL, CRYAA, CRYA1, GJA8, CX50, CAE1, GJA3, CX46, CZP3, CAE3, CCM1, CAM, KRIT1); Corneal clouding and dystrophy (APOA1, TGFBI, CSD2, CDGG1, CSD, BIGH3, CDG2, TACSTD2, TROP2, M1S1, VSX1, RINX, PPCD, PPD, KTCN, COL8A2, FECD, PPCD2, PIP5K3, CFD); Cornea plana congenital (KERA, CNA2); Glaucoma (MYOC, TIGR, GLC1A, JOAG, GPOA, OPTN, GLC1E, FIP2, HYPL, NRP, CYP1B1, GLC3A, OPA1, NTG, NPG, CYP1B1, GLC3A); Leber congenital amaurosis (CRB1, RP12, CRX, CORD2, CRD, RPGRIP1, LCA6, CORD9, RPE65, RP20, AIPL1, LCA4, GUCY2D, GUC2D, LCA1, CORD6, RDH12, LCA3); Macular dystrophy (ELOVL4, ADMD, STGD2, STGD3, RDS, RP7, PRPH2, PRPH, AVMD, AOFMD, VMD2). |

TABLE C

| CELLULAR FUNCTION | GENES |
|---|---|
| PI3K/AKT Signaling | PRKCE; ITGAM; ITGA5; IRAK1; PRKAA2; EIF2AK2; PTEN; EIF4E; PRKCZ; GRK6; MAPK1; TSC1; PLK1; AKT2; IKBKB; PIK3CA; CDK8; CDKN1B; NFKB2; BCL2; PIK3CB; PPP2R1A; MAPK8; BCL2L1; MAPK3; TSC2; ITGA1; KRAS; EIF4EBP1; RELA; PRKCD; NOS3; PRKAA1; MAPK9; CDK2; PPP2CA; PIM1; ITGB7; YWHAZ; ILK; TP53; RAF1; IKBKG; RELB; DYRK1A; CDKN1A; ITGB1; MAP2K2; JAK1; AKT1; JAK2; PIK3R1; CHUK; PDPK1; PPP2R5C; CTNNB1; MAP2K1; NFKB 1; PAK3; ITGB3; CCND1; GSK3A; FRAP1; SFN; ITGA2; TTK; CSNK1A1; BRAF; GSK3B; AKT3; FOXO1; SGK; HSP90AA1; RPS6KB1 |
| ERK/MAPK Signaling | PRKCE; ITGAM; ITGA5; HSPB1; IRAK1; PRKAA2; EIF2AK2; RAC1; RAP1A; TLN1; EIF4E; ELK1; GRK6; MAPK1; RAC2; PLK1; AKT2; PIK3CA; CDK8; CREB1; PRKCI; PTK2; FOS; RPS6KA4; PIK3CB; PPP2R1A; PIK3C3; MAPK8; MAPK3; ITGA1; ETS1; KRAS; MYCN; EIF4EBP1; PPARG; PRKCD; PRKAA1; MAPK9; SRC; CDK2; PPP2CA; PIM1; PIK3C2A; ITGB7; YWHAZ; PPP1CC; KSR1; PXN; RAF1; FYN; DYRK1A; ITGB1; MAP2K2; PAK4; PIK3R1; STAT3; PPP2R5C; MAP2K1; PAK3; ITGB3; ESR1; ITGA2; MYC; TTK; CSNK1A1; CRKL; BRAF; ATF4; PRKCA; SRF; STAT1; SGK |
| Glucocorticoid Receptor Signaling | RAC1; TAF4B; EP300; SMAD2; TRAF6; PCAF; ELK1; PK1; SMAD3; AKT2; IKBKB; NCOR2; UBE2I; PIK3CA; CREB1; FOS; HSPA5; NFKB2; BCL2; MAP3K14; STAT5B; PIK3CB; PIK3C3; MAPK8; BCL2L1; MAPK3; TSC22D3; MAPK10; NRIP1; KRAS; MAPK13; RELA; STAT5A; MAPK9; NOS2A; PBX1; NR3C1; |

TABLE C-continued

| CELLULAR FUNCTION | GENES |
|---|---|
| | PIK3C2A; CDKN1C; TRAF2; SERPINE1; NCOA3; MAPK14; TNF; RAF1; IKBKG; MAP3K7; CREBBP; CDKN1A; MAP2K2; JAK1; IL8; NCOA2; AKT1; JAK2; PIK3R1; CHUK; STAT3; MAP2K1; NFKB1; TGFBR1; ESR1; SMAD4; CEBPB; JUN; AR; AKT3; CCL2; MMP1; STAT1; IL6; HSP90AA1 |
| Axonal Guidance Signaling | PRKCE; ITGAM; ROCK1; ITGA5; CXCR4; ADAM 12; IGF1; RAC1; RAP1A; E1F4E; PRKCZ; NRP1; NTRK2; ARHGEF7; SMO; ROCK2; MAPK1; PGF; RAC2; PTPN11; GNAS; AKT2; PIK3CA; ERBB2; PRKCI; PTK2; CFL1; GNAQ; PIK3CB; CXCL12; PIK3C3; WNT11; PRKD1; GNB2L1; ABL1; MAPK3; ITGA1; KRAS; RHOA; PRKCD; PIK3C2A; ITGB7; GLI2; PXN; VASP; RAF1; FYN; ITGB1; MAP2K2; PAK4; ADAM 17; AKT1; PIK3R1; GLI1; WNT5A; ADAM10; MAP2K1; PAK3; ITGB3; CDC42; VEGFA; ITGA2; EPHA8; CRKL; RND1; GSK3B; AKT3; PRKCA |
| Ephrin Receptor Signaling | PRKCE; ITGAM; ROCK1; ITGA5; CXCR4; IRAK1; PRKAA2; EIF2AK2; RAC1; RAP1A; GRK6; ROCK2; MAPK1; PGF; RAC2; PTPN11; GNAS; PLK1; AKT2; DOK1; CDK8; CREB1; PTK2; CFL1; GNAQ; MAP3K14; CXCL12; MAPK8; GNB2L1; ABL1; MAPK3; ITGA1; KRAS; RHOA; PRKCD; PRKAA1; MAPK9; SRC; CDK2; PIM1; ITGB7; PXN; RAF1; FYN; DYRK1A; ITGB1; MAP2K2; PAK4, AKT1; JAK2; STAT3; ADAM10; MAP2K1; PAK3; ITGB3; CDC42; VEGFA; ITGA2; EPHA8; TTK; CSNK1A1; CRKL; BRAF; PTPN13; ATF4; AKT3; SGK |
| Actin Cytoskeleton Signaling | ACTN4; PRKCE; ITGAM; ROCK1; ITGA5; IRAK1; PRKAA2; EIF2AK2; RAC1; INS; ARHGEF7; GRK6; ROCK2; MAPK1; RAC2; PLK1; AKT2; PIK3CA; CDK8; PTK2; CFL1; PIK3CB; MYH9; DIAPH1; PIK3C3; MAPK8; F2R; MAPK3; SLC9A1; ITGA1; KRAS; RHOA; PRKCD; PRKAA1; MAPK9; CDK2; PIM1; PIK3C2A; ITGB7; PPP1CC; PXN; VIL2; RAF1; GSN; DYRK1A; ITGB1; MAP2K2; PAK4; PIP5K1A; PIK3R1; MAP2K1; PAK3; ITGB3; CDC42; APC; ITGA2; TTK; CSNK1A1; CRKL; BRAF; VAV3; SGK |
| Huntington's Disease Signaling | PRKCE; IGF1; EP300; RCOR1; PRKCZ; HDAC4; TGM2; MAPK1; CAPNS1; AKT2; EGFR; NCOR2; SP1; CAPN2; PIK3CA; HDAC5; CREB1; PRKC1; HSPA5; REST; GNAQ; PIK3CB; PIK3C3; MAPK8; IGF1R; PRKD1; GNB2L1; BCL2L1; CAPN1; MAPK3; CASP8; HDAC2; HDAC7A; PRKCD; HDAC11; MAPK9; HDAC9; PIK3C2A; HDAC3; TP53; CASP9; CREBBP; AKT1; PIK3R1; PDPK1; CASP1; APAF1; FRAP1; CASP2; JUN; BAX; ATF4; AKT3; PRKCA; CLTC; SGK; HDAC6; CASP3 |
| Apoptosis Signaling | PRKCE; ROCK1; BID; IRAK1; PRKAA2; EIF2AK2; BAK1; BIRC4; GRK6; MAPK1; CAPNS1; PLK1; AKT2; IKBKB; CAPN2; CDK8; FAS; NFKB2; BCL2; MAP3K14; MAPK8; BCL2L1; CAPN1; MAPK3; CASP8; KRAS; RELA; PRKCD; PRKAA1; MAPK9; CDK2; PIM1; TP53; TNF; RAF1; IKBKG; RELB; CASP9; DYRK1A; MAP2K2; CHUK; APAF1; MAP2K1; NFKB1; PAK3; LMNA; CASP2; BIRC2; TTK; CSNK1A1; BRAF; BAX; PRKCA; SGK; CASP3; BIRC3; PARP1 |
| B Cell Receptor Signaling | RAC1; PTEN; LYN; ELK1; MAPK1; RAC2; PTPN11; AKT2; IKBKB; PIK3CA; CREB1; SYK; NFKB2; CAMK2A; MAP3K14; PIK3CB; PIK3C3; MAPK8; BCL2L1; ABL1; MAPK3; ETS1; KRAS; MAPK13; RELA; PTPN6; MAPK9; EGR1; PIK3C2A; BTK; MAPK14; RAF1; IKBKG; RELB; MAP3K7; MAP2K2; AKT1; PIK3R1; CHUK; MAP2K1; NFKB1; CDC42; GSK3A; FRAP1; BCL6; BCL10; JUN; GSK3B; ATF4; AKT3; VAV3; RPS6KB1 |
| Leukocyte Extravasation Signaling | ACTN4; CD44; PRKCE; ITGAM; ROCK1; CXCR4; CYBA; RAC1; RAP1A; PRKCZ; ROCK2; RAC2; PTPN11; MMP14; PIK3CA; PRKCI; PTK2; PIK3CB; CXCL12; PIK3C3; MAPK8; PRKD1; ABL1; MAPK10; CYBB; MAPK13; RHOA; PRKCD; MAPK9; SRC; PIK3C2A; BTK; MAPK14; NOX1; PXN; VIL2; VASP; ITGB1; MAP2K2; CTNND1; PIK3R1; CTNNB1; CLDN1; CDC42; F11R; ITK; CRKL; VAV3; CTTN; PRKCA; MMP1; MMP9 |
| Integrin Signaling | ACTN4; ITGAM; ROCK1; ITGA5; RAC1; PTEN; RAP1A; TLN1; ARHGEF7; MAPK1; RAC2; CAPNS1; AKT2; CAPN2; PIK3CA; PTK2; PIK3CB; PIK3C3; MAPK8; CAV1; CAPN1; ABL1; MAPK3; ITGA1; KRAS; RHOA; SRC; PIK3C2A; ITGB7; PPP1CC; ILK; PXN; VASP; RAF1; FYN; ITGB1; MAP2K2; PAK4; AKT1; PIK3R1; |

TABLE C-continued

| CELLULAR FUNCTION | GENES |
|---|---|
| | TNK2; MAP2K1; PAK3; ITGB3; CDC42; RND3; ITGA2; CRKL; BRAF; GSK3B; AKT3 |
| Acute Phase Response Signaling | IRAK1; SOD2; MYD88; TRAF6; ELK1; MAPK1; PTPN11; AKT2; IKBKB; PIK3CA; FOS; NFKB2; MAP3K14; PIK3CB; MAPK8; RIPK1; MAPK3; IL6ST; KRAS; MAPK13; IL6R; RELA; SOCS1; MAPK9; FTL; NR3C1; TRAF2; SERPINE1; MAPK14; TNF; RAF1; PDK1; IKBKG; RELB; MAP3K7; MAP2K2; AKT1; JAK2; PIK3R1; CHUK; STAT3; MAP2K1; NFKB1; FRAP1; CEBPB; JUN; AKT3; IL1R1; IL6 |
| PTEN Signaling | ITGAM; ITGA5; RAC1; PTEN; PRKCZ; BCL2L11; MAPK1; RAC2; AKT2; EGFR; IKBKB; CBL; PIK3CA; CDKN1B; PTK2; NFKB2; BCL2; PIK3CB; BCL2L1; MAPK3; ITGA1; KRAS; ITGB7; ILK; PDGFRB; INSR; RAF1; IKBKG; CASP9; CDKN1A; ITGB1; MAP2K2; AKT1; PIK3R1; CHUK; PDGFRA; PDPK1; MAP2K1; NFKB1; ITGB3; CDC42; CCND1; GSK3A; ITGA2; GSK3B; AKT3; FOXO1; CASP3; RPS6KB1 |
| p53 Signaling | PTEN; EP300; BBC3; PCAF; FASN; BRCA1; GADD45A; BIRC5; AKT2; PIK3CA; CHEK1; TP53INP1; BCL2; PIK3CB; PIK3C3; MAPK8; THBS1; ATR; BCL2L1; E2F1; PMAIP1; CHEK2; TNFRSF10B; TP73; RB1; HDAC9; CDK2; PIK3C2A; MAPK14; TP53; LRDD; CDKN1A; HIPK2; AKT1; PIK3R1; RRM2B; APAF1; CTNNB1; SIRT1; CCND1; PRKDC; ATM; SFN; CDKN2A; JUN; SNAI2; GSK3B; BAX; AKT3 |
| Aryl Hydrocarbon Receptor Signaling | HSPB1; EP300; FASN; TGM2; RXRA; MAPK1; NQO1; NCOR2; SP1; ARNT; CDKN1B; FOS; CHEK1; SMARCA4; NFKB2; MAPK8; ALDH1A1; ATR; E2F1; MAPK3; NRIP1; CHEK2; RELA; TP73; GSTP1; RB1; SRC; CDK2; AHR; NFE2L2; NCOA3; TP53; TNF; CDKN1A; NCOA2; APAF1; NFKB1; CCND1; ATM; ESR1; CDKN2A; MYC; JUN; ESR2; BAX; IL6; CYP1B1; HSP90AA1 |
| Xenobiotic Metabolism Signaling | PRKCE; EP300; PRKCZ; RXRA; MAPK1; NQO1; NCOR2; PIK3CA; ARNT; PRKCI; NFKB2; CAMK2A; PIK3CB; PPP2R1A; PIK3C3; MAPK8; PRKD1; ALDH1A1; MAPK3; NRIP1; KRAS; MAPK13; PRKCD; GSTP1; MAPK9; NOS2A; ABCB1; AHR; PPP2CA; FTL; NFE2L2; PIK3C2A; PPARGC1A; MAPK14; TNF; RAF1; CREBBP; MAP2K2; PIK3R1; PPP2R5C; MAP2K1; NFKB1; KEAP1; PRKCA; EIF2AK3; IL6; CYP1B1; HSP90AA1 |
| SAPK/JNK Signaling | PRKCE; IRAK1; PRKAA2; EIF2AK2; RAC1; ELK1; GRK6; MAPK1; GADD45A; RAC2; PLK1; AKT2; PIK3CA; FADD; CDK8; PIK3CB; PIK3C3; MAPK8; RIPK1; GNB2L1; IRS1; MAPK3; MAPK10; DAXX; KRAS; PRKCD; PRKAA1; MAPK9; CDK2; PIM1; PIK3C2A; TRAF2; TP53; LCK; MAP3K7; DYRK1A; MAP2K2; PIK3R1; MAP2K1; PAK3; CDC42; JUN; TTK; CSNK1A1; CRKL; BRAF; SGK |
| PPAr/RXR Signaling | PRKAA2; EP300; INS; SMAD2; TRAF6; PPARA; FASN; RXRA; MAPK1; SMAD3; GNAS; IKBKB; NCOR2; ABCA1; GNAQ; NFKB2; MAP3K14; STAT5B; MAPK8; IRS1; MAPK3; KRAS; RELA; PRKAA1; PPARGC1A; NCOA3; MAPK14; INSR; RAF1; IKBKG; RELB; MAP3K7; CREBBP; MAP2K2; JAK2; CHUK; MAP2K1; NFKB1; TGFBR1; SMAD4; JUN; IL1R1; PRKCA; IL6; HSP90AA1; ADIPOQ |
| NF-KB Signaling | IRAK1; EIF2AK2; EP300; INS; MYD88; PRKCZ: TRAF6; TBK1; AKT2; EGFR; IKBKB; PIK3CA; BTRC; NFKB2; MAP3K14; PIK3CB; PIK3C3; MAPK8; RIPK1; HDAC2; KRAS; RELA; PIK3C2A; TRAF2; TLR4; PDGFRB; TNF; INSR; LCK; IKBKG; RELB; MAP3K7; CREBBP; AKT1; PIK3R1; CHUK; PDGFRA; NFKB1; TLR2; BCL10; GSK3B; AKT3; TNFAIP3; IL1R1 |
| Neuregulin Signaling | ERBB4; PRKCE; ITGAM; ITGA5: PTEN; PRKCZ; ELK1; MAPK1; PTPN11; AKT2; EGFR; ERBB2; PRKCI; CDKN1B; STAT5B; PRKD1; MAPK3; ITGA1; KRAS; PRKCD; STAT5A; SRC; ITGB7; RAF1; ITGB1; MAP2K2; ADAM17; AKT1; PIK3R1; PDPK1; MAP2K1; ITGB3; EREG; FRAP1; PSEN1; ITGA2; MYC; NRG1; CRKL; AKT3; PRKCA; HSP90AA1; RPS6KB1 |
| Wnt & Beta catenin Signaling | CD44; EP300; LRP6; DVL3; CSNK1E; GJA1; SMO; AKT2; PIN1; CDH1; BTRC; GNAQ; MARK2; PPP2R1A; WNT11; SRC; DKK1; PPP2CA; SOX6; SFRP2; ILK; LEF1; SOX9; TP53; MAP3K7; CREBBP; TCF7L2; AKT1; PPP2R5C; WNT5A; LRP5; CTNNB1; TGFBR1; CCND1; |

TABLE C-continued

| CELLULAR FUNCTION | GENES |
| --- | --- |
| | GSK3A; DVL1; APC; CDKN2A; MYC; CSNK1A1; GSK3B; AKT3; SOX2 |
| Insulin Receptor Signaling | PTEN; INS; EIF4E; PTPN1; PRKCZ; MAPK1; TSC1; PTPN11; AKT2; CBL; PIK3CA; PRKCI; PIK3CB; PIK3C3; MAPK8; IRS1; MAPK3; TSC2; KRAS; EIF4EBP1; SLC2A4; PIK3C2A; PPP1CC; INSR; RAF1; FYN; MAP2K2; JAK1; AKT1; JAK2; PIK3R1; PDPK1; MAP2K1; GSK3A; FRAP1; CRKL; GSK3B; AKT3; FOXO1; SGK; RPS6KB1 |
| IL-6 Signaling | HSPB1; TRAF6; MAPKAPK2; ELK1; MAPK1; PTPN11; IKBKB; FOS; NFKB2: MAP3K14; MAPK8; MAPK3; MAPK10; IL6ST; KRAS; MAPK13; IL6R; RELA; SOCS1; MAPK9; ABCB1; TRAF2; MAPK14; TNF; RAF1; IKBKG; RELB; MAP3K7; MAP2K2; IL8; JAK2; CHUK; STAT3; MAP2K1; NFKB1; CEBPB; JUN; IL1R1; SRF; IL6 |
| Hepatic Cholestasis | PRKCE; IRAK1; INS; MYD88; PRKCZ; TRAF6; PPARA; RXRA; IKBKB; PRKCI; NFKB2; MAP3K14; MAPK8; PRKD1; MAPK10; RELA; PRKCD; MAPK9; ABCB1; TRAF2; TLR4; TNF; INSR; IKBKG; RELB; MAP3K7; IL8; CHUK; NR1H2; TJP2; NFKB1; ESR1; SREBF1; FGFR4; JUN; IL1R1; PRKCA; IL6 |
| IGF-1 Signaling | IGF1; PRKCZ; ELK1; MAPK1; PTPN11; NEDD4; AKT2; PIK3CA; PRKCI; PTK2; FOS; PIK3CB; PIK3C3; MAPK8; IGF1R; IRS1; MAPK3; IGFBP7; KRAS; PIK3C2A; YWHAZ; PXN; RAF1; CASP9; MAP2K2; AKT1; PIK3R1; PDPK1; MAP2K1; IGFBP2; SFN; JUN; CYR61; AKT3; FOXO1; SRF; CTGF; RPS6KB1 |
| NRF2-mediated Oxidative Stress Response | PRKCE; EP300; SOD2; PRKCZ; MAPK1; SQSTM1; NQO1; PIK3CA; PRKCI; FOS; PIK3CB; PIK3C3; MAPK8; PRKD1; MAPK3; KRAS; PRKCD; GSTP1; MAPK9; FTL; NFE2L2; PIK3C2A; MAPK14; RAF1; MAP3K7; CREBBP; MAP2K2; AKT1; PIK3R1; MAP2K1; PPIB; JUN; KEAP1; GSK3B; ATF4; PRKCA; EIF2AK3; HSP90AA1 |
| Hepatic Fibrosis/Hepatic Stellate Cell Activation | EDN1; IGF1; KDR; FLT1; SMAD2; FGFR1; MET; PGF; SMAD3; EGFR; FAS; CSF1; NFKB2; BCL2; MYH9; IGF1R; IL6R; RELA; TLR4; PDGFRB; TNF; RELB; IL8; PDGFRA; NFKB1; TGFBR1; SMAD4; VEGFA; BAX; IL1R1; CCL2; HGF; MMP1; STAT1; IL6; CTGF; MMP9 |
| PPAR Signaling | EP300; INS; TRAF6; PPARA; RXRA; MAPK1; IKBKB; NCOR2; FOS; NFKB2; MAP3K14; STAT5B; MAPK3; NRIP1; KRAS; PPARG; RELA; STAT5A; TRAF2; PPARGC1A; PDGFRB; TNF; INSR; RAF1; IKBKG; RELB; MAP3K7; CREBBP; MAP2K2; CHUK; PDGFRA; MAP2K1; NFKB1; JUN; IL1R1; HSP90AA1 |
| Fc Epsilon RI Signaling | PRKCE; RAC1; PRKCZ; LYN; MAPK1; RAC2; PTPN11; AKT2; PIK3CA; SYK; PRKCI; PIK3CB; PIK3C3; MAPK8; PRKD1; MAPK3; MAPK10; KRAS; MAPK13; PRKCD; MAPK9; PIK3C2A; BTK; MAPK14; TNF; RAF1; FYN; MAP2K2; AKT1; PIK3R1; PDPK1; MAP2K1; AKT3; VAV3; PRKCA |
| G-Protein Coupled Receptor Signaling | PRKCE; RAP1A; RGS16; MAPK1; GNAS; AKT2; IKBKB; PIK3CA; CREB1; GNAQ; NFKB2; CAMK2A; PIK3CB; PIK3C3; MAPK3; KRAS; RELA; SRC; PIK3C2A; RAF1; IKBKG; RELB; FYN; MAP2K2; AKT1; PIK3R1; CHUK; PDPK1; STAT3; MAP2K1; NFKB1; BRAF; ATF4; AKT3; PRKCA |
| Inositol Phosphate Metabolism | PRKCE; IRAK1; PRKAA2; EIF2AK2; PTEN; GRK6; MAPK1; PLK1; AKT2; PIK3CA; CDK8; PIK3CB; PIK3C3; MAPK8; MAPK3; PRKCD; PRKAA1; MAPK9; CDK2; PIM1; PIK3C2A; DYRK1A; MAP2K2; PIP5K1A; PIK3R1; MAP2K1; PAK3; ATM; TTK; CSNK1A1; BRAF; SGK |
| PDGF Signaling | EIF2AK2; ELK1; ABL2; MAPK1; PIK3CA; FOS; PIK3CB; PIK3C3; MAPK8; CAV1; ABL1; MAPK3; KRAS; SRC; PIK3C2A; PDGFRB; RAF1; MAP2K2; JAK1; JAK2; PIK3R1; PDGFRA; STAT3; SPHK1; MAP2K1; MYC; JUN; CRKL; PRKCA; SRF; STAT1; SPHK2 |
| VEGF Signaling | ACTN4; ROCK1; KDR; FLT1; ROCK2; MAPK1; PGF; AKT2; PIK3CA; ARNT; PTK2; BCL2; PIK3CB; PIK3C3; BCL2L1; MAPK3; KRAS; HIF1A; NOS3; PIK3C2A; PXN; RAF1; MAP2K2; ELAVL1; AKT1; PIK3R1; MAP2K1; SFN; VEGFA; AKT3; FOXO1; PRKCA |
| Natural Killer Cell Signaling | PRKCE; RAC1; PRKCZ; MAPK1; RAC2; PTPN11; KIR2DL3; AKT2; PIK3CA; SYK; PRKCI; PIK3CB; PIK3C3; PRKD1; MAPK3; KRAS; PRKCD; PTPN6; PIK3C2A; LCK; RAF1; FYN; MAP2K2; PAK4; AKT1; PIK3R1; MAP2K1; PAK3; AKT3; VAV3; PRKCA |
| Cell Cycle: G1/S Checkpoint Regulation | HDAC4; SMAD3; SUV39H1; HDAC5; CDKN1B; BTRC; ATR; ABL1; E2F1; HDAC2; HDAC7A; RB1; HDAC11; |

TABLE C-continued

| CELLULAR FUNCTION | GENES |
| --- | --- |
| | HDAC9; CDK2; E2F2; HDAC3; TP53; CDKN1A; CCND1; E2F4; ATM; RBL2; SMAD4; CDKN2A; MYC; NRG1; GSK3B; RBL1; HDAC6 |
| T Cell Receptor Signaling | RAC1; ELK1; MAPK1; IKBKB; CBL; PIK3CA; FOS; NFKB2; PIK3CB; PIK3C3; MAPK8; MAPK3; KRAS; RELA, PIK3C2A; BTK; LCK; RAF1; IKBKG; RELB, FYN; MAP2K2; PIK3R1; CHUK; MAP2K1; NFKB1; ITK; BCL10; JUN; VAV3 |
| Death Receptor Signaling | CRADD; HSPB1; BID; BIRC4; TBK1; IKBKB; FADD; FAS; NFKB2; BCL2; MAP3K14; MAPK8; RIPK1; CASP8; DAXX; TNFRSF10B; RELA; TRAF2; TNF; IKBKG; RELB; CASP9; CHUK; APAF1; NFKB1; CASP2; BIRC2; CASP3; BIRC3 |
| FGF Signaling | RAC1; FGFR1; MET; MAPKAPK2; MAPK1; PTPN11; AKT2; PIK3CA; CREB1; PIK3CB; PIK3C3; MAPK8; MAPK3; MAPK13; PTPN6; PIK3C2A; MAPK14; RAF1; AKT1; PIK3R1; STAT3; MAP2K1; FGFR4; CRKL; ATF4; AKT3; PRKCA; HGF |
| GM-CSF Signaling | LYN; ELK1; MAPK1; PTPN11; AKT2; PIK3CA; CAMK2A; STAT5B; PIK3CB; PIK3C3; GNB2L1; BCL2L1; MAPK3; ETS1; KRAS; RUNX1; PIM1; PIK3C2A; RAF1; MAP2K2; AKT1; JAK2; PIK3R1; STAT3; MAP2K1; CCND1; AKT3; STAT1 |
| Amyotrophic Lateral Sclerosis Signaling | BID; IGF1; RAC1; BIRC4; PGF; CAPNS1; CAPN2; PIK3CA; BCL2; PIK3CB; PIK3C3; BCL2L1; CAPN1; PIK3C2A; TP53; CASP9; PIK3R1; RAB5A; CASP1; APAF1; VEGFA; BIRC2; BAX; AKT3; CASP3; BIRC3 |
| JAK/Stat Signaling | PTPN1; MAPK1; PTPN11; AKT2; PIK3CA; STAT5B; PIK3CB; PIK3C3; MAPK3; KRAS; SOCS1; STAT5A; PTPN6; PIK3C2A; RAF1; CDKN1A; MAP2K2; JAK1; AKT1; JAK2; PIK3R1; STAT3; MAP2K1; FRAP1; AKT3; STAT1 |
| Nicotinate and Nicotinamide Metabolism | PRKCE; IRAK1; PRKAA2; EIF2AK2; GRK6; MAPK1; PLK1; AKT2; CDK8; MAPK8; MAPK3; PRKCD; PRKAA1; PBEF1; MAPK9; CDK2; PIM1; DYRK1A; MAP2K2; MAP2K1; PAK3; NT5E; TTK; CSNK1A1; BRAF; SGK |
| Chemokine Signaling | CXCR4; ROCK2; MAPK1; PTK2; FOS; CFL1; GNAQ; CAMK2A; CXCL12; MAPK8; MAPK3; KRAS; MAPK13; RHOA; CCR3; SRC; PPP1CC; MAPK14; NOX1; RAF1; MAP2K2; MAP2K1; JUN; CCL2; PRKCA |
| IL-2 Signaling | ELK1; MAPK1; PTPN11; AKT2; PIK3CA; SYK; FOS; STAT5B; PIK3CB; PIK3C3; MAPK8; MAPK3; KRAS; SOCS1; STAT5A; PIK3C2A; LCK; RAF1; MAP2K2; JAK1; AKT1; PIK3R1; MAP2K1; JUN; AKT3 |
| Synaptic Long Term Depression | PRKCE; IGF1; PRKCZ; PRDX6; LYN; MAPK1; GNAS; PRKCI; GNAQ; PPP2R1A; IGF1R; PRKD1; MAPK3; KRAS; GRN; PRKCD; NOS3; NOS2A; PPP2CA; YWHAZ; RAF1; MAP2K2; PPP2R5C; MAP2K1; PRKCA |
| Estrogen Receptor Signaling | TAF4B; EP300; CARM1; PCAF; MAPK1; NCOR2; SMARCA4; MAPK3; NRIP1; KRAS; SRC; NR3C1; HDAC3; PPARGC1A; RBM9; NCOA3; RAF1; CREBBP; MAP2K2; NCOA2; MAP2K1; PRKDC; ESR1; ESR2 |
| Protein Ubiquitination Pathway | TRAF6; SMURF1; BIRC4; BRCA1; UCHL1; NEDD4; CBL; UBE2I; BTRC; HSPA5; USP7; USP10; FBXW7; USP9X; STUB1; USP22; B2M; BIRC2; PARK2; USP8; USP1; VHL; HSP90AA1; BIRC3 |
| IL-10 Signaling | TRAF6; CCR1; ELK1; IKBKB; SP1; FOS; NFKB2; MAP3K14; MAPK8; MAPK13; RELA; MAPK14; TNF; IKBKG; RELB; MAP3K7; JAK1; CHUK; STAT3; NFKB1; JUN; IL1R1; IL6 |
| VDR/RXR Activation | PRKCE; EP300; PRKCZ; RXRA; GADD45A; HES1; NCOR2; SP1; PRKCI; CDKN1B; PRKD1; PRKCD; RUNX2; KLF4; YY1; NCOA3; CDKN1A; NCOA2; SPP1; LRP5; CEBPB; FOXO1; PRKCA |
| TGF-beta Signaling | EP300; SMAD2; SMURF1; MAPK1; SMAD3; SMAD1; FOS; MAPK8; MAPK3; KRAS; MAPK9; RUNX2; SERPINE1; RAF1; MAP3K7; CREBBP; MAP2K2; MAP2K1; TGFBR1; SMAD4; JUN; SMAD5 |
| Toll-like Receptor Signaling | IRAK1; EIF2AK2; MYD88; TRAF6; PPARA; ELK1; IKBKB; FOS; NFKB2; MAP3K14; MAPK8; MAPK13; RELA; TLR4; MAPK14; IKBKG; RELB; MAP3K7; CHUK; NFKB1; TLR2; JUN |
| p38 MAPK Signaling | HSPB1; IRAK1; TRAF6; MAPKAPK2; ELK1; FADD; FAS; CREB1; DDIT3; RPS6KA4; DAXX; MAPK13; TRAF2; MAPK14; TNF; MAP3K7; TGFBR1; MYC; ATF4; IL1R1; SRF; STAT1 |
| Neurotrophin/TRK Signaling | NTRK2; MAPK1; PTPN11; PIK3CA; CREB1; FOS; PIK3CB; PIK3C3; MAPK8; MAPK3; KRAS; PIK3C2A; |

TABLE C-continued

| CELLULAR FUNCTION | GENES |
|---|---|
| | RAF1; MAP2K2; AKT1; PIK3R1; PDPK1; MAP2K1; CDC42; JUN; ATF4 |
| FXR/RXR Activation | INS; PPARA; FASN; RXRA; AKT2; SDC1; MAPK8; APOB; MAPK10; PPARG; MTTP; MAPK9; PPARGC1A; TNF; CREBBP; AKT1; SREBF1; FGFR4; AKT3; FOXO1 |
| Synaptic Long Term Potentiation | PRKCE; RAP1A; EP300; PRKCZ; MAPK1; CREB1; PRKCI; GNAQ; CAMK2A; PRKD1; MAPK3; KRAS; PRKCD; PPP1CC; RAF1; CREBBP; MAP2K2; MAP2K1; ATF4; PRKCA |
| Calcium Signaling | RAP1A; EP300; HDAC4; MAPK1; HDAC5; CREB1; CAMK2A; MYH9; MAPK3; HDAC2; HDAC7A; HDAC11; HDAC9; HDAC3; CREBBP; CALR; CAMKK2; ATF4; HDAC6 |
| EGF Signaling | ELK1; MAPK1; EGFR; PIK3CA; FOS; PIK3CB; PIK3C3; MAPK8; MAPK3; PIK3C2A; RAF1; JAK1; PIK3R1; STAT3; MAP2K1; JUN; PRKCA; SRF; STAT1 |
| Hypoxia Signaling in the Cardiovascular System | EDN1; PTEN; EP300; NQO1; UBE2I; CREB1; ARNT; HIF1A; SLC2A4; NOS3; TP53; LDHA; AKT1; ATM; VEGFA; JUN; ATF4; VHL; HSP90AA1 |
| LPS/IL-1 Mediated Inhibition of RXR Function | IRAK1; MYD88; TRAF6; PPARA; RXRA; ABCA1, MAPK8; ALDH1A1; GSTP1; MAPK9; ABCB1; TRAF2; TLR4; TNF; MAP3K7; NR1H2; SREBF1; JUN; IL1R1 |
| LXR/RXR Activation | FASN; RXRA; NCOR2; ABCA1; NFKB2; IRF3; RELA; NOS2A; TLR4; TNF; RELB; LDLR; NR1H2; NFKB1; SREBF1; IL1R1; CCL2; IL6; MMP9 |
| Amyloid Processing | PRKCE; CSNK1E; MAPK1; CAPNS1; AKT2; CAPN2; CAPN1; MAPK3; MAPK13; MAPT; MAPK14; AKT1; PSEN1; CSNK1A1; GSK3B; AKT3; APP |
| IL-4 Signaling | AKT2; PIK3CA; PIK3CB; PIK3C3; IRS1; KRAS; SOCS1; PTPN6; NR3C1; PIK3C2A; JAK1; AKT1; JAK2; PIK3R1; FRAP1; AKT3; RPS6KB1 |
| Cell Cycle: G2/M DNA Damage Checkpoint Regulation | EP300; PCAF; BRCA1; GADD45A; PLK1; BTRC; CHEK1; ATR; CHEK2; YWHAZ; TP53; CDKN1A; PRKDC; ATM; SFN; CDKN2A |
| Nitric Oxide Signaling in the Cardiovascular System | KDR; FLT1; PGF; AKT2; PIK3CA; PIK3CB; PIK3C3; CAV1; PRKCD; NOS3; PIK3C2A; AKT1; PIK3R1; VEGFA; AKT3; HSP90AA1 |
| Purine Metabolism | NME2; SMARCA4; MYH9; RRM2; ADAR; EIF2AK4; PKM2; ENTPD1; RAD51; RRM2B; TJP2; RAD51C; NT5E; POLD1; NME1 |
| cAMP-mediated Signaling | RAP1A; MAPK1; GNAS; CREB1; CAMK2A; MAPK3; SRC; RAF1; MAP2K2; STAT3; MAP2K1; BRAF; ATF4 |
| Mitochondrial Dysfunction | SOD2; MAPK8; CASP8; MAPK10; MAPK9; CASP9; PARK7; PSEN1; PARK2; APP; CASP3 |
| Notch Signaling | HES1; JAG1; NUMB; NOTCH4; ADAM17; NOTCH2; PSEN1; NOTCH3; NOTCH1; DLL4 |
| Endoplasmic Reticulum Stress Pathway | HSPA5; MAPK8; XBP1; TRAF2; ATF6; CASP9; ATF4; EIF2AK3; CASP3 |
| Pyrimidine Metabolism | NME2; AICDA; RRM2; EIF2AK4; ENTPD1; RRM2B; NT5E; POLD1; NME1 |
| Parkinson's Signaling | UCHL1; MAPK8; MAPK13; MAPK14; CASP9; PARK7; PARK2; CASP3 |
| Cardiac & Beta Adrenergic Signaling | GNAS; GNAQ; PPP2R1A; GNB2L1; PPP2CA; PPP1CC; PPP2R5C |
| Glycolysis/ Gluconeogenesis | HK2; GCK; GPI; ALDH1A1; PKM2; LDHA; HK1 |
| Interferon Signaling | IRF1; SOCS1; JAK1; JAK2; IFITM1; STAT1; IFIT3 |
| Sonic Hedgehog Signaling | ARRB2; SMO; GLI2; DYRK1A; GLI1; GSK3B; DYRKIB |
| Glycerophospholipid Metabolism | PLD1; GRN; GPAM; YWHAZ; SPHK1; SPHK2 |
| Phospholipid Degradation | PRDX6; PLD1; GRN; YWHAZ; SPHK1; SPHK2 |
| Tryptophan Metabolism | SIAH2; PRMT5; NEDD4; ALDH1A1; CYP1B1; SIAH1 |
| Lysine Degradation | SUV39H1; EHMT2; NSD1; SETD7; PPP2R5C |
| Nucleotide Excision Repair Pathway | ERCC5; ERCC4; XPA; XPC; ERCC1 |
| Starch and Sucrose Metabolism | UCHL1; HK2; GCK; GPI; HK1 |
| Aminosugars Metabolism | NQO1; HK2; GCK; HK1 |
| Arachidonic Acid Metabolism | PRDX6; GRN; YWHAZ; CYP1B1 |
| Circadian Rhythm Signaling | CSNK1E; CREB1; ATF4; NR1D1 |
| Coagulation System | BDKRB1; F2R; SERPINE1; F3 |
| Dopamine Receptor Signaling | PPP2R1A; PPP2CA; PPP1CC; PPP2R5C |
| Glutathione Metabolism | IDH2; GSTP1; ANPEP; IDH1 |

TABLE C-continued

| CELLULAR FUNCTION | GENES |
|---|---|
| Glycerolipid Metabolism | ALDH1A1; GPAM; SPHK1; SPHK2 |
| Linoleic Acid Metabolism | PRDX6; GRN; YWHAZ; CYP1B1 |
| Methionine Metabolism | DNMT1; DNMT3B; AHCY; DNMT3A |
| Pyruvate Metabolism | GLO1; ALDH1A1; PKM2; LDHA |
| Arginine and Proline Metabolism | ALDH1A1; NOS3; NOS2A |
| Eicosanoid Signaling | PRDX6; GRN; YWHAZ |
| Fructose and Mannose Metabolism | HK2; GCK; HK1 |
| Galactose Metabolism | HK2; GCK; HK1 |
| Stilbene, Coumarine and Lignin Biosynthesis | PRDX6; PRDX1; TYR |
| Antigen Presentation Pathway | CALR; B2M |
| Biosynthesis of Steroids | NQO1; DHCR7 |
| Butanoate Metabolism | ALDH1A1; NLGN1 |
| Citrate Cycle | IDH2; IDH1 |
| Fatty Acid Metabolism | ALDH1A1; CYP1B1 |
| Glycerophospholipid Metabolism | PRDX6; CHKA |
| Histidine Metabolism | PRMT5; ALDH1A1 |
| Inositol Metabolism | ERO1L; APEX1 |
| Metabolism of Xenobiotics by Cytochrome p450 | GSTP1; CYP1B1 |
| Methane Metabolism | PRDX6; PRDX1 |
| Phenylalanine Metabolism | PRDX6; PRDX1 |
| Propanoate Metabolism | ALDH1A1; LDHA |
| Selenoamino Acid Metabolism | PRMT5; AHCY |
| Sphingolipid Metabolism | SPHK1; SPHK2 |
| Aminophosphonate Metabolism | PRMT5 |
| Androgen and Estrogen Metabolism | PRMT5 |
| Ascorbate and Aldarate Metabolism | ALDH1A1 |
| Bile Acid Biosynthesis | ALDH1A1 |
| Cysteine Metabolism | LDHA |
| Fatty Acid Biosynthesis | FASN |
| Glutamate Receptor Signaling | GNB2L1 |
| NRF2-mediated Oxidative Stress Response | PRDX1 |
| Pentose Phosphate Pathway | GPI |
| Pentose and Glucuronate Interconversions | UCHL1 |
| Retinol Metabolism | ALDH1A1 |
| Riboflavin Metabolism | TYR |
| Tyrosine Metabolism | PRMT5, TYR |
| Ubiquinone Biosynthesis | PRMT5 |
| Valine, Leucine and Isoleucine Degradation | ALDH1A1 |
| Glycine, Serine and Threonine Metabolism | CHKA |
| Lysine Degradation | ALDH1A1 |
| Pain/Taste | TRPM5; TRPA1 |
| Pain | TRPM7; TRPC5; TRPC6; TRPC1; Cnr1; cnr2; Grk2; Trpa1; Pomc; Cgrp; Crf; Pka; Era; Nr2b; TRPM5; Prkaca; Prkacb; Prkar1a; Prkar2a |
| Mitochondrial Function | AIF; CytC; SMAC (Diablo); Aifm-1; Aifm-2 |
| Developmental Neurology | BMP-4; Chordin (Chrd); Noggin (Nog); WNT (Wnt2; Wnt2b; Wnt3a; Wnt4; Wnt5a; Wnt6; Wnt7b; Wnt8b; Wnt9a; Wnt9b; Wnt10a; Wnt10b; Wnt16); beta-catenin; Dkk-1; Frizzled related proteins; Otx-2; Gbx2; FGF-8; Reelin; Dab1; unc-86 (Pou4fl or Brn3a); Numb; Reln |

Embodiments of the invention also relate to methods and compositions related to silencing genes, or inducing or increasing expression of genes through altering the loop or domain in which thay are located.

Several further aspects of the invention relate to silencing genes having a defect, and inducing expression of other genomic copies of that same genein the genome that are not defective. Genes associated with a wide range of genetic diseases which are further described on the website of the National Institutes of Health under the topic subsection Genetic Disorders. The genetic brain diseases may include but are not limited to Adrenoleukodystrophy, Agenesis of the Corpus Callosum, Aicardi Syndrome, Alpers' Disease, Alzheimer's Disease, Barth Syndrome, Batten Disease, CADASIL, Cerebellar Degeneration, Fabry's Disease, Gerstmann-Straussler-Scheinker Disease, Huntington's Disease and other Triplet Repeat Disorders, Leigh's Disease, Lesch-Nyhan Syndrome, Menkes Disease, Mitochondrial Myopathies and NINDS Colpocephaly. These diseases are further described on the website of the National Institutes of Health under the subsection Genetic Brain Disorders.

In some embodiments, the condition may be neoplasia. In some embodiments, where the condition is neoplasia, the genes to be targeted (or he locus of the genes that is to be targeted) are any of those listed in Table A. In some embodiments, the condition may be Age-related Macular Degeneration. In some embodiments, the condition may be a Schizophrenic Disorder. In some embodiments, the condition may be a Trinucleotide Repeat Disorder. In some embodiments, the condition may be Fragile X Syndrome. In some embodiments, the condition may be a Secretase Related Disorder. In some embodiments, the condition may be a Prion—related disorder. In some embodiments, the condition may be ALS. In some embodiments, the condition may be a drug addiction. In some embodiments, the condition may be Autism. In some embodiments, the condition may be Alzheimer's Disease. In some embodiments, the condition may be inflammation. In some embodiments, the condition may be Parkinson's Disease.

It is envisaged that the present methods for interfering in chromatin looping is used to change the expression of disease associated proteins, or other proteins in a living cell, through modification of the contacts that the genes encoding these proteins have with other genes in a contact domain. Examples of disease associated proteins proteins associated with Parkinson's disease include but are not limited to α-synuclein, DJ-1, LRRK2, PINK1, Parkin, UCHL1, Synphilin-1, and NURR1.

Examples of addiction-related proteins may include ABAT for example.

Examples of inflammation-related proteins may include the monocyte chemoattractant protein-1 (MCP1) encoded by the Ccr2 gene, the C-C chemokine receptor type 5 (CCR5) encoded by the Ccr5 gene, the IgG receptor IIB (FCGR2b, also termed CD32) encoded by the Fcgr2b gene, or the Fc epsilon R1g (FCER1g) protein encoded by the Fcer1g gene, for example.

Examples of cardiovascular diseases associated proteins may include IL1B (interleukin 1, beta), XDH (xanthine dehydrogenase), TP53 (tumor protein p53), PTGIS (prostaglandin 12 (prostacyclin) synthase), MB (myoglobin), IL4 (interleukin 4), ANGPT1 (angiopoietin 1), ABCG8 (ATP-binding cassette, sub-family G (WHITE), member 8), or CTSK (cathepsin K), for example.

Examples of Alzheimer's disease associated proteins may include the very low density lipoprotein receptor protein (VLDLR) encoded by the VLDLR gene, the ubiquitin-like modifier activating enzyme 1 (UBA1) encoded by the UBA1 gene, or the NEDD8-activating enzyme E1 catalytic subunit protein (UBE1C) encoded by the UBA3 gene, for example.

Examples of proteins associated with Autism Spectrum Disorder may include the benzodiazapine receptor (peripheral) associated protein 1 (BZRAP1) encoded by the BZRAP1 gene, the AF4/FMR2 family member 2 protein (AFF2) encoded by the AFF2 gene (also termed MFR2), the fragile X mental retardation autosomal homolog 1 protein (FXR1) encoded by the FXR1 gene, or the fragile X mental retardation autosomal homolog 2 protein (FXR2) encoded by the FXR2 gene, for example.

Examples of proteins associated with Macular Degeneration may include the ATP-binding cassette, sub-family A (ABC1) member 4 protein (ABCA4) encoded by the ABCR gene, the apolipoprotein E protein (APOE) encoded by the APOE gene, or the chemokine (C-C motif) Ligand 2 protein (CCL2) encoded by the CCL2 gene, for example.

Examples of proteins associated with Schizophrenia may include NRG1, ErbB4, CPLX1, TPH1, TPH2, NRXN1, GSK3A, BDNF, DISC1, GSK3B, and combinations thereof.

Examples of proteins involved in tumor suppression may include ATM (ataxia telangiectasia mutated), ATR (ataxia telangiectasia and Rad3 related), EGFR (epidermal growth factor receptor), ERBB2 (v-erb-b2 erythroblastic leukemia viral oncogene homolog 2), ERBB3 (v-erb-b2 erythroblastic leukemia viral oncogene homolog 3), ERBB4 (v-erb-b2 erythroblastic leukemia viral oncogene homolog 4), Notch 1, Notch2, Notch 3, or Notch 4, for example.

Examples of proteins associated with a secretase disorder may include PSENEN (presenilin enhancer 2 homolog (C. elegans)), CTSB (cathepsin B), PSEN1 (presenilin 1), APP (amyloid beta (A4) precursor protein), APH1B (anterior pharynx defective 1 homolog B (C. elegans)), PSEN2 (presenilin 2 (Alzheimer disease 4)), or BACE1 (beta-site APP-cleaving enzyme 1), for example.

Examples of proteins associated with Amyotrophic Lateral Sclerosis may include SOD1 (superoxide dismutase 1), ALS2 (amyotrophic lateral sclerosis 2), FUS (fused in sarcoma), TARDBP (TAR DNA binding protein), VAGFA (vascular endothelial growth factor A), VAGFB (vascular endothelial growth factor B), and VAGFC (vascular endothelial growth factor C), and any combination thereof.

Examples of proteins associated with prion diseases may include SOD1 (superoxide dismutase 1), ALS2 (amyotrophic lateral sclerosis 2), FUS (fused in sarcoma), TARDBP (TAR DNA binding protein), VAGFA (vascular endothelial growth factor A), VAGFB (vascular endothelial growth factor B), and VAGFC (vascular endothelial growth factor C), and any combination thereof.

Examples of proteins related to neurodegenerative conditions in prion disorders may include A2M (Alpha-2-Macroglobulin), AATF (Apoptosis antagonizing transcription factor), ACPP (Acid phosphatase prostate), ACTA2 (Actin alpha 2 smooth muscle aorta), ADAM22 (ADAM metallopeptidase domain), ADORA3 (Adenosine A3 receptor), or ADRA1D (Alpha-1D adrenergic receptor for Alpha-1D adrenoreceptor), for example.

Examples of proteins associated with Immunodeficiency may include A2M [alpha-2-macroglobulin]; AANAT [arylalkylamine N-acetyltransferase]; ABCA1 [ATP-binding cassette, sub-family A (ABC1), member 1]; ABCA2 [ATP-binding cassette, sub-family A (ABC1), member 2]; or ABCA3 [ATP-binding cassette, sub-family A (ABC1), member 3]; for example.

Examples of proteins associated with Trinucleotide Repeat Disorders include AR (androgen receptor), FMR1 (fragile X mental retardation 1), HTT (huntingtin), or DMPK (dystrophia myotonica-protein kinase), FXN (frataxin), ATXN2 (ataxin 2), for example.

Examples of proteins associated with Neurotransmission Disorders include SST (somatostatin), NOS1 (nitric oxide synthase 1 (neuronal)), ADRA2A (adrenergic, alpha-2A-, receptor), ADRA2C (adrenergic, alpha-2C-, receptor), TACR1 (tachykinin receptor 1), or HTR2c (5-hydroxytryptamine (serotonin) receptor 2C), for example.

Examples of neurodevelopmental-associated sequences include A2BP1 [ataxin 2-binding protein 1], AADAT [aminoadipate aminotransferase], AANAT [arylalkylamine N-acetyltransferase], ABAT [4-aminobutyrate aminotransferase], ABCA1 [ATP-binding cassette, sub-family A (ABC1), member 1], or ABCA13 [ATP-binding cassette, sub-family A (ABC1), member 13], for example.

Further examples of preferred conditions treatable with the present system include may be selected from: Aicardi-Goutiéres Syndrome; Alexander Disease; Allan-Herndon-Dudley Syndrome; POLG-Related Disorders; Alpha-Mannosidosis (Type II and III); Alstrom Syndrome; Angelman; Syndrome; Ataxia-Telangiectasia; Neuronal Ceroid-Lipofuscinoses; Beta-Thalassemia; Bilateral Optic Atrophy and (Infantile) Optic Atrophy Type 1; Retinoblastoma (bilateral); Canavan Disease; Cerebrooculofacioskeletal Syndrome 1 [COFS1]; Cerebrotendinous Xanthomatosis; Cornelia de Lange Syndrome; MAPT-Related Disorders; Genetic Prion Diseases; Dravet Syndrome; Early-Onset Familial Alzheimer Disease; Friedreich Ataxia [FRDA]; Fryns Syndrome; Fucosidosis; Fukuyama Congenital Muscular Dystrophy; Galactosialidosis; Gaucher Disease; Organic Acidemias; Hemophagocytic Lymphohistiocytosis; Hutchinson-Gilford Progeria Syndrome; Mucolipidosis II; Infantile Free Sialic Acid Storage Disease; PLA2G6-Associated Neurodegeneration; Jervell and Lange-Nielsen Syndrome; Junctional Epidermolysis Bullosa; Huntington Disease; Krabbe Disease (Infantile); Mitochondrial DNA-Associated Leigh Syndrome and NARP; Lesch-Nyhan Syndrome; LIS1-Associated Lissencephaly; Lowe Syndrome; Maple Syrup Urine Disease; MECP2 Duplication Syndrome; ATP7A-Related Copper Transport Disorders; LAMA2-Related Muscular Dystrophy; Arylsulfatase A Deficiency; Mucopolysaccharidosis Types I, II or III; Peroxisome Biogenesis Disorders, Zellweger Syndrome Spectrum; Neurodegeneration with Brain Iron Accumulation Disorders; Acid Sphingomyelinase Deficiency; Niemann-Pick Disease Type C; Glycine Encephalopathy; ARX-Related Disorders; Urea Cycle Disorders; COL1A1/2-Related Osteogenesis Imperfecta; Mitochondrial DNA Deletion Syndromes; PLP1-Related Disorders; Perry Syndrome; Phelan-McDermid Syndrome; Glycogen Storage Disease Type II (Pompe Disease) (Infantile); MAPT-Related Disorders; MECP2-Related Disorders; Rhizomelic Chondrodysplasia *Punctata* Type 1; Roberts Syndrome; Sandhoff Disease; Schindler Disease—Type 1; Adenosine Deaminase Deficiency; Smith-Lemli-Opitz Syndrome; Spinal Muscular Atrophy; Infantile-Onset Spinocerebellar Ataxia; Hexosaminidase A Deficiency; Thanatophoric Dysplasia Type 1; Collagen Type VI-Related Disorders; Usher Syndrome Type I; Congenital Muscular Dystrophy; Wolf-Hirschhorn Syndrome; Lysosomal Acid Lipase Deficiency; and Xeroderma Pigmentosum.

Chronic administration of protein therapeutics may elicit unacceptable immune responses to the specific protein. The immunogenicity of protein drugs can be ascribed to a few immunodominant helper T lymphocyte (HTL) epitopes. Reducing the MHC binding affinity of these HTL epitopes contained within these proteins can generate drugs with lower immunogenicity (Tangri S, et al. ("Rationally engineered therapeutic proteins with reduced immunogenicity" J Immunol. 2005 Mar. 15; 174(6):3187-96.) In the present invention, the immunogenicity of the CRISPR enzyme in particular may be reduced following the approach first set out in Tangri et al with respect to erythropoietin and subsequently developed. Accordingly, directed evolution or rational design may be used to reduce the immunogenicity of the CRISPR enzyme (for instance a Cas9) in the host species (human or other species).

In plants, pathogens are often host-specific. For example, *Fusarium oxysporum*. f sp. *lycopersici* causes tomato wilt but attacks only tomato, and *F. oxysporum* f. *dianthii Puccinia graminis* f. sp. *tritici* attacks only wheat. Plants have existing and induced defenses to resist most pathogens. Mutations and recombination events across plant generations lead to genetic variability that gives rise to susceptibility, especially as pathogens reproduce with more frequency than plants. In plants there can be non-host resistance, e.g., the host and pathogen are incompatible. There can also be Horizontal Resistance, e.g., partial resistance against all races of a pathogen, typically controlled by many genes and Vertical Resistance, e.g., complete resistance to some races of a pathogen but not to other races, typically controlled by a few genes. In a Gene-for-Gene level, plants and pathogens evolve together, and the genetic changes in one balance changes in other. Accordingly, using Natural Variability, breeders combine most useful genes for Yield, Quality, Uniformity, Hardiness, Resistance. The sources of resistance genes include native or foreign Varieties, Heirloom Varieties, Wild Plant Relatives, and Induced Mutations, e.g., treating plant material with mutagenic agents. Using the present invention, plant breeders are provided with a new tool to alter gene expression in their plants. Accordingly, one skilled in the art can analyze the genome of sources of resistance genes, and in Varieties having desired characteristics or traits employ the present invention to induce the rise of resistance genes, with more precision than previous mutagenic agents and hence accelerate and improve plant breeding programs.

As will be apparent, it is envisaged that the present system can be used to target any polynucleotide sequence of interest. Some examples of conditions or diseases that might be usefully treated using the present system are included in the Tables above and examples of genes currently associated with those conditions are also provided there. However, the genes exemplified are not exhaustive.

E. Further Embodiments

Also disclosed is a system wherein information from one or more ligation junctions is used to identify regions of the genome that control or modulate spatial proximity relationships between nucleic acids. In some embodiments, the genomic regions identified establish chromatin loops. In some embodiments, the genomic regions identified demarcate or establish contiguous intervals of chromatin that display elevated proximity between loci within the intervals.

Further disclosed is a system for visualizing, such as system comprising hardware and/or software, the information from one or more ligation junctions. In some examples, the information from one or more ligation junctions is represented in a matrix with entries indicating frequency of interaction. In some examples, a user can dynamically zoom in and out, viewing interactions between smaller or larger pieces of the genome. In some examples, interaction matrices and other 1-D data vectors can be viewed and compared simultaneously. In some examples, the annotations of features can be superimposed on interaction matrices. In some examples, multiple interaction matrices can be simultaneously viewer and compared.

1. Target Ligation Junctions and Probes

As part of the in situ Hi-C technique, described herein, also disclosed are nucleic acids made of two or more end joined nucleic acids, target junctions, produced using the disclosed methods and amplification products thereof, such as RNA, DNA or a combination thereof. An isolated target junction is an end joined nucleic acid, wherein the junction encodes the information about the proximity of the two nucleic acid sequences that make up the target junction in a cell, for example as formed by the methods disclosed herein. The presence of an isolated target junction can be correlated with a disease state or environmental condition. For example, certain disease states may be caused and/or characterized by the differential formation of certain target junctions. Similarly isolated target junction can be correlated to an environmental stress or state, such as but not limited to heat shock, osmolarity, hypoxia, cold, oxidative stress, radiation, starvation, a chemical (for example a therapeutic agent or potential therapeutic agent) and the like.

This disclosure also relates, to isolated nucleic acid probes that specifically bind to target junction, such as a target junction indicative of a disease state or environmental condition. To recognize a target junction, a probe specifically hybridizes to the target junction both 5' and 3' of the site of the junction and spans the site of the target junction, or specifically hybridizes to probe-specific target sequences with the end joined nucleic acid fragments. In some example embodiments, the probe-specific target sequence is at least 50, at least 60, at least 70, at least 80, at least 90, at least 100, at least 110, at least 120, at least 130, at least 140, at least 150, at least 160, at least 170, at least 180, at least 190, or at least 200 base pairs long. In certain example embodiments, the specific nucleic acid sequence is within at least 50, at least 60, at least 70, at least, 80, at least 90, or at least 100 base pairs, in either the 5' or 3' direction, of a restriction site. In certain example embodiments, the specific nucleic sequence comprises less than ten repetitive bases. In certain other example embodiments, the GC content of the specific nucleic acid sequence is between 25% and 80%, between 40% and 70%, or between 50% and 60%.

In some embodiments, the probe is labeled, such as radiolabeled, fluorescently-labeled, biotin-labeled, enzymatically-labeled, or chemically-labeled. Non-limiting examples of the probe is an RNA probe, a DNA probe, a locked nucleic acid (LNA) probe, a peptide nucleic acid (PNA) probe, or a hybrid RNA-DNA probe. Also disclosed are sets of probes for binding to target ligation junction, as well as devices, such as nucleic acid arrays for detecting a target junction.

In embodiments, the total length of the probe, including end linked PCR or other tags, is between about 10 nucleotides and 200 nucleotides, although longer probes are contemplated. In some embodiments, the total length of the probe, including end linked PCR or other tags, is at least about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190 191, 192, 193, 194, 195, 196, 197, 198, 199 or 200.

In some embodiments the total length of the probe, including end linked PCR or other tags, is less then about 2000 nucleotides in length, such as less than about 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 500, 750, 1000, 1250, 1500, 1750, 2000 nucleotides in length or even greater. In some embodiments, the total length of the probe, including end linked PCR or other tags, is between about 30 nucleotides and about 250 nucleotides, for example about 90 to about 180, about 120 to about 200, about 150 to about 220 or about 120 to about 180 nucleotides in length. In some embodiments, a set of probes is used to target a specific target junction or a set of target junctions.

In some embodiments, the probe is detectably labeled, either with an isotopic or non-isotopic label, alternatively the target junction or amplification product thereof is labeled. Non-isotopic labels can, for instance, comprise a fluorescent or luminescent molecule, biotin, an enzyme or enzyme substrate or a chemical. Such labels are preferentially chosen such that the hybridization of the probe with target junction can be detected. In some examples, the probe is labeled with a fluorophore. Examples of suitable fluorophore labels are given above. In some examples, the fluorophore is a donor fluorophore. In other examples, the fluorophore is an accepter fluorophore, such as a fluorescence quencher. In some examples, the probe includes both a donor fluorophore and an accepter fluorophore. Appropriate donor/acceptor fluorophore pairs can be selected using routine methods. In one example, the donor emission wavelength is one that can significantly excite the acceptor, thereby generating a detectable emission from the acceptor.

An array containing a plurality of heterogeneous probes for the detection of target junctions are disclosed. Such arrays may be used to rapidly detect and/or identify the target junctions present in a sample, for example as part of a diagnosis. Arrays are arrangements of addressable locations on a substrate, with each address containing a nucleic acid, such as a probe. In some embodiments, each address corresponds to a single type or class of nucleic acid, such as a single probe, though a particular nucleic acid may be redundantly contained at multiple addresses. A "microarray" is a miniaturized array requiring microscopic examination for detection of hybridization. Larger "macroarrays" allow each address to be recognizable by the naked human eye and, in some embodiments, a hybridization signal is detectable without additional magnification. The addresses may be labeled, keyed to a separate guide, or otherwise identified by location.

Any sample potentially containing, or even suspected of containing, target joins may be used. A hybridization signal from an individual address on the array indicates that the probe hybridizes to a nucleotide within the sample. This system permits the simultaneous analysis of a sample by plural probes and yields information identifying the target junctions contained within the sample. In alternative embodiments, the array contains target junctions and the array is contacted with a sample containing a probe. In any such embodiment, either the probe or the target junction may be labeled to facilitate detection of hybridization.

Within an array, each arrayed nucleic acid is addressable, such that its location may be reliably and consistently determined within the at least the two dimensions of the array surface. Thus, ordered arrays allow assignment of the location of each nucleic acid at the time it is placed within the array. Usually, an array map or key is provided to correlate each address with the appropriate nucleic acid. Ordered arrays are often arranged in a symmetrical grid pattern, but nucleic acids could be arranged in other patterns (for example, in radially distributed lines, a "spokes and wheel" pattern, or ordered clusters). Addressable arrays can be computer readable; a computer can be programmed to correlate a particular address on the array with information about the sample at that position, such as hybridization or binding data, including signal intensity. In some exemplary computer readable formats, the individual samples or molecules in the array are arranged regularly (for example, in a Cartesian grid pattern), which can be correlated to address information by a computer.

An address within the array may be of any suitable shape and size. In some embodiments, the nucleic acids are suspended in a liquid medium and contained within square or rectangular wells on the array substrate. However, the nucleic acids may be contained in regions that are essentially triangular, oval, circular, or irregular. The overall shape of the array itself also may vary, though in some embodiments it is substantially flat and rectangular or square in shape.

Examples of substrates for the phage arrays disclosed herein include glass (e.g., functionalized glass), Si, Ge, GaAs, GaP, SiO2, SiN4, modified silicon nitrocellulose, polyvinylidene fluoride, polystyrene, polytetrafluoroethylene, polycarbonate, nylon, fiber, or combinations thereof. Array substrates can be stiff and relatively inflexible (for example glass or a supported membrane) or flexible (such as a polymer membrane). One commercially available product line suitable for probe arrays described herein is the Microlite line of MICROTITER® plates available from Dynex Technologies UK (Middlesex, United Kingdom), such as the Microlite 1+ 96-well plate, or the 384 Microlite+ 384-well plate.

Addresses on the array should be discrete, in that hybridization signals from individual addresses can be distinguished from signals of neighboring addresses, either by the naked eye (macroarrays) or by scanning or reading by a piece of equipment or with the assistance of a microscope (microarrays).

F. Kits

The agents, and other reagents disclosed herein for use in the disclosed methods can be supplied in the form of a kit. In such a kit, an appropriate amount of one or more of the agent is provided in one or more containers or held on a substrate. Components of the kit include agents for use as a medicament or for use in the treatment of a disorder in a human or animal subject in need thereof, wherein said agent comprises one or more sequence-specific DNA targeting agents selected from the group consisting of a CRISPR-Cas system, a zinc finger protein (ZFP), a zinc finger nuclease (ZFN), a transcription activator-like effector (TALE), a transcription activator-like effector nuclease (TALEN), a catalytically inactive CRISPR-Cas system, and a self-inactivating CRISPR/Cas system, wherein binding of the sequence-specific DNA targeting agents to the one or more genomic loci removes one or more existing chromatin loop or domain structures, introduces one or more new chromatin loop or domain structures, or modifies one or more existing chromatin loop or domain structures in a cell of said subject. Said agents comprise a DNA-targeting element comprising a nucleotide sequence that hybridizes to one or more CTCF or cohesin binding motifs or to a DNA target region in said chromatin DNA proximate to a location where one or more CTCF or cohesin binding motifs are to be introduced into the genome. Alternatively, the agents comprise a DNA-targeting element comprising a zinc finger motif that binds to one or more CTCF or cohesin binding motifs or to a DNA target region in said chromatin DNA proximate to a location where one or more CTCF or cohesin binding motifs are to be introduced into the genome. The agent may be encoded by a vector for delivering said agent to the nucleus of said cell, such as a viral vector. Suitable vectors include a lentiviral, adenoviral, adeno-associated viral, or herpes simplex virus vector.

A agent may be provided suspended in an aqueous solution or as a freeze-dried or lyophilized powder, for instance. The container(s) in which the agent are supplied can be any conventional container that is capable of holding the supplied form, for instance, microfuge tubes, ampoules, or bottles. The amount of agent supplied in the kit can be any appropriate amount, and may depend on the target market to which the product is directed. A kit may contain more than one different agent, such as 2, 3, 4, 5, 6, 7, 8, 9, 10, 11, 12, 13, 14, 15, 20, 25, 50, 100, or more agent. The instructions may include directions for genome editing using the agents, including methods for delivering the agent to the subjects. In certain embodiments, the kit includes nucleic acid probes for in sit Hi-C and/or Hi-C2 that hybridize to target junctions, and instructions for Hi-C mapping. The components of the kit may be packaged in, or, especially in the probes may me provided as in individual containers (for example, microtubules) or an array substrate (such as, a 96-well or 384-well microtiter plate). In particular embodiments, the kit includes prepackaged probes, such as probes suspended in suitable medium in individual containers (for example, individually sealed EPPENDORF® tubes) or the wells of an array substrate (for example, a 96-well microtiter plate sealed with a protective plastic film). In some embodiments, kits also may include the reagents necessary to carry out methods disclosed herein. In other particular embodiments, the kit includes equipment, reagents, and instructions for the methods disclosed herein.

III. Chromatin Extrusion Explains Key Features of Loop and Domain Formation in Wild-Type and Engineered Genomes We recently used in situ Hi-C to create kilobase-resolution 3D maps of mammalian genomes. Here, we combine these with new Hi-C, microscopy, and genome-editing experiments in order to study the physical structure of chromatin loops and domains. We find that the observed contact domains are inconsistent with the equilibrium state for an ordinary condensed polymer. Combining Hi-C data and novel mathematical theorems, we show that contact domains are also not consistent with a fractal globule. Instead, we use physical simulations to study two models for genome folding. In the first, inter-monomer attraction during polymer condensation leads to the formation of a "tension globule", a non-equilibrium state in which genome position correlates with spatial position along a linear axis. In the other, CTCF and cohesin act together to extrude loops during interphase. Both models are consistent with the observed contact domains and with the observation that contact domains tend to form inside loops. However, the extrusion model explains a far wider array of observations, such as why loops tend not to overlap and why the CTCF-binding motifs at pairs of loop anchors lie in the convergent orientation. Finally, we perform 13 genome-editing experiments examining the effect of altering CTCF-binding sites on chromatin folding. The convergent rule correctly predicts the affected loops in every case. Moreover, the extrusion model accurately predicts in silico the 3D maps resulting from each experiment using only the location of CTCF-binding sites in the WT. Thus, we show that it is possible to disrupt, restore, and move loops and domains using targeted mutations as small as a single base pair.

Stretched out from end to end, the human genome is over 2 meters long. Yet it must fold up to fit inside a nucleus that is only a few microns wide. At the smallest scale, this folding is well characterized: double-stranded DNA helices wrap around histone proteins, forming a nucleosome every ~200 bp (a beads-on-a-string configuration known as the "10 nm fiber") (Kornberg (1974) Science 184, 868-871; Kornberg and Lorch (1999) Cell 98, 285-294). At larger scales, the physical structure of chromatin is more mysterious.

One common hypothesis is that the 10 nm fiber is organized into a higher-order structure known as the "30 nm fiber," which has been observed in vitro but not in vivo (Finch and Klug (1976) Proc Natl Acad Sci USA 73, 1897-1901; Fussner et al. (2011) Trends in Biochem Sci 36, 1-6; Ghirlando and Felsenfeld (2013) Biopolymers 99, 225-232). In the most common model, individual nucleosomes are wound about a central cavity that runs axially along the length of the 30 nm fiber. Every six nucleosomes (roughly one kilobase of DNA) correspond to a full turn about this axial cavity, creating a solenoidal structure whose diameter is 30 nm. (Several alternative models of the specific positioning of nucleosomes in a 30 nm fiber have also been proposed.) Physical models of chromatin packing have implications for the stiffness of chromatin fibers. One way of describing the stiffness of a fiber is its Kuhn length: the minimum length of the fiber such that it is possible for the beginning and the end of the fiber segment to point in the same direction. All published estimates of which we are aware suggest, based on coarse-grained computer simulations, that the Kuhn length of a 30 nm fiber under nuclear conditions would range from 30-60 kb (Wedemann and Langowski (2002) Biophys J 82; Schiessel (2003) J Phys Condens Matter 15, R699-R774). Reliable estimates of the stiffness of chromatin fibers are essential for modeling higher-order chromatin folding mechanisms.

Another common notion, dating back to the 1970s, is that the human genome is partitioned into domains that are typically several hundred kilobases in length (Goldman (1988) Bioessays 9, 50-55). These studies have relied on many experimental modalities, such as chromatin sedimentation (Cook and Brazell (1975) J Cell Sci 19, 261-279; Hartwig (1982) Biochem Biophys Acta 698, 214-217), fluorescence microscopy (Zehnbauer and Vogelstein (1985) BioEssays 2, 52-54), and—in the last several years—genome-wide DNA proximity ligation data generated using Hi-C(Lieberman-Aiden et al. (2009) Science 326, 289-293; Dixon et al. (2012). Nature 485, 376-380; Sexton et al. (2012) Cell 148, 458-472). Based on Hi-C experiments (Lieberman-Aiden et al. (2009) supra; Sexton et al. (2012) Cell 148, 458-472; Zhang et al. (2012) Cell 148, 908-921) and analytical and computational estimates of equilibration time (Rosa and Everaers (2008) PLoS Comp Bio 4, e1000153), chromatin at the scale of domains is thought to be far from thermodynamic equilibrium. Overall, the internal structure of domains is not well understood (Lieberman-Aiden et al. (2009) supra; Sachs et al. (1995) PNAS 92, 2710-2714; Mateos-Langerak et al. (2009) Proc Natl Acad Sci USA 106, 3812-3817; Bohn and Heermann (2010) PloS One 5, e12218; Barbieri et al. (2012) Proc Natl Acad Sci USA 109, 16173-16178; Naumova et al. (2013) Science 342, 948-953).

A third feature of chromatin folding is the formation of loops, which bring pairs of genomic sites that lie far apart along the linear genome into close spatial proximity (Schleif (1992) Annual Rev biochem 61(1), 199-223.). Many aspects of chromatin looping are poorly understood, including how loops form and whether they assemble into higher-order hubs (Schleif (1992) supra; Bulger and Groudine (1999) Genes & development 13(19), 2465-2477).

We recently reported new, one-kilobase-resolution contact maps of the human genome (Rao et al. (2014) supra). These were created by using in situ Hi-C, which couples DNA-DNA proximity ligation in intact nuclei (nuclear ligation assay) with high-throughput sequencing (FIG. 1A). The maps—containing over 15 billion contacts—allowed us to annotate nearly 9,000 contact domains, which are contiguous genomic intervals in which there is an enhanced probability of contact among all loci. Contact domains range in size from tens of kilobases to several megabases, with a median size of 185 kb. The maps also allowed us to annotate over 10,000 loops. These loops typically lie between convergent DNA motifs (i.e., motifs pointing toward one another) that bind a complex containing CTCF and cohesin. Notably, we found that many contact domains are also "loop domains"—that is, contact domains whose boundaries are demarcated by the endpoints of a chromatin loop.

Here, we use our new maps to explore the physical structure of chromatin fibers, contact domains, and loops.

First, we demonstrate that chromatin fibers are highly bendable at distances of kilobases, rather than the ~60 kb expected for 30 nm fibers; this casts doubt on the widespread existence of 30 nm fibers in vivo and has significant consequences for the mechanism of loop formation.

Next, we combine Hi-C data, molecular dynamics simulations, and a novel analogue of McKean's dimension-doubling theorem for Brownian motion (McKean (1955) Duke Math J 22, 229-234) to explore how chromatin fibers fold inside contact domains. Consistent with our earlier work based on lower-resolution Hi-C maps, we find that the chromatin packing is inconsistent with an ordinary polymer at equilibrium. We demonstrate that the structure of non-equilibrium globules depends on the strength of the internal forces arising between monomers during the condensation process. When internal forces are weak, the result is isotropic: a fractal globule. When internal forces are sufficiently strong, tension along the polymer chain causes anisotropic condensation, and the resulting "tension globules" contain long intervals in which linear position along the polymer correlates with spatial position along a dominant axis. Notably, the tension globule closely resembles a non-equilibrium polymer model proposed by de Gennes (de Gennes (1985) J de Phys 46, 639-642). We find that the Hi-C data is consistent with a tension globule, but not with a strictly fractal structure. Using physical simulations, we show that loops inside tension globules can give rise to transient contact domains.

We then explore an intriguing suggestion of Nasmyth (Nasmyth (2001) Annu Rev Genet 35:673-745; Alipour and Marko (2012) Nucl Acids Res 1-11) who proposed that loops can form through the extrusion of flexible chromatin fibers by a cohesin-associated complex. Using physical simulations, we probe the chromatin state that would result from such a process, and show that loop extrusion leads to the spontaneous formation of stable contact domains between the loop anchors.

For both the tension globule model and the extrusion model, we show that physical simulations incorporating the locations of CTCF-binding sites seen in chromatin immunoprecipitation (ChIP) with sequencing (ChIP-Seq) data provide reasonable fits to our observed Hi-C data. However, the extrusion model has many appealing properties: it produces better fits to the data, does not require ad hoc assumptions, and explains why loops tend not to overlap and only form between convergent CTCF motifs.

Finally, we use CRISPR-mediated genome editing to delete and invert CTCF motifs at loop anchors. In all cases examined, we find that that the convergent rule correctly predicts which loops will disappear.

Chromatin is Bendable at the Kilobase Scale, Far Less Stiff than Predictions Based on a 30 nm Fiber At the smallest scale, models of chromatin structure rely on an estimate of the Kuhn length of a chromatin fiber (Rubinstein and Colby (2003) Polymer Physics (Oxford University Press)). Polymer theory predicts that higher order structures can only form at scales an order of magnitude larger than the Kuhn length. Because direct estimates of chromatin flexibility in vivo have not previously been available, inferences about the Kuhn length of chromatin have been based on theoretical, computational, and in vitro models (Ringrose et al. (1999) EMBO J 18, 6630-6641; Dekker et al. (2002) Science 295, 1306-1311; Bystricky et al. (2004) Proc Natl Acad Sci USA 101, 16495-16500).

To experimentally measure the Kuhn length of human chromatin in vivo, we examined the tendency of cross-linked, chromatinized DNA fragments, formed during the Hi-C protocol's initial restriction digestion step, to form single-fragment DNA cycles during the subsequent proximity ligation step. We found that restriction fragments shorter than 200 bp (the size of a nucleosome) rarely formed cycles, suggesting that they were too stiff to bend into a DNA circle. The probability of cyclization increased sharply for fragments between 100 and 800 bp long, and remained relatively constant for longer fragments (FIG. 1B). The results were similar for Hi-C experiments performed using MboI and DpnII (4-cutters, with cutting sites on average every 420 bp); HindIII and NcoI (6-cutters, with cutting sites on average every 3.6 kb and 4.0 kb respectively); and for experiments performed with and without crosslinking. These measurements imply that chromatin is bendable at the scale of individual nucleosomes, and suggest a Kuhn length of roughly 1 kb for chromatin fibers.

The estimates derived from our analysis of cyclization were consistent with the results of two other approaches, both of which yield upper bounds on Kuhn length. First, we examined chromatin bendability by measuring the probability, I(s), of contact between two loci as a function of the genomic distance, s, between them. Measuring I(s) can be useful in estimating polymer flexibility because the value of I(s) is maximal at the Kuhn length of a polymer and decreases monotonically as s increases. Using our in situ Hi-C data, we were able to reliably measure I(s) for the human genome at all distances larger than 5 kb (i.e., distances much longer than the typical 4-cutter restriction fragment). We found that I(s) exhibits monotonic decline at all distances probed. This implies that the Kuhn length of chromatin is less than 5 kb. Second, we note that in our initial report, biologically functional loops as short as 40 kb were visually obvious. At least at the specific loci involved in such loops, kilobase-length chromatin fibers must be capable of bending appreciably. Taken together, our findings imply that chromatin is highly flexible at the kilobase scale. They also suggest that contact domains, which range in size from 65 kb to 2.7 Mb, are large enough to be described using polymer models.

Notably, the Kuhn length observed in our data ($\approx 1$ kb) is incompatible with the estimated Kuhn length for the 30 nm fiber. This result suggests that 30 nm fibers, if they exist, are rare in human nuclear chromatin in vivo. (The flexibility of chromatin may also be relevant to the potential formation of loops by extrusion, as discussed below.)

Measurements of Contact Probability Using Genome-Wide Averages are Inconsistent with an Ordinary Polymer at Equilibrium In a previous study, we characterized the polymer-like behavior of chromatin regions at the megabase scale by analyzing the contact probability function, I(s), described above, based on Hi-C data, analytical estimates, and in silico studies. In particular, the data for human chromatin showed a power law relationship of the form $I(s) \propto s^{-\gamma}$ between 500 kb and 7 Mb, with $\gamma = 1.08$. We showed that values of $\gamma$ can be used to discriminate between distinct polymer states. Specifically, we noted that $\gamma = 1.08$ is inconsistent with the classic structure of a globular polymer at equilibrium (known as an "equilibrium globule", which has $\gamma = 1.5$). Interestingly, we found that the observed value of $\gamma$ is consistent with a dense, scale-invariant, isotropic, long-lived polymer state known as the fractal globule (Lieberman-Aiden et al. (2009) supra). Because the fractal globule's unknotted topology makes it easier to physically access individual genomic loci, it furnishes an appealing model for the structure of chromatin.

When we repeated the above analysis on our new, high-resolution maps, we observed a scaling of $\gamma = 1.27$ between 300 kb and 3 Mb. This slightly higher value is consistent with our previous conclusion that chromatin does not fold into an equilibrium globule. Moreover, the value $\gamma = 1.27$ falls within the range of values that has been predicted for a fractal globule (Lieberman-Aiden E (2010) Evolution and the Emergence of Structure. Ph.D. thesis, Harvard University).

Figure 2:
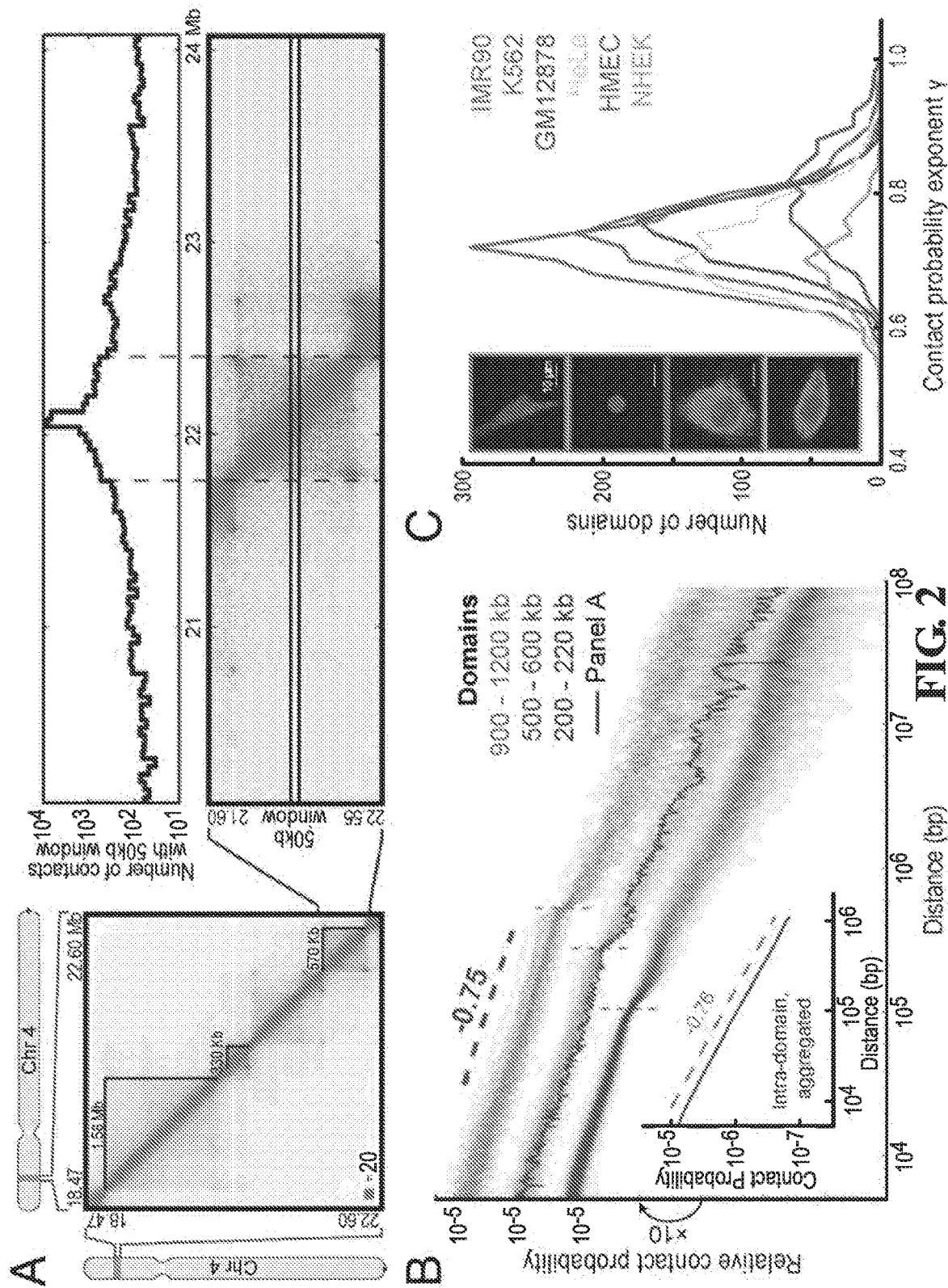
FIG. 2. Contact domains exhibit a consistent, non-equilibrium contact probability scaling with $\gamma \approx 0.75$. (A) Left: In our high-resolution in situ Hi-C maps, we observe contact domains ranging in size from tens of kilobases to several megabases. A sample region on chromosome 4 of GM12878 lymphoblastoid cells is shown. Right: Number of contacts (top) incident on a 50 kb window at the center of a domain (bottom). Our high-resolution maps enable measurement of contact probability relative to specific loci. (B) Contact probability versus distance along the genome for 473 individual domains, each measured with respect to a 50 kb locus at the center of a domain. A power law is consistently observed at intra-domain distances (reference slope of −0.75, grey dashed line). Vertical dashed lines indicate the approximate position of the domain boundary. A single black line shows contact probability for the window and domain highlighted in Panel A. Plots are grouped by domain size, but note that each group is vertically shifted by an order of magnitude for visual clarity. (C) Histogram of $\gamma$ values for all high-confidence contact domains larger than 300 kb across six human cell types. Inset: representative confocal microscopy images (maximum Z projections) of four cell types, showing chromatin (blue, DAPI stain) and cytoplasm (red, CellTracker CMTPX dye). Scale bar is 10 μm in all images. Values of $\gamma$ are consistent across cell types and are independent of nuclear volume.

Genome-Wide Measurements of Chromatin Folding Inside Individual Contact Domains Reveal a Polymer State Characterized by $\gamma = 0.75$ In our original Hi-C study, we could not discern local folding features at scales smaller than ~1 Mb. In our new study with far denser data, we had the opportunity to study folding within contact domains, which are contiguous genomic intervals in which there is an enhanced probability of contact among all loci (FIG. 2A). The median size of these contact domains is 185 kb. On closer examination, we found that folding measurements differ sharply within contact domains versus across contact domains.

We began by calculating Isame(s) using our genome-wide averaging technique, but only including pairs of loci that were in the same contact domain. Strikingly, the value of $\gamma$ that we obtained, 0.76 (FIG. 2E), was markedly lower than the value obtained using the full genome-wide average.

Next, we used our new maps, which contain 200- to 1000-fold more data, to measure the decay in contact probability with distance relative to a fixed DNA locus. So long as the locus was at least 50 kb long, we obtained highly reproducible estimates for $\gamma$ at any local position in the human genome. We focused on 1057 distinct 50 kb loci, each of which was situated at the midpoint of a high-confidence domain larger than 200 kb. The resulting contact probability plots consistently exhibited two distinct regimes. The first regime corresponded to declining contact frequency within a domain (FIG. 2B). Values of $\gamma$ observed in this regime centered on 0.75, with a standard deviation of 0.05. Values of 1 or larger were not seen (FIG. 2C). For points outside the domain, however, the contact probability continued to decline, but the power-law regularity disappeared, and was replaced by a more heterogeneous monotonic decline (FIG. 2B).

Our findings suggest that, because the frequency of contact between two loci declines markedly when a contact domain boundary is crossed, I(s)—which is calculated predominantly using pairs of loci separated by such a boundary—tends to overestimate γ for contact domains.

We wondered whether the distribution of γ for contact domains was dependent on the volume of the nucleus that contained them. To check, we compared four human cell types, examining their nuclei using both in situ Hi-C and confocal microscopy. Despite observing nearly three-fold variation in nucleus size (from smallest to largest, GM12878:237±84 μm3; IMR90:381±157 μm3; NHEK:440±90 μm3; HMEC:728±307 μm3), the intra-domain γ measurements were indistinguishable (FIG. 2D). The results did not vary significantly in different nuclear compartments (A/B) (12) or subcompartments (A1/A2/B1/B2/B3) (24). When we examined domains in CH12-LX mouse lymphoblasts, the results were also similar. The results were also robust to changes in cross-linking conditions.

Finally, we reasoned that, because the mechanism of site-directed recombination relies on the spatial proximity of pairs of DNA sites, the efficiency of site-directed recombinases might exhibit the same distance dependence observed above. We therefore re-examined published experiments probing the relationship between flippase recombination frequency in human cells and the genomic distance between the two Flippase Recognition Targets (Ringrose et al. (1999) supra). We found that the recombination frequency scaled as a power law with genomic distance, with γ =0.75.

Taken together, the results above suggest that chromatin folding within contact domains is characterized by a value of γ that is close to 0.75. We then sought to understand the implications of this exponent—in particular, whether the exponent is consistent with a fractal globule or whether it implies a different polymer state.

A New Mathematical Theorem Indicates that Chromatin Folding Inside Contact Domains is not Strictly Fractal A difficulty in interpreting experimental measurements of γ is the long-standing uncertainty about the values of γ that are consistent with a fractal globule. Approximate methods and physical simulations, including those described above and in our earlier work, have suggested values of γ that range from 1 to 1.2. However, no rigorous bounds have been obtained. We therefore sought to derive rigorous bounds on γ for a fractal globule.

Specifically, we proved mathematically that the value of γ lies between 1 and 2 for any fractal globule. To do so, we analyzed mathematical functions (denoted f) that continuously map (in other words, fold) the unit segment [0,1] into a higher-dimensional space. Specifically, we focused on fractal curves. These counterintuitive curves are generated by applying a simple folding rule to a simple initial state, and repeating this process ad infinitum. When the folding rule is applied identically at all scales, fractal curves have no characteristic length scale. Because they can continuously transform a 1-dimensional line into a higher dimensional object, such curves have been of interest to mathematicians ever since the first space-filling curves, which map the unit segment onto the unit square, were discovered by Giuseppe Peano (the "Peano curve," in 1890) and David Hilbert (the "Hilbert curve," in 1891). If the repetition process is terminated after only a finite number of steps, the resulting curve is dense, self-similar, and corresponds to a physically realizable polymer chain; for this reason, finite iterations of fractal curves, especially the Hilbert Curve, are often used to model the fractal globule (Schram et al. (2013) J Chem Phys 138, 224901/1-11). By deriving mathematical bounds on the possible values of γ that can be obtained from fractal curves, we can test whether the observed folding pattern of chromatin is consistent with a strict fractal globule.

When characterizing a fractal curve, a commonly used measure is the Minkowski (or "box-counting") dimension, denoted dim(X), which generalizes the common notion of dimension to non-integer values (Falconer (2003) Fractal geometry: mathematical foundations and applications (Wiley)). Just as the number of line segments with width 1/N needed to cover the 1-dimensional unit segment scales as N1, and the number of squares with width 1/N needed to cover the 2-dimensional unit square scales as N2, dim(X) is defined so that the number of boxes with width 1/N needed to cover X scales as Ndim(X). In this way, the Minkowski dimension can be computed for a mathematical set or measured for a physical object. For instance, the Minkowski dimension of a crumpled sheet of paper ($\approx$2.51) provides a measure of its packing density (Gomes (1987) J Phys 20, 283-284). The Minkowski dimension of the boundary of Great Britain ($\approx$1.25) is a measure of the roughness of its coastline (Mandelbrot (1967) Science 156, 636-638). The Minkowski dimension of a set can also be less than 1: for instance, the set of points in the unit interval whose decimal representation does not contain an odd digit (i.e., 0.86, 0.22222) has a Minkowski dimension of 0.699.

We proved mathematically that the process of folding the one-dimensional unit segment [0,1] into a d dimensional fractal curve scales the Minkowski dimension of all subsets of the segment uniformly, i.e., by a constant factor. That is, not only does the curve fold the one-dimensional unit segment into a d dimensional shape, but any k-dimensional subset of the unit segment will fold into a k*d dimensional shape. Our results can be summarized in the following theorem and corollary, whose proofs appear in the Supplemental Information:

Theorem: For any self-similar fractal curve $f([0,1])$, dim $f(X)=d\cdot\dim X$ for any $X\subseteq[0,1]$. (The proof is in two parts. First, we show that any fractal curve f is a 1/d-Hölder function, which gives an upper bound on dim X. Next, we construct a push-forward measure on f(X), which gives a lower bound on dim X. Both bounds are the same and therefore give the exact value. The full proofs of the theorem and corollary are provided in the Supplemental Information.)

Corollary: The contact probability of a fractal curve satisfies $I(s) \propto s^{-\gamma}$ with $\gamma = 2-(d_{surf}/d)$, where s is linear distance along the curve, $d_{surf}$ is the Minkowski dimension of the curve's surface (that is, the curve's roughness) and d is the Minkowski dimension of the curve as a whole.

Figure 3:
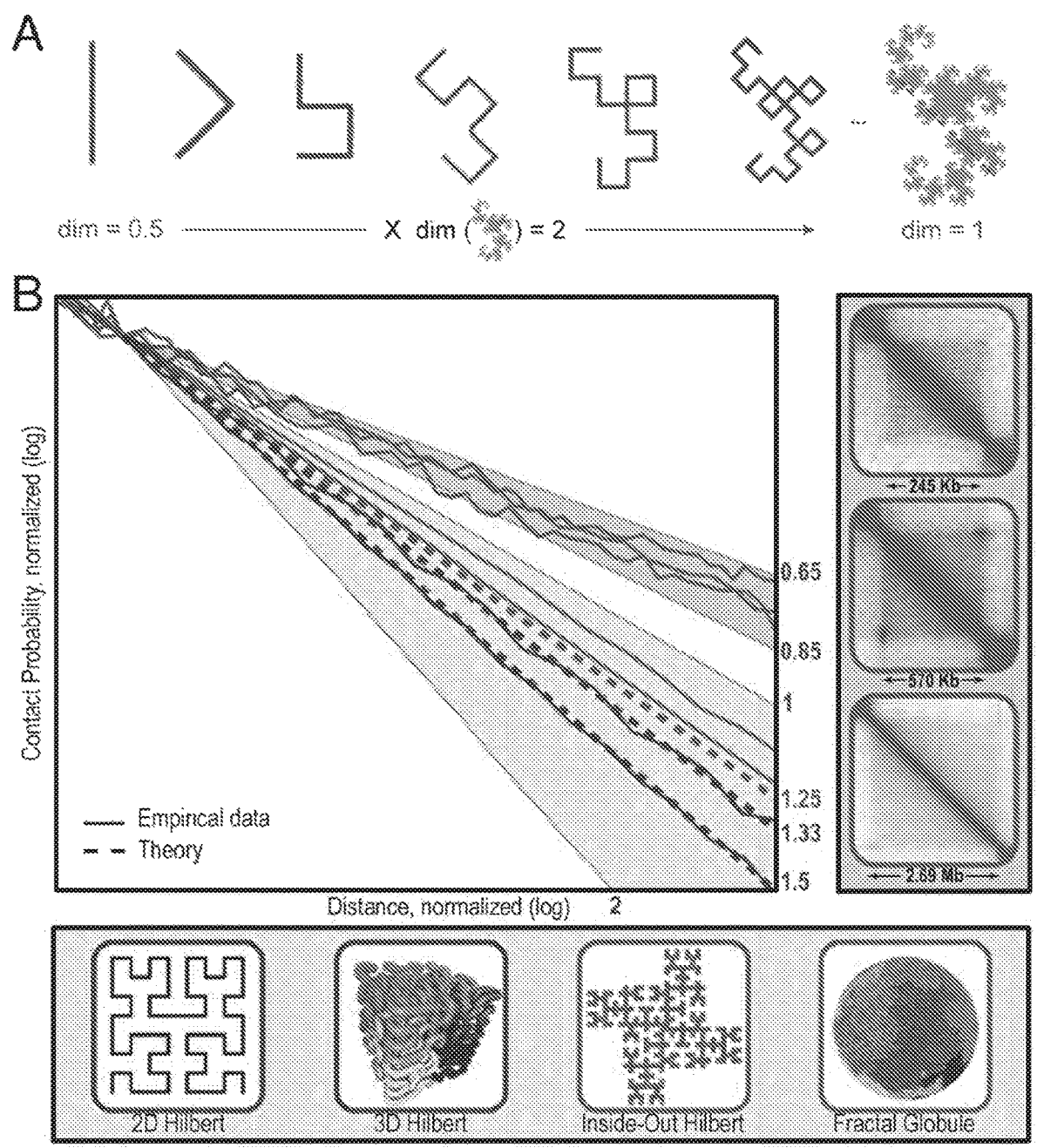
FIG. 3. A new mathematical theorem indicates that chromatin folding inside contact domains is not strictly fractal. (A) By successive application of a simple folding rule, we transform a one-dimensional line segment (left) into a two-dimensional Dragon curve (right). By applying our new mathematical theorem to the Dragon curve, we can deduce that, just as the curve doubles the dimension of the line segment, it must double the dimension of all subsets of the line segment. Thus, when we intersect the Dragon curve with a line to create a one-dimensional feature, the corresponding points in the original segment must have a Minkowski dimension of ½. A corollary of this theorem makes it possible to calculate the contact probability scaling exponent $\gamma$ for any fractal curve. (B) Contact probability vs. distance for various fractal curves and contact domains. Our theorem shows that contact probability scaling exponents of fractal curves obey $\gamma = 2 - (d_{surf}/d)$, where $d_{surf}$ is the dimension of the curve's surface and d is the dimension of its interior. Since $d_{surf}$ must be smaller than d, this implies that $1 < \gamma < 2$ (light blue highlight). In contrast, contact domains exhibit scalings between $\gamma = 0.85$ and $\gamma = 0.65$ (light red highlight). We illustrate this finding through a series of specific examples; for fractal curves, values obtained via simulation (solid lines) are compared to theoretical predictions (dashed lines). Bottom, left to right: 2D Hilbert curve (purple, $d_{surf}=1$, $d=2$, $\gamma=1.5$), 3D Hilbert curve (blue, $d_{surf}=2$, $d=3$, $\gamma=1.33$), Inside-Out Hilbert curve, rank 3 (teal, $d_{surf}=1.5$, $d=2$, $\gamma=1.25$), fractal globule (green). As the rank of an Inside-Out Hilbert curve increases, its boundary becomes nearly two dimensional and the value of $\gamma$ it yields draws close to, but never falls below, 1. Right, top to bottom: Three contact domains: Chr12: 46.2-46.4 Mb, Chr4: 21.8-22.4 Mb, and Chr5: 2.1-4.8 Mb.

An illustration of the theorem is the two-dimensional Dragon curve, which doubles the Minkowski dimension of all subsets in its domain (FIG. 3A). (This result is notable from the mathematical standpoint insofar as it is a deterministic analog of Henry McKean's well-known "dimension-doubling" theorem, which states that Brownian motion doubles the dimension of subsets (McKean H P (1955) supra).)

The corollary may be illustrated by measuring γ for classic fractal curves, such as the 2D Hilbert Curve (dsurf=1, d=2, γ =3/2; FIG. 3B, purple), the 3D Hilbert Curve (dsurf=2, d=3, γ =4/3; FIG. 3B, blue), and many others. The corollary also implies that, if a curve has an extremely rough surface (dsurf close to d), the value of γ can come arbitrarily close to unity. No such curves are known. As an illustrative example, we generalized the Hilbert Curve, constructing a class of 'inside-out' Hilbert Curves (FIG. 3B, teal) whose boundaries are arbitrarily rough and whose γ values come arbitrarily close to 1.

Most importantly, because 0≤dsurf/d<1, the corollary proves that γ for a fractal curve must lie between 1 and 2. Thus, our measurements of γ ≈0.75 inside contact domains (FIG. 3B, red) are inconsistent with the hypothesis that contact domains tend to form fractal globules.

Physical Simulations Suggest that γ =0.75 is Consistent with an Unknotted, Non-Equilibrium State that is Anisotropic Rather than Fractal Another way of exploring the significance of a particular value of γ is by computationally modeling chromatin as an extended homopolymer comprising numerous, identical monomers, each of which represents a fixed number of bases. By simulating the dynamics of a condensing polymer chain and the surrounding mixture under various physical assumptions, it is possible to test whether a particular set of conditions leads to a realistic γ value.

In our original models, we simulated an extremely simple condensation process in which the collapse of the polymer was driven by external forces, i.e., the crowding of a stretch of chromatin by other components of the nucleoplasm. Through an excluded volume interaction, these components crush the polymer chain into a smaller volume. Such forces can be modeled using a potential function that attracts all monomers equally toward a single point in space (Lieberman-Aiden et al. (2009) supra). Because this potential does not introduce a characteristic length scale into the simulations, the resulting dynamics are scale-invariant, and the polymers collapse isotropically into a fractal globule.

Notably, our earlier models did not examine the effects of internal interactions between the monomers themselves on the polymer condensation process. Attractive forces between individual nucleosomes have been observed in vitro by many groups (Clark and Kimura (1990) J Mol Bio 211, 883896; Cui and Bustamante (2000) Proc Natl Acad Sci USA 97, 127-132; Hansen (2003) Annu Rev Biophys Biomol Struct 31, 361-392; Luger and Hansen (2005) Current Opinion in Structural Biology 15, 188-196), and effective attractions between monomers are seen in all polymer globules, arising naturally when the polymer is immersed in a poor solvent (de Gennes (1985) supra; Halperin and Goldbart (1999) Phys Rev E 61(1): 565; Frisch and Verga (2002) Phys Rev E 66). Therefore, in the present study, we incorporated attractive forces between monomers using the classic Lennard-Jones potential. The Lennard-Jones potential is a model of intermolecular attractions that was originally developed to study van der Waals effects, and is commonly used to describe the attractive forces between nucleosomes in polymer simulations (Wedemann and Langowski (2002) supra; Langowski J, Heermann D (2007) Sem in Cell & Dev Bio 18, 659-667). We examined a class of systems in which both internal attractions between monomers and external crushing forces are present during the condensation process. The ratio of these forces is given by a single parameter, R, which represents the extent to which the system is governed by internal forces between the monomers themselves. In the course of our study, we varied R over roughly eight orders of magnitude.

We probed the condensation process using Langevin dynamics simulations. In this approach, random collisions between the solvent and the polymer are accounted for implicitly, through the use of parameters for both viscosity and temperature. We ran our simulations using the LAMMPS software package (Plimpton S (1995) J Comp Phys 117, 1-19), accelerated using graphical processing units (Brown W M, Wang P, Plimpton S J, Tharrington A N (2011) Comp Phys Comm 182, 898-911). Each monomer represented 1 kilobase, in order to match the above estimates of Kuhn length; the chain as a whole contained up to 10 Mb, or 10,000 monomers. For each condition, we ran at least 100 simulations from randomized starting configurations and calculated γ as a function of R for the resulting globular states.

Figure 4:
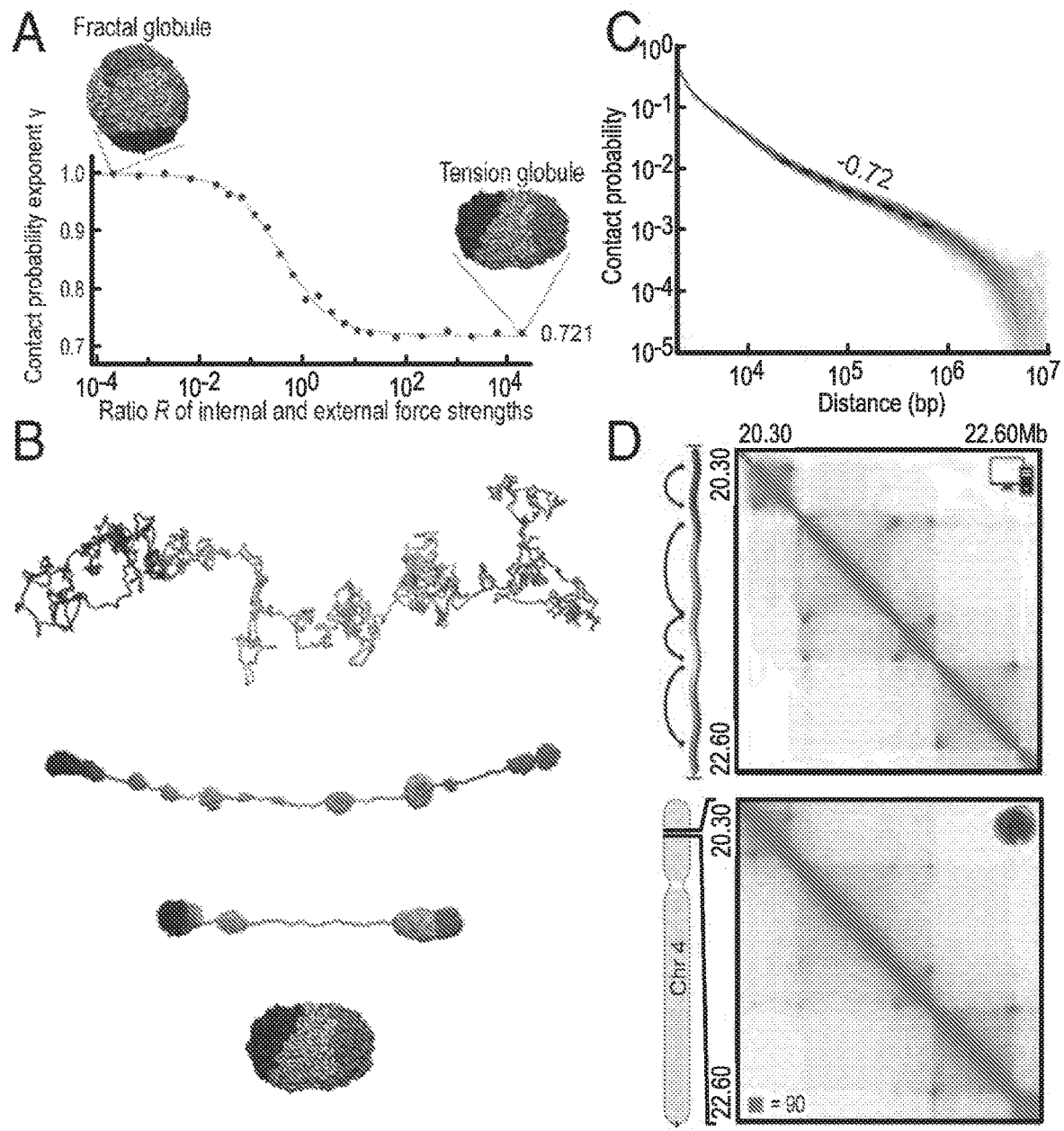
FIG. 4. The value of $\gamma$ obtained using Hi-C is consistent with a tension globule. (A) The value of $\gamma$ for a globule varies as the ratio of internal to external forces, R, is changed. Two broad regimes are observed. When external crowding dominates, polymers condense isotropically into a fractal globule (left). When internal forces dominate, tension along the polymer chain leads to anisotropic condensation, resulting in a tension globule (right). For all values of R, the resulting state is dense and unknotted. (B) Condensation of a 10 Mb tension globule. Internal forces first cause small globules to form along the extended chain. Next, tension along the chain causes the globules to concatenate in a linear fashion. (C) We show the contact probability for 450 tension globules, each of length 10 Mb, created in silico. For distances between 20 kb and 800 kb, a power law relating contact probability and distance is seen in each case. The average value of $\gamma$ is 0.726, with a standard deviation of 0.071. (D) When strong attractions are introduced between particular pairs of anchor monomers in a tension globule, a loop forms. Furthermore, contact domains spontaneously arise between the loop ends: all pairs of loci contained in the interval tend to form contacts with one another more frequently. Here, we model a region of chromosome 4 in GM12878 (Chr4: 20.3-22.6 Mb). The region contains 4 loop domains (left); the contact map can be recapitulated (right) using a tension globule containing 4 loops (black arcs). Simulation is performed with tethered ends.

Our simulations revealed a family of non-equilibrium states (FIG. 4A). When internal forces are weak (R<<1), the polymer collapse closely resembles the isotropic dynamics observed with pure external forces (R=0), and results in a fractal globule. However, because inter-monomeric attractions decay as the monomers move apart, internal forces introduce a length scale into the system. When they are sufficiently strong (R>>1), we find that the polymer condensation process transitions into an anisotropic regime: first, tiny globules form along an extended chain; then tension along the chain causes the globules to concatenate in a linear fashion (FIG. 4B). This model of polymer condensation was first postulated by the theorist de Gennes (de Gennes (1985) supra). The resulting state—which we dub a "tension globule"—is not scale-invariant. Instead, it contains long intervals in which genomic position is correlated with spatial position along a linear axis.

Importantly, the values of γ obtained for the condensed state differ depending on the regime. When R is small, γ (R) is slightly larger than unity, consistent with our earlier fractal globule simulations and with those of other groups. When R is large, γ (R) is roughly 0.72, consistent with our observations for contact domains (FIG. 4C). These two possibilities are connected by a region in parameter space where γ (R) transitions from one regime to the other. Interestingly, all of the non-equilibrium states in this family are dense and largely unknotted, features that had previously been associated only with fractal globules.

Our findings were robust to variations in numerous simulation parameters. In particular, we performed over 3000 simulations to confirm that the internal structure of tension globules, and the value of γ they display, was independent of the length of the polymer chain, the initial configuration of the chain, the solvent temperature, the viscosity, and the total simulation time. The results were also robust to the mechanism underlying the internal forces. They did not change significantly when we replaced the Lennard-Jones potential with a Yukawa potential, a model of screened electrostatic forces, in which the attractions decay much more rapidly with distance (Chodaparambil et al. (2007) Nat struc mol bio 14(11):1105-1107).

As with our mathematical analyses, our physical simulations again suggest that the structure of nuclear chromatin inside contact domains is not consistent with a fractal globule. However, our simulations show that the structure is consistent with a tension globule resulting from a condensation regime dominated by internal attractions between the monomers themselves.

Contact Domains Form Spontaneously Between the Anchors of a Loop During Condensation of a Tension Globule As noted in the introduction, one of the most surprising features of our in situ Hi-C maps is that contact domains often correspond to loops—that is, the two boundaries of the domain lie at the loop's two anchor loci, which are spatially proximate. We dubbed this common configuration a "loop domain." Typically, each anchor site contains a motif that binds a complex containing CTCF and cohesin. These motifs almost always occur in the convergent orientation, i.e., pointing toward one another. The ubiquity of this configuration suggests that the binding of CTCF and cohesin may be responsible for the formation of loops and domains at precise genomic coordinates.

We used our physical simulations to explore whether bringing together two anchor points followed by condensation into a tension globule might be sufficient to cause the intervening points to become a contact domain. Indeed, we found that the formation of a loop led to enhanced contact frequency between all pairs of loci in the interval demarcated by the two loop anchors, i.e., to the formation of a contact domain (FIG. 4D). These contact domains exhibited values of $Y$ that match our experimental observations ($Y=0.77\pm0.077$ for simulated domains, versus $Y=0.75\pm0.05$ for domains observed in Hi-C maps).

Thus, contact domains could arise through the formation of a tension globule in which the anchor points of a loop come into contact through diffusion in three dimensions, and this contact is stabilized by a protein complex containing CTCF and cohesin.

However, this model does not account for the fact that loops typically involve consecutive anchor points. Simple three-dimensional diffusion would tend to produce a tangle of overlapping loops (that is, a point in the interior of one loop anchored to a point outside the loop). It is also difficult to understand how such a model could lead to the strong tendency of CTCF/cohesin binding motifs at pairs of loop anchors to lie in a convergent orientation. We therefore considered alternative models for loop formation.

The Data are Consistent with Loop Formation by Extrusion Complexes

Figure 5:
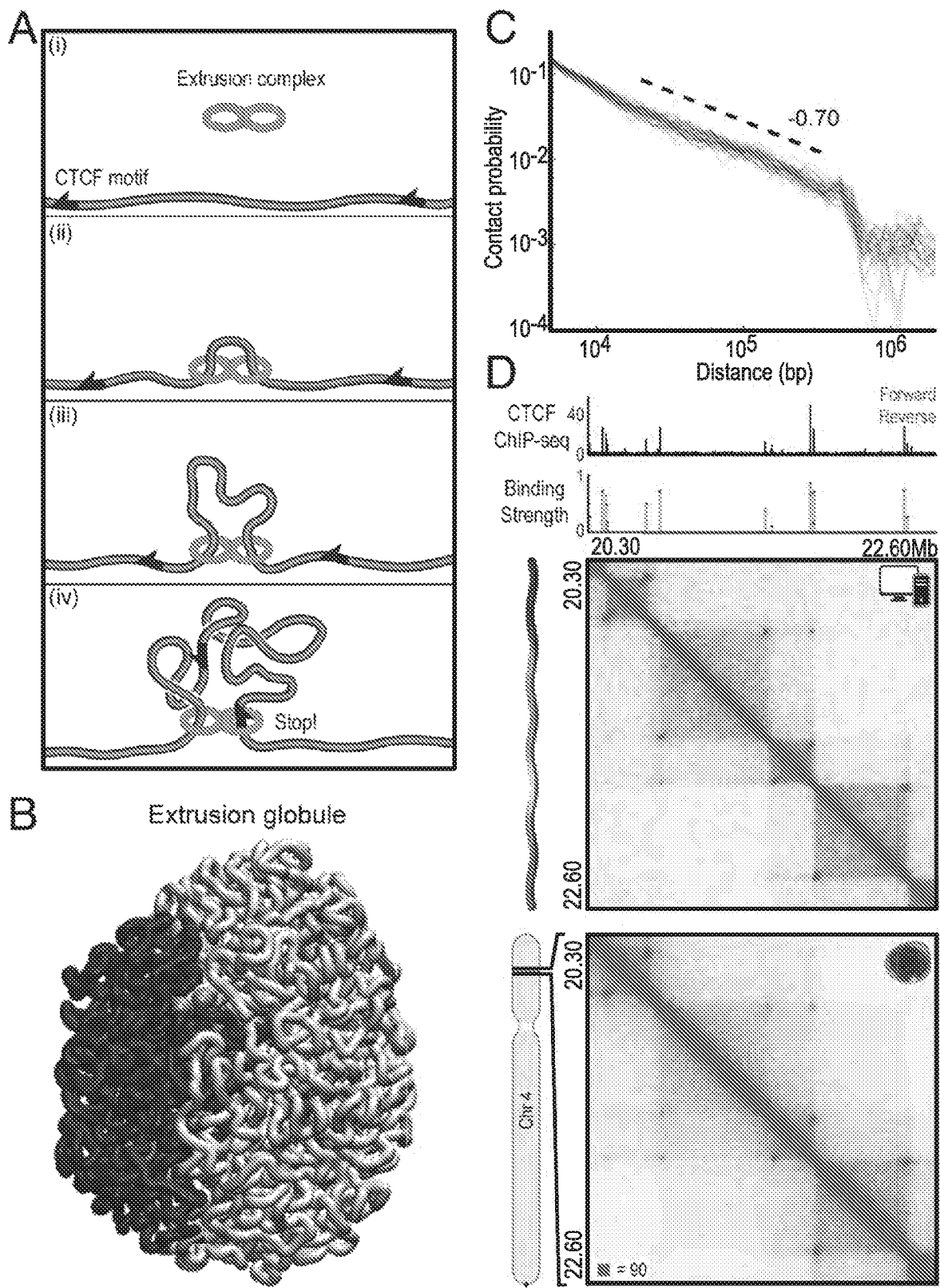
FIG. 5. A model based on loop extrusion makes it possible to accurately recapitulate Hi-C maps using only CTCF ChIP-Seq results. (A) Schematic of the loop extrusion model. The extrusion complex comprises CTCF and cohesin. It loads onto the fiber at a random locus, forming an extremely short-range loop (i, ii). As the two binding subunits move in opposite directions along the fiber, the loop grows. The extruded fiber forms a domain (iii). When the CTCF protein detects a motif on the appropriate strand, it will bind; stronger motifs increase the likelihood of a binding event. When CTCF binds, the sliding of the subunit is halted (iv). (B) Three-dimensional rendering of a 3 Mb extrusion simulation. The presence of a convergent CTCF anchors (at loci indicated using white spheres) leads to the formation of a loop; the interior of the loop forms a compact, spatially segregated domain (highlighted). (C) Contact probability for 12 domains of length 1 Mb, created in silica using loop extrusion. Contact probability is measured at a 100 kb locus at the center of the domain. For distances between 5 kb and 400 kb, a power law relating contact probability and distance is seen in each case. The average value of y is 0.72, with a standard deviation of 0.06. (D) Our extrusion model can be used to recapitulate Hi-C experimental results directly from CTCF ChIP-Seq data. As an example, we show a 2.3 Mb region from chromosome 4 of GM12878. CTCF ChIP-Seq signals are normalized and converted into binding probabilities for the simulated extrusion complex. Each peak is assigned a forward (green) or reverse (red) orientation based on the strand of the CTCF motif associated with the ChIP-Seq peak. Extrusion simulations yield an ensemble of 3D polymer configurations; contact maps for the simulated ensemble (top) faithfully recapitulate the features observed in our kilobase resolution Hi-C experiments (bottom), including the position of domains and loops. A member of the ensemble was shown in panel B.

Nasmyth (Nasmyth K (2001) Annu Rev Genet 35:673-745; Alipour E, Marko J F (2012) Nucl Acids Res 1-11) proposed a model based on an "extrusion complex" (composed of proteins and possibly other biomolecules) containing two DNA binding subunits that are physically tethered together. The extrusion complex is loaded onto chromatin at a single locus; initially, its subunits are bound to nearby DNA elements, forming a tiny chromatin loop between them. Next, DNA is extruded through the subunits such that the two subunits move in opposite directions with respect to the genome: one forward, one reverse. (Of course, the subunits are not moving with respect to one another in 3D space, since they are part of a single complex.) As a result, a growing loop is extruded until the extrusion complex—whose processivity is assumed to be finite—eventually dissociates from DNA (FIG. 5A, i-iii).

We explored the behavior of extrusion complexes in our simulations as follows. The extrusion complexes are bound to the polymer at a density that depends on their concentration, and they dissociate at a rate that depends on their processivity. Extrusion complexes cannot pass through one another. If the loops produced by neighboring extrusion complexes are immediately adjacent at any point (i.e., the DNA element in the forward subunit of one extrusion complex is too close to the DNA element in the reverse subunit of the next extrusion complex), then one of the two colliding complexes falls off.

We added one novel feature to Nasmyth's model, based on our observations about the role and orientation of CTCF/cohesin motifs. We designated certain monomers as anchors, and assigned each anchor a forward or reverse orientation. We assume that the DNA binding subunits of the extrusion complex preferentially recognize specific DNA sequences and have orientations, with one recognizing forward anchors and one recognizing reverse anchors. Under these assumptions, the extrusion process proceeds in the following way: the progress of the forward subunit of an extrusion complex may be halted by a forward anchor, but not by a reverse anchor; and conversely the progress of the reverse subunit of an extrusion complex may be halted by a reverse anchor, but not by a forward anchor (FIG. 5A, iv). In short, the two subunits recognize the presence of a particular motif on a particular DNA strand—such as an appropriately oriented CTCF/cohesin motif—by more tightly binding the target DNA element, and halting the extrusion process through the subunit.

We began by simulating a polymer containing pairs of convergent anchors 1 Mb apart. When an extrusion complex landed between the anchors, it began extruding a loop until its subunits eventually arrived at the two anchor monomers. At this point, the extrusion came to a halt, yielding a "persistent loop" between the anchors: i.e., a loop that was present for a protracted period (FIG. 5B). Eventually, the extrusion complex dissociated from the polymer. When we examined the contact maps for the polymers in our simulation, we made three observations. First, a prominent peak was present between the two anchors, reflecting the formation of a persistent loop. Second, extrusion of the chromatin fiber led to enhanced contact frequency between all pairs of loci in the interval between the two anchors, i.e., to the formation of a contact domain. Finally, we found that these contact domains exhibit extremely linear contact probability scalings with values of $Y$ that match our experimental observations ($Y=0.72\pm0.06$ for simulated domains, versus $Y=0.75\pm0.05$ for domains observed in Hi-C maps; FIG. 5C). These findings reflect the equilibrium state of a long polymer immersed in a solvent containing extrusion complexes. They were extremely robust, and did not depend on the inter-monomeric potential (external or internal) and the initial condition (fractal globule, tension globule, or extended filament). When we modeled more complex arrangements of loop anchors, we found that pairs of convergent anchors led to both persistent loops and contact domains with realistic $Y$ values.

In contrast to the model in which tension globules form by condensation with loop anchors finding each other by diffusion, the extrusion model with oriented DNA-binding/recognition subunits has many attractive features.

Intra-Domain Distances Measured by 3D-FISH Match Simulation Results for Both Tension Globules and the Extrusion Model We examined whether the tension globule model and extrusion model recapitulate spatial distances observed experimentally. We examined 4 pairs of loci using 3D-FISH. Each pair lay in a single domain; the genomic distance between the loci ranged from 320 kb to nearly a megabase. We measured at least 50 3D distances for each locus pair. We compared the resulting distributions to distributions for monomers at a comparable distance from one another obtained using our simulations of both tension globules and extrusion models. In both cases, we found that the simulated distributions matched the experimental distributions almost as closely (Kolmogorov-Smirnov statistic with tension globule: 0.15; K-S statistic with extrusion model: 0.19) as experimental replicates matched one another (K-S statistic: 0.18). Thus, both models not only accurately recapitulate the observed contact probabilities, but they also recapitulate the observed distribution of 3D distance measurements.

The Network of Loops Contains Hundreds of Isolated Cliques, Consistent with Chromatin Rosettes Formed by Consecutive Extrusion Complexes Finally, we explored higher-order relationships among the location of loops. To probe these relationships, we constructed a "loop network" for GM12878 lymphoblastoid cells. The nodes of this network are genomic loci containing at least 1 loop anchor, and its edges indicate the presence of a loop connecting the incident loci. We then sought to find network motifs—patterns of nodes and edges whose frequency was higher than expected.

Figure 6:
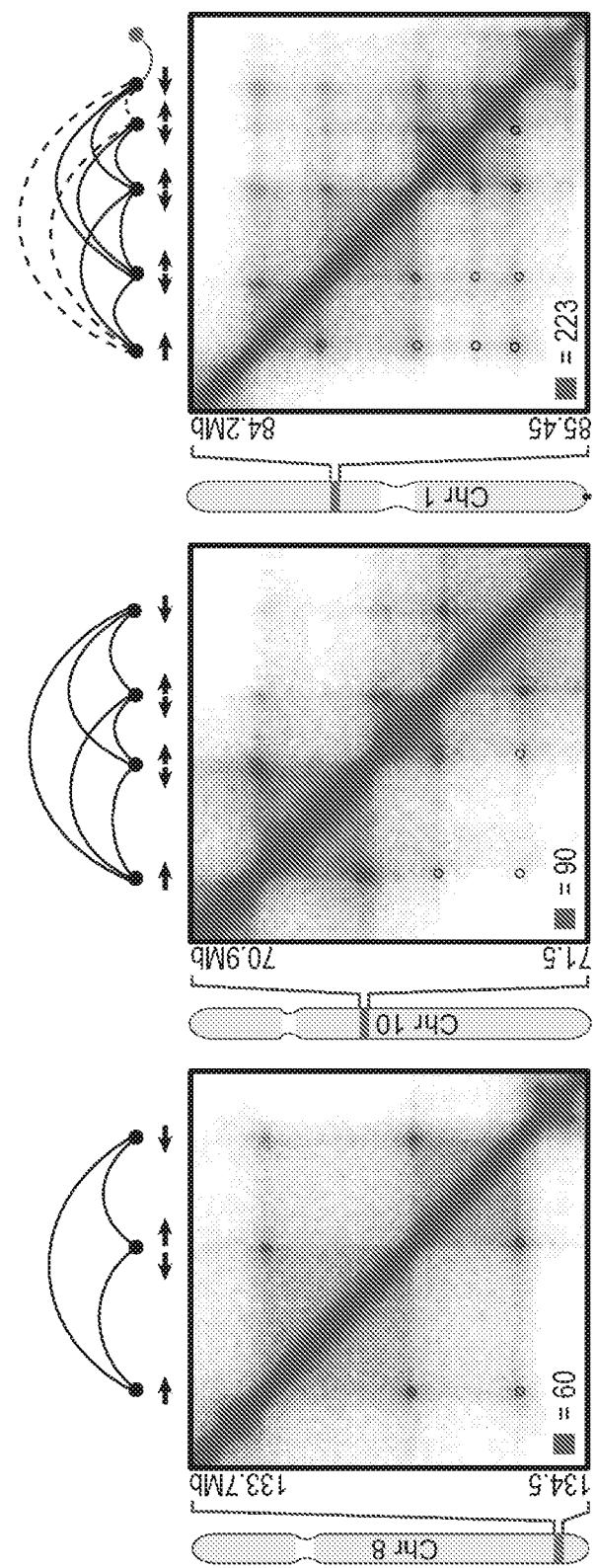
FIG. 6. Analysis of loop networks reveals many isolated cliques, which may correspond to chromatin rosettes. We show cliques of size three (top), four (middle), and five (bottom), both using network representations (left) and in the Hi-C contact map (right). Nodes in the network correspond to loop anchor loci. Black edges indicate a loop called in (Rao et al., 2014). Dashed lines indicate a loop called using a more relaxed threshold. The clique on the bottom is nearly isolated; it shows an additional loop (grey) connecting a locus in the clique to a locus outside the clique.
Figure 7:
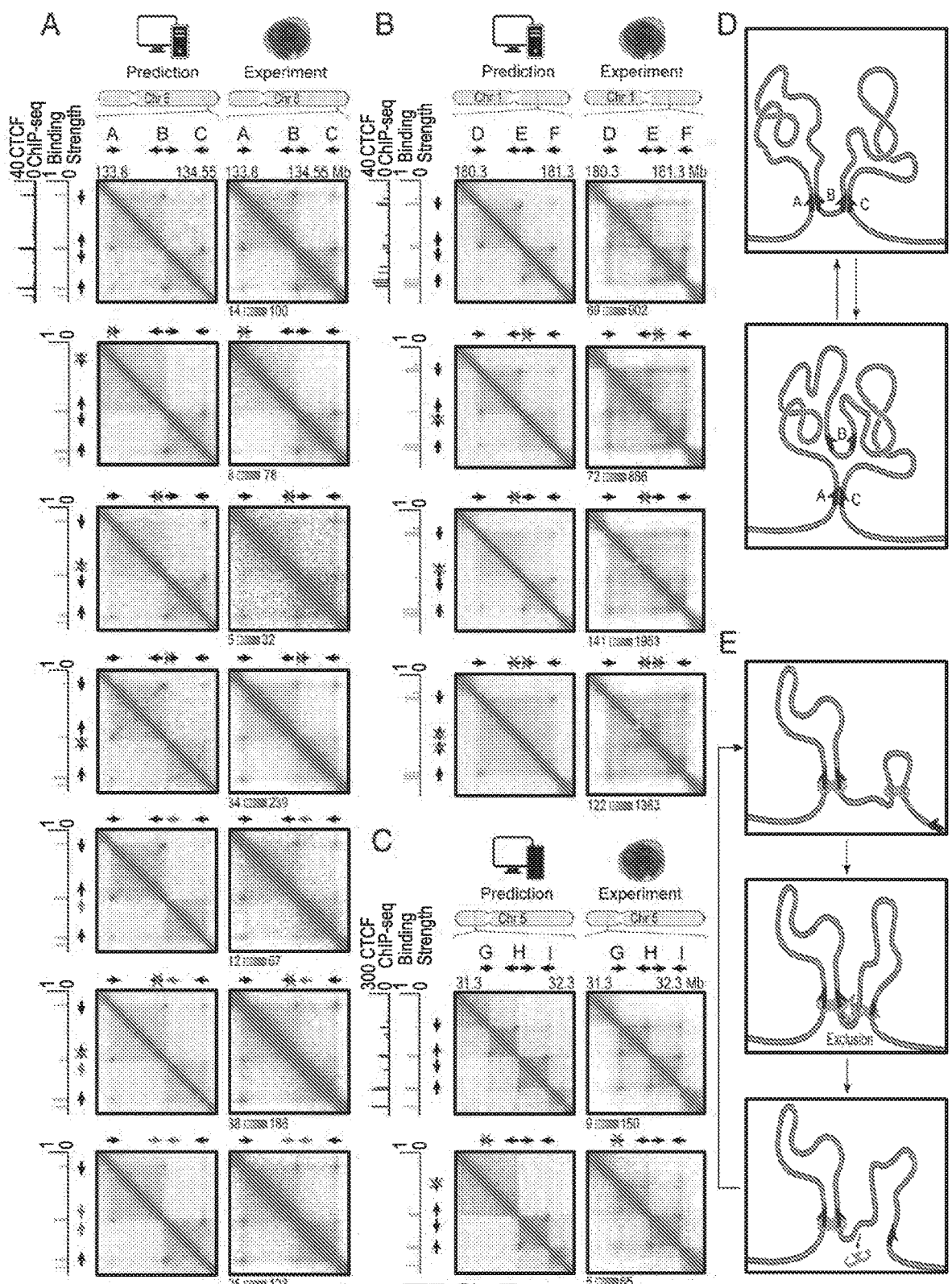
FIG. 7. Genome editing of CTCF motifs allows reengineering of loops in accordance with the convergent rule; the resulting contact maps can be predicted in silico using extrusion simulations. (A) Results of CRISPR/Cas9-based genome editing experiments at chr8:133.8-134.55 Mb in HAP1 cells. Extrusion simulations (Left) and experimental data (Right) are shown. (A, first row) Contact map for the WT locus, calculated using in silico simulations (Left), closely matches the map observed using Hi-C2 experiments (Right). (A, second row) Deletion of A/Forward eliminates the A-B and A-C loops and the contact domain boundary at locus A. The predictions of our in silico simulations (Left) closely match the contact map observed using Hi-C2 experiments (Right). All parameters in this and subsequent simulations of mutant regions use exactly the same parameters as the simulations of the corresponding WT contact map. The only difference in the mutant simulation is the modification of the appropriate CTCF-binding site (in this case, deletion of A/Forward). (A, third row) Deletion of B/Reverse eliminates the A-B loop. (A, fourth row) Deletion of B/Forward eliminates the B-C loop. (A, fifth row) Inversion of B/Forward eliminates the B-C loop. (A, sixth row) Simultaneous deletion of B/Reverse and inversion of B/Forward eliminates the B-C loop. (B) Similar series of results for chromosome 1 (180.3-181.3 Mb). Notably, the elimination of one loop anchor motif at the middle locus fails to eliminate either the D-E or E-F contact domain. When both loop anchor motifs are eliminated, both the D-E and E-F contact domains disappear. (C) We disrupted a forward CTCF motif by inserting a single base at chromosome 5: 31,581,788. Two loops are disrupted. The domain boundary moves to a nearby, weak CTCF site. Because the binding at this new site was weaker than the threshold value, this new boundary was not predicted by our extrusion simulations. (D) Our data suggest that the region shown in A is typically found in one of two states in wild-type cells. In the first state, both the A-B and B-C loop domains are present, but the A-C loop domain is absent. In the second, only the A-C loop domain is present. The data suggests a similar decomposition for the region in B. (E) Extrusion can explain the formation of exclusion domains. In this example, an extrusion complex forms a loop between adjacent motifs in the convergent orientation. Downstream, a second CTCF motif in the reverse orientation is unoccupied. Obstructed on both sides, extrusion complexes landing in the interval between the two reverse motifs tend to remain inside the interval. This leads to the formation of a domain.

We were particularly interested in 'isolated cliques' in the loop network. An isolated clique consists of a set of N≥3 loci such that any pair in the set is connected by a loop (i.e., the set is a 'clique') but none of the loci are connected by loops with loci outside the set (i.e., the set is 'isolated') (FIG. 6).

To identify isolated cliques, we allowed for errors in loop calling. Because an isolated clique of size N has N(N−1)/2 loops, even a small false negative rate will prevent the recognition of large cliques. To account for false negatives, we allowed cliques in which up to N−2 of the N(N−1)/2 loops satisfy a less stringent threshold than used in our standard loop annotation procedure (Rao et al. (2014) supra).

We found that isolated cliques were dramatically enriched in the loop network. For instance, in GM12878 we observed 206 isolated cliques with 3 nodes (9-fold enrichment), 16 cliques with 4 nodes (28-fold), and 1 clique with 5 nodes (161-fold). (The enrichments are relative to an ensemble of randomized control networks analyzed under the same procedures.)

We also re-analyzed the data after allowing for a small number of loops (≤N−2) between loci inside the clique and loci outside the clique. The number of isolated cliques identified rises substantially: in GM12878, we observed 567 isolated cliques with 3 nodes (6.2-fold enrichment relative to an ensemble of randomized control networks analyzed under the same criteria), 86 cliques with 4 nodes (12-fold), 5 cliques with 5 nodes (14-fold), and one clique with 6 nodes (41-fold).

These cliques had several notable features. First, they typically (in 63% of cases) involved a series of consecutive loops, i.e., the clique loci were positioned one-after-another in the human genome, with no other loop anchors intervening. This feature is consistent with the fact that loops tend not to overlap. Second, the clique loci exhibited a highly characteristic pattern of CTCF binding. The first clique locus (the locus closest to the p-terminus of the chromosome) typically contained a bound CTCF motif in the forward orientation (97%, an 4.3-fold enrichment). The last clique locus contained a bound CTCF motif in the reverse orientation (97%, an 4.1-fold enrichment). The middle clique loci typically contained a pair of nearby CTCF motifs pointing away from one another (in 52% of cases, a 6.1-fold enrichment; median distance: 4.6 kb), such that the first motif pointed toward the preceding clique locus and the second motif pointed toward the subsequent clique locus. This divergent configuration at clique loci is thus consistent with the convergent rule for CTCF looping that we recently described. It is also consistent with the requirement that loops cannot overlap, even if the overlap is small.

One possible interpretation of these isolated cliques is the formation of a "chromatin rosette" comprising a set of consecutive loops whose anchors are all simultaneously co-located at a single spatial hub. As such, our data suggest hundreds of possible chromatin rosettes located in an interphase human genome. The existence of rosettes has been proposed by several groups (Sachs R, Engh G, Trask B, Yokota H, Hearst J (1995) PNAS 92, 2710-2714; León P, Macaya G (1983) Chromosoma 88(4): 307-314), and the presence of other types of hubs has been carefully documented at individual loci such as beta-globin (Splinter E et al. (2006) Genes Dev 20(17):2349-54).

Interestingly, the extrusion model predicts that the genomic intervals inside chromatin loops can be nearly adjacent in the genomic sequence, but cannot overlap. This is precisely what is seen in a chromatin rosette. In contrast, the model of anchor points being brought together by diffusion is less likely to produce rosettes.

It is important to emphasize one major limitation of our analysis. While the pattern of higher-order relationships among loops is consistent with the possibility of chromatin rosettes occurring in individual nuclei, our data are based on pairwise contacts across an ensemble of cells. From these data, we cannot tell whether the various loops in an isolated clique occur simultaneously in individual nuclei. Of course, it is possible that some of our cliques reflect simultaneous loops, whereas others do not.

Both Models can be Used to Recapitulate Hi-C Experimental Results Given the Locations of CTCF Binding Next, we sought to explore whether our models could be used to recapitulate Hi-C experimental results in silico using CTCF ChIP-Seq data alone.

We began by using the extrusion model to simulate the folding of a 2.3 Mb target region on chromosome 4 (20.3-22.6 Mb). Our algorithm created an in silico representation of the region as a uniform polymer and then added forward and reverse anchors placed at the binding sites of CTCF observed in experimental ChIP-Seq data for the region. The strength of each anchor (i.e., the likelihood that a subunit on the appropriate strand would halt when sliding across the anchor) reflected the amplitude of the CTCF peak. The orientation of each anchor was assigned based on the strand of the CTCF motif associated with the peak. The algorithm did not use Hi-C data as an input. We then simulated the results of exposing this model polymer to a solvent containing extrusion complexes, which functioned as described in our extrusion model. We found that the contact matrix resulting from these simulations closely resembled the contact matrix obtained using Hi-C experiments (FIG. 5D, Pearson's r=0.964). In particular, the position of peaks and contact domains in the simulated matrix corresponded to what was observed in our kilobase resolution Hi-C experiment, and appropriate γ values were obtained inside contact domains. When we repeated this procedure for other target regions, the results were similar.

Next, we sought to simulate the same target region using the tension globule model. As before, we identified peaks in CTCF ChIP-Seq data, and assigned each peak an orientation based on the strand of the CTCF motif associated with the peak. In order to achieve a reasonable correspondence with experimental results, we had to impose a number of rules and fit various parameters: loops were only allowed between pairs of convergent peaks, and the likelihood of such a loop depended on: (i) the strength of the peaks; (ii) the distance between the peaks; and (iii) the number and strength of intervening CTCF peaks. We fit the parameters so that the frequencies of the loops matched the frequencies estimated from ChIP-Seq data. The results of the simulation were similar to the results of Hi-C experiments (Pearson's r=0.922).

Importantly, the tension globule model differs from the extrusion model in that achieving a good fit requiring imposing various ad hoc penalties, which do not correspond to any natural processes in three-dimensional diffusion. Even so, the fit was not as accurate as the fit produced by simulations based on loop extrusion. By contrast, the extrusion model involved much more natural assumptions.

Genome Editing of CTCF/Cohesin Motifs Disrupts Corresponding Loops and Contact Domains In our Hi-C data, the formation of loops is strongly associated with the presence of a pair of CTCF motifs in the convergent orientation. Both of the physical models described above suggest that these motifs play a causal role in loop formation.

To study the formation of loops experimentally, we used CRISPR/Cas9-based genome editing to modify CTCF motifs in a targeted fashion and then explored the resulting changes in loop structure.

We focused on HAP1, a human, haploid, fibroblast-like cell line, because the use of a haploid cell line avoids the issues raised by allelic heterogeneity for both Hi-C and CRISPR experiments. We generated an in situ Hi-C map of wild-type HAP1 cells, with 1.1B reads. We annotated 8,334 loops and 4,332 contact domains in the map.

Based on this map, we chose to study a target region on chromosome 8 containing three loci: A (133.9 Mb), B (134.2 Mb), and C (134.5 Mb). Each pair of these three loci form loops with one another, consistent with the presence of a hub. CTCF sites are present at each locus in accordance with the convergent rule: locus A has a forward-oriented CTCF motif (dubbed A/Forward); locus B has a reverse-oriented CTCF motif (B/Reverse) followed by a forward-oriented motif (B/Forward) (the two motifs do not overlap); and locus C has a reverse-oriented motif (C/Reverse). All three loops are associated with contact domains.

Under the convergent rule, we would predict that deleting the B/Forward site would disrupt the loop between B and C but have no effect on the other two loops. In particular, disruption would not affect the loop between A and B, which, according to the convergent CTCF rule, would be anchored at B/Reverse rather than B/Forward. To test this hypothesis, we performed genome editing to create a deletion in the B/Forward motif and grew a clonal population of the resulting cells. We then repeated the in situ Hi-C experiment on the disrupted cells, and mapped loops genome-wide. As predicted by the convergent rule, the loop from B to C was disrupted. The A/B and A/C loops were not affected. More generally, we did not observe significant alteration of any loop, genome-wide, in the mutant cells, with the exception of the B/C loop.

We then used genome-editing to test additional predictions of the convergent rule. To reduce sequencing costs, we developed an inexpensive way to monitor the results only in the target region by performing HYbrid Capture on the in situ Hi-C library, a method we dubbed "Hi-C2". (We validated the Hi-C2 method by applying it to wild-type HAP1 and our B/Forward deletion mutant, and confirmed that the results were equivalent to those obtained using ordinary in situ Hi-C.)

We tested two further predictions of the convergent rule in the target region: (i) inversion of the B/Forward site should have the same effect as deletion of the site—namely, the B/C loop should disappear; and (ii) deletion of B/Reverse should lead to the disappearance of the A/B loop. In both cases, the experimental Hi-C2 data matched these predictions.

Next, we probed a second target region, on chromosome 1, containing three loci: D (@180.5 Mb), E(@180.8 Mb), and F(@181.1 Mb) whose contact map was again consistent with the presence of a hub: all three were connected to one another by loop domains; each loop is associated with CTCF motifs in the convergent orientation. As before, deletion of E/Forward led to the disappearance of the E/F loop. When we took the E/Forward mutant and further deleted E/Reverse, the D/E loop disappeared. The D/F loop remained, as predicted by the convergent rule.

Finally, we targeted a third region, on chromosome 5, containing three loci: G (@180.5 Mb), H (@180.8 Mb), and I (@181.1 Mb) whose contact map was again consistent with the presence of a hub. We inserted a single base pair into the G/Forward site, thereby disrupting the CTCF binding site. Both the G/H loop and the G/I loop disappeared.

In every single case above, the convergent rule predicted exactly which loops would be affected by a genome editing experiment. These results confirm that convergent CTCF sites play a causal role in the formation of loops, and show that it is possible to re-engineer chromatin loops in a targeted fashion.

It is noteworthy that the experiments described above targeted isolated cliques in HAP1, similar to those revealed in our network analysis of GM12878. If the loops in these cliques had been simultaneous, disruption of only one loop would be impossible. (If loops A/B and A/C are present simultaneously, then B and C must also be in close proximity.) Our ability to disrupt B/C alone, without eliminating either A/B or A/C (and the similar findings when we disrupted loops A/B and E/F) suggests that, in the case of the two cliques in question, the loops are not simultaneous.

These experiments also shed light on the mechanisms of contact domain formation. In all but two cases, the disruption of loops led to the attenuation, but not the disappearance, of the contact domain spanned by the loop. This behavior is not expected under the tension globule model, which would predict the complete disappearance of the contact domain. However, it may be associated with a behavior seen in our extrusion simulations. In our extrusion simulations, a genomic interval bounded by two loop anchors that do not loop to one another still forms a domain, since the sliding of extrusion complexes in the interval can be impeded by other extrusion complexes whose subunits occupy the loop anchors. In fact, the cases where contact domains remained after editing of a loop anchor locus are examples of this scenario: they were all cases in which two loop anchor motifs were present at the locus (forward and reverse), but only one motif—and only one loop—was disrupted. In order to completely eliminate a domain in our extrusion simulations, it is necessary to disrupt all loop anchor motifs located at the domain's boundary, so that the boundary locus ceases to be a loop anchor. Strikingly, this behavior is seen in our editing experiments. The disruption of the forward motif at G, a locus which contains no other loop anchor motif, led to the disappearance of the contact domain bounded at G. Similarly, the simultaneous disruption of both E/Forward and E/Reverse, leaving no other loop anchor motifs at locus E, led to the disappearance of both the D/E and E/F domains. As such, there is a strong correspondence between the contact maps obtained experimentally in our genome editing experiments and the contact maps predicted by our loop extrusion simulations. Our results suggest that it may be possible to re-engineer contact domains in a targeted fashion.

DISCUSSION

With the dramatic improvements in resolution that can be achieved using in situ Hi-C, it is now possible to probe the physical and mechanical properties of chromatin genome-wide. Our results illuminate the structure of chromatin at multiple scales: chromatin fibers, contact domains, and loops.

At the smallest scale, the winding of DNA around histones has long been known to form the flexible 10 nm fiber. This fiber is widely believed to coil into the larger, stiffer 30 nm fiber, although recent studies using microscopy, electron spectroscopy, and X-ray scattering have failed to find evidence for 30 nm fibers in vivo (Fussner E et al. (2012) EMBO Rep 13, 992-996; Joti Y et al. (2012) Nucleus 3, 404-410; Nishino Y et al. (2012) EMBO J 31, 1644-1653; Ricci M A, Manzo C, Garcia-Parajo M, Lakadamyali M, Cosma M P (2015) Cell 160, 1145-1158). Our Hi-C data allows us to measure the Kuhn length, or bendability, of chromatin fibers, and to thereby compare the mechanical properties of fibers in vivo to the values predicted under various models. Strikingly, we find that chromatin fibers are highly bendable, with a Kuhn length of roughly 1 kb. This value is far smaller than what would be expected for a 30 nm fiber (30-60 kb) (Wedemann and Langowski (2002) supra; Schiessel (2003) supra), suggesting that 30 nm fibers, if they exist, are rare in intact chromatin. Interestingly, our findings suggest that, at the scale of the typical gene (~15 kb), chromatin is highly flexible. This observation is broadly relevant to physical models of loop formation, transcription, and replication. Of particular relevance for the present study, the flexibility of chromatin fibers inferred from our experimental Hi-C data is compatible with (and essential for) loop and domain formation through extrusion.

In our original Hi-C study (Lieberman-Aiden et al. (2009) supra), we probed the physical structure of chromatin at the megabase scale by calculating the relationship between the 1D distance separating two loci, s, and the probability of physical contact between them, I(s). Because the size of our dataset was limited, we performed this calculation using a genome-wide average. For values of s between 500 kb and 7 Mb, we found power-law behavior: specifically, $I(s) \propto s^{-\gamma}$ with $\gamma = 1.08$. This value of $\gamma$ was inconsistent with an ordinary condensed polymer at equilibrium (for which $\gamma = 1.5$) but is consistent with a fractal globule. Fractal globules are an appealing model for chromatin because they are dense and unknotted, suggesting how chromatin can be tightly packed while remaining physically accessible. The value of the genome-wide average has been reproduced in many subsequent studies, including this one, with similar results.

In our recent Hi-C experiments at kilobase resolution (Rao et al. (2014) supra), we observed a large number of contact domains (median length, 200 kb) that together partition the genome. In the present study, we explore the structure of chromatin inside individual domains by exploiting the vastly higher resolution of our new maps to calculate I(s), in a locus-specific fashion, genome-wide. The contact probability exhibits a power-law behavior at fine scale, but with a different exponent, $\gamma = 0.75$, than that observed from our low-resolution genome-wide average. We show that this value is robust across domains, cell types, and species, and is independent of nuclear volume. It is also robust to changes in experimental conditions, such as the use or the specific conditions of crosslinking. Notably, we find that measurements of $\gamma$ obtained from averages over larger scales overestimate the value of $\gamma$ within domains, because the contact frequency declines sharply when a domain boundary is crossed. When only pairs of loci that lie in the same domain are included, we show that genome-wide averages also yield a value of $\gamma = 0.75$.

The value $\gamma = 0.75$ is inconsistent with an ordinary polymer at equilibrium. To rigorously determine whether such a value could be consistent with a fractal globule architecture for individual domains, we proved a novel mathematical theorem describing how the Minkowski (fractal) dimension of a set changes when the set is mapped using a fractal curve. As a corollary, we find that values of $\gamma$ inside a fractal globule must lie between 1 and 2, implying that chromatin inside domains is inconsistent with the fractal globule model. Interestingly, our theoretical observations highlight the growing potential of genomic datasets to suggest increasingly sophisticated mathematical results in areas seemingly unrelated to biology. In the present case, our theorem provides a deterministic analog of a well-known result by McKean for Brownian motion (McKean H P (1955) Duke Math J 22, 229-234). Moreover, we illustrate our corollary by constructing a novel variant of the famous Hilbert curve, first described by David Hilbert in 1891. In Hilbert's original construction, a 1D curve snakes continuously through a smooth-bounded 2D square, filling all points as it passes. Our "Inside-Out" Hilbert curve snakes through a 2D shape with arbitrarily rough fractal boundaries. Our findings suggest that the study of genome folding as a whole may—perhaps unexpectedly—serve as a fruitful catalyst for discoveries in mathematics.

Another way of interpreting values of $\gamma$ is by using physical simulations to identify polymer states with similar $\gamma$ values. In our original Hi-C study, we showed that a polymer that was crushed by external forces naturally folds into a fractal globule with a value of $\gamma = 1$. However, there is also evidence that attractive forces exist between nucleosomes and other chromatin components. Therefore, in the present work, we considered the possibility that internal forces—attractions between pairs of monomers—may also play a role. Specifically, we used molecular dynamics simulations to probe the condensation of a polymer in response to a combination of external and internal forces. We found that varying the ratio of internal and external forces results in a family of possible structures, all of which are dense and unknotted. Within this family, two dominant regimes are observed. At one extreme—when external forces dominate—the result of the condensation process is symmetric, yielding a classic fractal globule with $\gamma = 1$. At the other extreme—when internal forces dominate—tension arises along the polymer chain, leading to anisotropic condensation with $\gamma = 0.72$. Thus, the value of $\gamma$ observed in these "tension globules" closely matches the value of $\gamma$ observed in Hi-C contact domains. Tension globules contain long stretches in which position along the polymer in 1D correlates with position along a linear axis in 3D, and closely resemble a non-equilibrium polymer state first postulated by de Gennes. When we explored the consequences of loop formation in a tension globule, we found that it leads to the formation of a contact domain and does not affect the value of $\gamma$. Taken together, the kilobase-resolution maps published in our recent report are consistent with the existence of tension globules in which loops are associated with the formation of contact domains.

Nonetheless, the tension globule model has important drawbacks. These drawbacks emerge from the putative mechanism of loop formation in a tension globule, which is the classic model of loop formation through diffusion. In this model, looping proteins (such as CTCF) initially bind to DNA anchor motifs. When diffusion brings two anchors into close spatial proximity, the proteins dimerize, forming a chromatin loop between the anchor motifs. This diffusive process may take a long time, and would tend to lead to a tangle of overlapping loops. It is also hard to understand, in a diffusive model, why the CTCF/cohesin motifs at pairs of loop anchors must lie in the convergent orientation.

To overcome these limitations, we explore a different model of loop formation based on a proposal by Nasmyth (Nasmyth K (2001) Annu Rev Genet 35:673-745; Alipour E, Marko J F (2012) Nucl Acids Res 1-11), who hypothesized that loops form during metaphase chromosome condensation through the action of an extrusion complex comprising two tethered DNA binding subunits, each of which extrude DNA as they slide—relative to the genome—in opposite directions. He specifically suggested that such a process might involve cohesin proteins, which form a tripartite ring that can slide along DNA and chromatin. To date, little direct evidence has been observed in support of this model.

We show, by means of physical simulations, that the extrusion of a loop leads to the formation of a contact domain between the loop's two anchors, whose $\gamma$ value closely matches the value seen in our Hi-C maps. The kilobase-resolution Hi-C maps are thus consistent with both models (and may be consistent with other models as well).

In fact, we show that simulations with both models can be used to recapitulate the results of Hi-C experiments, using only data about CTCF-binding sites from ChIP-Seq. The contact matrices resulting from such simulations correlate strongly with the results of kilobase-resolution Hi-C experiments at short range (<2 Mb), and there is a strong correspondence between the position of peaks and contact domains in our simulations and their position in actual Hi-C experiments. Notably, the tension globule simulations required ad hoc penalties for loops between non-consecutive CTCF motifs, and yielded less accurate results.

Figure 8:
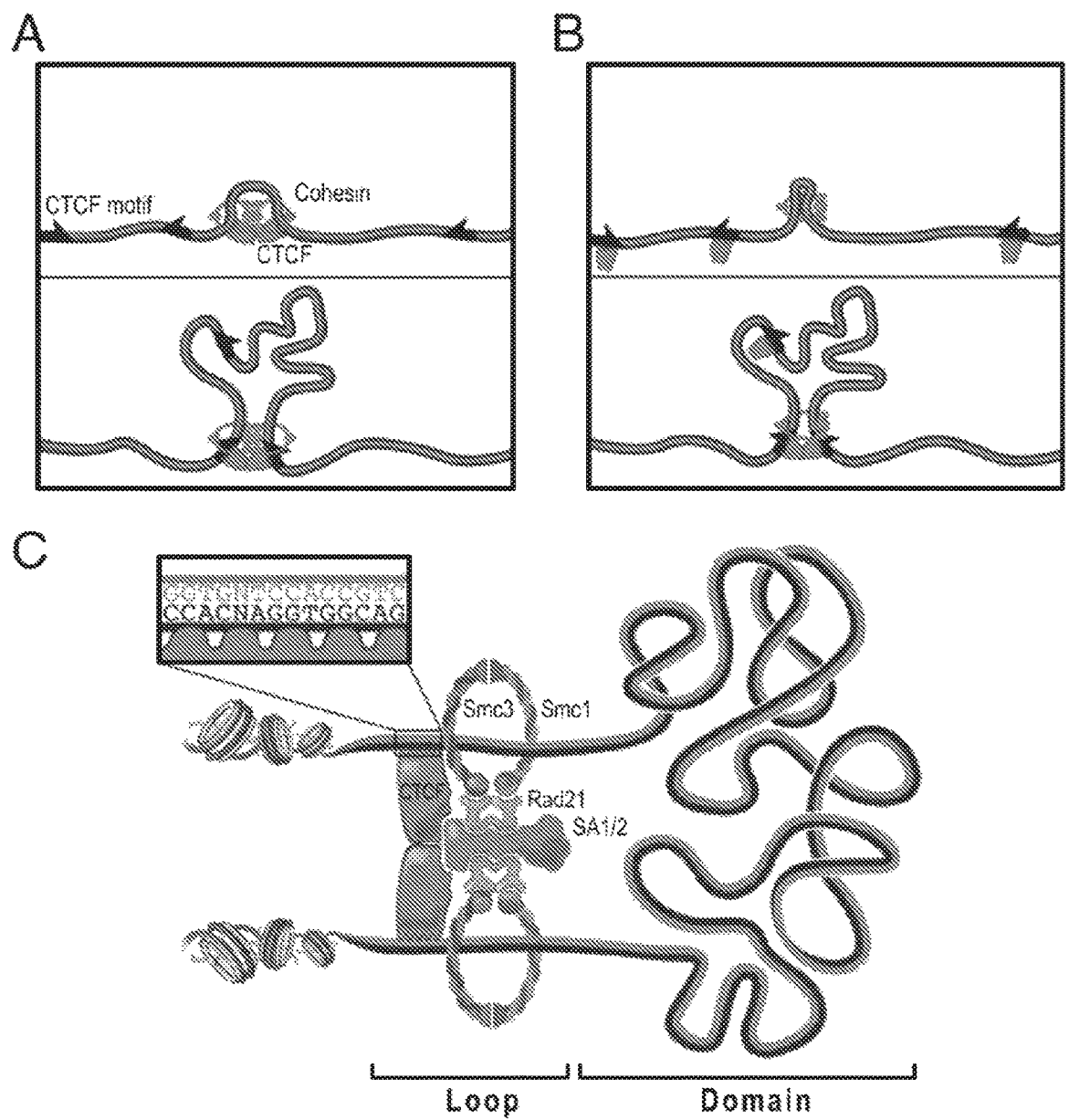
FIG. 8. We hypothesize that loops are formed during interphase by an extrusion mechanism comprising CTCF and cohesin. Here, we illustrate possible models for the extrusion complex. (A) In one model, the complex includes two DNA-binding subunits, each comprising a cohesin ring and a CTCF protein. When the complex is loaded onto DNA, a tiny loop forms. The two subunits engage the chromatin fiber in an antisymmetrical fashion, with their CTCF proteins facing the outside of the loop, scanning opposite DNA strands. The loop expands without knotting as the subunits slide in opposite directions. The interior of the loop forms a contact domain. When the CTCF proteins find a target motif on the appropriate strand, they can bind, arresting the progress of the subunit. Eventually, the extrusion complex dissociates. As multiple complexes land, extrude, and dissociate, loops and domains form. (B) In a second model, the sliding of cohesin alone leads to extrusion. Independently, CTCF proteins bind to their motif in an oriented fashion. When the cohesin ring encounters a CTCF protein, the extrusion process either continues or halts, depending on the orientation of CTCF. (C) Detailed view of the model in A. Other models are possible. Notably, it is unclear how many CTCF proteins and cohesin rings participate in a single extrusion complex, or whether the complex is part of a larger structure. All extrusion models predict that focal chromatin interactions mediated by CTCF must be intrachromosomal.

Several possibilities exist for the structure of the extrusion complex. One possibility is that the extrusion complex comprises two cohesin rings and two CTCF proteins (FIG. 8). The complex is loaded onto DNA via loading of the cohesin rings at adjacent DNA sites and the simultaneous binding of the CTCF proteins nearby. Each CTCF/cohesin pair serves as a single DNA binding subunit. These subunits extrude DNA in opposing directions: one is a forward subunit, and the other is a reverse subunit.

Because DNA strands are intrinsically oriented (5'→3), the forward and reverse subunits must engage the two DNA anchor sites in antisymmetric fashion in order for them to slide in opposite directions. Although additional structural studies would be needed to confirm this hypothesis, we can use ChIP-Seq to look for antisymmetric behavior in the relative positioning of CTCF and Cohesin with respect to chromatin loop anchors. Despite the fact that both proteins are associated with the same DNA motif, we find that they exhibit antisymmetric behavior: CTCF tends to be positioned near the motif, towards the outside of a loop, whereas RAD21 and SMC3 are positioned approximately 20 bp away, towards the loop interior. In other words, the CTCF/cohesin motif at a loop anchor points away from the centroid of the CTCF peak and toward the centroid of the RAD21 and SMC3 peaks. This supports the notion that the forward and reverse subunits engage DNA in antisymmetric fashion, and suggests that the cohesin ring trails behind the CTCF protein as they slide along DNA, with the CTCF protein serving as a "brake" that is capable of stalling the extrusion process.

If the extrusion complex subunits engage DNA antisymmetrically, then, as chromatin is extruded, the zinc fingers of the two CTCF proteins track along opposite strands of the DNA double helix. Sliding continues in either direction until it is either slowed or stopped by the presence of a CTCF motif on the appropriate strand (FIG. 5A).

Of course, there are other possible models. For instance, the extrusion complex may include CTCF, but not cohesin. In such a model, cohesin binding would occur only after an extrusion complex containing CTCF has formed a long-range loop. Alternatively, the extrusion complex may include cohesin, but not CTCF. In such a model, CTCF proteins bind independently to their target motif, and either permit or prevent the sliding of cohesin rings depending on their orientation.

Although both the tension globule and the extrusion model are consistent with our kilobase-resolution maps, the latter model both (i) leads to better simulation results, and (ii) more importantly, naturally explains two key features not explained by the tension globule. First, extruded loops cannot overlap, whereas simple diffusion is likely to result in substantial overlap and entanglement. In fact, we rarely observe overlapping loops in our data (4-fold depletion). Instead, the putative rosettes suggest that consecutive loops span adjacent but non-overlapping genomic intervals. Second, the extrusion model can explain why loops must lie between convergent CTCF motifs.

Our physical simulations fail to explain one important feature of Hi-C data: the observation that contact domains fall into at least two compartments and six subcompartments, each consisting of loci that tend to show similar patterns of long-range interactions. Compartmentalization, seen in humans and many other species, manifests as a plaid arrangement in Hi-C maps. The fact that these compartments are not recapitulated by our simulations indicates that, although CTCF and cohesin help establish loop anchors and contact domain boundaries, other mechanisms are responsible for positioning each contact domain in the appropriate nuclear neighborhood. In particular, we have previously reported that compartments and subcompartments tend to be associated with distinctive chromatin modifications.

Our work also demonstrates that it is possible to re-engineer loops and domains in a targeted fashion by modifying a small number of bases in the CTCF/cohesin motifs that lie at loop anchors. The effect on the loops depends on the orientation of the CTCF/cohesin motif, consistent with the convergent rule for looping described in our previous report. We show that inserting a single base pair is sufficient to eliminate multiple loops and domains, thereby affecting genome folding at the megabase scale. Moreover, we show that our extrusion model simulations can predict the Hi-C contact map of an engineered locus using only binding sites for CTCF in wild-type cells as input.

The ability to read out the 3D structure of a genome has improved rapidly in recent years. As shown by our genome-editing experiments, it may now be possible to not only "read" 3D-folding patterns, but to write them. Going forward, the ability to interpret what we read and write in terms of physical mechanisms remains a central challenge, and it will be important to devise experimental tests that can directly distinguish between the possible models of chromatin structure. These tests will likely include efforts to interfere with the function of CTCF and cohesin. In some examples, the methods described herein can be used for engineering genomes in 3D, 3D prediction (how will it fold); de novo genome assembly for whole genomes; reading and writing genomes in 3D and predicting structures as well as many other applications.

All documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

For the purpose of clarity and a concise description, features are described herein as part of the same or separate embodiments. However, it will be appreciated that the scope of the invention may include embodiments having combinations of all or some of the features described.

The following examples are provided to illustrate certain particular features and/or embodiments. These examples should not be construed to limit the invention to the particular features or embodiments described.

EXAMPLES

Example 1

The inventors used the disclosed methods, termed in situ Hi-C (an improved method for probing the three-dimensional architecture of Genomes) to construct haploid and diploid maps of nine cell types. The densest, in human lymphoblastoid cells, contains 4.9 billion contacts, achieving 1-kilobase resolution. The inventors found that genomes are partitioned into local domains, which are associated with distinct patterns of histone marks and segregate into six sub-compartments. The inventors identified ~10,000 loops. These loops frequently link promoters and enhancers, correlate with gene activation, and show conservation across cell types and species. Loop anchors typically occur at domain boundaries and bind CTCF. CTCF sites at loop anchors occur predominantly (>90%) in a convergent orientation, with the asymmetric motifs 'facing' one another. The inactive X-chromosome splits into two massive domains and contains large loops anchored at CTCF-binding repeats.

The spatial organization of the human genome is known to play an important role in the transcriptional control of genes (Bickmore, Annual review of genomics and human genetics 14, 67-84, 2013; Cremer and Cremer, Nature Rev Genet 2, 292-301, 2001; Sexton et al., Nature structural & molecular biology 14, 1049-1055, 2007). Yet important questions remain, like how distal regulatory elements, such as enhancers, affect promoters and how insulators can abrogate these effects (Banerji et al., Cell 27, 299-308, 1981; Blackwood and Kadonaga, Science (New York, N.Y.) 281, 60-63, 1998; Gaszner and Felsenfeld, Nature Reviews: Genetics 7, 703-713, 2006). Both phenomena are thought to involve the formation of protein-mediated "loops" that bring pairs of genomic sites that lie far apart along the linear genome into proximity (Schleif, Annual review of biochemistry 61, 199-223, 1992).

Over the past quarter-century, various methods have emerged to assess the three-dimensional architecture of the nucleus in vivo (Gerasimova et al., Molecular cell 6, 1025-1035, 2000; Mukherjee et al., Cell 52, 375-383, 1988), including nuclear ligation assay and chromosome conformation capture (3C), which analyze contacts made by a single locus (Cullen et al., Science 261, 203-206, 1993; Dekker et al., Science 295, 1306-1311, 2002; Murrell et al., Nature genetics 36, 889-893, 2004; Tolhuis et al., Molecular cell 10, 1453-1465, 2002), extensions such as 5C for examining several loci simultaneously (Dostie et al., Genome research 16, 1299-1309, 2006), and methods such as CHIA-PET for examining all loci bound by a specific protein (Fullwood et al., Nature 462, 58-64, 2009). The inventors had previously developed Hi-C, which combines DNA-DNA proximity ligation with highthroughput sequencing to interrogate all pairs of loci across a genome (Lieberman-Aiden et al., Science 326, 289-293, 2009).

Disclosed herein is a new and unique method, dubbed in situ Hi-C, in which proximity ligation is performed in intact nuclei. The protocol facilitates generation of much denser Hi-C maps. The maps reported here comprise 5 terabases of sequence data recording over 15 billion contacts; they are larger, by an order of magnitude, than all published Hi-C datasets combined. Using single nucleotide polymorphisms (SNPs), we also construct diploid maps corresponding to each chromosomal homolog. The maps provide a picture of genomic architecture with resolution down to 1 kilobase. They show that the genome is partitioned into domains that are associated with particular patterns of histone marks and that segregate into six sub-compartments, distinguished by unique long range contact patterns. Using the maps, the inventors have identified ~10,000 distinct loops across the genome and study their properties, including their strong association with gene activation. Strikingly, the vast majority of loop anchors bind CTCF. Moreover, the two CTCF motifs that occur at the anchors of a loop are found in a convergent orientation—that is, with the asymmetric CTCF motifs 'facing' one another—over 90% of the time. The diploid maps show that the inactive X chromosome is partitioned into two massive domains, and contains large loops anchored at CTCF-binding repeats.

Results

In Situ Hi-C Methodology and Maps

Figure 11:
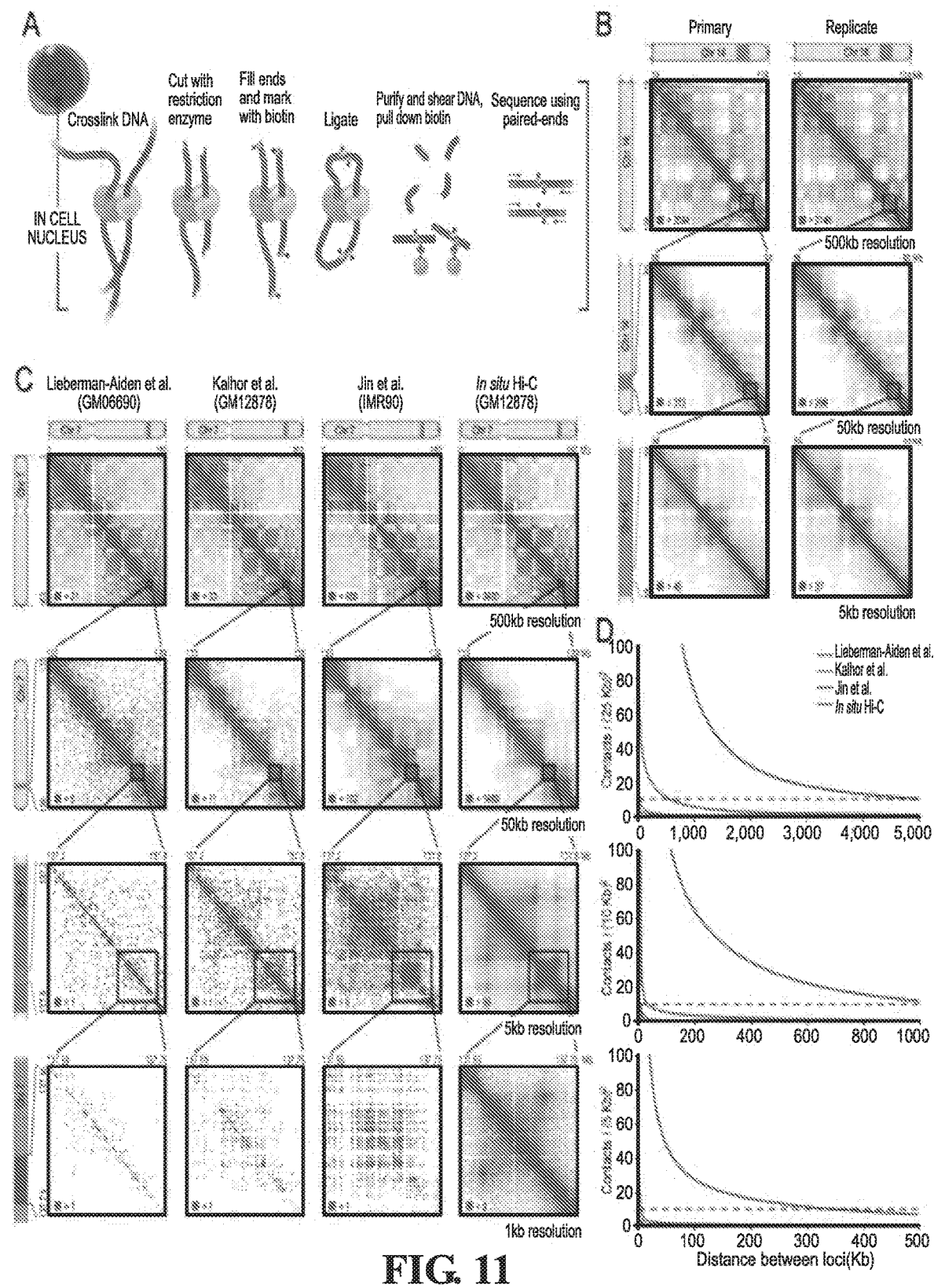
FIG. 11. In situ Hi-C was used to map over 15 billion chromatin contacts across nine cell types in human and mouse, achieving 1 kilobase resolution in human lymphoblastoid cells. (A) During in situ Hi-C, DNA-DNA proximity ligation is performed in intact nuclei. (B) Contact matrices from chromosome 14: the whole chromosome, at 500 Kb resolution (top); 86-96 Mb/50 Kb resolution (middle); 94-95 Mb/5 Kb resolution (bottom). Left: GM12878, primary experiment; Right: replicate. The 1D regions corresponding to a contact matrix are indicated in the diagrams above and at left. The intensity of each pixel represents the normalized number of contacts between a pair of loci. Maximum intensity is indicated in the lower left of each panel. (C) Is a comparison in situ HI-C++ generated map of chromosome 7 in GM12878 (last column) to earlier Hi-C maps: Lieberman-Aiden et al., Science 326, 289-293, 2009; Kalhor et al., Nature biotechnology 30, 90-98, 2012, and Jin et al. (D) Mean contacts per pixel vs distance, at various resolutions, compared to published Hi-C experiments (dashed line=10).

As implemented in this Example, the disclosed in situ Hi-C protocol involves cross-linking cells with formaldehyde; permeabilizing them with nuclei intact; digesting DNA with a suitable 4-cutter restriction enzyme (such as MboI); filling the 5'-overhangs while incorporating a biotinylated nucleotide; ligating the resulting blunt-end fragments; shearing the DNA; capturing the biotinylated ligation junctions with streptavidin beads; and analyzing the resulting fragments with paired-end sequencing (FIG. 11A).

The protocol has three major advantages over the original Hi-C protocol (here called dilution Hi-C). First, in situ ligation reduces the frequency of spurious contacts due to random ligation in dilute solution—as evidenced by a lower frequency of junctions between mitochondrial and nuclear DNA. Second, the protocol is much faster, requiring three days instead of seven. Third, it enables higher resolution and more efficient cutting of chromatinized DNA, for instance, through the use of a 4-cutter (MboI) rather than a 6-cutter (typically, HindIII).

A Hi-C map is a list of DNA-DNA contacts produced by a Hi-C experiment. By partitioning the linear genome into "loci" of fixed size (e.g., bins of 1 Mb or 1 Kb), the Hi-C map can be represented as a "contact matrix" M, where the entry Mi,j is the number of contacts observed between locus Li and locus Lj. (A "contact" is a read pair that remains after we exclude reads that do not align uniquely to the genome, that correspond to unligated fragments, or that are duplicates.) The contact matrix can be visualized as a heatmap, whose entries are called "pixels". An "interval" refers to a (one-dimensional) set of consecutive loci; the contacts between two intervals thus form a "rectangle" or "square" in the contact matrix. "Matrix resolution" is defined as the locus size used to construct a particular contact matrix and "map resolution" as the smallest locus size such that 80% of loci have at least 1000 contacts. The map resolution describes the finest scale at which one can reliably discern local features in the data.

Contact Maps Spanning 9 Cell Lines Containing Over 15 Billion Contacts.

The inventors constructed in situ Hi-C maps of 9 cell lines in human and mouse. Whereas the original Hi-C experiments had a map resolution of 1 Mb, these maps have a resolution of 1 Kb or 5 Kb, demonstrating the surprising improvement. The largest map, in human GM12878 B-lymphoblastoid cells, aggregates the results of nine biological replicate experiments derived from independent cell cultures. It contains 4.9 billion pairwise contacts and has map resolution of 950 bp ("kilobase resolution"). This map was used to construct contact matrices with locus sizes ranging from 2.5 Mb to 1 Kb. The inventors also generated eight in situ Hi-C maps at 5 kb resolution, using cell lines representing all human germ layers (IMR90, HMEC, NHEK, K562, HUVEC, HeLa, and KBM7) as well as mouse Blymphoblasts (CH12-LX). Each of these maps contains between 395M and 1.1B contacts. To test reproducibility, a comparison was made of "primary" GM12878 map (2.6 billion contacts from a single culture) to a "replicate" map (2.3 billion contacts aggregated from experiments on eight other samples). The results were strongly correlated both visually and statistically (Pearson's R>0.998, 0.996, 0.96 and 0.85 at matrix resolutions of 500, 50, 5, and 1 Kb; P-values throughout are negligible unless stated) (FIG. 11B-D). Biological replicates were compared in IMR90, HMEC, K562, KBM7, and CH12-LX with similar results. To ensure that the results were comparable with those of previous Hi-C experiments, an original dilution Hi-C protocol was used to generate a map of GM12878 with 3.2 billion contacts; the in situ and dilution Hi-C showed high reproducibility (R>0.96,0.90, 0.87 at 500,50,25 Kb). This procedure was repeated in IMR90, HMEC, NHEK, HUVEC, CH12-LX with similar results. The inventors also performed 112 supplementary Hi-C experiments using three different protocols (in situ Hi-C, dilution Hi-C, and Tethered Conformation Capture) while varying a wide array of conditions such as crosslinking time, restriction enzyme, ligation volume/time, and biotinylated nucleotide. The experiments demonstrated that the findings presented herein were robust to particular experimental conditions (see the sections on loop calling). In total, 201 independent Hi-C experiments were successfully performed. To identify fine-scale features in Hi-C maps, it is essential to account for non-uniformities in coverage due to the number of restriction sites at a locus or the accessibility of those sites to cutting (Cournac et al., BMC genomics 13, 436, 2012; Hu et al., Bioinformatics (Oxford, England) 28, 3131-3133, 2012; Imakaev et al., Nature methods 9, 999-1003, 2012; Lieberman-Aiden et al., Science 326, 289-293, 2009; Yaffe and Tanay, Nature genetics 43, 1059-1065, 2011). Either circumstance would increase the number of restriction fragments at the locus available for ligation, and thus the frequency of contacts involving the locus and any other locus. These non-uniformities were accounted for by normalizing each contact matrix using a matrix-balancing algorithm due to Knight and Ruiz (Knight and Ruiz, IMA Journal of Numerical Analysis, 2012). Three other published Hi-C bias-correction methods were also used (Cournac et al., BMC genomics 13, 436, 2012; Imakaev et al., Nature methods 9, 999-1003, 2012; Lieberman-Aiden et al., Science 326, 289-293, 2009); all produced similar results.

The Genome is Partitioned into Small Domains with Consistent Patterns of Chromatin.

It was next sought to use the vastly higher (200- to 1000-fold) map resolution of the present data to re-examine the three-dimensional partitioning of the genome. In earlier experiments at 1 Mb map resolution, large squares of enhanced contact frequency tiling the diagonal of the contact matrices were seen. These squares partitioned the genome into 5-20 Mb intervals, which we here call "megadomains." On opposite sides of a megadomain boundary, the contact frequency between pairs of loci drops sharply. Megadomains are very frequently preserved across cell types.

It was also found that individual 1 Mb loci could be assigned to one of two long-range contact patterns, which are termed herein Compartments A and B, with loci in the same compartment showing more frequent interaction. Megadomains—and the associated squares along the diagonal—arise when all of the 1 Mb loci in an interval exhibit the same genome-wide contact pattern (Kalhor et al., Nature biotechnology 30, 90-98, 2012; Lieberman-Aiden et al., Science 326, 289-293, 2009; Sexton et al., Cell 148, 458-472, 2012). Compartment A is highly enriched for open chromatin, and correlates strongly with DNaseI accessibility, active genes, and H3K36me3. Compartment B is enriched for closed chromatin.

Figure 12:
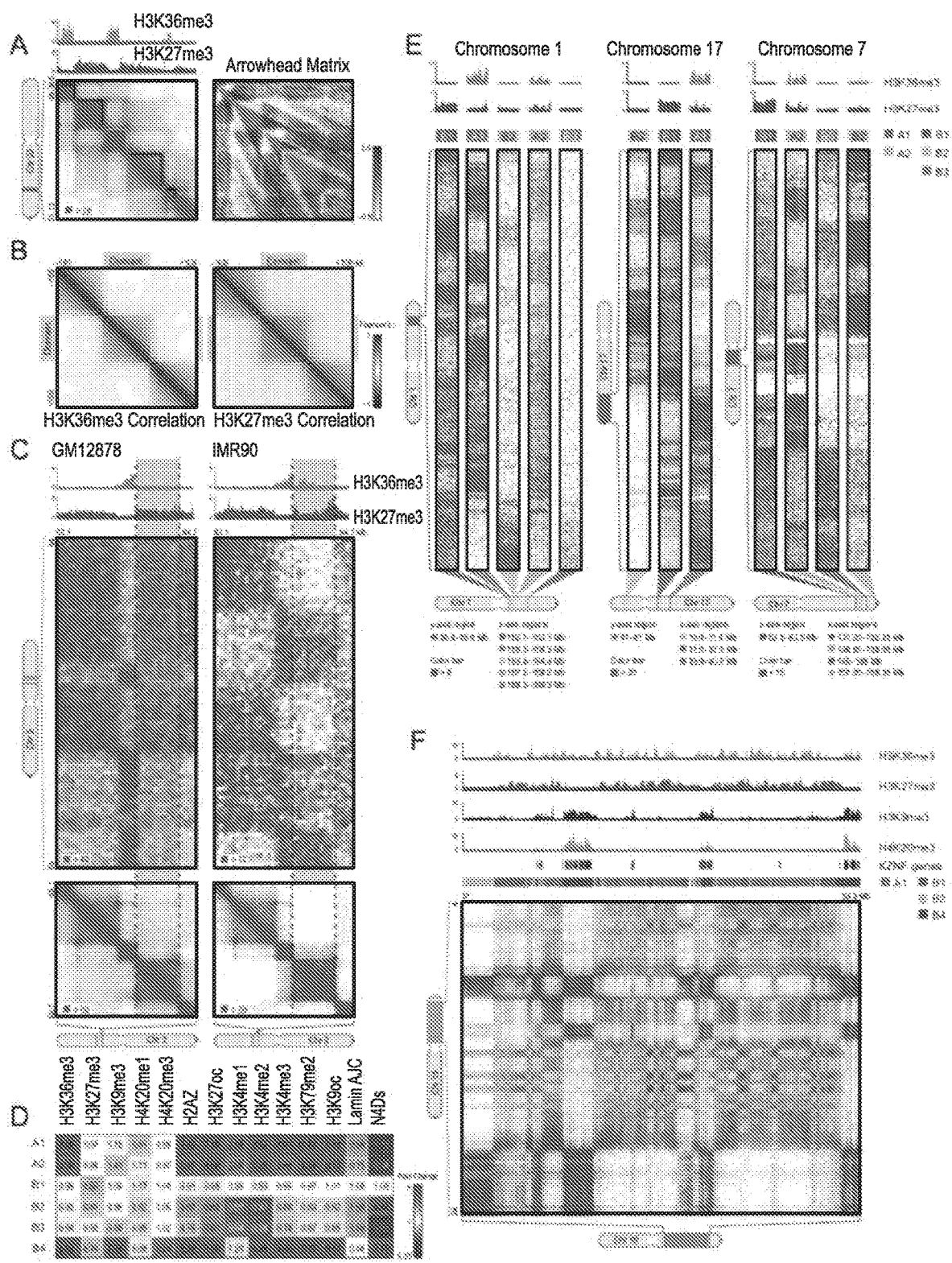
FIG. 12. The genome is partitioned into domains that segregate into nuclear subcompartments, corresponding to different patterns of histone modifications. (A) Thousands of domain are annotated (left, black highlight) using the arrowhead transformation (right), which converts domains into arrowhead-shaped motifs (example in yellow). (B) Pearson correlation matrices of the histone mark signal between pairs of loci inside, and within 100 Kb of, a domain. Left: H3K36me3; Right: H3K27me3. (C) Conserved domains on chromosome 3 in GM12878 (left) and IMR90 (right). In GM12878, the highlighted domain (gray) is enriched for H3K27me3 and depleted for H3K36me3. In IMR90, the situation is reversed. Marks at flanking domains are the same in both: the domain to the left is enriched for H3K36me3 and the domain to the right is enriched for H3K27me3. The flanking domains have long-range contact patterns which differ from one another and are preserved in both cell types. In IMR90, the central domain is marked by H3K36me3 and its long-range contact pattern matches the similarly-marked domain on the left. In GM12878, it is decorated with H3K27me3, and the long-range pattern switches, matching the similarly-marked domain to the right. Diagonal submatrices, 10 Kb resolution; long-range interaction matrices, 50 Kb resolution. (D) Each of the six long-range contact patterns we observe exhibits a distinct epigenetic profile. All epigenetic data is from ENCODE experiments in GM12878 except nuclear lamin (derived from skin fibroblast cells) and NAD (HeLa). See Table S8. Each subcompartment also has a visually distinctive contact pattern. (E) Each example shows part of the long-range contact patterns for several nearby genomic intervals lying in different compartments. (F) A large contiguous region on chromosome 19 contains intervals in subcompartments A1, B1, B2, and B4.

In the new, higher resolution maps presented herein, the inventors observed many small squares of enhanced contact frequency that tile the diagonal of each contact matrix (FIG. 12A). A dynamic programming algorithm was used to annotate these domains genome-wide. (Results using a previously published domain-calling algorithm (Dixon et al., 2012) were similar.) The observed domains range in size from 40 Kb to 3 Mb (median size 185 Kb). As with megadomains, there is an abrupt drop in contact frequency (33%) for pairs of loci on opposite sides of the domain boundary. Domains are very frequently preserved across cell type. The presence of smaller domains in Hi-C maps is consistent with other recent reports (Dixon et al., Nature 485, 376-380, 2012; Nora et al., Nature 485, 381-385, 2012; Sexton et al., Cell 148, 458-472, 2012), although the domains observed here are considerably smaller, likely due to the much larger dataset. Changes in histone marks at a domain are associated with changes in long-range contact pattern Loci within a domain show strongly correlated chromatin states for eight different histone modifications (H3K36me3, H3K27me3, H3K4me1, H3K4me2, H3K4me3, H3K9me3, H3K79me2, and H4K20me1) based on data from the ENCODE project in GM12878 cells (Consortium, 2011; Consortium et al., 2012). By contrast, loci at comparable distance but residing in different domains showed much less correlation in chromatin state (FIG. 12B). Strikingly, changes in a domain's chromatin state are often accompanied by changes in the long-range contact pattern of domain loci (i.e., the pattern of contacts between loci in the domain and other loci genome-wide), indicating that changes in chromatin pattern are accompanied by shifts in a domain's nuclear neighborhood (FIG. 12C).

There are at Least Six Nuclear Subcompartments with Distinct Patterns of Histone Modifications Next, it was sought to characterize the long-range contact patterns in the data. Loci were partitioned into categories based on long-range contact patterns alone, using four independent approaches: manual annotation, and three objective clustering algorithms (HMM, K-means, Hierarchical). All gave similar results. The biological meaning of these categories was then investigated.

When the data was analyzed at low matrix resolution (1 Mb), the earlier finding of two compartments (A and B) was reproduced. At high resolution (25 Kb), however, strong evidence was found for at least five "subcompartments" defined by their long-range interaction patterns, both within and between chromosomes. The median length of an interval lying completely within a subcompartment was 300 Kb.

Although the five subcompartments are defined solely based on their Hi-C interaction patterns, they show distinctive properties with respect to both their genomic and epigenomic content. Two of the five interaction patterns are strongly correlated with loci in compartment A. The loci exhibiting these patterns were labeled as belonging to subcompartments A1 and A2. Both A1 and A2 are gene dense, have highly expressed genes, harbor activating chromatin marks such as H3K36me3, H3K79me2, H3K27ac and H3K4me1 and are depleted at the nuclear envelope and at nucleolus associated domains (NADs). (See FIG. 12D,E) A2 is more strongly associated with the presence of H3K9me3 than A1, and the genes residing in A2 tend to be longer (2.4-fold). The other three interaction patterns (labeled B1, B2, and B3) are strongly correlated with loci in compartment B, and show very different properties. Subcompartment B1 correlates positively with H3K27me3 and negatively with H3K36me3, suggestive of facultative heterochromatin (FIG. 12D,E). Subcompartment B2 includes 62% of pericentromeric heterochromatin (3.8-fold enrichment) and is enriched at the nuclear envelope (1.8-fold) and at NADs (4.6-fold). Subcompartment B3 tends to lack all of the above-noted marks, suggesting ordinary heterochromatin; it is enriched at the nuclear envelope (1.6-fold), but strongly depleted at NADs (76-fold). (See FIG. 12D) Upon closer visual examination, we noticed the presence of a sixth pattern on chromosome 19 (FIG. 12F). The genome-wide clustering algorithm missed this pattern because it spans only 11 Mb, or 0.3% of the genome. When the algorithm was repeated on chromosome 19 alone, the additional pattern was detected. Because this sixth pattern correlates with the Compartment B pattern, it was labeled it B4. Subcompartment B4 comprises a handful of regions, each of which contain many KRAB-ZNF superfamily genes. (B4 contains 130 of the 278 KRAB-ZNF genes in the genome, a 65-fold enrichment). As noted in previous studies (Barski et al., Cell 129, 823-837, 2007; Hahn et al., PLoS One, 2011), these regions exhibit a distinctive chromatin pattern, with strong enrichment for both activating chromatin marks, such as H3K36me3, and heterochromatin-associated marks, such as H3K9me3 and H4K20me3.

In principle, the fact that domains lying in the same subcompartment exhibit similar chromatin marks might reflect either that (i) spatial proximity enhances the spread of histone modifications, or (ii) similarity of histone modifications helps bring about spatial proximity.

Approximately 10,000 Peaks Mark the Position of Chromatin Loops

Figure 13:
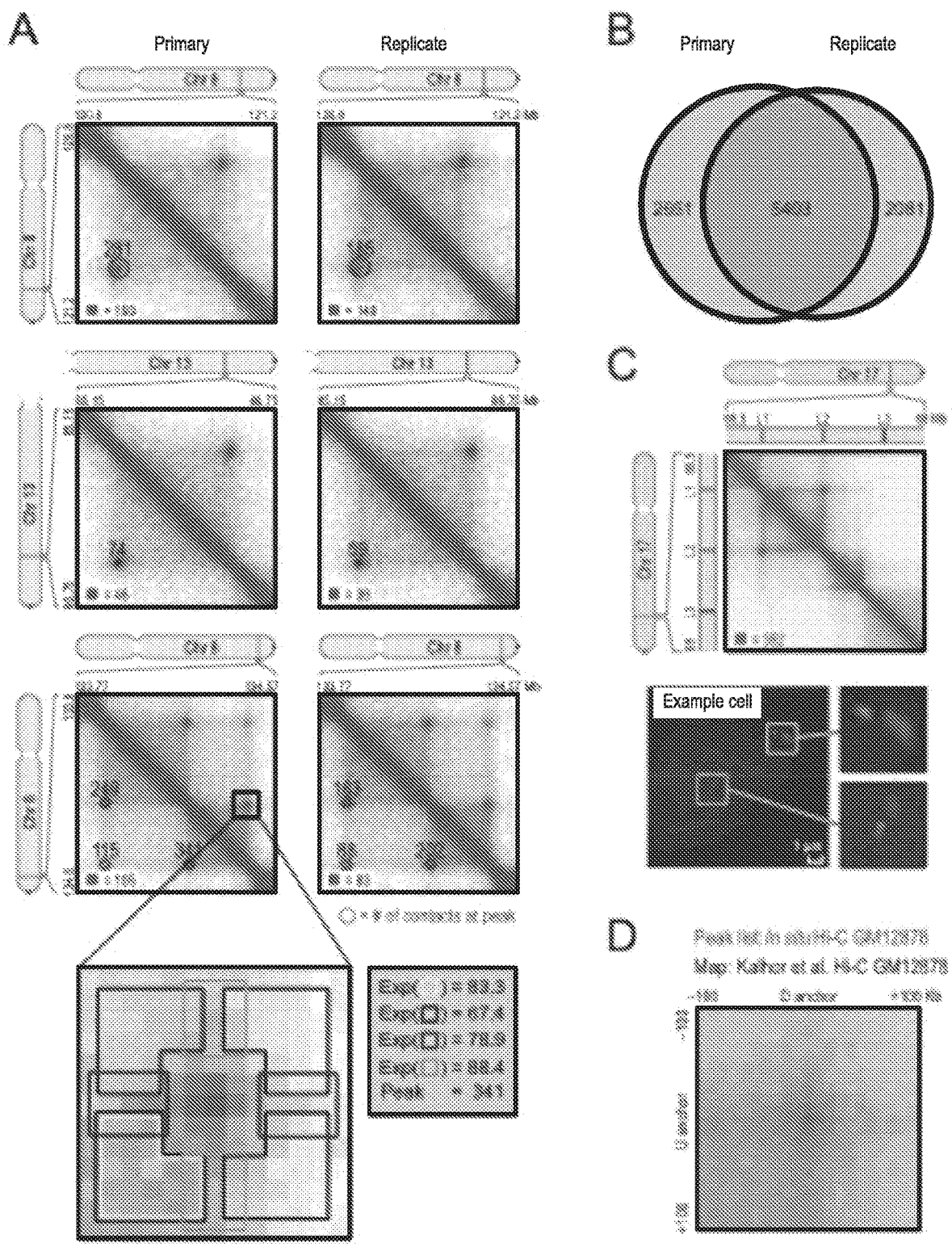
FIG. 13. The inventors identified thousands of chromatin loops genome-wide using a local background model. (A) The inventors identified peaks by detecting pixels that are enriched with respect to four local neighborhoods (blowout): horizontal (blue), vertical (green), lower-left (yellow), and donut (black). These "peak" pixels are marked with blue circles (radius=20 Kb) in the lower-left of each heatmap. The number of raw contacts at each peak is indicated. Left: primary GM12878 map; Right: replicate; annotations are completely independent. All contact matrices in these figures are 10 Kb resolution unless noted. (B) Overlap between replicates. (C) (Top) Location of 3D-FISH probes (Bottom) Example cell. (D) APA plot shows the aggregate signal from the 9948 GM12878 loops was made by summing submatrices surrounding each peak in a low-resolution GM12878Hi-C map due to Kalhor et al., Nature biotechnology 30, 90-98, 2012.
Figure 14:
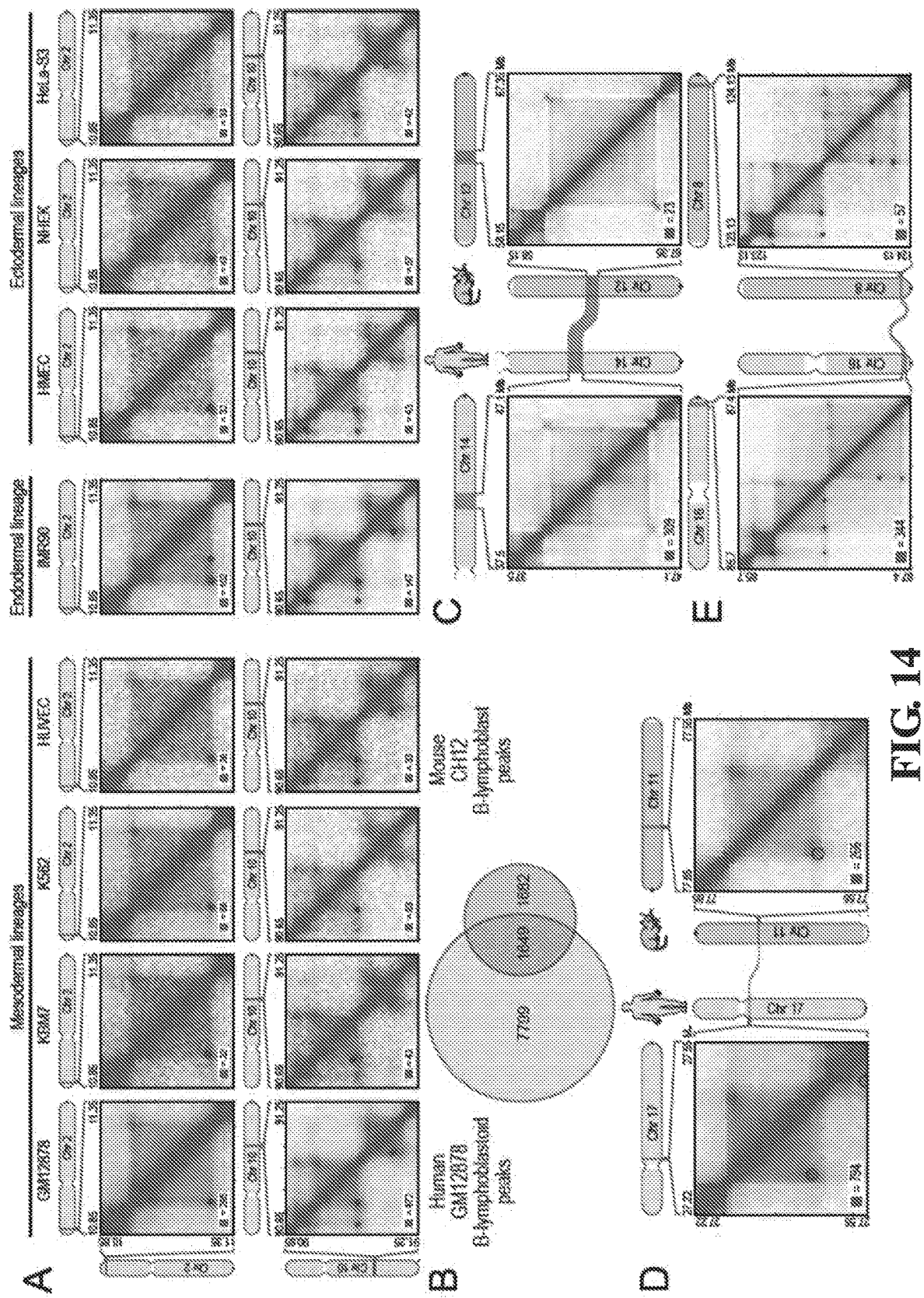
FIG. 14. Loops are often preserved across cell types and from human to mouse. (A) Examples of peak and domain preservation across cell types. Annotated peaks are circled in blue. All annotations are completely independent. (B) Of the 3331 loops we annotate in mouse CH12-LX, 1649 (50%) are orthologous to loops in human GM12878. (C-E) Conservation of threedimensional structure in synteny blocks.

It was next sought to identify the positions of chromatin loops by using an algorithm to search for pairs of loci that show significantly closer proximity with one another than with the loci lying between them (FIG. 13A). Such pairs correspond to pixels with higher contact frequency than typical pixels in their neighborhood. These pixels are referred to as "peaks" in the Hi-C heatmap, and to the corresponding pair of loci as "peak loci". Peaks reflect the presence of chromatin loops, with the peak loci being the anchor points of the chromatin loop. (Because contact frequencies vary across the genome, peak pixels are defined relative to the local background. Of Note, some papers have sought to define peaks relative to the genome-wide average. This choice is problematic because, for example, many pixels within a domain may be reported as peaks despite showing no locally distinctive proximity.). The algorithm detected 9448 peaks in the in situ Hi-C map for GM12878 at 5 kb map resolution. These peaks are associated with a total of 12,903 distinct peak loci (some peak loci are associated with more than one peak). The vast majority of peaks (98%) reflected loops between loci that are less than 2 Mb apart. (Examining the primary and replicate maps separately, 8054 peaks were found in the former and 7484 peaks in the latter, with 5403 in both lists. The differences were almost always the result of conservative peak-calling criteria.) As an independent confirmation that peak loci have greater physical proximity than neighboring locus pairs, 3D-FISH (Beliveau et al., Proceedings of the National Academy of Sciences of the United States of America 109, 21301-21306, 2012) was performed on 4 loops. In each case, two peak loci, L1 and L2, were compared with a control locus, L3, that lies an equal distance away from L2 but on the opposite side (FIG. 13C). In all cases, the distance between L1 and L2 was consistently shorter than the distance between L2 and L3. It was also confirmed that the list of peaks was consistent with previously published Hi-C maps. Although earlier maps contained too few contacts to reliably call individual peaks, the inventors developed a method called Aggregate Peak Analysis (APA) that compares the aggregate enrichment of the peak set in these low-resolution maps to the enrichment seen when the peaks are translated in any direction. APA showed strong consistency between the loop calls and all six previously published Hi-C datasets for lymphoblastoid cell lines (Kalhor et al., Nature biotechnology 30, 90-98, 2012; Lieberman-Aiden et al., Science 326, 289-293, 2009; FIG. 13D). Finally, it was demonstrated that the list of peaks was robust to particular protocol conditions by performing APA analysis on a GM12878 dilution Hi-C map, and on the 112 supplemental Hi-C experiments exploring a wide range of protocol variants. Enrichment was seen in every single experiment.

Conservation of Peaks Among Human Cell Lines and Across Evolution

The inventors also identified peaks in the other six human cell lines (IMR90, HMEC, NHEK, K562, HUVEC, HeLa, and KBM7). Because these maps contain fewer contacts, sensitivity is reduced, and fewer peaks are observed (ranging from 2634 to 8040). Notably, APA analysis showed strong consistency between these peak calls and the dilution Hi-C maps reported here (in IMR90, HMEC, HUVEC, and NHEK), as well as with all previously published Hi-C maps in these cell types. Overall, it was found that peaks were strongly conserved across cell types (FIG. 14A): approximately half of the peaks found in any given cell type were also found in GM12878. We also compared peaks across species. In CH12-LX mouse B-lymphoblasts, we identified 2927 high-confidence domains and 3331 peaks. There was a strong correspondence between orthologous regions in GM12878 and CH12-LX. Overall, 50% of peaks and 45% of domains called in mouse were also called in humans, suggesting strong conservation of three-dimensional genome structure across the mammals (FIG. 14B-E).

Figure 15:
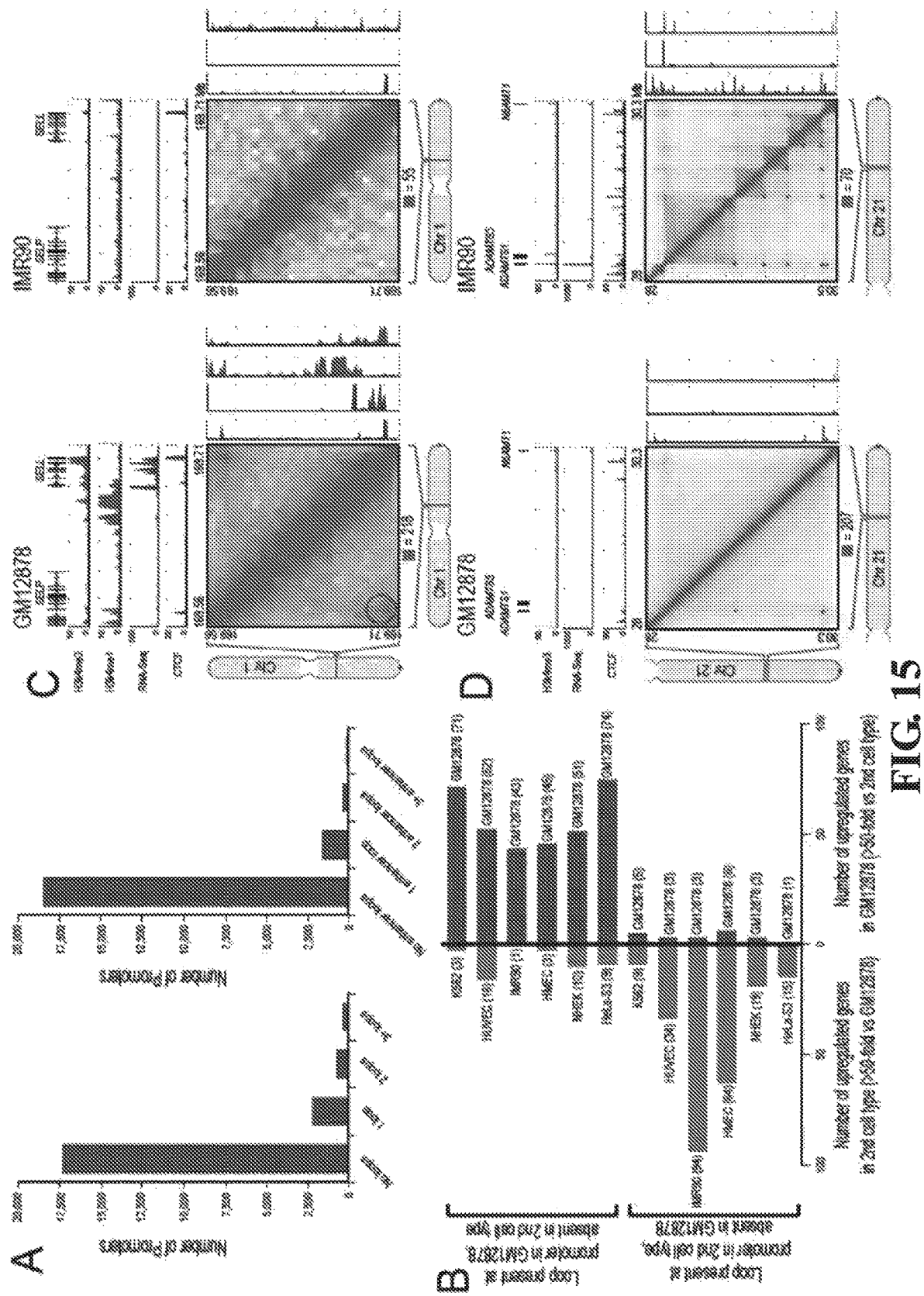

Loops Anchored at a Promoter are Associated with Enhancers and Increased Gene Activation Various lines of evidence indicate that many of the observed loops, defined by the peaks, are associated with gene regulation. First, the peaks frequently have a known promoter at one peak locus (as annotated by ENCODE's ChromHMM), and a known enhancer at the other (FIG. 15A). For instance, 2854 of the 9448 peaks in our GM12878 map bring together known promoters and known enhancers (30%, vs. 7% expected by chance). These peaks include well-studied promoter-enhancer loops, such as at MYC (chr8:128.35-128.75 Mb) and alpha-globin (chr16:0.15-0.22 Mb). Second, genes whose promoters are associated with a loop are much more highly expressed (6-fold). Third, the presence of cell type-specific peaks is associated with changes in gene expression.

Although peaks are strongly correlated across cell types, there were also many cases in which a peak was present in one cell type but not another. When we examined RNA-Seq data produced by ENCODE (ENCODE Consortium, 2011; ENCODE Consortium et al., 2012), it was found that the appearance of a loop in a cell type was frequently accompanied by the activation of a gene whose promoter overlapped one of the peak loci. For instance, 510 loops were observed in IMR90 that were clearly absent in GM12878. The corresponding peak loci overlapped the promoters of 94 genes that were markedly upregulated in IMR90 (>50-fold difference in RNA level), but of only 3 genes that were markedly upregulated in GM12878 (31-fold depletion). Conversely, 557 loops were found in GM12878 that were clearly absent in IMR90. The corresponding peak loci overlapped the promoters of 43 genes that were markedly upregulated in GM12878, but of only 1 gene that was markedly upregulated in IMR90: a 43-fold depletion. When GM12878 was compared to the five other human cell types for which ENCODE RNA-Seq data was available (all but KBM7), the results were very similar (FIG. 15B). One example of a cell-type specific loop is anchored at the promoter of the SELL gene, which encodes L-selectin, a lymphocyte-specific surface marker that is expressed in GM12878 but not IMR90 (FIG. 15C). Gene activation is occasionally accompanied by the emergence of a cell-type specific network of peaks. FIG. 15D illustrates the case of ADAMTS1, which encodes a protein involved in fibroblast migration. The gene is expressed in IMR90, where its promoter is involved in six loops. In GM12878, it is not expressed, and the promoter is involved in only two loops. Many of the IMR90 peak loci form transitive peaks with one another, suggesting that the ADAMTS1 promoter and the six distal sites may all be spatially co-located.

Peaks Frequently Demarcate the Boundaries of Domains

Figure 16:
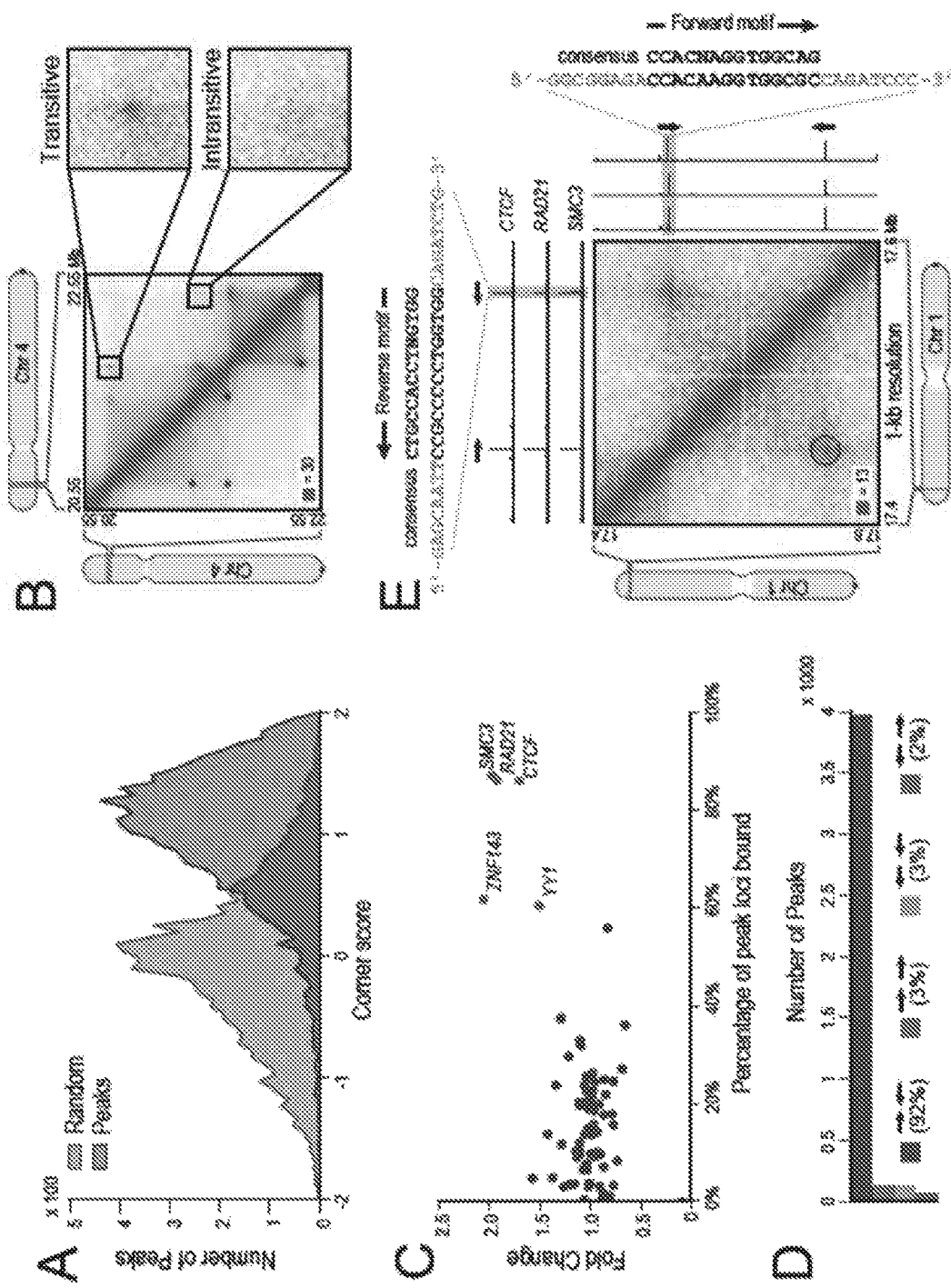
FIG. 16. Many loops demarcate domains; the vast majority of loops are anchored at a pair of convergent CTCF/RAD21/SMC3 binding sites. (A) Histograms of corner score for peak pixels vs. random pixels with an identical distance distribution. (B) Contact matrix for chr4:20.55 Mb-22.55 Mb in GM12878, showing examples of transitive and intransitive looping behavior. (C) % of peak loci bound vs. fold enrichment for 76 DNA-binding proteins. (D) The pairs of CTCF motifs that anchor a loop are nearly all found in the convergent orientation. (E) A peak on chromosome 1 and corresponding ChIP-Seq tracks. Both peak loci contain a single site bound by CTCF, RAD21, and SMC3. The CTCF motifs at the anchors exhibit a convergent orientation.

A large fraction of peaks (38%) coincide with the corners of a domain—that is, the peak loci are located at domain boundaries (FIG. 16A). Conversely, a large fraction of domains (39%) had peaks in their corner. Moreover, the appearance of a loop is usually (in 65% of cases) associated with the appearance of a domain demarcated by the loop. Because this configuration is so common, we will use the term "loop domain" to refer to domains whose endpoints form a chromatin loop.

In some cases, adjacent loop domains (bounded by peak loci L1-L2 and L2-L3, respectively) exhibit transitivity—that is, L1 and L3 also correspond to a peak. In these situations, the three loci may simultaneously co-locate at a single spatial position. However, many peaks do not exhibit transitivity, suggesting that the loci may not co-locate simultaneously. FIG. 16B shows a region on chromosome 4 exhibiting both configurations. It was also found that overlapping loops are strongly disfavored: pairs of loops L1-L3 and L2-L4 (where L1, L2, L3 and L4 occur consecutively in the genome) are found far less often than expected under a random model.

The Vast Majority of Peaks are Associated with Pairs of CTCF Motifs in a Convergent Orientation It was next asked whether peaks are associated with specific proteins. We therefore examined the results of 86 ChIP-Seq experiments performed by ENCODE in GM12878 (ENCODE Consortium, 2011; ENCODE Consortium et al., 2012). Strikingly, it was found that the vast majority of peak loci are bound by the insulator protein CTCF (86%) and the cohesin subunits RAD21 (86%) and SMC3 (87%) (FIG. 8C). Indeed, most peak loci contain a unique DNA site containing a CTCF binding motif, to which all three proteins (CTCF, SMC3, and RAD21) were bound (5-fold enrichment). We were thus able to associate most of the peak loci (6991 of 12,903) with a specific CTCF binding site "anchor". The consensus DNA sequence for CTCF binding sites is typically written as 5'-CCACNAGGTGGCAG-3' (SEQ ID NO: 16). Because the sequence is not palindromic, each CTCF site has an orientation; we designate the consensus motif above as the 'forward' orientation. Thus, a pair of CTCF sites on the same chromosome can have four possible orientations: (1) same direction on one strand; (2) same direction on the other strand; (3) convergent on opposite strands; and (4) divergent on opposite strands. If CTCF sites were randomly oriented, one would expect all 4 orientations to occur equally often. But when we examined the 4322 peaks in GM12878 where the two corresponding peak loci each contained a single CTCF binding motif, we found a stunning result: the vast majority (92%) of motif pairs are convergent (FIG. 16D,E). Overall, the presence, at pairs of peak loci, of bound CTCF sites in the convergent orientation was enriched 102-fold over random expectation. Notably, the convergent orientation was overwhelmingly more frequent than the divergent orientation, despite the fact that divergent motifs also lie on opposing strands: in GM12878, the counts were 3971-78 (51-fold enrichment of convergent vs. divergent); in IMR90, 1456-5 (291-fold); in HMEC, 968-11 (88-fold); in K562, 723 to 2 (362-fold); in HUVEC, 671-4 (168-fold); in HeLa, 301-3 (100-fold); in NHEK, 556-9 (62-fold); and in CH12, 625-8 (78-fold). This surprising pattern suggests that a pair of CTCF sites in the convergent orientation on opposite strands is required for the formation of a loop. The observation that looped CTCF sites occur in the convergent orientation also allows us to analyze peak loci containing multiple CTCF-bound motifs to predict which motif instance plays a role in a given loop. In this way, we can associate nearly two-thirds of peak loci (8175 of 12,903, or 63.4%) with a single CTCF binding site. The specific orientation of CTCF sites at observed peaks provides strong evidence that our peak calls are biologically correct. Because randomly chosen CTCF pairs would exhibit each of the four orientations with equal probability, the near-perfect association between our loop calls and the particular orientation could not occur by chance (p<10-1900). In addition, the presence of CTCF and RAD21 sites at many of our peaks provides an opportunity to compare our results to three recent CHIA-PET experiments reported by the ENCODE consortium (in GM12878 and K562) in which ligation junctions bound to CTCF (resp. RAD21) were isolated and analyzed. We found strong concordance with our results in all three cases.

Figure 17:
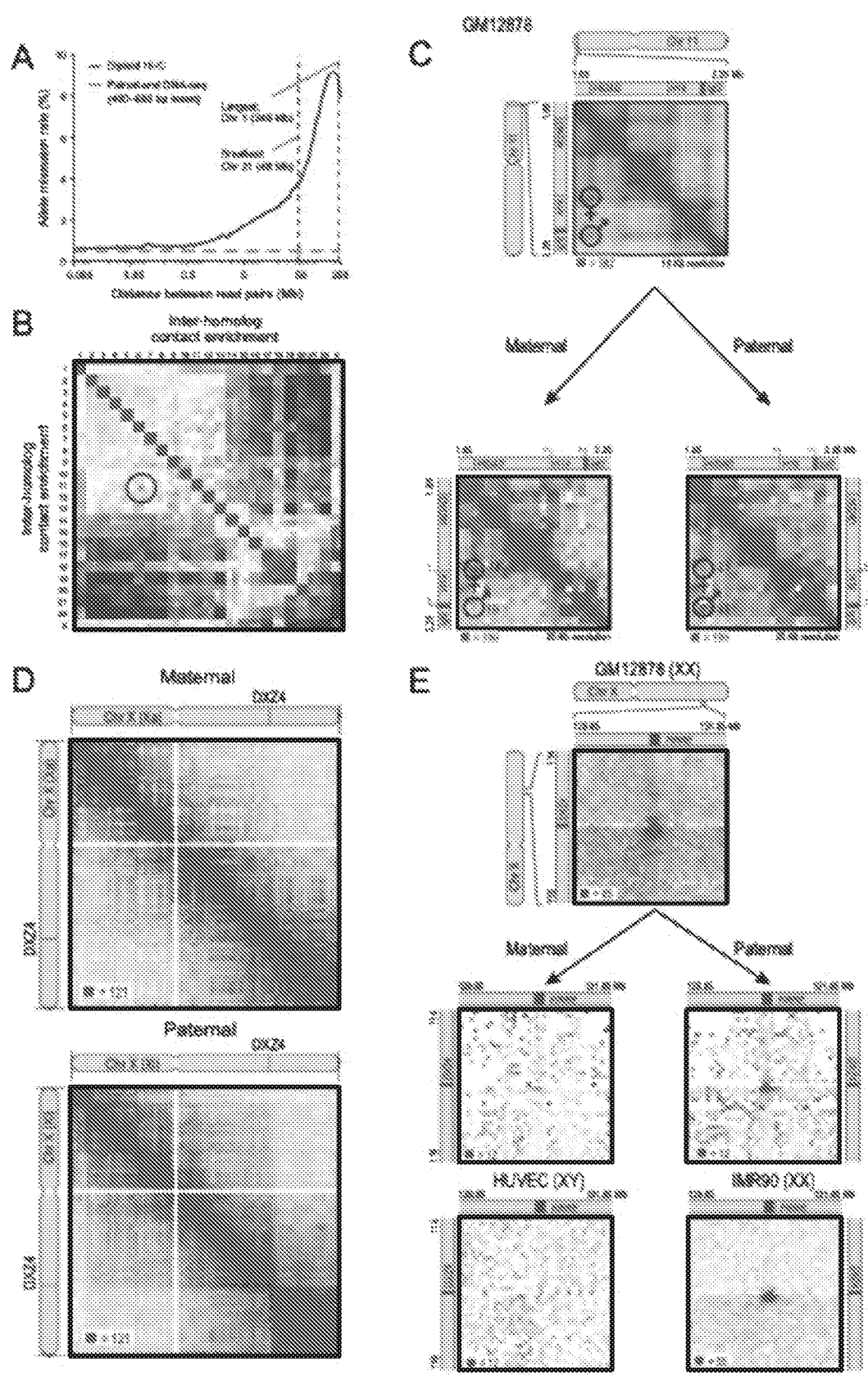
FIG. 17. Diploid Hi-C maps reveal superdomains and superloops anchored at CTCF-binding repeats on the inactive X chromosome. (A) The frequency of mismatch (maternal-paternal) in SNP allele assignment vs distance between two paired read alignments. Intrachromosomal read pairs are overwhelmingly intramolecular. (B) Preferential interactions between homologs. Left/top is maternal; right/bottom is paternal. The aberrant contact frequency between 6p and 11p (circle) reveals a translocation. (C) Top: In our unphased Hi-C map of GM12878, the inventors observed two loops joining both the promoter of the maternally-expressed H19 and the promoter of the paternally-expressed Igf2 to a distal locus, HIDAD. Using diploid Hi-C maps, the inventors phase these loops: the HIDAD-H19 loop is present only on the maternal homolog (left) and the HDAD-Igf2 loop is present only on the paternal homolog (right). (D) The inactive (paternal) copy of chromosome X (bottom) is partitioned into two massive "superdomains" not seen in the active (maternal) copy (top). DXZ4 lies at the boundary. (E) The "superloop" between FIRRE and DXZ4 is present in the GM12878 haploid map (top), in the paternal GM12878 map (middle right), and in the map of the female cell line IMR90 (bottom right); it is absent from the maternal GM12878 map (middle left) and the map of the male HUVEC cell line (bottom left).

Diploid Hi-C Maps Reveals Homolog-Specific Features, Including Imprinting-Specific Loops and Massive Domains and Loops on the Inactive X-Chromosome Because many of our reads overlap SNPs, it is possible to assign contacts to specific chromosomal homologs. Using GM12878 SNP-phasing data (Gil et al., Nature 491, 2012), we found that we could frequently assign reads to either the maternal or paternal homolog (FIG. 17A). Using these assignments, we constructed a "diploid" Hi-C map of GM12878 comprising both maternal (238M contacts) and paternal (240M) maps. We studied these maps for differences between homologous chromosomes in contact frequencies, domain structure, and loop structure. For autosomes, the maternal and paternal homologs exhibit very similar inter- and intrachromosomal contact profiles (Pearson's R>0.998, P value negligible). One interchromosomal difference was notable: an elevated contact frequency between the paternal homologs of chromosome 6 and 11 that is consistent with an unbalanced translocation fusing chr11q:73.5 Mb and all distal loci (a stretch of over 60 Mb) to the telomere of chromosome 6p (FIG. 17B). The signal intensity suggests that the translocation is present in between 1.2% and 5.6% of our cells. We tested this prediction by karyotyping 100 GM12878 cells using Giemsa staining and found three abnormal chromosomes, each showing the predicted translocation, der(6)t(6,11)(pter;q) (Fig. S40-S41). Notably, the Hi-C data reveal that the translocation involves the paternal homologs, which cannot be determined with ordinary cytogenetic methods. We also observed differences in loop structure between homologous autosomes at some imprinted loci. For instance, the H19/Igf2 locus on chromosome 11 is a well-characterized case of genomic imprinting. In our unphased maps, we clearly see two loops from a single distal locus at 1.72 Mb (which binds CTCF in the forward orientation) to loci located near the promoters of both H19 and Igf2 (both of which bind CTCF in the reverse orientation, i.e., the above consensus motif lies on the opposite strand; see FIG. 17C). We refer to this distal locus as the H19/Igf2 Distal Anchor Domain (HIDAD). Our diploid maps reveal that the loop to the H19 region is present on the maternal chromosome (from which H19 is expressed), but the loop to the Igf2 region is absent or greatly attenuated. The opposite pattern is found on the paternal chromosome (from which Igf2 is expressed). Most strikingly, differences were seen on the diploid intra-chromosomal maps of chromosome X. The paternal X chromosome, which is usually inactive in GM12878, is partitioned into two massive domains (0-115 Mb and 115-155.3 Mb). These "superdomains" are not seen in the active, maternal X (FIG. 17D). When we examined the unphased maps of chromosome X for the karyotypically normal female cell lines in our study (GM12878, IMR90, HMEC, NHEK), the superdomains on X were evident, although the signal was markedly attenuated by the superposition of signals from active and inactive X chromosomes. When we examined the male HUVEC cell line and the haploid KBM7 cell line, we saw no evidence of superdomains. Interestingly, the boundary between the superdomains (ChrX: 115 Mb+/−500 Kb) lies near the macrosatellite repeat DXZ4 (ChrX: 114,867, 433-114,919,088) near the middle of Xq. DXZ4 is a CpG-rich tandem repeat that is conserved across primates and monkeys and encodes a long non-coding RNA. In males and on the active X, DXZ4 is heterochromatic, hyper-methylated and does not bind CTCF. On the inactive X, DXZ4 is euchromatic, hypo-methylated, and binds CTCF. DXZ4 has been hypothesized to play a role in reorganizing chromatin during X inactivation (Chadwick, 2008). There were also significant differences in loop structure between the chromosome X homologs. We observed 27 extremely large "superloops," each spanning between 7 and 74 Mb, present only on the inactive X chromosome in the diploid map (FIG. 17E). The superloops were also seen in all 4 unphased maps from karyotypically normal XX cells, but were absent in unphased maps from X0 and XY cells. Two of the superloops (chrX:56.8 Mb-DXZ4 and DXZ4-130.9 Mb) have been reported previously, and their presence on the inactive X alone has been confirmed using multiple methods (Horakova et al., Human molecular genetics 21, 4367-4377, 2012). Like the peak loci of most other loops, nearly all the superloop anchors bind CTCF (25 of 26). The six anchor regions most frequently associated with superloops are very large (up to 200 kb). Four of these anchor regions contain whole lncRNA genes: loc550643; XIST; DXZ4; and FIRRE. Three (loc550643, and DXZ4, and FIRRE) contain CTCF-binding tandem repeats that only bind CTCF on the inactive homolog. DISCUSSION The in situ Hi-C protocol allowed us to probe genomic architecture with extremely high resolution; in the case of GM12878 lymphoblastoid cells, better than 1 kb. We observe the presence of domains that were too small to be seen in our original Hi-C maps, which had resolution of 1 Mb (Lieberman-Aiden et al., Science 326, 289-293, 2009). Loci within a domain interact frequently with one another, have similar patterns of chromatin modifications, and exhibit similar long-range contact patterns. Domains tend to be conserved across cell types and between human and mouse. Strikingly, when the pattern of chromatin modifications associated with a domain changes, the domain's long-range contact pattern also changes. The domains exhibit six distinct patterns of long-range contacts (subcompartments), which subdivide the two compartments that we had reported based on low resolution data. The subcompartments are each associated with distinct chromatin patterns. It is possible that the chromatin patterns play a role in bringing about the long-range contact patterns, or vice versa. High-resolution in situ Hi-C data makes it possible to create a genome-wide catalog of chromatin loops. We identified loops by looking for pairs of loci that have significantly more contacts with one another than they do with other nearby loci. In our densest map, GM12878 lymphoblastoid cells, we observe 9448 loops. We note that our annotation identifies fewer loops than were reported in several recent high throughput studies. The key reason is that we call peaks only when a pair of loci shows elevated contact frequency relative to the local background—that is, when the peak pixel is enriched as compared to other pixels in its neighborhood. In contrast, several previous studies have defined peaks by comparing the contact frequency at a pixel to the genome-wide average. This latter definition is problematic because many pixels within a domain can be annotated as peaks despite showing no local increase in contact frequency. Previous papers using the latter definition imply the existence of more than 100,000 or even more than 1 million peaks. The loops we observe have many interesting properties. First, most loops are short (<2 Mb). Second, loops are strongly conserved across cell types and between human and mouse. Third, promoter-enhancer loops are common and are strongly associated with gene activation. Fourth, loops often demarcate domains, and may establish them. Fifth, loops tend not to overlap. Sixth, loops are closely associated with the presence of CTCF and the cohesin subunits RAD21 and SMC3; each of these proteins is found at over 86% of loop anchors. The most striking property of loops is that the pair of CTCF motifs present at the loop anchors occurs in a convergent orientation in >90% of cases (vs. 25% expected by chance). The importance of motif orientation between loci that are separated by, on average, 360 Kb is unexpected and must bear on the mechanism by which CTCF and cohesin form loops, which likely involves CTCF dimerization. Experiments in which the presence or orientation of CTCF sites is altered should shed light on this mechanism. Such experiments may also enable the engineering of loops, domains, and other chromatin structures.

We also created diploid Hi-C maps, by using polymorphisms to assign contacts to distinct chromosomal homologs. We find that the inactive X chromosome is partitioned into two large "superdomains" whose boundary lies near the locus of the lncRNA DXZ4 (Chadwick, 2008).

We also detect a network of extremely long-range (7-74 Mb) "superloops", the strongest of which are anchored at locations containing lncRNA genes (loc550643, XIST, DXZ4, and FIRRE). With the exception of XIST, all of these lncRNAs contain CTCF-binding tandem repeats that bind CTCF only on the inactive X. We hypothesize that Xi-specific CTCF binding participates in the formation of these massive chromatin structures. Just as loops bring distant DNA loci into close spatial proximity, we find that they bring disparate aspects of DNA biology—domains, compartments, chromatin marks, and genetic regulation—into close conceptual proximity. As our understanding of the physical connections between DNA loci continues to improve, our understanding of the relationships between these broader phenomena will deepen.

EXPERIMENTAL PROCEDURES

In Situ Hi-C Protocol

All cell lines used were cultured following the manufacturer's recommendations. Cells were crosslinked with 1% formaldehyde for 10 minutes at room temperature. In situ Hi-C was performed by permeabilizing 2-5M nuclei. DNA was digested with 100 units of MboI (or DpnII), the ends of restriction fragments were labeled using biotinylated nucleotides, and were then ligated in a small volume. After reversal of crosslinks, ligated DNA was purified and sheared to a length of roughly 400 basepairs, at which point ligation junctions were pulled down with streptavidin beads and prepped for high-throughput Illumina® sequencing. Dilution Hi-C was performed as in (Lieberman-Aiden et al., Science 326, 289-293, 2009).

3D-FISH

FISH probes were designed using the OligoPaints database. DNA-FISH was performed as described in (Beliveau et al., Proceedings of the National Academy of Sciences of the United States of America 109, 21301-21306, 2012), with minor modifications.

Hi-C Data Pipeline

All sequence data was produced using Illumina® paired-end sequencing. Sequence data was processed using a custom pipeline that was optimized for parallel computation on a cluster. The pipeline uses BWA (Li and Durbin, Bioinformatics (Oxford, England) 26, 589-595, 2010) to map each read end separately to the b37 or mm9 reference genomes; removes duplicate and near-duplicate reads; removes reads that map to the same fragment; and filters the remaining reads based on mapping quality score. Contact matrices were generated at base-pair delimited resolutions of 2.5 Mb, 1 Mb, 500 Kb, 250 Kb, 100 Kb, 50 Kb, 25 Kb, 10 Kb, and 5 Kb, as well as fragment-delimited resolutions of 500f, 200f, 100f, 50f, 20f, 5f, 2f, and 1f. For the largest data sets, the file also contains a 1 Kb contact matrix. Normalized contact matrices are produced at all resolutions using (Knight and Ruiz, IMA Journal of Numerical Analysis, 2012).

Annotation of Domains

To annotate domains, a novel "arrowhead" transformation was applied, defined as $A_{i,i+d}=(M^*_{i,i-d}-M^*_{i,i+d})/(M^*_{i,i-d}+M^*_{i,i+d})$. $M^*$ denotes the normalized contact matrix. This transformation can be thought of as equivalent to calculating a matrix equal to $-1*(observed/expected-1)$, where the expected model controls for local background and distance from the diagonal in the simplest possible way: the "expected" value at $i,i+d$ is simply the mean observed value at $i,i-d$ and $i,i+d$. $A_{i,i+d}$ will be strongly positive if and only if locus $i-d$ is inside a domain and locus $i+d$ is not. If the reverse is true, $A_{i,i+d}$ will be strongly negative. If the loci are both inside or both outside a domain, $A_{i,i+d}$ will be close to zero. Consequently, if there is a domain at $[a,b]$, we find that A takes on very negative values inside a triangle whose vertices lie at $[a,a]$, $[a,b]$, and $[(a+b)/2,b]$, and very positive values inside a triangle whose vertices lie at $[(a+b)/2,b]$, $[b,b]$, and $[b,2b-a]$. The size and positioning of these triangles creates the arrowhead-shaped feature that replaces each domain in $M^*$. A "corner score" matrix, indicating each pixel's likelihood of lying at the corner of a domain, is efficiently calculated from the arrowhead matrix using dynamic programming.

Assigning Loci to Subcompartments

To cluster loci based on long-range contact patterns, we constructed a 100 Kb resolution contact matrix comprising a subset of the interchromosomal contact data. Loci on odd chromosomes appeared on the rows, and loci from the even chromosomes appeared on the columns. (Chromosome X was excluded.) This matrix was clustered using the Python package scikit. To generate annotation of subcompartment B4, the 100 kb interchromosomal matrix for chromosome 19 was constructed and clustered separately, using the same procedure.

Annotation of Peaks

The peak-calling algorithm examines each pixel in a Hi-C contact matrix and compares the number of contacts in the pixel to the number of contacts in a series of regions surrounding the pixel. The algorithm thus identifies pixels $M^*_{i,j}$ where the contact frequency is higher than expected, and where this enrichment is not the result of a larger structural feature. For instance, ruling out the possibility that the enrichment of pixel $M^*_{i,j}$ is the result of Li and Lj lying in the same domain by comparing the pixel's contact count to an expected model derived by examining the "lower-left" neighborhood. (The "lower-left" neighborhood samples pixels $M_{i',j'}$ where $i \leq i' \leq j' \leq j$; if a pixel is in a domain, these pixels will necessarily be in the same domain.) It is requires that the pixel being tested contain at least 50% more contacts than expected, and that this enrichment be statistically significant after correcting for multiple hypothesis testing (FDR<10%). The same criteria are applied to three other neighborhoods. To be labeled an "enriched pixel," a pixel must therefore be significantly enriched relative to four neighborhoods: (i) pixels to its lower-left; (ii) pixels to its left and right; (iii) pixels above and below; and (iv) a donut surrounding the pixel of interest (FIG. 6A). Using this approach, numerous enriched pixels were identified across the genome. The enriched pixels tend to form contiguous interaction regions comprising 5-20 pixels each. We define the "peak pixel" (or simply the "peak") to be the pixel in an interaction region with the largest number of contacts. Because over 10 billion (10 Kb)2 pixels must be examined, this calculation requires weeks of CPU time to execute. To accelerate it, a highly parallelized implementation was created using general-purpose graphical processing units, resulting in a 200-fold speedup relative to initial, CPU-based approach.

Aggregate Peak Analysis

APA is performed on 10 Kb resolution contact matrices. To measure the aggregate enrichment of a set of putative peaks in a contact matrix, we plot the sum of a series of submatrices derived from that contact matrix. Each of these submatrices is a 210 Kb×210 Kb square centered at a single putative peak in the upper triangle of the contact matrix. The resulting APA plot displays the total number of contacts that lie within the entire putative peak set at the center of the matrix; the entry immediately to the right of center corresponds to the total number of contacts in the pixel set obtained by shifting the peak set 10 Kb to the right; the entry two positions above center corresponds to an upward shift of 20 Kb, and so on. Focal enrichment across the peak set in aggregate manifests as larger values at the center of the APA plot. APA analyses only include peaks whose loci are at least 300 Kb apart.

Example 2

Comparison of results obtained for In situ determination of nucleic acid proximity as described herein and a Hi-C protocol. As shown herein, the disclosed methods yield a result with greater complexity, which indicates more interactions that can be mapped and consequently more information. In other words, 'complexity' . . . this is the number of total contacts/datapoints produced by the experiment, thus the greater number of data points, the more information is extracted from each trial. In addition, method disclosed herein provide more the 'large' reads, which correspond to a long distance intrachromosomal contact. These contacts are the most informative ones, as they can pin down the long range interactions in the cell. The data presented herein demonstrate that the methods disclosed herein are superior than the previous Hi-C methods. The methods and protocols disclosed below are non-limiting examples of the methods disclosed herein and variation on the protocols in envisioned, such as the times, temperatures, and specific reagents used. Some steps maybe omitted and others added.

In Situ Hi-C Protocol Prepped for Illumina Sequencing

Crosslinking

1) Grow two to five million cells under recommended culture conditions to about 80% confluence. Pellet suspension cells or detached adherent cells by centrifugation at 300×G for 5 min.
2) Resuspend cells in fresh medium at concentration of $1 \times 10^6$ cells per 1 ml media. In a fume hood, add freshly made formaldehyde solution to a final concentration of 1%. Incubate at room temperature for 10 min with mixing. In some examples, no crosslinking is performed and the proximity relationships between nucleic acids are maintained via other means, for example by embedding nuclei in agarose.
3) Add 2.5M glycine solution to a final concentration of 0.2M to quench the reaction. Incubate at room temperature for 5 min on rocker.
4) Centrifuge for 5 min at 300×g at 4° C. Discard supernatant into an appropriate collection container.
5) Resuspend cells in 1 ml of cold 1×PBS and spin for 5 min at 300×g at 4° C. Discard supernatant and flash-freeze cell pellets in liquid nitrogen or dry ice/ethanol.
6) Either proceed to the rest of the protocol or store cell pellets at −80° C.

Lysis and Restriction Digest

7) Combine 250 μl of ice-cold Hi-C lysis buffer (10 mM Tris-HCl pH8.0, 10 mM NaCl, 0.2% Igepal CA630) with 50 μl of protease inhibitors (Sigma, P8340). Add to one cross-linked pellet of cells.
8) Incubate cell suspension on ice for >15 minutes. Centrifuge at 2500×G for 5 minutes. Discard the supernatant.
9) Wash pelleted nuclei once with 500 μl of ice-cold Hi-C lysis buffer.
10) Gently resuspend pellet in 50 μl of 0.5% sodium dodecyl sulfate (SDS) and incubate at 62° C. for 5-10 minutes.
11) After heating is over, add 145 μl of water and 25 μl of 10% Triton® X-100 (Sigma, 93443) to quench SDS. Mix well, avoiding excessive foaming. Incubate at 37° C. for 15 minutes.
12) Add 25 μl of 10×NEBuffer2 and 100 U of MboI restriction enzyme (New England Biolabs (NEB, R0147)) and digest chromatin for at least 2 h or overnight at 37° C. with rotation.

In some examples, Hi-C can be performed with an additional centrifugation step added after restriction (step 12) and prior to fill-in.

Marking of DNA Ends, Proximity Ligation, and Crosslink Reversal

13) Incubate at 62° C. for 20 minutes, then cool to room temperature.
14) To fill in the restriction fragment overhangs and mark the DNA ends with biotin, add 50 μl of fill-in master mix:
   37.5 μl of 0.4 mM biotin-14-dATP (Life Technologies, 19524-016)
   1.5 μl of 10 mM dCTP
   1.5 μl of 10 mM dGTP
   1.5 μl of 10 mM dTTP
   8 μl of 5 U/ul DNA Polymerase I, Large (Klenow) Fragment (NEB, M0210)
15) Mix by pipetting and incubate at 37° C. for 45 min-1.5 hours with rotation.
16) Add 900 μl of ligation master mix:
   663 μl of water
   120 μl of 10×NEB T4 DNA ligase buffer (NEB, B0202)
   100 μl of 10% Triton X-100
   12 μl of 10 mg/ml Bovine Serum Albumin (100×BSA)
   5 μl of 400 U/μl T4 DNA Ligase (NEB, M0202)
17) Mix by inverting and incubate at room temperature for 4 hours with slow rotation.
18) Degrade protein by adding 50 μl of 20 mg/ml proteinase K (NEB, P8102) and 120 μl of 10% SDS and incubate at 55° C. for 30 minutes.
   (In some examples nuclei can be pelleted after ligation (step 17) and then resuspended, both to remove random ligations that may have occurred in solution and to reduce the overall volume for ease of handling.)
19) Add 130 μl of 5M sodium chloride and incubate at 68° C. for at least 1.5 hours or overnight.

DNA Shearing and Size Selection

20) Cool tubes at room temperature.
21) Split into two 750 μl aliquots in 2 ml tubes and add 1.6× volumes of pure ethanol and 0.1× volumes of 3M sodium acetate, pH 5.2, to each tube. Mix by inverting and incubate at −80° C. for 15 minutes.
22) Centrifuge at max speed, 2° C. for 15 minutes. Keeping tubes on ice after spinning, carefully remove the supernatant by pipetting.
23) Resuspend, combining the two aliquots, in 800 μl of 70% ethanol. Centrifuge at max speed for 5 minutes.
24) Remove all supernatant and wash the pellet once with 800 μl of 70% ethanol.
25) Dissolve pellet in 130 μl of 1× Tris buffer (10 mM Tris-Cl, pH 8) and incubate at 37° C. for 15 minutes to fully dissolve DNA.
26) To make the biotinylated DNA suitable for high-throughput sequencing using Illumina sequencers, shear to a size of 300-500 bp using the following parameters:
   Instrument: Covaris LE220 (Covaris, Woburn, Mass.)
   Volume of Library: 130 μl in a Covaris microTUBE Fill Level: 10
Duty Cycle: 15
PIP: 500
Cycles/Burst: 200
Time: 58 seconds 27) Transfer sheared DNA to a fresh 1.5 ml tube. Wash the Covaris vial with 70 µl of water and add to the sample, bringing the total reaction volume to 2000 Run a 1:5 dilution of DNA on a 2% agarose gel to verify successful shearing. For libraries containing fewer than $2 \times 10^6$ cells, the size selection using AMPure XP beads described in the next steps could be performed on final amplicons rather than before pull-down.
28) Warm a bottle of AMPure XP beads (Beckman Coulter, A63881) to room temperature. To increase yield, AMPure XP beads can be concentrated by removing some of the clear solution before the beads are mixed for use in the next steps.
29) Add exactly 110 µl (0.55× volumes) of beads to the reaction. Mix well by pipetting and incubate at room temperature for 5 minutes.
30) Separate on a magnet. Transfer clear solution to a fresh tube, avoiding any beads. The supernatant will contain fragments shorter than 500 bp.
31) Add exactly 30 µl of fresh AMPure XP beads to the solution. Mix by pipetting and incubate at room temperature for 5 minutes.
32) Separate on a magnet and keep the beads. Fragments in the range of 300-500 bp will be retained on the beads.
33) Keeping the beads on the magnet, wash twice with 700 pi of 70% ethanol without mixing.
34) Leave the beads on the magnet for 5 minutes to allow remaining ethanol to evaporate.
35) To elute DNA, add 300 µl of 1× Tris buffer, gently mix by pipetting, incubate at room temperature for 5 minutes, separate on a magnet, and transfer the solution to a fresh 1.5 ml tube
36) Quantify DNA by Qubit dsDNA High Sensitivity Assay (Life Technologies, Q32854) and run undiluted DNA on a 2% agarose gel to verify successful size selection.

Biotin Pull-Down and Preparation for Illumina Sequencing
Perform all steps in low-bind tubes.
37) Prepare for biotin pull-down by washing 150 µl of 10 mg/ml Dynabeads MyOne Streptavidin T1 beads (Life technologies, 65602) with 400 µl of 1× Tween Washing Buffer (1×TWB: 5 mM Tris-HCl (pH 7.5); 0.5 mM EDTA; 1M NaCl; 0.05% Tween 20). Separate on a magnet and discard the solution.
38) Resuspend the beads in 300 µl of 2× Binding Buffer (2×BB: 10 mM Tris-HCl (pH 7.5); 1 mM EDTA; 2M NaCl) and add to the reaction. Incubate at room temperature for 15 minutes with rotation to bind biotinylated DNA to the streptavidin beads.
39) Separate on a magnet and discard the solution.
40) Wash the beads by adding 600 µl of 1×TWB and transferring the mixture to a new tube. Heat the tubes on Thermomixer at 55° C. for 2 min with mixing. Reclaim the beads using a magnet. Discard supernatant.
41) Repeat wash.
42) Resuspend beads in 100 ul 1×NEB T4 DNA ligase buffer (NEB, B0202) and transfer to a new tube. Reclaim beads and discard the buffer.
43) To repair ends of sheared DNA and remove biotin from unligated ends, resuspend in 100 µl of master mix: 88 µl of 1×NEB T4 DNA ligase buffer with 10 mM ATP 2 µl of 25 mM dNTP mix
5 µl of 10 U/µl NEB T4 PNK (NEB, M0201)
4 µl of 3 U/µl NEB T4 DNA polymerase I (NEB, M0203)
1 µl of 5 U/µl NEB Klenow fragment of DNA polymerase I (NEB, M0210)
44) Incubate at room temperature for 30 minutes. Separate on a magnet and discard the solution.
45) Wash the beads by adding 600 µl of 1×TWB and transferring the mixture to a new tube. Heat the tubes on Thermomixer at 55° C. for 2 min with mixing. Reclaim the beads using a magnet. Discard supernatant.
46) Repeat wash.
47) Resuspend beads in 100 µl 1×NEBuffer 2 and transfer to a new tube. Reclaim beads and discard the buffer.
48) Resuspend in 100 µl of dATP attachment master mix:
90 µl of 1×NEBuffer 2
5 µl of 10 mM dATP
5 µl of 5 U/µl NEB Klenow exo minus (NEB, M0212)
49) Incubate at 37° C. for 30 minutes. Separate on a magnet and discard the solution.
50) Wash the beads by adding 600 µl of 1×TWB and transferring the mixture to a new tube. Heat the tubes on Thermomixer at 55° C. for 2 min with mixing. Reclaim the beads using a magnet. Discard supernatant.
51) Repeat wash.
52) Resuspend beads in 100 µl 1× Quick ligation reaction buffer (NEB, B6058) and transfer to a new tube. Reclaim beads and discard the buffer.
53) Resuspend in 50 µl of 1×NEB Quick ligation reaction buffer.
54) Add 2 µl of NEB DNA Quick ligase (NEB, M2200). Add 3 µl of an Illumina indexed adapter. Record the sample-index combination. Mix thoroughly.
55) Incubate at room temperature for 15 minutes. Separate on a magnet and discard the solution.
56) Wash the beads by adding 600 µl of 1×TWB and transferring the mixture to a new tube. Heat the tubes on Thermomixer at 55° C. for 2 min with mixing. Reclaim the beads using a magnet. Remove supernatant.
57) Repeat wash.
58) Resuspend beads in 100 µl 1× Tris buffer and transfer to a new tube. Reclaim beads and discard the buffer.
59) Resuspend in 50 µl of 1× Tris buffer.

Final Amplification and Purification
60) Amplify the Hi-C library directly off of the T1 beads with 4-12 cycles, using Illumina primers and protocol. In some examples to avoid PCR inhibition, one can detach DNA from the streptavidin beads by heating at 98° C. for 10 minutes after step 59 and then removing the beads with a magnet.)
61) After amplification is complete, bring the total library volume to 250 µl.
62) Separate on a magnet. Transfer the solution to a fresh tube and discard the beads.
63) Warm a bottle of AMPure XP beads to room temperature. Gently shake to resuspend the magnetic beads. Add 175 µl of beads to the PCR reaction (0.7× volumes). Mix by pipetting and incubate at room temperature for 5 minutes.
64) Separate on a magnet and remove the clear solution.
65) Keeping the beads on the magnet, wash once with 700 µl of 70% ethanol without mixing.
66) Remove ethanol completely. To remove traces of short products, resuspend in 100 µl of 1× Tris buffer and add 70 µl more of AMPure XP beads. Mix by pipetting and incubate at room temperature for 5 minutes.
67) Separate on a magnet and remove the clear solution.
68) Keeping the beads on the magnet, wash twice with 700 µl of 70% ethanol without mixing.
69) Leave the beads on the magnet for 5 minutes to allow remaining ethanol to evaporate.
70) Add 25-50 µl of 1× Tris buffer to elute DNA. Mix by pipetting, incubate at room temperature for 5 minutes, separate on a magnet, and transfer the solution to a freshly labeled tube. The result is a final in situ Hi-C library ready to be quantified and sequenced using an Illumina sequencing platform.

In situ Hi-C can be performed on cells embedded in agar plugs as follows:

After lysis (above protocol, step 11), nuclei can be resuspended in 100 µl 2× NEBuffer2 and mixed with 100 µl molten 2% NuSieve agarose (Lonza, 5009) and allowed to solidify into an agarose plug. The nuclei embedded in agar are restricted overnight in 500 µl 1× NEBuffer2 with 100 U of MboI at 37° C.

After restriction, the buffer is discarded and the agar plug is washed twice with 1 ml of 1×NEB T4 DNA ligase buffer for 30 min at 37° C. The buffer is discarded and the agar plug is submerged in 0.5 ml fill-in reaction mix:

398 µl of water
50 µl of 10×NEB T4 DNA ligase buffer
37.5 µl of 0.4 mM biotin-14-dATP
1.5 µl of 10 mM dCTP
1.5 µl of 10 mM dGTP
1.5 µl of 10 mM dTTP
10 µl of 5 U/µl DNA Polymerase I, Large (Klenow) Fragment The library is incubated for 1.5 hours at room temperature. After incubation, 2000 U of T4 DNA Ligase are added to the reaction and the library is ligated at room temperature for 4 hours.

After ligation, the buffer is discarded and the agar plug is washed twice with 1 ml of 1×NEB β-agarase I buffer (NEB, B0392) for 30 min at 37° C. The buffer is removed and the agarose is melted by incubation at 68° C. for 10 minutes. Liquid agarose is equilibrated at 42° C. for 15 minutes. The agarose was digested with 4 U of β-Agarase I (NEB, M0392) at 42° C. for 1 hour. Next, the crosslinks can be reversed and all subsequent steps are performed following the standard in situ Hi-C protocol beginning at step 18.

In Situ Determination of Nucleic Acid Proximity as Determined by the Inventors for Cell Line GM12878.
Library complexity: 5,013,218,921
Inter: 26,989,930 (21.29%)
Intra: 99,786,882 (78.71%)
Small: 28,929,777 (22.82%)
Large: 70,857,049 (55.89%)
In Situ Determination of Nucleic Acid Proximity as Determined by the Inventors for Cell Line IMR-90.
Library Complexity: 4,539,616,093
Inter: 23,982,997 (19.20%)
Intra: 100,952,857 (80.80%)
Small: 25,712,979 (20.58%)
Large: 75,237,444 (60.22%)
Hi-C Methodology as Described in McCord et al., Genome Res. Vol. 23 No. 2, Pp 260-269, 2013, which is Specifically Incorporated Herein by Reference in its Entirety (See Example 3)
Library complexity: 601,980,531
Inter: 11,681,267 (22.38%)
Intra: 40,503,943 (77.62%)
Small: 34,209,456 (65.55%)
Large: 6,292,643 (12.06%)
Hi-C Methodology as Described in Rickman et al., PNAS, USA, Vol. 109 No. 23, Pp 9083-9088, 2012, which is Specifically Incorporated Herein by Reference in its Entirety (See Example 4).
Library complexity: 107,614,087
Inter: 17,204,445 (36.84%)
Intra: 29,500,589 (63.16%)
Small: 17,708,289 (37.92%)
Large: 11,783,647 (25.23%)

Example 3

Analysis of Human Fibroblasts Using Hi-C

This example describes the analysis of human fibroblasts using the Hi-C methodology as described in McCord et al., Genome Res. Vol. 23 no. 2, pp 260-269, 2013.

Cell Lines

The three primary fibroblast cell lines used in the Hi-C experiments were HGADFN167 (HGPS), HGFDFN168 (Father, normal), and AG08470 (Age control, normal). Additional fibroblast lines were used in EZH2 RT-qPCR analysis, and these cell lines were HGADFN169 (HGPS), HGADFN164 (HGPS), HGADFN155 (HGPS), and HGFDFN090 (normal). AG08470 was obtained from Coriell, and the other cell lines were obtained from the Progeria Research Foundation. These primary human dermal fibroblasts were cultured in MEM (Invitrogen/GIBCO) supplemented with 15% fetal bovine serum (FBS) (Invitrogen) and 2 mM L-glutamine.

Hi-C Library Preparation 20 million cells from an HGPS cell line (HGADFN167) at two increasing passages (p17 and 19), as well as from two normal fibroblast cell lines at similar passages (HGFDFN168-p18 and AG08470-p20) were crosslinked in 1% formaldehyde. HGFDFN168-p18 is the father of the HGPS patient HGADFN167, and AG08470 is an age matched, unrelated child. Hi-C was performed essentially as described previously (Lieberman-Aiden et al. 2009). Cells were lysed, and chromatin was digested with HindIII. Digested ends were filled in with biotinylated dCTP and then ligated for 4 hours at 16 C. After reversing the formaldehyde crosslinks by incubation at 65° C. with Proteinase K overnight and removing unligated biotinylated ends with T4 DNA polymerase, the DNA was fragmented by Covaris sonication to an average size of 200 bp and then the ideal size for Illumina sequencing (100-300 bp) was selected by Ampure fractionation. The DNA ends were repaired and 'A'-tailed and then biotinylated junctions were pulled down using MyOne streptavidin beads. Illumina paired end adapters were ligated onto the DNA ends and then the fragments were PCR amplified for the minimum number of cycles necessary to generate 10 nM final DNA concentration.

Hi-C Data Processing

Samples were sequenced on an Illumina GAIT instrument using the Paired End 75 bp module. Sequencing reads from the Hi-C experiment were mapped to the hg18 genome using Bowtie2 using the "very-sensitive" settings in an iterative procedure as follows: first, the 5' 25 bp of each sequence was mapped, and then any reads that were unmapped or not mapped uniquely were extended to 30 bp, then 35 bp, etc. until the maximum length of the sequence was reached. This procedure aids in mapping sequences that read through a ligation junction near their 3' end and whose full length sequence would thus be unmappable. Aligned reads were assigned to restriction fragments and filtered to discard duplicate read pairs (PCR over-amplification products) and molecules for which both ends map to the same restriction fragment.

Restriction fragments shorter than 100 bp or longer than 100 kb as well as those with the top 0.5% of read counts were removed. After these filtering steps, 10-20 million valid interaction pairs were obtained for each sample. Reads were assigned to genomic bins of 200 kb, according to the center of their corresponding restriction fragment. The binned interaction maps were then corrected for systematic biases by equalizing the total coverage (1D sum across the matrix) of every bin in the genome using 50 iterations of a normalization procedure previously described (Imakaev et al. 2012; Zhang et al. 2012). The final data was then smoothed with a 1 Mb bin size and 200 kb step size.

HI-C Data Analysis and Comparison to Other Datasets

Open and closed chromatin compartments were identified as previously described (Lieberman-Aiden et al. 2009). Briefly, the expected number of Hi-C reads between bins separated by each genomic distance was calculated using a loess-smoothed average over the dataset. The log ratio of observed Hi-C reads to this expected value was then calculated. The Pearson correlation between the patterns of chromosomal interactions at each pair of bins was then calculated, and this correlation matrix was used to perform Principal Components Analysis. The eigenvector of the first principal component was then plotted as the compartment assignment, with positive values corresponding to regions of high gene density ("compartment A" or "open chromatin") and negative values corresponding to regions of low gene density ("compartment B" or "closed chromatin"). The gene density was determined by calculating the number of genes in each bin according to the UCSC Known Canonical table of human genes.

Example 4

Analysis of Human Fibroblasts Using Hi-C

This example describes the analysis of RWPE1-ERG and RWPE1-GFP cell lines.

Human Cell Lines.

RWPE1 and DU145 cells were obtained from ATCC and maintained according to the manufacturer's protocol using isogenic cell lines overexpress either truncated ERG (most commonly encoded isoform based on TMPRSS2-ERG fusion).

Hi-C Library Generation.

Fifty million RWPE1-ERG or RWPE1-GFP cells were fixed and processed to generate Hi-C libraries. Briefly, cells were cross-linked and the chromatin was digested with HindIII, ligated after fill-in with biotin-conjugated dCTP, and purified using streptavidivin-conjugated magnetic beads. The Hi-C libraries were then paired-end sequenced using an Illumina GAIIx platform, resulting in replicate-combined 158.5 million and 159.2 million paired-end DNA sequence reads from RWPE1-ERG and RWPE1-GFP, respectively.

Hi-C

Fifty million RWPE1-ERG or RWPE1-GFP cells were fixed and processed to generate Hi-C libraries as previously reported. Briefly, cells were cross-linked, and the chromatin was digested with HindIII, ligated after fill-in with biotin-conjugated dCTP, and purified using streptavidivin-conjugated magnetic beads.

SI Computational Analysis

Sequence Alignment and Extraction of Hi-C Interactions.

We aligned the two ends of the 54-bp paired reads separately to the reference human genome hg18 (NCBI build 36), using the BWA aligner.

Reads mapped ambiguously to multiple locations on the genome were discarded. We further filtered out clonal reads caused by PCR artifacts on the basis of the 5' and 3' read positions, removed nonligated DNA fragments, and retained ones with consistent expected placement relative to HindIII enzyme digestion sites. In total, we obtained more than 32 million intra- and interchromosomal interactions in each cell line.

Example 5

Hybrid Capture Hi-C

As implemented in this Example, the disclosed example embodiment involves generating a probe set to detect target ligation junctions, the probes in the probe set comprising one or more labeled nucleotides. The probes in the probe set are designed to target sequences within a certain distance of known restriction sites in the genome to be analyzed. Ligation junctions are formed as described previously with the exception that labeled nucleotides do not have to be incorporated to fill in the overhanging fragmented ends. The generated probe set is allowed to hybridize to the formed ligation junctions and the one or more labeled nucleotides in the hybridized probed are then used to isolate the one or more end joined nucleic fragments (junctions). To determine the sequence of the target junction is then determined using nucleic acid sequencing.

i. Probe Design

To design probes targeting a particular region for HYbrid Capture Hi-C(Hi-C$^2$), all restriction sites within the target region were identified. Since Hi-C ligation junctions occur between restriction sites, bait probe sequences were designed to target sequences within a certain distance of the identified restriction sites present in the target region. In this particular embodiment MboI restrictions sites were used. Specifically, a first pass was performed scanning all 120 bp sequences with one end within 80 bp of a restriction site and selecting, for each restriction end (i.e. both upstream and downstream of the restriction site), the closest 120 bp sequence to the restriction site that had fewer than 10 repetitive bases (as determined by the repeat masked hg19 genome downloaded from UCSC) and had between 50% and 60% GC content. If there was no probe satisfying those criteria, the closest probe with between 40% and 70% GC content but satisfying all the other above criteria was retained. The GC content bounds were chosen based on the hybridization bias data known in the art.

After the first pass, one probe from any pair of probes that overlapped was removed. Gaps in the probe coverage were identified, for example intervals larger than 110 bp, and any restriction sites falling within those gaps identified. Additional 120 bp probes were then searched using the following relaxed set of criteria. For each restriction site within a gap, all 120 bp sequences with one end within 110 bp of a restriction site were scanned and the closest sequence to the restriction site that had fewer than 20 repetitive bases and had between 40 and 70% GC content was selected. After the second pass, gaps in the probe coverage of at least 110 bp were identified. For gaps that fell within 5 kb windows in the target region that were covered by fewer than 5 probes, a third probe design pass was performed. For each restriction site within these low coverage gaps, all 120 bp sequences with one end within 110 bp of a restriction site were scanned and the closest sequence to the restriction site that had fewer than 25 repetitive bases and had between 25% and 80% GC content was selected.

ii. Probe Construction

Custom synthesized pools of 150 bp (120 bp+15 bp primer sequence on either end) single stranded oligodeoxynucleotides were obtained from CustomArray, Inc. (Bothell, Wash.). The oligonucleotides were of the general form TCGCGCCCATAACTCN$_{120}$CTGAGGGTCCGCCTT (SEQ ID NO: 1) for Region 1, ATCGCACCAGCGTGTN$_{120}$CACTGCGGCTCCTCA (SEQ ID NO: 2) for Region 2, and CCTCGCCTATCCCATN$_{120}$CACTACCGGGGTCTG (SEQ ID NO: 3) for Region 3. Region-specific sub-pools were first amplified from the overall CustomArray oligo pool using the following mix and PCR profile:

| | |
|---|---|
| 2 ul | oligo pool (160 ng) |
| 6 ul | Primer 1 (10 uM) |
| 6 ul | Primer 2 (10 uM) |
| 36 ul | H2O |
| 50 ul | 2X Phusion master mix |
| 100 ul | TOTAL |

Amplify for 10-18 cycles using the following PCR profile:

| | |
|---|---|
| 98 C. for 30 s | |
| 98 C. for 10 s | |
| 55 C. for 30 s | |
| 72 C. for 30 s | cycle 10-18 times |
| 72 for 7 min | |
| hold at 4 C. | | where Primer 1 was CTGGGATCGCGCCCATAACTC (SEQ ID NO: 4) for Region 1, CTGGGAATCGCACCAGCGTGT (SEQ ID NO: 5) for Region 2, CTGGGACCTCGCCTATCCCAT (SEQ ID NO: 6) for Region 3 and Primer 2 was CGTGGAAAGGCGGACCCTCAG (SEQ ID NO: 7) for Region 1, CGTGGATGAGGAGCCGCAGTG (SEQ ID NO: 8) for Region 2, CGTGGACAGACCCCGGTAGTG (SEQ ID NO: 9) for Region 3.

After the initial amplification of the region-specific sub-pool, a 1×SPRI clean up was performed on the 162 bp PCR product to remove primers and primer-dimers. We then performed a second PCR amplification to add a T7 promoter, using the following mix and PCR profile:

| | |
|---|---|
| 2 ul | first PCR product |
| 12 ul | Primer 1 - T7 (10 uM) |
| 12 ul | Primer 2 (10 uM) |
| 74 ul | H2O |
| 100 ul | 2X Phusion master mix |
| 200 ul | TOTAL |

Amplify for 12-18 cycles using the following PCR profile:

| | |
|---|---|
| 98 C. for 30 s | |
| 98 C. for 10 s | |
| 55 C. for 30 s | |
| 72 C. for 30 s | cycle 12-18 times |
| 72 for 7 min | |
| hold at 4 C. | | where Primer 1-T7 was GGATTCTAATACGACTCACTATAGGGTCGCGCCCATAACTC (SEQ ID NO: 10) for Region 1, GGATTCTAATACGACTCACTATAGGGATCGCACCAGCGTGT (SEQ ID NO: 11) for Region 2, and GGATTCTAATACGACTCACTATAGGGCCTCGCCTATCCCA (SEQ ID NO: 12) for Region 3.

After the second PCR, once again, a 1×SPRI clean up to purify the 182 bp PCR product was performed. The purified second PCR product was then used as the template in a MAXIScript T7 transcription reaction (Ambion) as follows:

| | |
|---|---|
| Xul | purified DNA template (1 ug) |
| 10 ul | T7 enzyme mix |
| 10 ul | 10X transcription buffer |
| 5 ul | 10 mM ATP |
| 5 ul | 10 mM CTP |
| 5 ul | 10 mM GTP |
| 4 ul | 10 mM UTP |
| 1 ul | 10 mM Biotin-16-UTP |
| Yul | H2O |
| 100 ul | TOTAL |

After incubating the reaction for at least 90 minutes at 37 C, 1 ul of TURBO DNase 1 was added and incubated at 37 C.° for 15 minutes to remove template DNA. An aliquot of 1 ul of 0.5M EDTA was added to stop the reaction and unincorporated nucleotides were removed and the RNA desalted by purifying the RNA probes using a Zymo Oligo Clean and Concentrator column (following manufacturer's instructions). The RNA yield was typically 5-15 ug of RNA per reaction, so the concentration of the RNA prior to the column cleanup using a Qubit RNA assay was measured in order to determine whether to use one or two columns (the capacity of one of the Zymo columns is 10 ug). For long-term storage of the RNA probes, 1 U/ul of SUPERase-In RNase inhibitor (Ambion) was added and the probes were stored at −80 C.

iii. Hybrid Selection

Final in situ Hi-C libraries were assessed for quality using the metrics outlined in Rao et al. Cell. 2014 159(7):1665-80. High quality libraries of sufficient complexity were selected for hybrid capture. 500 ng of Hi-C library was used as the pond for the hybrid selection reaction; libraries were diluted to a concentration of 20 ng/ul (i.e. 25 ul of library was used). For a few libraries that were under 20 ng/ul in concentration, as low as 250 ng total was used (still in 25 ul).

For the hybridization reaction, 25 ul of pond was mixed with 2.5 ug (1 ul) of Cot-1 DNA (Invitrogen) and bug (1 ul) of salmon sperm DNA (Stratagene). The DNA mixture was heated to 95 C for 5 minutes and then held at 65 C for at least 5 minutes. After at least 5 minutes at 65 C, 33 ul of prewarmed (65 C) hybridization buffer (10×SSPE, 10×Denhardt's buffer, 10 mM EDTA, and 0.2% SDS) and 6 ul of RNA probe mixture (500 ng of RNA probes, 20 U of SUPERase-In RNase inhibitor; prewarmed at 65 C for 2 minutes) were added to the DNA library for a total volume of ~66 ul. This mixture was incubated at 65 C in a thermocycler for 24 hours.

After 24 hours at 65 C, 50 ul of streptavidin beads (Dynabeads MyOne Streptavidin T1, Life Technologies) were washed three times in 200 ul of Bind-and-Wash buffer (1M NaCl, 10 mM Tris-HCl, pH 7.5, and 1 mM EDTA) and then resuspended in 134 ul of Bind-and-Wash buffer. The beads were added to the hybridization mixture and incubated for 30 minutes at room temperature (with occasional mixing to prevent the beads from settling). After 30 minutes, the beads were separated with a magnet and the supernatant discarded. The beads were then washed once with 200 ul low-stringency wash buffer (1×SSC, 0.1% SDS) and incubated for 15 minutes at room temperature. After 15 minutes, the beads were separated on a magnet and the supernatant discarded. The beads were then washed three times in high-stringency wash buffer (0.1×SSC, 0.1% SDS) at 65 C for 10 minutes, each time separating the beads with a magnet and discarding the supernatant.

After the last wash, the DNA was eluted off the beads by resuspending in 50 ul of 0.1M NaOH and incubating for 10 minutes at room temperature. After 10 minutes, the beads were separated on a magnet and the supernatant was transferred to a fresh tube with 50 ul of 1M Tris-HCl, pH 7.5 (to neutralize the NaOH).

To desalt the DNA, we performed a 1×SPRI cleanup using 3× concentrated SPRI beads (taking 3 volumes of SPRI bead/solution mix, separating on a magnet, discarding 2 volumes of SPRI solution and resuspending the beads in the remaining 1 volume). We eluted the DNA in 22.5 ul of 1× Tris buffer (10 mM Tris-HCl, pH 8.0).

In order to prep the Hi-C2 library for sequencing, we added 25 ul of 2× Phusion and 2.5 ul of Illumina primers and amplified the library for 12-18 cycles. After PCR, we performed two 0.7×SPRI cleanups to remove primers, etc. and then quantified the libraries for sequencing.

iv. Hi-C$^2$ Data Processing

Hi-C2 libraries were sequenced to a depth of between ~600K-60M reads (on average, 7.8M reads). All data was initially processed using the pipeline published in Rao et al. (2014). However, additional processing was needed to properly normalize the Hi-C2 data.

Normalization is an important problem to address in the analysis and interpretation of all proximity ligation experiments. It was previously shown that matrix balancing with the KR algorithm is an effective tool for properly normalizing Hi-C data (Rao and Huntley, et al. Cell 2014). However, one requirement of the KR algorithm is the requirement of a square symmetric matrix. As hybrid selection strongly enriches for certain rows of the matrix corresponding to the target region, there are large regions of the overall matrix that are extremely sparse (entries corresponding to interactions between two non-target loci). As a result, performing KR matrix balancing on the overall matrix generated by a Hi-C2 experiment does not efficiently correct both first-order hybrid selection target-enrichment biases and second-order hybridization biases within the target region.

To deal with this, a previously generated high resolution genome-wide in situ Hi-C map of wild-type of Hap1 was used to normalize the data. Since all genome-editing perturbations were made within the region targeted using Hi-C2, for every Hi-C2 dataset, data from the genome-wide wild-type Hap1 map corresponding to regions of the chromosome-wide matrix where both loci fall outside of the target region were spiked in. Spiked data was added such that the average coverage of a locus in the overall chromosome-wide matrix was equal to the average coverage of loci within the target region. By spiking in data from the wild-type map where expectation is to see no change (since there were no perturbations), the first-order bias from hybrid-selection target enrichment could be removed, and KR matrix balancing used on the entire chromosome-wide matrix (which is no longer extremely sparse) to correct the second-order hybridization biases. Several different flavors of this normalization scheme may be implemented yielding extremely similar results; they are described below. The example methods described below may be used to normalize the data.

Raw gap-filling: For a given resolution, the average intrachromosomal coverage of the loci within the target region (defined as the entire interval tiled by probes not specifically the loci that were covered by a probe) was calculated from the raw uncorrected Hi-C2 matrix. Similarly, the average intrachromosomal coverage of all loci was calculated from the raw uncorrected genome-wide Hap1 wild-type Hi-C map. A matrix consisting of all entries corresponding to two loci that were both outside the target region was constructed from the raw uncorrected genome-wide Hap1 Hi-C map. This matrix was multiplied by the ratio of the average coverage of loci within the target region in the Hi-C2 data to the average coverage of all loci from the genome-wide Hap1 wild-type Hi-C data and then summed with the Hi-C2 matrix (thereby filling in the extremely sparse areas of the Hi-C2 matrix). This summed matrix was then corrected with the KR matrix balancing algorithm. The resulting normalization factors were used as correction factors for the Hi-C2 data.

KR gap-filling: The KR gap-filling normalization was performed similarly to the method described above, but to avoid corrected Hi-C biases and Hi-C2 biases together, the method above was performed on KR normalized data. Specifically, the KR correction factors derived from the genome-wide Hap1 wild-type Hi-C map were used to perform an initial correction of the Hi-C2 data. After the initial correction, the average intrachromosomal coverage of the loci within the target region (defined as the entire interval tiled by probes not specifically the loci that were covered by a probe) was calculated from the Hi-C2 matrix. Similarly, the average intrachromosomal coverage of all loci was calculated from the corrected genome-wide Hap1 wild-type Hi-C map. A matrix consisting of all entries corresponding to two loci that were both outside the target region was constructed from the raw uncorrected genome-wide Hap1 Hi-C map. This matrix was multiplied by the ratio of the average coverage of loci within the target region in the Hi-C2 data to the average coverage of all loci from the genome-wide Hap1 wild-type Hi-C data and then summed with the Hi-C2 matrix (thereby filling in the extremely sparse areas of the Hi-C2 matrix). This summed matrix was then corrected with the KR matrix balancing algorithm. The resulting normalization factors may be used as correction factors for the Hi-C2 data.

Raw gap-filling with rescaling: Filling in the sparse areas of the Hi-C2 matrix corrects for first order target enrichment biases from hybrid capture to some extent, but does not account for the fact that differential enrichments may be present for entries of the matrix corresponding to one on-target loci and one off-target loci vs. entries corresponding to two on-target loci. To address this, the ratio of the number of contacts formed between the locus and off-target loci to the number of contacts formed between the locus and other on-target loci using the genome-wide Hap1 wild-type Hi-C data was first calculated before performing gap-filling as in the above methods. The same ratio was then calculated using the Hi-C2 data. The ratio of these ratios provided a scaling factor for each on-target locus which was then used to scale all entries in the Hi-C2 matrix corresponding to contacts between the on-target locus and off-target loci. After performing this correction, the method from above was followed, i.e. a matrix consisting of all entries corresponding to two loci that were both outside the target region was constructed from the raw uncorrected genome-wide Hap1 Hi-C map. This matrix was multiplied by the ratio of the average coverage of loci within the target region in the Hi-C2 data (using the rescaled Hi-C2 data) to the average coverage of all loci from the genome-wide Hap1 wild-type Hi-C data and then summed with the Hi-C2 matrix (thereby filling in the extremely sparse areas of the Hi-C2 matrix). This summed matrix was then corrected with the KR matrix balancing algorithm. The resulting normalization factors were used as correction factors for the Hi-C2 data.

KR gap-filling with rescaling: This method is the same as method c, except that as in method b, the Hi-C2 data was initially corrected with the KR factors derived from the Hap1 genome-wide wild-type Hi-C matrix and the KR corrected wild-type Hi-C data was used for gap-filling.

Raw gap-filling with rescaling and thresholding: It was noted that for a few very sparse (under-covered) rows in the Hi-C2 data, the normalization methods would actually overcorrect, leading to highly-covered streak artifacts in the data. In order to remove these artifacts, a final filtering step was added where loci with a normalization factor (C) of less than 0.33 (where Mi,j is divided by Ci and Cj to get the corrected entry M*i,j) were thresholded so that their normalization factors were raised to 0.33 (this was implemented after the KR matrix balancing was run, not as a constraint during the running of the algorithm). The threshold of 0.33 was chosen based on empirical observation of rows that led to streaky artifacts. This method is the same as method c except with the aforementioned thresholding.

KR gap-filling with rescaling and thresholding: This method is the same as method d except with the addition of the thresholding described in method.

Example 6

Genome Engineering Workflow

As described in this example, the example method comprises (i) identifying chromatin loops (ii) identifying unique, correctly oriented CTCF motifs within loop anchors (iii) rationally designing a CRISPR guide RNA or multiple guide RNAs to cut within or around the CTCF motif while optimizing for cutting efficiency and minimizing off-target effects, (iv) optionally designing homology directed repair (HDR) templates to specifically invert or replace the CTCF motif, (v) transfecting cells with the Cas9 and the guide RNA(s) (and optionally the HDR template), (vi) sorting single transfected cells via fluorescence-activated cell sorting (FACS), (vii) growing up and genotyping clonal populations of cells, (viii) selecting clonal cell lines with mutations disrupting the CTCF motif (or in the case of HDR, the specific desired mutation), (ix) performing in situ Hi-C on the selected mutated cell lines, and (x) performing hybrid selection on the in situ Hi-C libraries for a region around the targeted CTCF motif to generate Hi-C2 libraries that can easily and cheaply be sequenced to read off the effects of the mutations on genome folding.

While the CRISPR experiments where performed in the Hap1 cell line in order to read off the effects of the mutations without having to worry about allelic heterozygosity, this method is easily adaptable to other cell lines, as long as one has a reasonable means for identify chromatin loops. The steps in our workflow are described in detail below. Likewise this method may be adapted to modify regulatory elements other than CTCF motifs.

i. Experimental Design

Three regions containing triple-hubs (three loci A, B and C with all pair-wise loops present) were chosen for thorough dissection. The regions were chosen such that they showed extremely similar patterns of chromatin folding to GM12878 and IMR90, so that ChIP-Seq data from those cell lines could be used to identify precise motifs in loop anchors to target as well as to simulate folding in the regions.

The three hubs were chosen such that unique anchors (as defined in Rao and Huntley, et al. [Cell 2014]) were present at least at the middle loop anchor and ideally at one of the upstream or downstream loop anchors as well. Motifs in loop anchors were identified using FIMO (Grant et al. Bioinformatics 2011) using the CTCF motif position weight matrices (PWMs) from Kim, et al. (Cell 2007) and Schmidt, et al. (Cell 2011). The hubs were chosen such that all loops were clearly anchored by correctly oriented motifs. Motifs to target via CRISPR were only chosen if they were clearly unique among the correctly oriented motifs in a ChIP-Seq binding site (i.e. there was only one motif present or only one motif that was clearly the strongest match when compared against both PWMs and in the case of the middle loop anchor, the reverse CTCF motif corresponding to the A-B loop was upstream of the forward CTCF motif corresponding to the B-C loop).

ii. Guide RNA and HDR Template Design

Guide RNAs were designed using one of two strategies. Either a single guide RNA was designed to cut inside the target CTCF motif, or two guide RNAs were designed to cut both sides flanking the target CTCF motif.

Prospective guide RNAs were screened using the cutting efficiency scoring schemes known in the art. Wherever possible, guides with cutting efficiency scores of 0.4 or lower were avoided, and guide RNAs with scores of lower than 0.25 were discarded altogether. Wherever possible, guides ranked as high quality guides by the Hsu off target assessment algorithm were used. In a few cases, where no high quality guide was identified or when the cutting efficiency as ranked by the Doench, et al algorithm was extremely low, a mid-quality guide (with respect to off-targets) was used.

Guide RNAs for all mutations are listed in Table 1 below.

All the HDR templates used in this study were ssODNs (Ran et al., Nat Prot 2013), either 200 bp (IDT ultramers) or 100 bp (Invitrogen custom DNA oligonucleotides) in size. They were designed such that they contained the 20 bp CTCF motif inverted (or a new 20 bp CTCF motif), flanked by homology arms either 90 bp or 40 bp in size.

TABLE 1

Genotype information, targeted motifs and guideRNAs for all mutant clones

| Genotype ID | Genotype | Size | Location | Motif Location | Guide RNAs (PAM in bold) |
|---|---|---|---|---|---|
| Clone001 | R1-A deletion | 17 bp | chr8:133,887,888-133,887,904 | chr8:133,887,891-133,887,910 | TCACAGCTATTTCCACAAGAGGG (SEQ ID NO: 17) |
| Clone002 | R1-B reverse deletion | 142 bp | chr8:134,215,261-134,215,402 | chr8:134,215,312-134,215,331 | GCCCGGGAGCTTTCAGGACAGGG; (SEQ ID NO: 18) GCTCACGGAGCACTTGCCCAGGG (SEQ ID NO: 19) |

TABLE 1-continued

Genotype information, targeted motifs and guideRNAs for all mutant clones

| Genotype ID | Genotype | Size | Location | Motif Location | Guide RNAs (PAM in bold) |
|---|---|---|---|---|---|
| Clone003 | R1-B forward deletion | 159 bp | chr8:134,221,611-134,221,769 | chr8:134,221,674-134,221,693 | GGAAAACCCTCTGGACCCCAGGG; (SEQ ID NO: 20) AGAAGTCCTCCCTTGGACAGGGG (SEQ ID NO: 21) |
| Clone004 | R1-B forward inversion | 159 bp | chr8:134,221,611-134,221,769 | chr8:134,221,674-134,221,693 | GGAAAACCCTCTGGACCCCAGGG; (SEQ ID NO: 22) AGAAGTCCTCCCTTGGACAGGGG (SEQ ID NO: 23) |
| Clone005 | R1-B forward inversion; B reverse insertion | inversion-inversion: 159 bp, insertion-1 bp | chr8:134,221,611-134,221,769; insertion: chr8:134,215,324-134,215,325 | B reverse: chr8:134,215,312-134,215,331; B forward: chr8:134,221,674-134,221,693 | B forward: GGAAAACCCTCTGGACCCCAGGG; (SEQ ID NO: 24) AGAAGTCCTCCCTTGGACAGGGG; B reverse: CACCTAGATACTCCACCAGGGGG (SEQ ID NO: 25) |
| Clone006 | R1-B forward inversion; reverse-B reverse inversion | forward-159 bp, reverse-20 bp | forward: chr8:134,221,611-134,221,769; reverse: chr8:134,215,331-134,215,330 | B reverse: chr8:134,215,312-134,215,331; B forward: chr8:134,221,674-134,221,693 | B forward: GGAAAACCCTCTGGACCCCAGGG; (SEQ ID NO: 26) AGAAGTCCTCCCTTGGACAGGGG; (SEQ ID NO: 27) B reverse: CACCTAGATACTCCACCAGGGGG (SEQ ID NO: 28) |
| Clone007 | R2-E forward deletion | 7 bp | chr1:180,851,240-180,851,246 | chr1:180,851,233-180,851,252 | CCTTGTTAGTTACCAGCAGAGGG (SEQ ID NO: 29) |
| Clone008 | R2-E forward deletion | 1 bp deletion, 2 bp insertion | chr1:180,851,240-180,851,241 | chr1:180,851,233-180,851,252 | CCTTGTTAGTTACCAGCAGAGGG (SEQ ID NO: 30) |
| Clone009 | R2-E forward deletion | 4 bp | chr1:180,851,237-180,851,240 | chr1:180,851,233-180,851,252 | CCTTGTTAGTTACCAGCAGAGGG (SEQ ID NO: 31) |
| Clone010 | R2-E forward deletion | 10 bp | chr1:180,851,238-180,851,247 | chr1:180,851,233-180,851,252 | CCTTGTTAGTTACCAGCAGAGGG (SEQ ID NO: 32) |
| Clone011 | R2-E reverse deletion | 16 bp | chr1:180,832,497-180,832,512 | chr1:180,832,502-180,832,521 | TTTTAACTTTTGCCATCAGGTGG (SEQ ID NO: 33) |
| Sanborn Rao-2015-Clone012 | R2-E forward inversion | 20 bp | chr1:180,851,233-180,851,252 | chr1:180,851,233-180,851,252 | CCTTGTTAGTTACCAGCAGAGGG (SEQ ID NO: 34) |
| Clone013 | R2-E forward-forward 1 bp deletion; reverse-E reverse 16 bp deletion | forward-1 bp, reverse-16 bp | forward: chr1:180,851,241-180,851,242; reverse: chr1:180,832,497-180,832,512 | E reverse: chr1:180,832,502-180,832,521; E forward: chr1:180,851,233-180,851,252 | E forward: CCTTGTTAGT-TACCAGCAGAGGG; (SEQ ID NO: 35) E reverse: TTTTAACTTTTGCCATCAGGTGG (SEQ ID NO: 36) |

TABLE 1-continued

Genotype information, targeted motifs and guideRNAs for all mutant clones

| Genotype ID | Genotype | Size | Location | Motif Location | Guide RNAs (PAM in bold) |
|---|---|---|---|---|---|
| Clone014 | R2-E forward-forward deletion; reverse-E reverse deletion | 5 bp, reverse-16 bp | forward: chr1:180,851,239-180,851,243; reverse: chr1:180,832,497-180,832,512 | E reverse: chr1:180,832,502-180,832,521; E forward: chr1:180,851,233-180,851,252 | E forward: CCTTGTTAGT-TACCAGCAGAGGG; (SEQ ID NO: 37) E reverse: TTTTAACTTTTGCCATCAGGTGG (SEQ ID NO: 38) |
| Clone015 | R2-E forward-forward deletion; reverse-E reverse deletion | 7 bp, reverse-10 bp | forward: chr1:180,851,240-180,851,246; reverse: chr1:180,832,504-180,832,513 | E reverse: chr1:180,832,502-180,832,521; E forward: chr1:180,851,233-180,851,252 | E forward: CCTTGTTAGT-TACCAGCAGAGGG; (SEQ ID NO: 39) E reverse: TTTTAACTTTTGCCATCAGGTGG (SEQ ID NO: 40) |
| Clone016 | R2-E forward replaced with E reverse motif | 20 bp | chr1:180,851,233-180,851,252 | chr1:180,851,233-180,851,252 | CCTTGTTAGTTACCAGCAGAGGG (SEQ ID NO: 41) |
| Clone017 | R3-G insertion | 1 bp | chr5:31,581,788-31,581,789 | chr5:31,581,776-31,581,795 | TCTGGTAGTCTAGGGCCACCTGG (SEQ ID NO: 42) |
| Clone018 | R3-H forward deletion | 37 bp | chr5:31,825,777-31,825,813 | chr5:31,825,779-31,825,798 | CAGCACAGTTGAATTCCCAGTGG; (SEQ ID NO: 43) ATTCAGTTAAGTTTATTCCACGG (SEQ ID NO: 44) | iii. Cell Culture and Transfection

Hap1 cells (Horizon Genomics) were cultured according to manufacturer's conditions. 24 hours before transfection, 0.9M Hap1 cells were plated in each well of a 6 well plate. After 24 hours, when the cells were roughly 60% confluent, the cells were transfected with the pSpCas9(BB)-2A-GFP (px458) plasmid. Guide RNAs were cloned into the plasmid using known protocols.

The Hap1 cells were transfected (in antibiotic free media) with 3 ug of DNA using Turbofectin according to manufacturer's instructions (a 3:1 ratio of Turbofectin to DNA was used; 9 ul of Turbofectin for 3 ug of DNA). For single guide RNAs, 3 ug of the Cas9-gRNA plasmid was used. For double guide RNA mediated deletions, 1.5 ug of each Cas9-gRNA plasmid was used. For HDR, either 1.5 ug of Cas9-gRNA plasmid and 3 ul 10 uM 200 bp ssODN or 1.875 ug Cas9-gRNA plasmid and 3.75 ul 10 uM 100 bp ssODN were used. For HDR experiments, the culture media was supplemented with 0.1 uM SCR7 (Chu et al., Nat Biotech 2015, Maruyama et al., Nat Biotech 2015) 12-24 hours after transfection.

24-48 hours after transfection, GFP+ cells were sorted via FACS (PI was also added to filter for dead cells). Transfection efficiencies were usually between 5 and 10%. Populations of 500-10,000 cells were screened for gRNA cutting efficiency or for HDR efficiency to judge roughly how many clones would need to be screened. Single cells were sorted into individual wells of a 96-well plate and allowed to grow for 10-14 days. After that, roughly 32-96 clones were screened per transfection.

iv. Mutation Strategy

Deletions were obtained either via a single guide RNA-mediated cut within the CTCF motif or via two guide RNAs-mediated double strand breaks on either side of the CTCF motif. In the case of the single guide RNA mediated cuts, clones were screened for mutations that were as small as possible, but also highly likely to completely disrupt CTCF binding (as judged by the strength of the motif match before and after mutation). Mutations that were likely to completely abrogate CTCF binding were selected for expansion. Mutations generated via two double strand breaks were all generated by Horizon Genomics and clones containing the region between the two guide RNAs either cut out or inverted were selected for expansion. Clones targeted with HDR were screened for the 20 bp inversion or 20 bp replacement and successfully targeted clones were selected for expansion.

v. In Situ Hi-C on Mutated Cell Lines

Expanded mutant clones were crosslinked and subsequently in situ Hi-C was performed on the pellets as described herein. On average, 4.3 in situ Hi-C libraries were generated per mutated cell line for a total of 56 in situ Hi-C libraries.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of this disclosure and these claims.

Example 7

Dynamics of Chromatin Loops and Structures During Hematopoietic Differentiation and Immune Response We have previously shown, and pointed out herein above that we have successfully created a genome-wide catalog of chromatin loops using kilobase-resolution Hi-C maps, and noted that the vast majority of loops are demarcated by a pair of loop anchor sites containing CTCF-binding motifs. At 64% of loop anchor sites, we could identify the single CTCF motif responsible for anchoring the loop with single-base-pair resolution. Stunningly, the orientation of the CTCF sites was highly nonrandom: in >90% of cases, the sites were convergent, i.e., the CTCF motifs point towards one another. We herein tested if disrupting the ability of CTCF protein to bind chromatin at specific anchors would result in disruption of the corresponding loops.

We have now tested this in two different ways. First, we used CRISPR-mediated genome editing to engineer individual loops, modifying CTCF binding motifs in highly targeted fashion (i.e., 10 bp deletions). We confirmed that these alterations disrupt CTCF binding and, moreover, found that they cause expected changes to chromatin looping, as measured by in situ Hi-C (See Example 7A). Second, we mutated three of the zinc-finger domains in CTCF proteins in a manner that disrupts CTCF's ability to bind to a large fraction of its binding sites in wild-type cells. Hundreds of these binding sites were located at loop anchors throughout the genome. Strikingly, disruption of CTCF binding sites at loop anchors consistently resulted in disruption of the corresponding loop (See Example 7B).

Example 7A. Engineering Individual Loops by Removing and Introducing CTCF Anchors Using CRISPR We used in situ Hi-C to map loops genome-wide in HAP1 cells (a human, haploid, fibroblast-like cell line), and combined this data with the results of CTCF ChIP-Seq experiments in order to identify the corresponding loop anchors. We then used CRISPR-mediated genome-editing to create 19 mutant cell lines containing highly specific edits to CTCF motifs at loop anchors. These include both disruptions, which eliminate a CTCF motif, and inversions, which eliminate a motif on one strand and replace it with a motif pointing in the other direction (i.e., on the other strand). Finally, we confirmed the expected effect on looping by repeating the in situ Hi-C experiment and observing which loops are affected.

For example, we examined a set of loops connecting three loci on chromosome 1: A (@180.5 Mb), B (@180.8 Mb), and C (@181.1 Mb). In the wild-type, a forward-oriented CTCF motif is observed at A (dubbed A/Fwd); at B, a reverse-oriented CTCF motif (B/Rev) is followed by a forward-oriented motif (B/Fwd) (the two motifs do not overlap); and finally, a reverse-oriented motif is seen at C (C/Rev). Corresponding loops are seen joining A and B (specifically, A/Fwd and B/Rev); B and C (specifically, B/Fwd and C/Rev); and A and C (specifically, A/Fwd and C/Rev).

We therefore hypothesized that the disruption of the B/Fwd motif would disrupt the loop between B and C but have no effect on the other two loops. Notably, we predicted that the disruption would not affect the loop between A and B, which, based on the convergent CTCF rule, must be anchored and B/Rev rather than B/Fwd.

Figure 18:
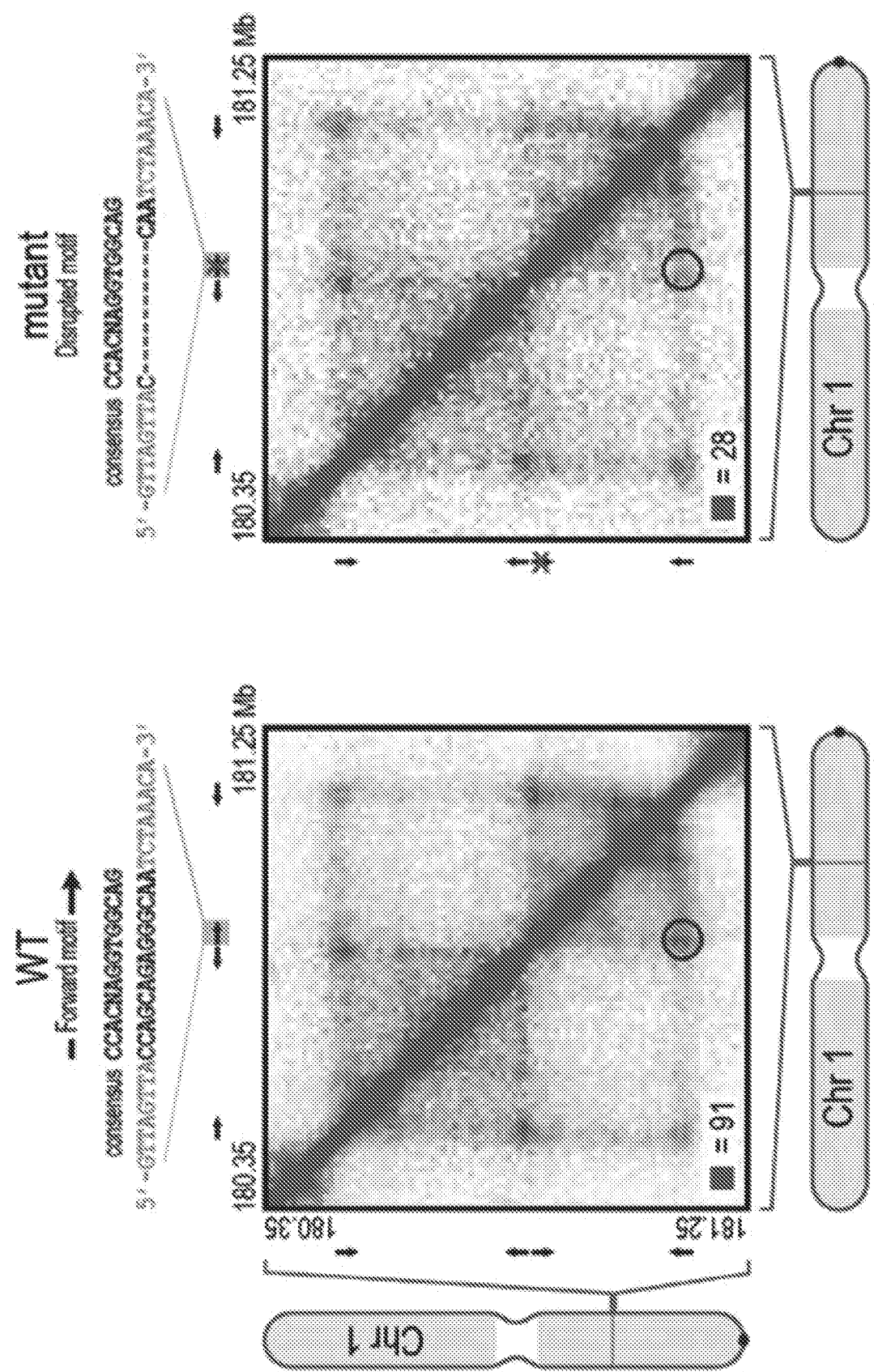
FIG. 18. Hi-C maps of a set of loops connecting three loci on chromosome 1 in WT (left panel) and CRISPR mutant (right panel). The three loci include: A (@180.5 Mb), B (@180.8 Mb), and C (@181.1 Mb). In the wild-type, a forward-oriented CTCF motif is observed at A (dubbed A/Fwd); at B, a reverse-oriented CTCF motif (B/Rev) is followed by a forward-oriented motif (B/Fwd) (the two motifs do not overlap); and finally, a reverse-oriented motif is seen at C (C/Rev). Corresponding loops are seen joining A and B (specifically, A/Fwd and B/Rev); B and C (specifically, B/Fwd and C/Rev); and A and C (specifically, A/Fwd and C/Rev). Disruption of the B/Fwd motif by CRISPR-mediated genome editing to create a 10 bp deletion in the B/Fwd motif (deleting chr1:180,851,237-180,851,246), disrupts the loop between B and C but has no effect on the other two loops. No significant alteration of any loop, genome-wide, in the mutant cells was observed, with the exception of the targeted B/C loop. This illustrates the capacity to engineer loops in a targeted fashion. The experiment is described in in more detail Example 7A.

To test this hypothesis, we used CRISPR-mediated genome editing to create a 10 bp deletion in the B/Fwd motif (deleting chr1:180,851,237-180,851,246), and grew a clonal population of the resulting cells. We then repeated the in situ Hi-C experiment on the disrupted cells. Strikingly, the loop from B to C was disrupted; the A/B and A/C loops were not affected. More generally, we did not observe significant alteration of any loop, genome-wide, in the mutant cells, with the exception of the B/C loop which we had intended to target. This dramatically illustrates the convergent rule and highlights our capacity to engineer loops in an extremely targeted fashion. The results of this experiment are depicted in FIG. 18.

Example 7B. Altering Looping Patterns Genome-Wide by Engineering Mutant CTCF Proteins CTCF binds DNA through 11 zinc finger domains (ZF1-ZF11). Together, these zinc finger domains determine the DNA sites to which CTCF can bind. We reasoned that modifying these zinc finger domains would alter CTCF binding genome-wide. The resulting changes in CTCF binding was expected to lead to two effects: (1) corresponding changes in loop formation, consistent with the convergent rule; (2) disruption of contact domains established by these loops.

We mutated the CTCF gene in CH12 murine B-lymphoblasts, disrupting three zinc fingers, ZF9-11. CTCF ChIP-Seq experiments confirmed that these mutations led to alterations in CTCF binding genome-wide. These changes clearly affected CTCF binding at hundreds of loop anchors. Strikingly, the disruption of CTCF binding at loop anchors consistently disrupted the corresponding loops and domains, in accordance with the convergent CTCF rule.

Figure 19:
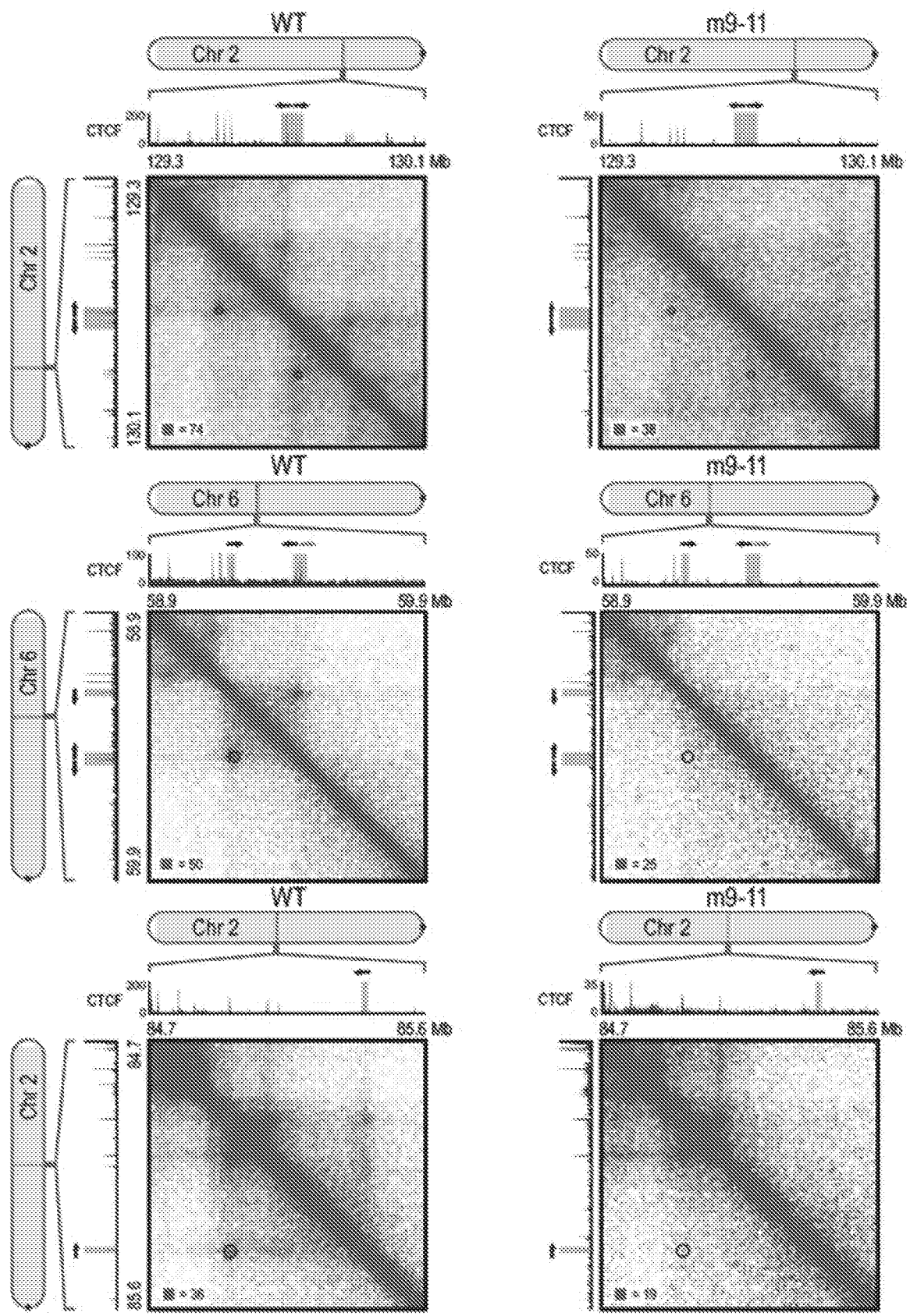
FIG. 19. Hi-C maps of a set of loops showing removal of loops in three different loci on chromosomes 2 and 6 using WT (left panels) and mutant CTFC protein (right panels). The CTCF gene in CH12 murine B-lymphoblasts was mutated, disrupting three zinc fingers, ZF9-11. These mutations led to alterations in CTCF binding genome-wide. These changes clearly affected CTCF binding at hundreds of loop anchors. The disruption of CTCF binding at loop anchors consistently disrupted the corresponding loops and domains, in accordance with the convergent CTCF rule. The experiment is described in in more detail Example 7B.

Several examples are shown in FIG. 19 and described below. In the example at the top of FIG. 11, a pair of loops on chromosome 2 (A to B and B to C) is anchored at four motifs (A/Fwd to B/Rev & B/Fwd to C/Rev) in wild-type CH12 cells. In the CH12 mutants, CTCF no longer binds to B/Rev or B/Fwd, though it continues to bind to A/Fwd and C/Rev. It is shown that both loops disappear, as do the contact domains that they demarcated. In the example shown in the middle of FIG. 19, wild-type CH12 cells exhibit a loop between a pair of convergent CTCF sites on chromosome 6. This loop demarcates a contact domain. In the mutant cells, CTCF no longer binds to either anchor; the loop and contact domain both disappear. In the example shown at bottom of FIG. 19, wild-type CH12 cells exhibit a loop between a pair of convergent CTCF sites on chromosome 2. Again, this loop demarcates a contact domain. In mutant cells, CTCF continues to bind one anchor, but not the other. Again, the loop and contact domain disappear.

Example 8. Deletion of DXZ4 on the Human Inactive X Chromosome Eliminates Superdomains and Impairs Gene Silencing During interphase, the inactive X chromosome (Xi) adopts an unusual 3D configuration known as the Barr body and is largely transcriptionally silent. Despite the importance of X inactivation, little is known about the 3D configuration of Xi and its relationship to gene silencing. We recently showed that in humans, Xi exhibits two distinctive structural features. First, Xi is partitioned into two huge intervals, called superdomains, such that pairs of loci in each superdomain show an enhanced contact frequency with one another. The boundary between the two superdomains lies near DXZ4 (Rao et al. Cell 159, 1665-1680 (2014)), a macrosatellite repeat spanning ~300 kb, whose Xi allele extensively binds the protein CTCF. Second, Xi exhibits extremely large loops, up to 77 Mb long, called superloops. DXZ4 lies at the anchor of several superloops. Here, we use 3D mapping to study the structure of Xi, focusing on the role of DXZ4. We show that superloops and superdomains are conserved across mammals. We develop a novel variant of our in situ Hi-C protocol, dubbed COLA (COncatamer Ligation Assay) to probe the higher order structures formed by the superloops. In COLA, in situ proximity ligation of multiple extremely short fragments produced by the enzyme CviJI is used to efficiently map simultaneous proximity among three or more loci. Using data from Hi-C and COLA, we demonstrate that DXZ4 and other superloop anchors tend to co-locate simultaneously within the same cells, a result that is confirmed by 3D-FISH. Finally, we examine the effects of deleting DXZ4 from Xi in human cells. Using in situ Hi-C, microscopy, and RNA-FISH, we show that superdomains and superloops disappear; that Xi frequently dissociates into multiple separate structures; and that transcriptional silencing on Xi is compromised. Deletion of DXZ4 from the active X chromosome (Xa) has no such effect. Thus, DXZ4 is essential for proper folding and silencing of Xi.

In our previous work describing the structure of Xi, we used DNA polymorphisms to assign in situ Hi-C reads to specific chromosomal homologs in order to create a diploid Hi-C map for human GM12878 cells (Rao et al. Cell 159, 1665-1680 (2014)). We showed that Xi has a distinctive superstructure consisting of superdomains and superloops. DXZ4 is situated at the boundary of the superdomains. It also lies at the anchor of superloops to XIST, FIRRE, LOC550643 (Horakova et al. Hum Mol Genet, doi:dds270 [pii]10.1093/hmg/dds270 (2012)) (which we here dub the Inactive-X CTCF-binding Contact Element, ICCE), and a previously uncharacterized locus at ChrX:75350000-75400000 (which we here dub x75).

We also observed that this Xi superstructure co-exists with compartmentalization, a feature of interphase genome folding that we described in our original study introducing Hi-C. Compartmentalization refers to the tendency of genomic loci to segregate into one of a handful of spatial neighborhoods in the nucleus. Loci in the same compartment exhibit a similar pattern of contacts genome-wide, giving rise to a contact map with a "plaid" appearance. Because loci in the same compartment form contacts with one another more frequently, contiguous genomic domains comprising loci in the same compartment (which are typically ~300 kb long) manifest as squares of enhanced contact frequency along the diagonal of a Hi-C map.

Figure 20:
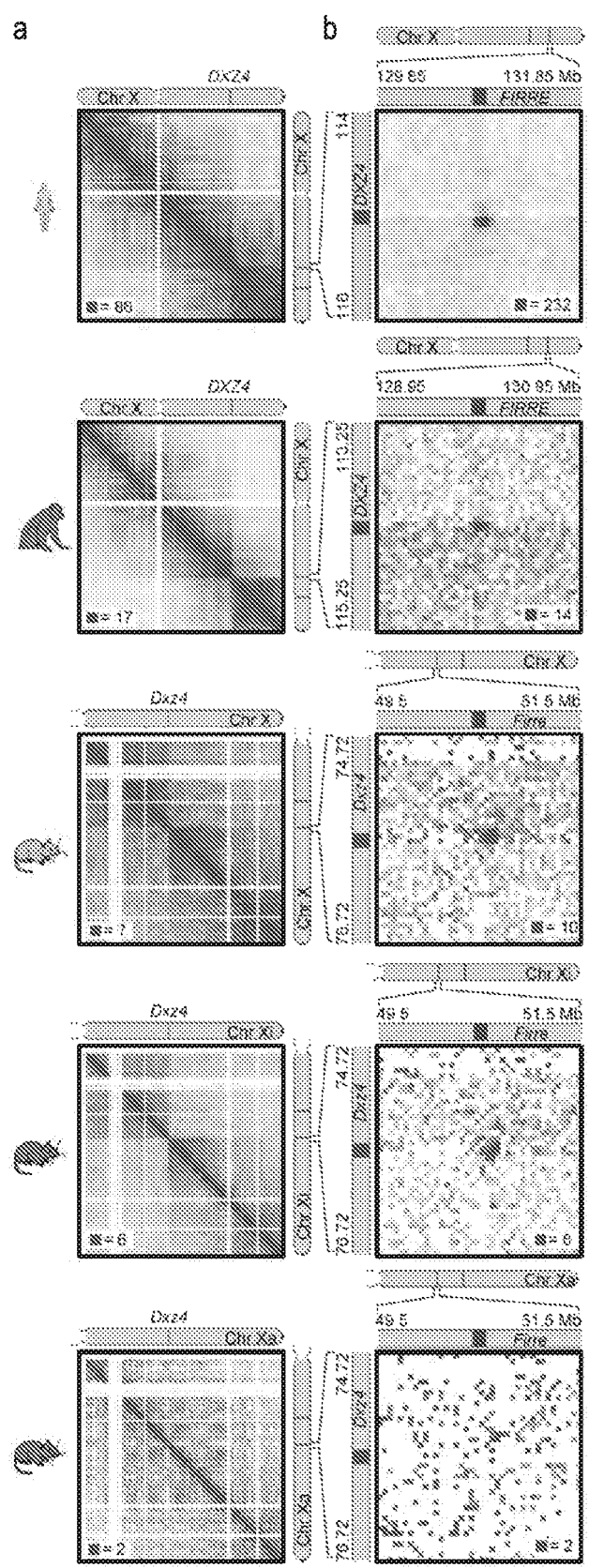
FIG. 20: Xi superstructure is conserved across human, rhesus macaque, and mouse. a, Superdomain on Xi is conserved across human, rhesus macaque, and mouse. The boundary of the superdomains lies at DXZ4 and its orthologs. In our diploid Hi-C maps of mouse, the superdomain is only seen on Xi. (Resolution: 100 kb.) b, A superloop forms between DXZ4 and FIRRE in human. Superloops are present at orthologous positions in rhesus macaque, and mouse. In our diploid Hi-C maps of mouse, the superloop is only seen on Xi. (Resolution: 50 kb.)

To explore whether the Xi superstructure is conserved among mammals, we applied Hi-C to cells from mouse and rhesus macaque. For mouse, we studied the female Patski cell line (Lingenfelter et al. Nat Genet 18, 212-213). Because the Patski cell line was derived from an interspecies hybrid cross [Mus musculus×Mus spretus], it has a high heterozygosity rate (1 in ~64 bases) that facilitates assignment of a large fraction of alignable reads (49%) to particular chromosome homologs. Superdomains were apparent in the maps of Xi, but absent from maps of Xa (FIG. 20a). Notably, despite extensive rearrangement of the murine X chromosome relative to its human counterpart, Dxz4 was again located at the boundary between the superdomains (chrX: 75.7-75.8 Mb, mm10) (Horakova et al. Genome Biol 13, R70, doi:10.1186/gb-2012-13-8-r70 (2012)). (While this manuscript was in preparation, this point was also noted by Minajigi and colleagues (Science, doi:10.1126/science.aab2276 (2015)) in a different murine cell line.) We also observed superloops between Dxz4 and Firre, Dxz4 and Xist, and Dxz4 and x75 (FIG. 20b).

There was one important difference, however, between the human and murine Xi maps. Compartment structure was almost entirely absent in the murine Xi: the Hi-C map of Xi did not have a plaid appearance and square domains were not seen along its diagonal. The absence of compartmentalization may be a feature specific to mice or may be a result of the cell lines chosen in this and our prior study.

When we performed in situ Hi-C in female fibroblasts derived from rhesus macaque (GM08312), we observed superdomains (FIG. 20a) whose boundary lies at the macaque DXZ4 locus (chrX: 114.2-114.3 Mb, rheMac2)16, as well as a prominent superloop linking the macaque orthologs of DXZ4 and FIRRE (FIG. 20b).

Taken together, our contact maps of human, rhesus macaque and mouse suggest that Xi superstructure is widely conserved across eutherian mammals. Because DXZ4's genomic context differs greatly in mouse and human, these findings support a functional role for DXZ4 in determining the placement of superloop anchors and of the superdomain boundary.

Next, we sought to characterize the structure formed by DXZ4 and other superloop anchors in greater detail. Specifically, we wondered whether superloops tend to occur simultaneously in the same cell, which would suggest the existence of a spatial hub on Xi at which all superloop anchors co-locate.

To explore this question, we re-examined our recently published Hi-C dataset, specifically the 21 billion reads that were derived from female human cell lines (Rao et al. Cell 159, 1665-1680 (2014)). Although most Hi-C reads bring together two nearby fragments, the procedure can sometimes result in the ligation of three or more nearby fragments. To explore higher order spatial relationships that cannot be interrogated using pairwise contacts, we searched our Hi-C data for reads containing sequences drawn from three genomic loci, indicating that the loci simultaneously co-localized in a single cell nucleus. Although such reads were rare (~1 in 2056), the size of the dataset enabled us to find over 10 million unique "triples", each exhibiting high-quality alignments (MAPQ.10) to three widely separated loci (all pairwise distances >20 kb) on the same chromosome. The data also contain about 4.6 million unique quadruples and 892 unique quintuples.

Because each triple (A-B-C) implies the proximity of three pairs of loci (A-B, A-C, B-C), we assessed the quality of the triple contacts by creating matrices of the implied pairwise contacts. These matrices closely resembled matrices derived from ordinary, pairwise Hi-C data suggesting that the higher-order contacts observed using in situ Hi-C reflect genuine patterns of nuclear proximity.

Figure 21:
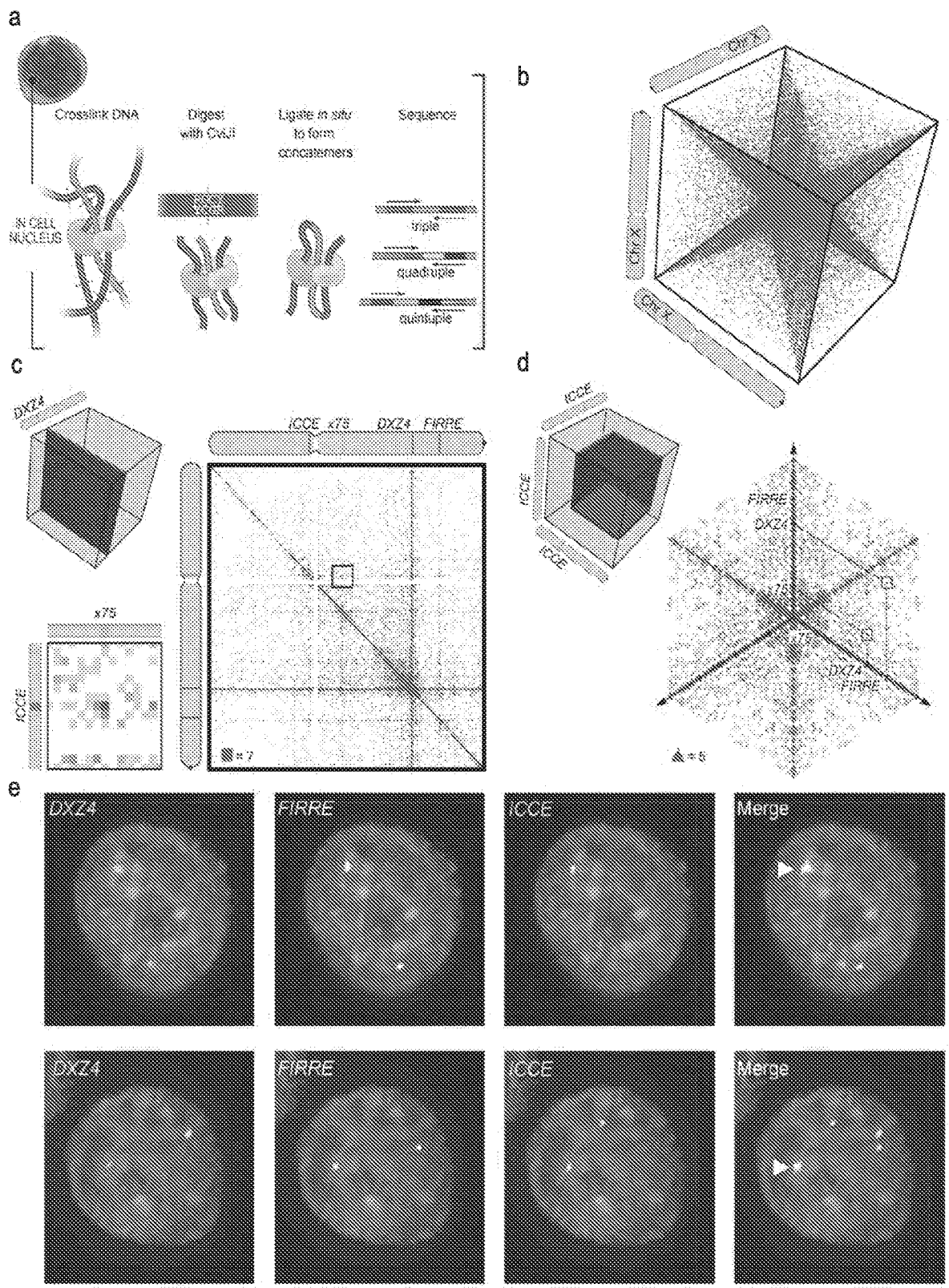
FIG. 21: The DXZ4-FIRRE and ICCE-DXZ4 loops tend to occur simultaneously, forming a hub on Xi. a, COLA, a modification of in situ Hi-C, creates concatemers of multiple fragments. b, Contact triples visualized as a 3D contact tensor. c, A planar cut of the contact tensor at DXZ4 examines all triples that DXZ4 participates in. Enrichment at ×75(-DXZ4)-FIRRE indicates that these superloop anchors collocate. (Resolution: 800 kb.) d, An alternate cut of the tensor, examining ICCE triples. Superloop triples (ICCE-)DXZ4-FIRRE and (ICCE-)×75-FIRRE are highlighted. (Resolution: 2 Mb.) e, Representative examples of direct-labeled 3-color DNA FISH in 46,XX GM12878 show collocation of ICCE-DXZ4-FIRRE. FISH signals overlay DAPI (blue) and are merged in the far-right panel. White arrowhead indicates 3-way overlap on one X-chromosome.

To probe these relations in greater detail, we extended the in situ Hi-C method by using a restriction enzyme that digests chromatin into much finer fragments, thus increasing the chances that a read contains intervals from three or more fragments. In this procedure, dubbed COLA (COncatamer Ligation Assay), chromatin is digested using CviJI, which cleaves RGCY sites between the G and C, leaving blunt ends that are ligated in situ (FIG. 21a). This procedure leads to much finer fragments (average distance between motifs: 64 bp) than ordinary in situ Hi-C. We sequenced 276M paired-end reads from a COLA library generated using human GM12878 lymphoblastoid cells. We found that the matrix of pairwise contacts obtained using COLA closely resembled the contact matrix obtained using ordinary in situ Hi-C experiments in GM12878. However, COLA is much more efficient at generating higher-order contacts; in particular, the frequency of triples is 12 times as high (1 in 122) as in ordinary in situ Hi-C. (The frequency of triples in COLA libraries was 61-fold higher than in dilution Hi-C experiments.) Our COLA maps of GM12878 contributed an additional 2,272,943 unique triples, 251,048 unique quadruples, and 1447 unique quintuples. Such higher order contacts are naturally represented and visualized as an n-dimensional matrix, or tensor. Because the number of entries in this tensor is proportional to the size of the interrogated genome raised to the nth power, the tensor is extraordinarily sparse. Features of chromosome organization manifest inside this tensor as n-dimensional shapes. For instance, the bright diagonal seen in 2-dimensional contact matrices naturally manifests as an n-dimensional hyperstar (FIG. 21b).

Because the tensor was so sparse, we did not expect that it would reveal simultaneity patterns for pairs of ordinary loops. However, because the DXZ4-FIRRE and ICCE-DXZ4 superloops involve extremely large anchors (up to 300 kb), and produce far more signal than typical loops, we reasoned that it might be possible to determine whether these two superloops tended to occur simultaneously.

We found that our tensor contained a cluster of 4 triples corresponding to the triad of loci ICCE-DXZ4-FIRRE. (Note that, because all three loci are tandem repeats, we included triples that did not align uniquely so long as all of the possible alignments fell in the same locus.) Given the extreme sparsity of the contact tensor, the odds that even a single contact would overlap these exact positions at random is <2%. (Our model for random contacts controls for both locus size and pairwise distance between loci.) Seeing 4 triples represents an enrichment of 300-fold over random expectation (p=1.4*10-9). The ICCE-DXZ4-FIRRE voxel was also very strongly enriched with respect to its local, 3D neighborhood. Similarly, we noticed a cluster of 4 triples at the triad ICCE-x75-DXZ4 (a 154-fold enrichment, p=1.8*10-8) (FIG. 21c, FIG. 21d).

To obtain independent evidence that DXZ4, FIRRE, and ICCE tend to simultaneously co-localize on Xi, we used 3D-FISH. When we examined X chromosomes in male lymphoblastoid cells (GM06992), we did not find a single case in which all three loci co-localized (out of 217 chromosomes examined). For X chromosomes in the female GM12878 cell line, we observed co-localization of all three loci in 9 of 224 cases (4%; p=0.0036, Fisher's exact test). Because females contain both Xa and Xi, this suggests that all 3 loci overlap 8% of the time on Xi (vs. 0% on Xa) (FIG. 21e). Because typical pairs of nearby (<1 Mb) loci in the same loop tend to overlap less than 25% of the time when probed using 3D-FISH (Rao et al. Cell 159, 1665-1680 (2014)), an observed overlap frequency of 8% among three loci spread across a chromosome is extremely high.

Taken together, these findings suggest that the DXZ4, FIRRE, and ICCE loci on Xi tend to co-locate at a single spatial position, i.e., that they form a hub.

Figure 22:
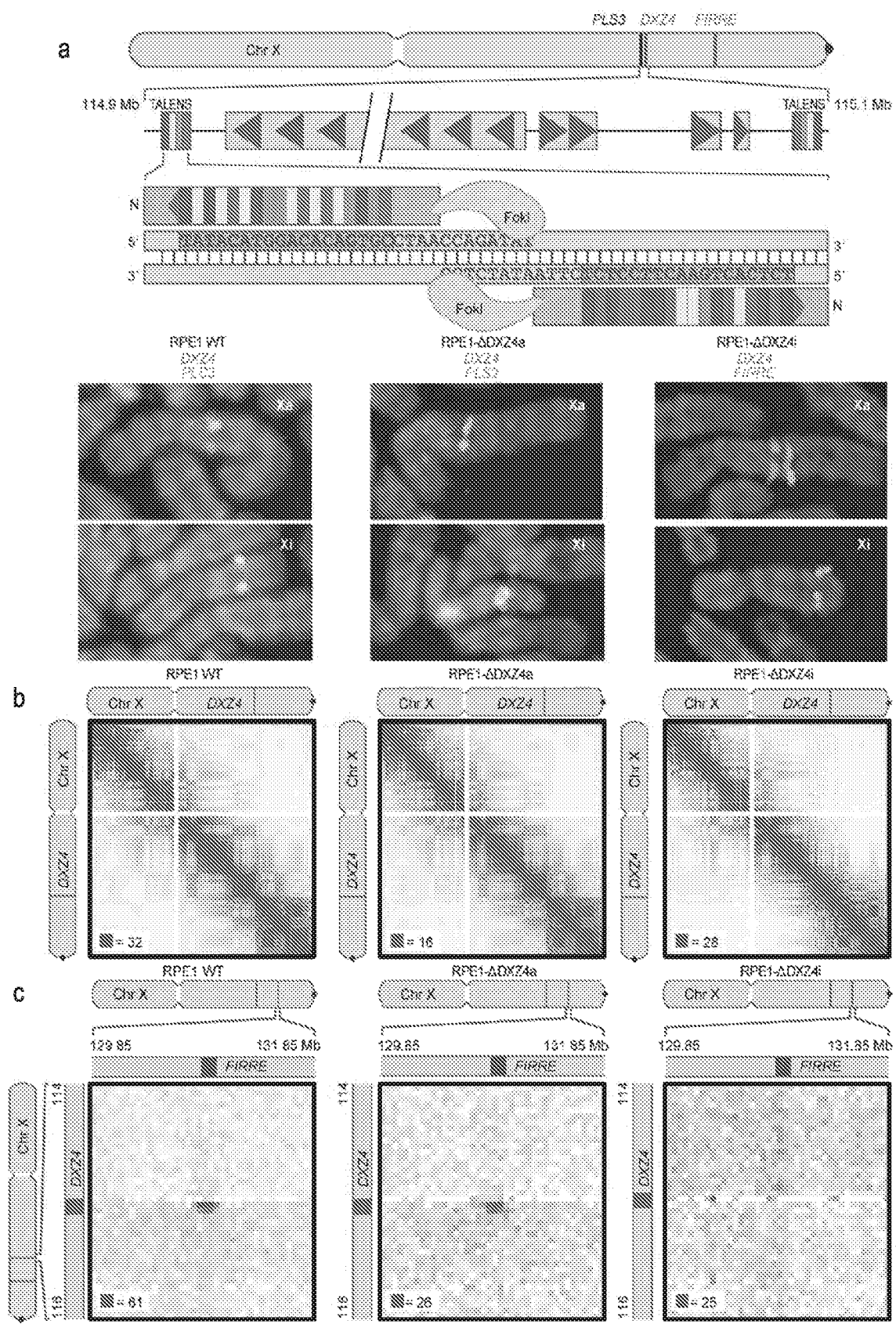
FIG. 22: Deletion of DXZ4 eliminates 344 Xi superstructure. a, We used TALEN pairs targeting an inverted repeat flanking DXZ4 to create mutants lacking DXZ4 on Xa (RPE1-ΔDXZ4a, middle) and Xi (RPE1-ΔDXZ4i, right). Loss of DXZ4 from Xa or Xi is shown by direct-labeled DNA FISH on dropped metaphase chromosomes from the parental and mutant clones. Chromosomes are counterstained with DAPI (Grey). Xa is longer than Xi due to an X:10 translocation at the tip of Xq. b, Superdomains are present in wild type RPE1 cells (left) and remain after DXZ4 is deleted on Xa (middle). Deleting DXZ4 on Xi eliminates superdomains. (Resolution: 100 kb.) c, The DXZ4-FIRRE superloop is present in wild type RPE1 (left) and in RPE1-ΔDXZ4a (middle), but disappears in RPE1-ΔDXZ4i (right). (Resolution: 50 kb.)

Finally, we explored the effect of deleting DXZ4 on the superstructures characterized above. We designed a pair of TALENs (a class of nucleases with a customizable DNA-binding motif) that target two unique inverted repeats flanking the DXZ4 locus (FIG. 22a). Simultaneous cutting at both ends of the locus resulted in loss of the intervening DNA, including DXZ4. We isolated clones of RPE1, a retinal pigment epithelial cell line derived from human females, which lacked DXZ4 on either Xi (RPE1-ƒ¢DXZ4i) or Xa (RPE1-ƒ¢DXZ4a). (See FIG. 22a) We precisely defined the extent of the 183 deletions by sequencing the deletion product.

We then used in situ Hi-C to create 3D genome maps of all three cell lines (RPE1, RPE1-ƒ¢DXZ4i, and RPE1-ƒ¢DXZ4a). Both the wild-type RPE1 cells and the RPE1-ƒ¢DXZ4a mutants exhibited superdomains and superloops, closely resembling both one another and previous high-resolution in situ Hi-C maps from human females. In contrast, the RPE1-ƒ¢DXZ4i cells exhibited neither superdomains nor superloops (FIG. 22b, 22c).

Figure 23:
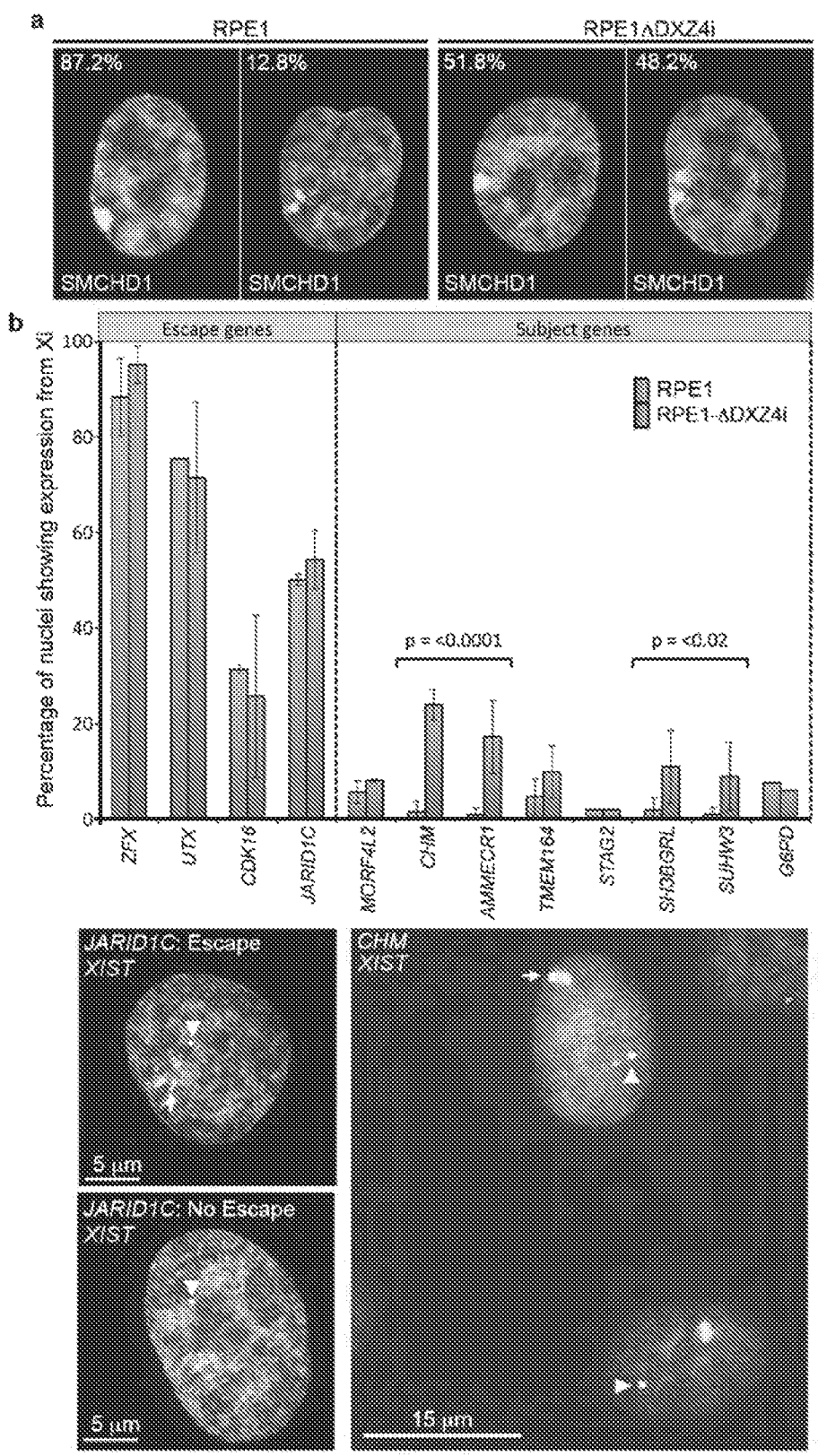
FIG. 23: Deletion of DXZ4 interferes with transcriptional silencing on Xi. a, Indirect immunofluorescence showing representative results for RPE1 and RPE1-ΔDXZ4i cells. SMCHD1, shown in Red, stains Xi; DAPI, shown in Grey, indicates the extent of the nucleus. Frequencies of each configuration are shown. The separation of Xi into multiple chromatin bodies are seen much more frequently after deletion of DXZ4. b, Top: Percentage of cells with expression of the indicated gene from Xi. Each data-point is derived from between 101-140 nuclei comprising two replicate RNA-FISH experiments. Standard deviations are shown; p-values were obtained using Fisher's exact test (2-tailed). Bottom: Examples of the scoring procedure. Escape or non-escape is determined by comparing the RNA-FISH signal from a gene of interest (Green) to the signal from XIST (Red), which coats Xi. White arrows indicate the Xi allele; white arrowheads indicate Xa.
Figure 24:
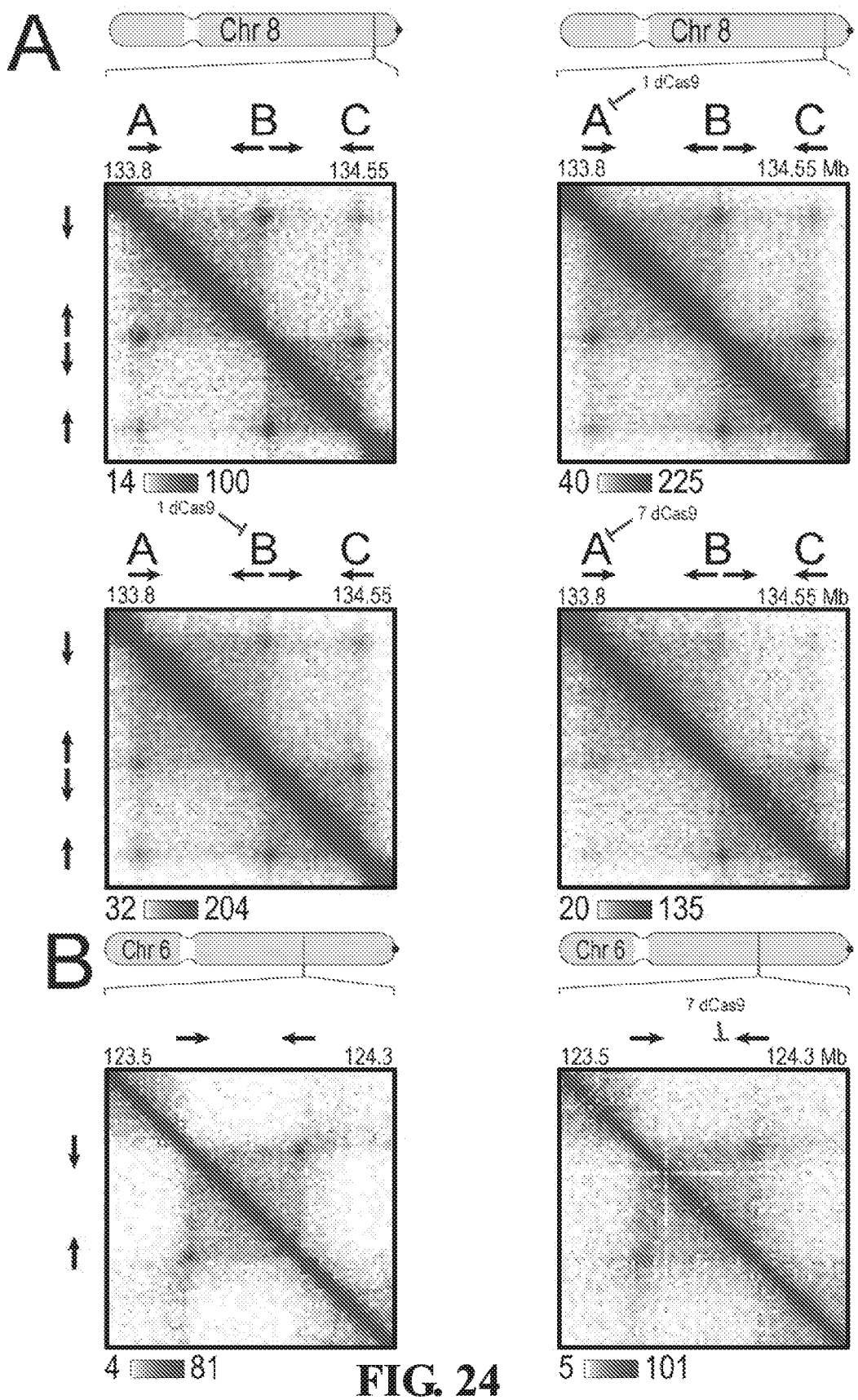
FIG. 24: dCas9 can be used to reengineer chromatin loop and domain structures in an inducible manner. (A) first row, Hi-C$^2$ contact map for the WT locus at chr8:133.8-134-55 Mb in Hap1 cells. first row, right, block of the A forward CTCF motif with a single dCas9/gRNA combo results in loop attenuation but does not completely abolish either the A-B or A-C loops. second row, left, block of the B reverse CTCF motif with a single dCas9/gRNA combo results in loop attenuation but does not completely abolish the A-B loop. second row, right, block of the A loop anchor (including CTCF motif itself) with 7 dCas9/gRNAs eliminates both the A-B and A-C loops. (B) left, Hi-C contact map for the WT locus at chr6:123.5-124.3 Mb in Hap1 cells, righ, tiling of 7 dCas9/gRNAs from chr6:123.925-123.930 Mb (>100 kb from either loop anchor) leads to attenuation of loop formation.

We confirmed the abnormal Xi structure in RPE1-ƒ¢DXZ4i cells using microscopy. To visualize Xi during interphase, we employed immunofluorescence using antibodies against SMCHD1, which is known to coat Xi17. In wild-type RPE1 cells, only a small fraction of cells (12.8%, n=258) exhibited multiple chromatin bodies (i.e., discrete fluorescent volumes). In contrast, nearly half of RPE1-ƒ¢DXZ4i mutant cells exhibited multiple chromatin bodies (48.2%, n=224; p=<0.0001, Fisher fs exact test) (FIG. 23a). These findings indicate that, in the absence of DXZ4, the structural cohesion of Xi is broadly compromised.

We used RNA-FISH to check whether deletion of DXZ4 affects transcription from Xi.

First, we examined eight genes that are silent on Xi in wild-type RPE1 cells (AMMECR1, CHM, G6PD, MORF4L2, SH3BGRL, STAG2, SUHW3, and TMEM164). Strikingly, we found that four of these genes (AMMECR1, CHM, SH3BGRL, SUHW3) were reactivated in a significant number of cells. The reactivated genes were dispersed throughout Xi.

Next, we examined four genes that escape inactivation in wild-type RPE1 cells (ZFX, UTX, CDK16, and JARID1C). The deletion had no effect on expression of these genes. These data suggest that deletion of DXZ4 interferes with maintenance of X chromosome silencing, possibly through the disruption of Xi superstructure (FIG. 23b).

In summary, we find that the position of DXZ4 with respect to superloop anchors and the superdomain boundary on Xi is broadly conserved across eutherian mammals; that DXZ4, FIRRE, ICCE, and possibly other loci appear to simultaneously co-locate to form a superhub comprising superloop anchors on Xi; and that the deletion of DXZ4 eliminates superdomains and disrupts the superstructure of Xi. Our study thus demonstrates that DXZ4 is crucial for proper inactivation of the X chromosome. The mechanism by which DXZ4 and other elements combine to establish the distinctive 3D structure of Xi and contribute to transcriptional silencing may well be de to CTCF. Given the role of CTCF in establishing chromatin loops, it is noteworthy that a given allele of the DXZ4 locus comprises between 10 and 100 copies of a repeat element containing a CTCF motif, and that these CTCF motifs are the only sequences in DXZ4 showing evidence of strong purifying selection. This finding suggests that, just as individual CTCF motifs can establish loops and domains at the megabase scale, large arrays of CTCF motifs may establish loops and domains at the chromosome scale. It also suggests that the insertion of DXZ4 elements in new contexts may produce genomic folds on the scale of whole chromosomes.

Methods

TALENs.

TALENs were assembled using FLASH essentially as described 19. Activity at the proximal and distal inverted repeat sequence was assessed using the Surveyor assay (Transgenomic)20 with oligonucleotide sequences CAACCCCACAGGGAGAACT (SEQ ID NO: 45) and ACTTTCATTTTCAGGTCAGAC (SEQ ID NO: 46) for the proximal side, and CTTTTCTTCTCAGGTTACAGT (SEQ ID NO: 47) and TCAATCACACAAGGGAAATGC (SEQ ID NO: 48) for the distal side.

Isolation and Characterization of RPE1-ÄDXZ4a and RPE1-ÄDXZ4i.

TALEN expression constructs were introduced into hTERT-RPE1 cells (Clontech Laboratories, No. C4000-1) using a 4D-Nucleofector™ (Lonza Group Ltd.). Twenty-four hours post-Nucleofection, cells were seeded to 24-well plates at a density of 25 cells/well. At 50% confluence, 50% of cells from each row were pooled and genomic DNA isolated before screening for deletion of DXZ4 using oligonucleotides CAACAGCAATTTCAGTAAGGTG (SEQ ID NO: 49) and GATCTGGTCAAAATCAGAGAT (SEQ ID NO: 50). Genomic DNA was isolated from cells in individual wells of positive rows and re-screened for DXZ4 deletions. Cells from positive wells were then seeded into 96-well plates at a density of 0.25 cells/well. Screening of pooled rows was performed as above. TA cloning and sequencing the deletion PCR product determined the exact nature of the DXZ4 deletion for RPE1-ÄDXZ4a and RPE1-ÄDXZ4i. Assignment of the deletion to Xa or Xi was achieved by FISH analysis on metaphase chromosomes using a direct-labeled DXZ4 probe (Spectrum Red, Abbott Molecular) in combination with a second X-linked direct labeled BAC probe (Spectrum Green, Abbott Molecular). hTERT-RPE1 have an X:10 translocation on Xa at Xq28 making Xq substantially longer on Xa compared to Xi. Metaphase chromosome preparation and FISH were performed essentially as described previously (McLaughlin & Chadwick, Genome Biology 12, R37 (2011)).

In Situ Hi-C Protocol.

We performed 20 in situ Hi-C experiments as described previously (Rao et al. Cell 159, 1665-1680 (2014)).

COLA Protocol

Five million cells were cross-linked for 10 minutes with 1% formaldehyde. Nuclei were permeabilized. DNA was digested with CviJI in CviJI reaction buffer and ligated with T4 DNA ligase. The library was enriched for ligation products after proximity ligation using size selection on an agarose gel. The library was prepared for sequencing with the Illumina platform.

DNA & RNA FISH.

Three-color DNA FISH was performed on B-Lymphocyte cell lines GM12878 and GM06992 that were obtained from the Coriell Institute for Medical Research. Direct labeled probes were prepared by nick translation and included BAC clones 2272M5 for DXZ4 (Alexa Fluor 647, Invitrogen Corporation), RP11-754H22 for FIRRE (Spectrum Green, Abbott Molecular) and RP11-818117 for ICCE (Spectrum Red, Abbott Molecular). DNA FISH was performed essentially as described 11. RNA FISH was performed using a direct-labeled XIST probe (Spectrum Red, Abbott Molecular) combined with direct-labeled BAC clones (Spectrum Green, Abbott Molecular) as described previously (Horakova, et al. Hum Mol Genet, doi:dds270 [pii]10.1093/hmg/dds270 (2012).).

Immunofluorescence.

Indirect immunofluorescence used rabbit anti-SMCHD1 polyclonal antibodies (Bethyl Laboratories Inc., A302-872A) at 1íg/ml essentially as described previously (McLaughlin & Chadwick, Genome Biology 12, R37 (2011)). Conjugate secondary antibodies (Alexa-Fluor®) were obtained from Life Technologies Corporation. DNA was counterstained using the VECTASHIELD® mounting medium with DAPI from VECTOR Laboratories. Imaging was performed on an Olympus IX71 operated by the DeltaVision pDV, deconvolved with softWoRx 5.5.1 (DeltaVision), and compiled using Adobe Photoshop CS6 (Adobe Systems).

DXZ4 Xa and Xi Allele Size Determination.

Pulsed field gel electrophoresis, Southern blotting, hybridization and detection were performed essentially as described previously.

Hi-C Data Pipeline.

Read files were processed as described 6. Reads for the human, mouse, and macaque cell lines were aligned to hg19, mm10, and rheMac2, respectively.

Diploid Hi-C Pipeline

The Patski cell line is a female mouse embryonic kidney 436 fibroblast obtained from a $M.\ spretus \times C57BL/6J$ hybrid mouse (obtained courtesy of the Disteche Lab, UW). The maternal (C57BL/6J) X chromosome is always the inactive X. To create two diploid maps, we followed the procedure described previously (Rao et al. Cell 159, 1665-1680 (2014)), using SNPs obtained from the Welcome Trust Sanger Institute to distinguish reads on the different alleles. Of 780,701,963 total reads, we were able to phase 117,412,620.

Higher-Order Contact Analysis Pipeline

In total, we examined 78 published Hi-C libraries from 6 different female cell lines, in addition to the GM12878 COLA library. As described previously (Rao et al. Cell 159, 1665-1680 (2014)), the Hi-C data pipeline annotates Hi-C contacts that map to three or more places in the genome as abnormal, and these are usually discarded from 2-d contact map analysis. For the current higher order contact analysis, we examined these chimeric contacts to create a list of triples, quadruples, and quintuples in the genome. Due to the overwhelming contribution of triples as compared to other chimeras further analysis was limited to triples.

In order to ensure that no duplicate triple reads entered the analysis, we first created a 'pseudo genome', concatenating all of the triple reads. We then used bwa to align each of the individual chimeric triples to the pseudo genome. Reads which aligned to multiple places (alpha $<=0.04$) were discarded as duplicates.

For the most stringent filtering of higher order contacts, we required that all alignments were high-quality (MAPQ>10), all loci were on the same chromosome, and that the distance between any pair of loci was at least 20 kb. Since DXZ4, FIRRE, and ICCE comprise tandem repeats, this filtering strategy threw out 459 most of the relevant reads at these superloop anchors, so we developed a second filtering strategy for the superloop collocation analysis. For this analysis, reads with MAPQ=0 were included. Reads that did not align uniquely but landed on superloop anchors were then manually examined to ensure that all alignments fell within the identified superloop anchor.

The enrichment analysis of superloop triple data was performed with respect to a global and a local expected model, using a Poisson distribution for significance testing. In the global model, the expected number of reads was calculated based on the number of triples with anchors separated by the same distances as the superloop anchors in question. Due to the fact that the global model does not account for possible biases due to pairwise contacts we also calculated an expected value based on the local neighborhood of the superloop triple (local model). The strategy we employed closely follows that of HiCCUPs described previously (Rao et al. Cell 159, 1665-1680 (2014)).

Example 9—Protocol to Block Chromatin Loop Anchors with dCas9

Anchor identification: Chromatin loop anchors are identified to single basepair resolution by applying HiCCUPS, a GPGPU accelerated loop identification algorithm we developed, on data generated using the Hi-C protocol, followed by identification of unique CTCF motifs lying under the anchors leveraging ChIP-Seq data for CTCF, cohesin, and/or other proteins bound at loop anchors (Rao and Huntley et al, Cell 2014; Durand and Shamim et al, Cell Systems 2016).

Guide RNA design: CRISPR guide RNAs were designed to target loop anchor motifs or to tile the ~5 kb region containing the loop anchor motif (including a gRNA targeting the motif itself). Prospective guide RNAs were screened using the cutting efficiency scoring scheme from Doench, et al (Nat Biotech 2015) and the off-target scoring scheme from Hsu, et al (Nat Biotech 2013). Wherever possible, guides with cutting efficiency scores of 0.4 or lower were avoided, and guide RNAs with scores of lower than 0.25 were discarded altogether. Wherever possible, guides ranked as high quality guides by the Hsu off-target assessment algorithm were used. In a few cases, where no high quality guide was identified or when the cutting efficiency as ranked by the Doench, et al algorithm was extremely low, a midquality guide (with respect to off-targets) was used. Guide RNAs tiling the ~5 kb around a loop anchor motif were designed such that each guide RNA was 500-1000 basepairs apart and one guide RNA targeted the motif itself.

Cloning: Guide RNAs were cloned into a plasmid based on pX330 plasmid (with dCas9 instead of Cas9) from the Feng Zhang lab (Cong et al, Science 2013). When multiple guide RNAs were to be used simultaneously (i.e. when tiling a loop anchor), the guide RNAs were multiplexed into the same plasmid, each under the control of its own U6 promoter. (Each guide RNA was cloned into a plasmid based on the pX330 plasmid and then the plasmids were combined into an acceptor plasmid via Golden Gate assembly.) To generate plasmids for stable integration of the guide RNA cassettes, the guide RNA cassettes were further cloned into a PiggyBac transposon (in order to be stably integrated into the genome when transfected into cells along with a Piggy-Bac transposase). In addition, a dCas9-2A-GFP cassette (Kabadi et al, Nucleic Acids Research 2014), was cloned into a PiggyBac transposon (along with a hygromycin selection cassette).

Transient transfection: Hap1 cells (Horizon Genomics) were cultured according to manufacturer's conditions. 24 hours before transfection, 0.9M Hap1 cells were plated in each well of a 6 well plate. After 24 hours, when the cells were roughly 60% confluent, the cells were transfected with the plasmid containing the guide RNA (or multiplex guide RNA) cassette and dCas9. If the dCas9 was fused to a GFP, then only this plasmid was transfected; otherwise, a plasmid with a GFP cassette was cotransfected to mark successfully transfected cells. The Hap1 cells were transfected (in antibiotic free media) with 3 μg of DNA using Turbofectin according to manufacturer's instructions (a 3:1 ratio of Turbofectin to DNA was used; 9 μl of Turbofectin for 3 μg of DNA). 24-48 hours after transfection, GFP+ cells were sorted via FACS (PI was also added to filter for dead cells). Transfection efficiencies were usually between 5 and 10%.

Sorted cells were crosslinked with 1% formaldehyde for 10 minutes at room temperature in order to perform the in situ Hi-C protocol.

Stable integration: We first generated Hap1 cells stably expressing dCas9 by transfecting PiggyBac-dCas9-2A-GFP as above along with a tamoxifen inducible PiggyBac transposase plasmid (also containing an mCherry cassette). 24 hours after transfection, tamoxifen was added to induce the tranposase. 48 hours after transfection, GFP+/mCherry+ double positive cells were sorted and allowed to grow for 24 more hours in the presence of tamoxifen. 1 week after transfection, hygromycin selection (600 ug/mL of Hygromycin B) was started to select for cells with dCas9-2A-GFP stably integrated. This Hap1-dCas9 cell line was then transfected with a PiggyBac-guideRNA (or PiggyBac-multiplex gRNA) plasmid; this plasmid also had a constitutive mCherry selection marker. Transfection and induction of integration were performed as above. GFP+/mCherry+ populations were crosslinked for in situ Hi-C as well as GFP+/mCherry+clones isolated via serial dilution.

In situ Hi-C: in situ Hi-C was performed as in Rao and Huntley, et al (Cell 2014).

Hi-C$^2$: Hi-C$^2$ was performed as in Sanborn and Rao, et al (PNAS 2015). The following is reproduced from there:

i. Probe Design

To design probes targeting a particular region for HYbrid Capture Hi-C(Hi-C$^2$), we first identified all restriction sites within the target region. Since Hi-C ligation junctions occur between restriction sites, we designed our bait probe sequences to target sequences within a certain distance of the (MboI) restriction sites present in our target region. Specifically, we performed a first pass, scanning all 120 bp sequences with one end within 80 bp of a restriction site and selecting, for each restriction end (i.e. both upstream and downstream of the restriction site), the closest 120 bp sequence to the restriction site that had fewer than 10 repetitive bases (as determined by the repeat masked hg19 genome downloaded from UCSC) and had between 50% and 60% GC content. If there was no probe satisfying those criteria, the closest probe with between 40% and 70% GC content but satisfying all the other above criteria was retained. The GC content bounds were chosen based on the hybridization bias data presented in (28). After the first pass, we removed one probe from any pair of probes that overlapped. We then identified any gaps in the probe coverage (intervals larger than 110 bp) and identified any restriction sites falling within those gaps. We then searched for additional 120 bp probes with a looser set of criteria: For each restriction site within a gap, we scanned all 120 bp sequences with one end within 110 bp of a restriction site and selected the closest sequence to the restriction site that had fewer than 20 repetitive bases and had between 40% and 70% GC content. After the second pass, we once again identified gaps of at least 110 bp in the probe coverage. For gaps that fell within 5 kb windows in the target region that were covered by fewer than 5 probes, we performed a third probe design pass. For each restriction site within these low coverage gaps, we scanned all 120 bp sequences with one end within 110 bp of a restriction site and selected the closest sequence to the restriction site that had fewer than 25 repetitive bases and had between 25% and 80% GC content.

15 bp primer sequences (unique for each region) were appended to either end of the 120 bp probe sequence in order to allow for synthesis of all probes together in one oligo pool and subsequent amplification of region-specific sub-pools (see below).

ii. Probe Construction

Custom synthesized pools of 150 bp (120 bp+15 bp primer sequence on either end) single stranded oligodeoxynucleotides were obtained from CustomArray, Inc. (Bothell, Wash.). Region-specific sub-pools were first amplified from the overall CustomArray oligo pool using the following mix and PCR profile:

2 µl oligo pool (160 ng)
6 µl Primer 1 (10 µM)
6 µl Primer 2 (10 µM)
36 µl H2O
50 µl 2× Phusion master mix
100 µl TOTAL
Amplify for 10-18 cycles using the following PCR profile:
98 C for 30 s
98 C for 10 s
55 C for 30 s
72 C for 30 s cycle 10-18 times
72 for 7 min
hold at 4 C After the initial amplification of the region-specific sub-pool, a 1×SPRI clean up was performed on the 162 bp PCR product to remove primers and primer-dimers. We then performed a second PCR amplification to add a T7 promoter, using the following mix and PCR profile:

2 µl first PCR product
12 µl Primer 1-T7 (10 µM)
12 µl Primer 2 (10 µM)
74 µl H2O
100 µl 2× Phusion master mix
200 µl TOTAL
Amplify for 12-18 cycles using the following PCR profile:
98 C for 30 s
98 C for 10 s
55 C for 30 s
72 C for 30 s cycle 12-18 times
72 for 7 min
hold at 4 C After the second PCR, once again, we performed a 1×SPRI clean up to purify the 182 bp PCR product. We then used the purified second PCR product as the template in a MAXIScript T7 transcription reaction (Ambion) as follows:

X µl purified DNA template (1 ug)
10 µl T7 enzyme mix
10 µl 10× transcription buffer
5 µl 10 mM ATP
5 µl 10 mM CTP
5 µl 10 mM GTP
4 µl 10 mM UTP
1 µl 10 mM Biotin-16-UTP
Y µl H2O
100 µl TOTAL After incubating the reaction for at least 90 minutes at 37° C., we added 1 µl of TURBO DNase 1 and incubated at 37° C. for 15 minutes to remove template DNA. We added 1 µl of 0.5M EDTA to stop the reaction and removed unincorporated nucleotides and desalted the RNA by purifying using a Zymo Oligo Clean and Concentrator column (following manufacturer's instructions). Our RNA yield was typically 5-15 µg of RNA per reaction, so we measured the concentration of the RNA prior to the column cleanup using a Qubit RNA assay in order to determine whether to use one or two columns (the capacity of one of the Zymo columns is 10 µg). For long-term storage of the RNA probes, we added 1 U/µl of SUPERase-In RNase inhibitor (Ambion) and stored at −80 C.

iii. Hybrid Selection

Final in situ Hi-C libraries were assessed for quality using the metrics outlined in Rao and Huntley, et al (Cell 2014). High quality libraries of sufficient complexity were selected for hybrid capture. 500 ng of Hi-C library was used as the pond for the hybrid selection reaction; libraries were diluted to a concentration of 20 ng/µl (i.e. 25 µl of library was used). For a few libraries that were under 20 ng/µl in concentration, as low as 250 ng total was used (still in 25 µl).

For the hybridization reaction, 25 µl of pond was mixed with 2.5 µg (1p1) of Cot-1 DNA (Invitrogen) and 10 µg (1 µl) of salmon sperm DNA (Stratagene). The DNA mixture was heated to 95° C. for 5 minutes and then held at 65° C. for at least 5 minutes. After at least 5 minutes at 65° C., 33 µl of prewarmed (65° C.) hybridization bu_er (10×SSPE, 10×Denhardt's buffer, 10 mM EDTA, and 0.2% SDS) and 6 µl of RNA probe mixture (500 ng of RNA probes, 20 U of SUPERase-In RNase inhibitor; prewarmed at 65° C. for 2 minutes) were added to the DNA library for a total volume of 660 This mixture was incubated at 65° C. in a thermocycler for 24 hours. After 24 hours at 65° C., 50 µl of streptavidin beads (Dynabeads MyOne Streptavidin T1, Life Technologies) were washed three times in 200 µl of Bind-and-Wash buffer (1M NaCl, 10 mM Tris-HCl, pH 7.5, and 1 mM EDTA) and then resuspended in 134 µl of Bind-and-Wash buffer. The beads were added to the hybridization mixture and incubated for 30 minutes at room temperature (with occasional mixing to prevent the beads from settling). After 30 minutes, the beads were separated with a magnet and the supernatant discarded. The beads were then washed once with 200 µl low-stringency wash buffer (1×SSC, 0.1% SDS) and incubated for 15 minutes at room temperature. After 15 minutes, the beads were separated on a magnet and the supernatant discarded. The beads were then washed three times in high-stringency wash buffer (0.1×SSC, 0.1% SDS) at 65° C. for 10 minutes, each time separating the beads with a magnet and discarding the supernatant. After the last wash, the DNA was eluted o_ the beads by resuspending in 50 µl of 0.1M NaOH and incubating for 10 minutes at room temperature. After 10 minutes, the beads were separated on a magnet and the supernatant was transferred to a fresh tube with 50 µl of 1M Tris-HCl, pH 7.5 (to neutralize the NaOH). To desalt the DNA, we performed a 1×SPRI cleanup using 3× concentrated SPRI beads (taking 3 volumes of SPRI bead/solution mix, separating on a magnet, discarding 2 volumes of SPRI solution and resuspending the beads in the remaining 1 volume). We eluted the DNA in 22.5 µl of 1× Tris buffer (10 mM Tris-HCl, pH 8.0). In order to prep the Hi-C2 library for sequencing, we added 25 µl of 2× Phusion and 2.5 µl of Illumina primers and amplified the library for 12-18 cycles. After PCR, we performed two 0.7×SPRI cleanups to remove primers, etc. and then quantified the libraries for sequencing.

Protocol to Block Loop Extrusion with dCas9:

Loop identification: Loops were identified with HiC-CUPS (Rao and Huntley, et al Cell 2014) as above.

Guide RNA design: CRISPR guide RNAs were designed to tile a ~5 kb region in between the two loop anchors and sufficiently far (>100 kb) from either anchor. Prospective guide RNAs were screened using the cutting efficiency scoring scheme from Doench, et al (Nat Biotech 2015) and the off-target scoring scheme from Hsu, et al (Nat Biotech 2013). Wherever possible, guides with cutting efficiency scores of 0.75 or lower were avoided, and guide RNAs with scores of lower than 0.25 were discarded altogether. Wherever possible, guides ranked as high quality guides by the Hsu off-target assessment algorithm were used. In a few cases, where no high quality guide was identified or when the cutting efficiency as ranked by the Doench, et al algorithm was extremely low, a midquality guide (with respect to off-targets) was used. Guide RNAs tiling the ~5 kb were designed such that each guide RNA was 500-1000 basepairs apart and alternated between the Watson and Crick strands.

Cloning, transfection, integration, in situ Hi-C and Hi-C² were performed as above.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of this disclosure and these claims.

We claim:

1. A method to modify one or more existing chromatin loops or contact domains in a target region of chromatin DNA inside the nucleus of a eukaryotic cell,
   wherein the target region of chromatin DNA is being extruded by each of the two subunits of a CCCTC-binding factor (CTCF) and/or cohesin-comprising extrusion complex in opposite direction with respect to the genome and wherein the target region of chromatin DNA comprises a forward and reverse CTCF or cohesin binding motif in convergent orientation on opposite strands of the extruded chromatin DNA,
   said method comprising targeting one or more catalytically inactive CRISPR-Cas systems or Cas proteins to a CTCF or cohesin binding motif or within 150,000 base pairs of a CTCF or cohesin binding motif in said target region in the nucleus of the cell, wherein the catalytically inactive CRISPR-Cas systems or Cas proteins bind to a target site in the target region and are not capable of recruiting any additional biological or enzymatic activity to the target site, to thereby prevent the extrusion of at least one chromatin strand through the extrusion complex.

2. The method of claim 1, wherein said catalytically inactive CRISPR-Cas systems or Cas proteins are targeted to a location between the forward and reverse CTCF or cohesin binding motifs at an existing loop or contact domain boundary.

3. The method of claim 2, wherein said catalytically inactive CRISPR-Cas systems or Cas proteins are targeted to a location within 1000 base pairs following an existing forward CTCF or cohesin binding motif.

4. The method of claim 1, wherein the CTCF or cohesin binding motif is the CTCF motif.

5. The method according to claim 1, wherein said method further comprises the step of performing in situ Hi-C on said cell prior to or following said targeting, thereby generating an in situ Hi-C library, wherein in situ Hi-C comprises performing Hi-C in intact nuclei, and wherein said in situ Hi-C method identifies target chromatin loop modification sites or monitors the result of chromatin loop or contact domain modification in the target region.

6. The method of claim 5, further comprising detecting changes in gene expression and/or changes in cell phenotype after said targeting.

7. The method of claim 5, further comprising hybridizing probes specific to ligation junctions in the target region and isolating the hybridized probes.

8. The method of claim 5, wherein said in situ Hi-C comprises the steps of:
   a. generating a 3D contact map of the genome of said cell; and
   b. identifying a target modification site from the 3D contact map, wherein the target modification site comprises either an existing loop or contact domain or a modified loop or contact domain.

9. The method of claim 8, wherein said method further comprises the steps of:
   c. generating a set of vectors wherein each vector encodes one or more chromatin loop perturbations, wherein expression of one or more vectors in the set of vectors results in removal of one or more existing chromatin loops or domains, introduction of one or more new chromatin loops or domains, or modification of one or more existing loops or domains at one of the identified target modification sites;

d. delivering each vector in the set of vectors to a different cell or cell population to determine an impact of the introduced chromatin loop perturbations on cell function; and e. identifying the one or more vectors in the set of vectors that introduce the one or more chromatin perturbations.

10. The method of claim 1, wherein targeting the one or more catalytically inactive CRISPR-Cas systems or Cas proteins to the nucleus of a cell comprises:
   i. delivering one or more vectors encoding the one or more catalytically inactive CRISPR-Cas systems or Cas proteins; or
   ii. delivering a cell-permeable reagent comprising the one or more catalytically inactive CRISPR-Cas systems or Cas proteins.

11. The method of claim 10, wherein the one or more vectors are delivered in vivo.

12. The method of claim 10, wherein the one or more catalytically inactive CRISPR-Cas systems or Cas proteins are under the inducible control of a vector promoter.

13. The method of claim 12, wherein the vector promoter is a tissue-specific promoter or a promoter that is ubiquitously expressed.

14. The method of claim 10, wherein the one or more vectors encoding the one or more catalytically inactive CRISPR-Cas systems or Cas proteins comprise a viral vector.

15. The method of claim 14, wherein the viral vector is selected from the group consisting of lentiviral, adenoviral, adeno-associated viral, and herpes simplex virus vectors.

16. The method of claim 10, wherein said cell-permeable reagent comprises a pyrrole-imidazole polyamide.

17. The method of claim 1, wherein the one or more catalytically inactive CRISPR-Cas systems or Cas proteins target one or more existing CTCF or cohesin binding motifs.

18. The method of claim 1, wherein said target region comprises genes the expression of which is to be modified, and wherein modification of the existing chromatin loop or contact domain alters expression of one or more of said genes.

19. The method of claim 18, wherein one or more of the genes is associated with a disease.

20. The method of claim 19, wherein the one or more of the genes is an oncogene or tumor suppressor gene.

21. The method of claim 20, wherein a target region associated with aberrant expression of an oncogene is targeted, whereby expression of the oncogene is repressed; or wherein a target region associated with aberrant expression of a tumor suppressor is targeted, whereby expression of the tumor suppressor is activated.

22. The method of claim 19, wherein the disease is a genetic disease associated with genomic imprinting, whereby an imprinted gene is unsilenced or a gene is silenced by establishing imprinting.

23. The method of claim 1, wherein the target region comprises a virus integration site of an infectious virus, and/or
   wherein the target region is associated with improved yields, disease resistance, drought resistance or salt tolerance in plant or animals.

24. The method of claim 23, wherein the virus is a retrovirus, an adenovirus, an adeno-associated virus (AAV), a lentivirus or a herpesvirus.

25. The method of claim 1, wherein the cell is a mammalian cell, or wherein the cell is a plant cell.

26. The method of claim 1, wherein the extrusion complex comprises one or more members selected from the group consisting of CTCF, SA1/2, Smc3, Smc1, cohesin and Rad21.

27. The method of claim 1, wherein two or more catalytically inactive CRISPR-Cas systems or Cas proteins are targeted to a 5 kb region containing a CTCF or cohesin binding motif, wherein the CTCF or cohesin binding motif is targeted.

28. The method of claim 27, wherein 2-7 catalytically inactive CRISPR-Cas systems or Cas proteins are targeted to the region.

29. The method of claim 28, wherein the catalytically inactive CRISPR-Cas systems or Cas proteins are targeted to sequences 500-1000 base pairs apart in the region and wherein the sequences targeted alternate between sequences on opposite strands in the chromatin DNA.

30. The method of claim 1, wherein two or more catalytically inactive CRISPR-Cas systems or Cas proteins are targeted to a 5 kb region in between two CTCF or cohesin binding motifs and at least 100 kb from either CTCF or cohesin binding motif.

31. The method of claim 30, wherein 2-7 catalytically inactive CRISPR-Cas systems or Cas proteins are targeted to the region.

32. The method of claim 31, wherein the catalytically inactive CRISPR-Cas systems or Cas proteins are targeted to sequences 500-1000 base pairs apart in the region and wherein the sequences targeted alternate between sequences on opposite strands in the chromatin DNA.

* * * * *

UNITED STATES PATENT AND TRADEMARK OFFICE
CERTIFICATE OF CORRECTION

| | |
|---|---|
| PATENT NO. | : 11,214,800 B2 |
| APPLICATION NO. | : 15/753318 |
| DATED | : January 4, 2022 |
| INVENTOR(S) | : Erez Lieberman Aiden et al. |

It is certified that error appears in the above-identified patent and that said Letters Patent is hereby corrected as shown below:

On the Title Page

On the page 3, in Column 1, under "Other Publications", Line 55, delete "fora" and insert -- for a --.

On the page 3, in Column 1, under "Other Publications", Line 56, delete "Xinactivation" and insert -- X inactivation --.

In the Specification

In Column 4, Line 26, delete "CTCT" and insert -- CTCF --.

In Column 4, Line 27, delete "dCa9" and insert -- dCas9 --.

In Column 6, Line 24, delete "complex" and insert -- complex. --.

In Column 6, Line 34, delete "a a" and insert -- a --.

In Column 7, Line 32, delete "chromain" and insert -- chromatin --.

In Column 7, Line 33, delete "diwth" and insert -- with --.

In Column 8, Line 10, delete "the the" and insert -- the --.

In Column 9, Line 38, delete "HiC" and insert -- Hi-C --.

In Column 11, Line 8, delete "said said" and insert -- said --.

In Column 11, Line 14, delete "said said" and insert -- said --.

In Column 16, Line 26, delete "threedimensional" and insert -- three-dimensional --.

Signed and Sealed this
Eighteenth Day of July, 2023

Katherine Kelly Vidal
*Director of the United States Patent and Trademark Office*

In Column 17, Line 31, delete "in in" and insert -- in --.

In Column 17, Line 34, delete "CTFC" and insert -- CTCF --.

In Column 17, Line 42, delete "in in" and insert -- in --.

In Column 20, Line 22, delete "indiation" and insert -- indication --.

In Column 23, Line 8, delete "the an" and insert -- an --.

In Column 23, Line 27, delete "2,2′disulfonic" and insert -- 2,2′-disulfonic --.

In Column 23, Line 35, delete "trifluoromethylcouluarin (Coumaran" and insert -- trifluoromethylcoumarin (Coumarin --.

In Column 23, Line 36, delete "diaminidino" and insert -- diamidino --.

In Column 24, Line 32, delete "US2014" and insert -- US 2014 --.

In Column 25, Line 3, delete "Febuary" and insert -- February --.

In Column 26, Line 63, delete "and or" and insert -- and/or --.

In Column 27, Line 65, delete "galactosylqueosine," and insert -- galactosylqueuosine, --.

In Column 27, Line 66, delete "N~6-sopentenyladenine," and insert -- N6-isopentenyladenine, --.

In Column 28, Lines 2-3, delete "methoxyarninomethyl" and insert -- methoxyaminomethyl --.

In Column 28, Line 3, delete "mannosylqueosine," and insert -- mannosylqueuosine, --.

In Column 28, Line 6, delete "queosine," and insert -- queuosine, --.

In Column 29, Line 35, delete "Intersciences." and insert -- Interscience. --.

In Column 29, Line 47, delete "Intersciences" and insert -- Interscience --.

In Column 30, Line 55, delete "that that" and insert -- that --.

In Column 31, Line 23, delete "2d" and insert -- $2^{nd}$ --.

In Column 31, Line 25, delete "3d" and insert -- $3^{rd}$ --.

In Column 31, Line 36, delete "limiting" and insert -- limiting. --.

In Column 34, Line 44, delete "with out" and insert -- without --.

CERTIFICATE OF CORRECTION (continued)
U.S. Pat. No. 11,214,800 B2

In Column 36, Lines 21-22, delete "gluteraldehyde." and insert -- glutaraldehyde. --.

In Column 42, Line 19, delete "then" and insert -- than --.

In Column 42, Line 25, delete "10,000" and insert -- ~10,000 --.

In Column 43, Line 51, delete "complext" and insert -- complex --.

In Column 43, Line 52, delete "faciliating" and insert -- facilitating --.

In Column 47, Line 30, delete "1 10" and insert -- 110 --.

In Column 47, Line 35, delete "1 10" and insert -- 110 --.

In Column 47, Line 36, delete "I 50" and insert -- 150 --.

In Column 49, Line 35, delete "inactived" and insert -- inactivated --.

In Column 49, Line 38, delete "interfer" and insert -- interfere --.

In Column 49, Line 67, delete "complext" and insert -- complex --.

In Column 50, Line 26, delete "Erez" and insert -- Erez. --.

In Column 50, Line 33, delete "interest" and insert -- interest. --.

In Column 53, Line 29, delete "the the" and insert -- the --.

In Column 54, Line 63, delete "serumfree" and insert -- serum-free --.

In Column 55, Line 27, delete "intrarterially," and insert -- intraarterially, --.

In Column 64, Line 20, delete "response)" and insert -- response). --.

In Column 64, Line 51, delete "4 C." and insert -- 4° C. --.

In Column 65, Line 7, delete "2 μmon-" and insert -- 2 μmol/L- --.

In Column 67, Line 2, delete "the the" and insert -- the --.

In Column 68, Line 11, delete "minoalcohol" and insert -- aminoalcohol --.

In Column 69, Line 24, delete "particles" and insert -- nanoparticles --.

In Column 69, Line 33, delete "acetampinophen," and insert -- acetaminophen, --.

CERTIFICATE OF CORRECTION (continued)
U.S. Pat. No. 11,214,800 B2

In Column 70, Line 31, delete "dimyristyloxlpropyl" and insert -- dimyristyloxypropyl --.

In Column 72, Line 19, delete "NHSester)" and insert -- NHS-ester) --.

In Column 72, Line 52, delete "unregulated" and insert -- upregulated --.

In Column 72, Line 67, delete "the the" and insert -- the --.

In Column 74, Line 65, delete "particle" and insert -- nanoparticle --.

In Column 75, Line 23, delete "siRNARVG" and insert -- siRNA-RVG --.

In Column 77, Line 16, delete "1,2-distearoryl" and insert -- 1,2-distearoyl --.

In Column 77, Line 46, delete "the the" and insert -- the --.

In Column 77, Line 59, delete "3-N-[(wmethoxypoly(ethylene" and insert -- 3-N-[(ω-methoxypoly(ethylene --.

In Column 78, Line 15, delete "N,Ndimethylaminopropane" and insert -- N,N-dimethylaminopropane --.

In Column 79, Line 17, delete "Niotechnology," and insert -- Biotechnology, --.

In Column 80, Lines 17-18, delete "the the" and insert -- the --.

In Column 80, Line 20, delete "particles" and insert -- nanoparticles --.

In Column 80, Line 30, delete "particles" and insert -- nanoparticles --.

In Column 80, Line 42, delete "The the" and insert -- The --.

In Column 82, Line 30, delete "serumfree" and insert -- serum-free --.

In Column 82, Line 55, delete "serumfree" and insert -- serum-free --.

In Column 82, Line 55, delete "1)36" and insert -- þ36 --.

In Column 82, Line 59, delete "1)36" and insert -- þ36 --.

In Column 83, Line 7, delete "in in" and insert -- in --.

In Column 83, Line 8, delete "teachints" and insert -- teachings --.

In Column 83, Line 13, delete "the the" and insert -- the --.

CERTIFICATE OF CORRECTION (continued)
U.S. Pat. No. 11,214,800 B2

In Column 83, Line 30, delete "intrarterially," and insert -- intraarterially, --.

In Column 84, Line 17, delete "the the" and insert -- the --.

In Column 84, Line 35, delete "the the" and insert -- the --.

In Column 85, Line 43, delete "and or" and insert -- and/or --.

In Column 86, Line 42, delete "the the" and insert -- the --.

In Column 86, Line 54, delete "the the" and insert -- the --.

In Column 86, Line 66, delete "the the" and insert -- the --.

In Column 87, Lines 8-9, delete "the the" and insert -- the --.

In Column 89, Line 55, delete "and and" and insert -- and --.

In Columns 97-98, Line 27, delete "PAK4," and insert -- PAK4; --.

In Columns 99-100, Line 62, delete "PRKCZ:" and insert -- PRKCZ; --.

In Columns 99-100, Line 65, delete "TLR4:" and insert -- TLR4; --.

In Columns 99-100, Line 69, delete "ITGA5:" and insert -- ITGA5; --.

In Columns 99-100, Line 78, delete "SFRP2:" and insert -- SFRP2; --.

In Columns 101-102, Line 13, delete "NFKB2:" and insert -- NFKB2; --.

In Columns 103-104, Line 8, delete "RELA," and insert -- RELA; --.

In Columns 103-104, Line 8, delete "RELB," and insert -- RELB; --.

In Columns 105-106, Line 22, delete "ABCA1," and insert -- ABCA1; --.

In Column 107, Line 65, delete "thay" and insert -- they --.

In Column 108, Line 62, delete "genein" and insert -- gene in --.

In Column 109, Line 12, delete "he" and insert -- the --.

In Column 109, Line 33, delete "proteins proteins" and insert -- proteins --.

In Column 109, Line 49, delete "12" and insert -- I2 --.

CERTIFICATE OF CORRECTION (continued)  Page 6 of 8
U.S. Pat. No. 11,214,800 B2

In Column 109, Line 60, delete "benzodiazapine" and insert -- benzodiazepine --.

In Column 110, Line 28, delete "VAGFA" and insert -- VEGFA --.

In Column 110, Line 29, delete "VAGFB" and insert -- VEGFB --.

In Column 110, Line 30, delete "VAGFC" and insert -- VEGFC --.

In Column 110, Line 35, delete "VAGFA" and insert -- VEGFA --.

In Column 110, Line 36, delete "VAGFB" and insert -- VEGFB --.

In Column 110, Line 37, delete "VAGFC" and insert -- VEGFC --.

In Column 112, Line 3, delete "dianthii" and insert -- dianthi --.

In Column 113, Line 65, delete "then" and insert -- than --.

In Column 119, Line 12, delete "that that" and insert -- that --.

In Column 133, Line 42, delete "(5′→3)," and insert -- (5′→3′), --.

In Column 137, Lines 16-17, delete "Blymphoblasts" and insert -- B-lymphoblasts --.

In Column 139, Line 11, delete "FIG. 12D,E)" and insert -- FIGS. 12D, E) --.

In Column 139, Lines 18-19, delete "(FIG. 12D,E)." and insert -- (FIGS. 12D, E). --.

In Column 143, Line 12, delete "(pter;q) (Fig. S40-S41)." and insert -- (pter;q). --.

In Column 148, Line 24, delete "U/ul" and insert -- U/µl --.

In Column 149, Line 8, delete "2000" and insert -- 200 µl. --.

In Column 149, Line 38, delete "tube" and insert -- tube. --.

In Column 150, Line 14, delete "NEBuffer 2" and insert -- NEBuffer2 --.

In Column 150, Line 17, delete "NEBuffer 2" and insert -- NEBuffer2 --.

In Column 151, Line 65, delete "3)" and insert -- 3). --.

In Column 152, Line 44, delete "16 C." and insert -- 16° C. --.

In Column 152, Line 57, delete "GAIT" and insert -- GAII --.

CERTIFICATE OF CORRECTION (continued)
U.S. Pat. No. 11,214,800 B2

In Column 153, Line 55, delete "streptavidivin" and insert -- streptavidin --.

In Column 153, Line 66, delete "streptavidivin" and insert -- streptavidin --.

In Column 155, Line 27, delete "98 C" and insert -- 98° C. --.

In Column 155, Line 28, delete "98 C" and insert -- 98° C. --.

In Column 155, Line 29, delete "55 C" and insert -- 55° C. --.

In Column 155, Line 30, delete "72 C" and insert -- 72° C. --.

In Column 155, Line 32, delete "4 C" and insert -- 4° C. --.

In Column 155, Line 61, delete "98 C" and insert -- 98° C. --.

In Column 155, Line 62, delete "98 C" and insert -- 98° C. --.

In Column 155, Line 63, delete "55 C" and insert -- 55° C. --.

In Column 155, Line 64, delete "72 C" and insert -- 72° C. --.

In Column 155, Line 66, delete "4 C." and insert -- 4° C. --.

In Column 165, Line 28, delete "Hi-C(See" and insert -- Hi-C (See --.

In Column 167, Line 13, delete "(COncatamer" and insert -- (COncatemer --.

In Column 168, Line 63, delete "(COncatamer" and insert -- (COncatemer --.

In Column 170, Line 52, delete "may well be de to CTCF." and insert -- may well be due to CTCF. --.

In Column 171, Line 65, delete "lig/ml" and insert -- 1 ig/ml --.

In Column 172, Line 24, delete "Welcome" and insert -- Wellcome --.

In Column 173, Line 29, delete "midquality" and insert -- mid-quality --.

In Column 174, Line 9, delete "tranposase." and insert -- transposase. --.

In Column 175, Line 16, delete "98 C" and insert -- 98° C. --.

In Column 175, Line 17, delete "98 C" and insert -- 98° C. --.

In Column 175, Line 18, delete "55 C" and insert -- 55° C. --.

CERTIFICATE OF CORRECTION (continued)
U.S. Pat. No. 11,214,800 B2

In Column 175, Line 19, delete "72 C" and insert -- 72° C. --.

In Column 175, Line 21, delete "4 C" and insert -- 4° C. --.

In Column 175, Line 34, delete "98 C" and insert -- 98° C. --.

In Column 175, Line 35, delete "98 C" and insert -- 98° C. --.

In Column 175, Line 36, delete "55 C" and insert -- 55° C. --.

In Column 175, Line 37, delete "72 C" and insert -- 72° C. --.

In Column 175, Line 39, delete "4 C" and insert -- 4° C. --.

In Column 176, Line 10, delete "(1p1)" and insert -- (1 µl) --.

In Column 176, Line 18, delete "660" and insert -- 660 µl. --.

In Column 176, Line 66, delete "midquality" and insert -- mid-quality --.

```
                        SEQUENCE LISTING

<160> NUMBER OF SEQ ID NOS: 50

<210> SEQ ID NO 1
<211> LENGTH: 150
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (16)..(135)
<223> OTHER INFORMATION: n is a, c, g, or t

<400> SEQUENCE: 1
tcgcgcccat aactcnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnctgag ggtccgcctt                                       150

<210> SEQ ID NO 2
<211> LENGTH: 150
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (16)..(135)
<223> OTHER INFORMATION: n is a, c, g, or t

<400> SEQUENCE: 2
atcgcaccag cgtgtnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnncactg cggctcctca                                       150

<210> SEQ ID NO 3
<211> LENGTH: 150
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (16)..(135)
<223> OTHER INFORMATION: n is a, c, g, or t

<400> SEQUENCE: 3
cctcgcctat cccatnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnncacta ccggggtctg                                       150

<210> SEQ ID NO 4
<211> LENGTH: 21
<212> TYPE: DNA
<213> ORGANISM: Artificial Sequence
```

```
<220> FEATURE:
<223> OTHER INFORMATION: Synthetic primer

<400> SEQUENCE: 4
ctgggatcgc gcccataact c                                           21

<210> SEQ ID NO 5
<211> LENGTH: 21
<212> TYPE: DNA
<213> ORGANISM: Artificial Sequence
<220> FEATURE:
<223> OTHER INFORMATION: Synthetic primer

<400> SEQUENCE: 5
ctgggaatcg caccagcgtg t                                           21

<210> SEQ ID NO 6
<211> LENGTH: 21
<212> TYPE: DNA
<213> ORGANISM: Artificial Sequence
<220> FEATURE:
<223> OTHER INFORMATION: Synthetic primer

<400> SEQUENCE: 6
ctgggacctc gcctatccca t                                           21

<210> SEQ ID NO 7
<211> LENGTH: 21
<212> TYPE: DNA
<213> ORGANISM: Artificial Sequence
<220> FEATURE:
<223> OTHER INFORMATION: Synthetic primer

<400> SEQUENCE: 7
cgtggaaagg cggaccctca g                                           21

<210> SEQ ID NO 8
<211> LENGTH: 21
<212> TYPE: DNA
<213> ORGANISM: Artificial Sequence
<220> FEATURE:
<223> OTHER INFORMATION: Synthetic primer

<400> SEQUENCE: 8
cgtggatgag gagccgcagt g                                           21

<210> SEQ ID NO 9
<211> LENGTH: 21
<212> TYPE: DNA
<213> ORGANISM: Artificial Sequence
<220> FEATURE:
<223> OTHER INFORMATION: Synthetic primer

<400> SEQUENCE: 9
cgtggacaga ccccggtagt g                                           21

<210> SEQ ID NO 10
<211> LENGTH: 41
<212> TYPE: DNA
<213> ORGANISM: Artificial Sequence
<220> FEATURE:
<223> OTHER INFORMATION: Synthetic primer

<400> SEQUENCE: 10
ggattctaat acgactcact atagggtcgc gcccataact c                     41
```

<210> SEQ ID NO 11
<211> LENGTH: 41
<212> TYPE: DNA
<213> ORGANISM: Artificial Sequence
<220> FEATURE:
<223> OTHER INFORMATION: Synthetic primer

<400> SEQUENCE: 11
ggattctaat acgactcact atagggatcg caccagcgtg t           41

<210> SEQ ID NO 12
<211> LENGTH: 40
<212> TYPE: DNA
<213> ORGANISM: Artificial Sequence
<220> FEATURE:
<223> OTHER INFORMATION: Synthetic primer

<400> SEQUENCE: 12
ggattctaat acgactcact atagggcctc gcctatccca             40

<210> SEQ ID NO 13
<211> LENGTH: 14
<212> TYPE: DNA
<213> ORGANISM: Artificial Sequence
<220> FEATURE:
<223> OTHER INFORMATION: Synthetic consensus sequence for CTCF binding
      sites
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 13
ccgcgnggng gcag                                         14

<210> SEQ ID NO 14
<211> LENGTH: 288
<212> TYPE: PRT
<213> ORGANISM: Artificial Sequence
<220> FEATURE:
<223> OTHER INFORMATION: N-terminal capping region

<400> SEQUENCE: 14

Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
            20                  25                  30

Ser Pro Pro Ala Gly Gly Pro Leu Asp Gly Leu Pro Ala Arg Arg Thr
        35                  40                  45

Met Ser Arg Thr Arg Leu Pro Ser Pro Ala Pro Ser Pro Ala Phe
    50                  55                  60

Ser Ala Asp Ser Phe Ser Asp Leu Leu Arg Gln Phe Asp Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg
                100                 105                 110

Ala Ala Asp Ala Pro Pro Pro Thr Met Arg Val Ala Val Thr Ala Ala
            115                 120                 125

```
Arg Pro Pro Arg Ala Lys Pro Ala Pro Arg Arg Ala Ala Gln Pro
    130                 135                 140

Ser Asp Ala Ser Pro Ala Ala Gln Val Asp Leu Arg Thr Leu Gly Tyr
145                 150                 155                 160

Ser Gln Gln Gln Glu Lys Ile Lys Pro Lys Val Arg Ser Thr Val
                165                 170                 175

Ala Gln His His Glu Ala Leu Val Gly His Gly Phe Thr His Ala His
                180                 185                 190

Ile Val Ala Leu Ser Gln His Pro Ala Ala Leu Gly Thr Val Ala Val
            195                 200                 205

Lys Tyr Gln Asp Met Ile Ala Ala Leu Pro Glu Ala Thr His Glu Ala
    210                 215                 220

Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
                245                 250                 255

Thr Gly Gln Leu Leu Lys Ile Ala Lys Arg Gly Val Thr Ala Val
                260                 265                 270

Glu Ala Val His Ala Trp Arg Asn Ala Leu Thr Gly Ala Pro Leu Asn
    275                 280                 285
```

<210> SEQ ID NO 15
<211> LENGTH: 183
<212> TYPE: PRT
<213> ORGANISM: Artificial Sequence
<220> FEATURE:
<223> OTHER INFORMATION: C-terminal capping region

<400> SEQUENCE: 15

```
Arg Pro Ala Leu Glu Ser Ile Val Ala Gln Leu Ser Arg Pro Asp Pro
1               5                   10                  15

Ala Leu Ala Ala Leu Thr Asn Asp His Leu Val Ala Leu Ala Cys Leu
                20                  25                  30

Gly Gly Arg Pro Ala Leu Asp Ala Val Lys Lys Gly Leu Pro His Ala
            35                  40                  45

Pro Ala Leu Ile Lys Arg Thr Asn Arg Arg Ile Pro Glu Arg Thr Ser
    50                  55                  60

His Arg Val Ala Asp His Ala Gln Val Val Arg Val Leu Gly Phe Phe
65                  70                  75                  80

Gln Cys His Ser His Pro Ala Gln Ala Phe Asp Asp Ala Met Thr Gln
                85                  90                  95

Phe Gly Met Ser Arg His Gly Leu Leu Gln Leu Phe Arg Arg Val Gly
                100                 105                 110

Val Thr Glu Leu Glu Ala Arg Ser Gly Thr Leu Pro Pro Ala Ser Gln
            115                 120                 125

Arg Trp Asp Arg Ile Leu Gln Ala Ser Gly Met Lys Arg Ala Lys Pro
    130                 135                 140

Ser Pro Thr Ser Thr Gln Thr Pro Asp Gln Ala Ser Leu His Ala Phe
145                 150                 155                 160

Ala Asp Ser Leu Glu Arg Asp Leu Asp Ala Pro Ser Pro Met His Glu
                165                 170                 175

Gly Asp Gln Thr Arg Ala Ser
                180
```

<210> SEQ ID NO 16
<211> LENGTH: 14

```
<212> TYPE: DNA
<213> ORGANISM: Artificial Sequence
<220> FEATURE:
<223> OTHER INFORMATION: Synthetic consensus DNA sequence for CTCF
      binding sites
<220> FEATURE:
<221> NAME/KEY: misc_feature
<222> LOCATION: (5)..(5)
<223> OTHER INFORMATION: n is a, c, g, or t

<400> SEQUENCE: 16
ccacnaggtg gcag                                                         14

<210> SEQ ID NO 17
<211> LENGTH: 23
<212> TYPE: DNA
<213> ORGANISM: Artificial Sequence
<220> FEATURE:
<223> OTHER INFORMATION: Guide RNA for mutant clone 001

<400> SEQUENCE: 17
tcacagctat ttccacaaga ggg                                               23

<210> SEQ ID NO 18
<211> LENGTH: 23
<212> TYPE: DNA
<213> ORGANISM: Artificial Sequence
<220> FEATURE:
<223> OTHER INFORMATION: Guide RNA for mutant clone 002

<400> SEQUENCE: 18
gcccgggagc tttcaggaca ggg                                               23

<210> SEQ ID NO 19
<211> LENGTH: 23
<212> TYPE: DNA
<213> ORGANISM: Artificial Sequence
<220> FEATURE:
<223> OTHER INFORMATION: Guide RNA for mutant clone 002

<400> SEQUENCE: 19
gctcacggag cacttgccca ggg                                               23

<210> SEQ ID NO 20
<211> LENGTH: 23
<212> TYPE: DNA
<213> ORGANISM: Artificial Sequence
<220> FEATURE:
<223> OTHER INFORMATION: Guide RNA for mutant clone 003

<400> SEQUENCE: 20
ggaaaaccct ctggacccca ggg                                               23

<210> SEQ ID NO 21
<211> LENGTH: 23
<212> TYPE: DNA
<213> ORGANISM: Artificial Sequence
<220> FEATURE:
<223> OTHER INFORMATION: Guide RNA for mutant clone 003

<400> SEQUENCE: 21
agaagtcctc ccttggacag ggg                                               23

<210> SEQ ID NO 22
<211> LENGTH: 23
<212> TYPE: DNA
<213> ORGANISM: Artificial Sequence
```

```
<220> FEATURE:
<223> OTHER INFORMATION: Guide RNA for mutant clone 004

<400> SEQUENCE: 22
ggaaaaccct ctggaccccca ggg                                              23

<210> SEQ ID NO 23
<211> LENGTH: 23
<212> TYPE: DNA
<213> ORGANISM: Artificial Sequence
<220> FEATURE:
<223> OTHER INFORMATION: Guide RNA for mutant clone 004

<400> SEQUENCE: 23
agaagtcctc ccttggacag ggg                                               23

<210> SEQ ID NO 24
<211> LENGTH: 23
<212> TYPE: DNA
<213> ORGANISM: Artificial Sequence
<220> FEATURE:
<223> OTHER INFORMATION: Guide RNA for mutant clone 005 - B forward
      inversion

<400> SEQUENCE: 24
ggaaaaccct ctggaccccca ggg                                              23

<210> SEQ ID NO 25
<211> LENGTH: 23
<212> TYPE: DNA
<213> ORGANISM: Artificial Sequence
<220> FEATURE:
<223> OTHER INFORMATION: Guide RNA for mutant clone 005 - B reverse
      inversion

<400> SEQUENCE: 25
cacctagata ctccaccagg ggg                                               23

<210> SEQ ID NO 26
<211> LENGTH: 23
<212> TYPE: DNA
<213> ORGANISM: Artificial Sequence
<220> FEATURE:
<223> OTHER INFORMATION: Guide RNA for mutant clone 006 - B forward
      inversion

<400> SEQUENCE: 26
ggaaaaccct ctggaccccca ggg                                              23

<210> SEQ ID NO 27
<211> LENGTH: 23
<212> TYPE: DNA
<213> ORGANISM: Artificial Sequence
<220> FEATURE:
<223> OTHER INFORMATION: Guide RNA for mutant clone 006

<400> SEQUENCE: 27
agaagtcctc ccttggacag ggg                                               23

<210> SEQ ID NO 28
<211> LENGTH: 23
<212> TYPE: DNA
<213> ORGANISM: Artificial Sequence
<220> FEATURE:
<223> OTHER INFORMATION: Guide RNA for mutant clone 006 - B reverse
      inversion
```

```
<400> SEQUENCE: 28
cacctagata ctccaccagg ggg                                              23

<210> SEQ ID NO 29
<211> LENGTH: 23
<212> TYPE: DNA
<213> ORGANISM: Artificial Sequence
<220> FEATURE:
<223> OTHER INFORMATION: Guide RNA for mutant clone 007

<400> SEQUENCE: 29
ccttgttagt taccagcaga ggg                                              23

<210> SEQ ID NO 30
<211> LENGTH: 23
<212> TYPE: DNA
<213> ORGANISM: Artificial Sequence
<220> FEATURE:
<223> OTHER INFORMATION: Guide RNA for mutant clone 008

<400> SEQUENCE: 30
ccttgttagt taccagcaga ggg                                              23

<210> SEQ ID NO 31
<211> LENGTH: 23
<212> TYPE: DNA
<213> ORGANISM: Artificial Sequence
<220> FEATURE:
<223> OTHER INFORMATION: Guide RNA for mutant clone 009

<400> SEQUENCE: 31
ccttgttagt taccagcaga ggg                                              23

<210> SEQ ID NO 32
<211> LENGTH: 23
<212> TYPE: DNA
<213> ORGANISM: Artificial Sequence
<220> FEATURE:
<223> OTHER INFORMATION: Guide RNA for mutant clone 010

<400> SEQUENCE: 32
ccttgttagt taccagcaga ggg                                              23

<210> SEQ ID NO 33
<211> LENGTH: 23
<212> TYPE: DNA
<213> ORGANISM: Artificial Sequence
<220> FEATURE:
<223> OTHER INFORMATION: Guide RNA for mutant clone 011

<400> SEQUENCE: 33
ttttaacttt tgccatcagg tgg                                              23

<210> SEQ ID NO 34
<211> LENGTH: 23
<212> TYPE: DNA
<213> ORGANISM: Artificial Sequence
<220> FEATURE:
<223> OTHER INFORMATION: Guide RNA for mutant clone 012

<400> SEQUENCE: 34
ccttgttagt taccagcaga ggg                                              23

<210> SEQ ID NO 35
<211> LENGTH: 23
```

```
<212> TYPE: DNA
<213> ORGANISM: Artificial Sequence
<220> FEATURE:
<223> OTHER INFORMATION: Guide RNA for mutant clone 13 - E forward
      deletion

<400> SEQUENCE: 35
ccttgttagt taccagcaga ggg                                              23

<210> SEQ ID NO 36
<211> LENGTH: 23
<212> TYPE: DNA
<213> ORGANISM: Artificial Sequence
<220> FEATURE:
<223> OTHER INFORMATION: Guide RNA for mutant clone 013 - E reverse
      deletion

<400> SEQUENCE: 36
ttttaacttt tgccatcagg tgg                                              23

<210> SEQ ID NO 37
<211> LENGTH: 23
<212> TYPE: DNA
<213> ORGANISM: Artificial Sequence
<220> FEATURE:
<223> OTHER INFORMATION: Guide RNA for mutant clone 014 - E forward
      deletion

<400> SEQUENCE: 37
ccttgttagt taccagcaga ggg                                              23

<210> SEQ ID NO 38
<211> LENGTH: 23
<212> TYPE: DNA
<213> ORGANISM: Artificial Sequence
<220> FEATURE:
<223> OTHER INFORMATION: Guide RNA for mutant clone 014 - E reverse
      deletion

<400> SEQUENCE: 38
ttttaacttt tgccatcagg tgg                                              23

<210> SEQ ID NO 39
<211> LENGTH: 23
<212> TYPE: DNA
<213> ORGANISM: Artificial Sequence
<220> FEATURE:
<223> OTHER INFORMATION: Guide RNA for mutant clone 015 - E forward
      deletion

<400> SEQUENCE: 39
ccttgttagt taccagcaga ggg                                              23

<210> SEQ ID NO 40
<211> LENGTH: 23
<212> TYPE: DNA
<213> ORGANISM: Artificial Sequence
<220> FEATURE:
<223> OTHER INFORMATION: Guide RNA for mutant clone 015 - E reverse
      deletion

<400> SEQUENCE: 40
ttttaacttt tgccatcagg tgg                                              23

<210> SEQ ID NO 41
<211> LENGTH: 23
<212> TYPE: DNA
```

```
<213> ORGANISM: Artificial Sequence
<220> FEATURE:
<223> OTHER INFORMATION: Guide RNA for mutant clone 016

<400> SEQUENCE: 41
ccttgttagt taccagcaga ggg                                               23

<210> SEQ ID NO 42
<211> LENGTH: 23
<212> TYPE: DNA
<213> ORGANISM: Artificial Sequence
<220> FEATURE:
<223> OTHER INFORMATION: Guide RNA for mutant clone 017

<400> SEQUENCE: 42
tctggtagtc tagggccacc tgg                                               23

<210> SEQ ID NO 43
<211> LENGTH: 23
<212> TYPE: DNA
<213> ORGANISM: Artificial Sequence
<220> FEATURE:
<223> OTHER INFORMATION: Guide RNA for mutant clone 018

<400> SEQUENCE: 43
cagcacagtt gaattcccag tgg                                               23

<210> SEQ ID NO 44
<211> LENGTH: 23
<212> TYPE: DNA
<213> ORGANISM: Artificial Sequence
<220> FEATURE:
<223> OTHER INFORMATION: Guide RNA for mutant clone 018

<400> SEQUENCE: 44
attcagttaa gtttattcca cgg                                               23

<210> SEQ ID NO 45
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 45
caaccccaca gggagaact                                                    19

<210> SEQ ID NO 46
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 46
actttcattt tcaggtcaga c                                                 21

<210> SEQ ID NO 47
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 47
cttttcttct caggttacag t                                                 21
```

```
<210> SEQ ID NO 48
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 48
tcaatcacac aagggaaatg c                                                  21

<210> SEQ ID NO 49
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 49
caacagcaat ttcagtaagg tg                                                 22

<210> SEQ ID NO 50
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 50
gatctggtca aaatcagaga t                                                  21
```